US010626471B2

(12) United States Patent
Pichaud et al.

(10) Patent No.: US 10,626,471 B2
(45) Date of Patent: Apr. 21, 2020

(54) GENE SIGNATURES OF INFLAMMATORY DISORDERS THAT RELATE TO THE LIVER

(71) Applicants: ENTEROME, Paris (FR); INSTITUT NATIONAL DE LA RECHERCHE AGRONOMIQUE, Paris (FR)

(72) Inventors: Matthieu Pichaud, Paris (FR); Pierre Rimbaud, Bordeaux (FR); Stanislav Ehrlich, Orsay (FR)

(73) Assignees: ENTEROME, Paris (FR); INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 0 days.

(21) Appl. No.: 15/972,620

(22) Filed: May 7, 2018

(65) Prior Publication Data

US 2018/0251819 A1 Sep. 6, 2018

Related U.S. Application Data

(62) Division of application No. 14/435,750, filed as application No. PCT/EP2013/071793 on Oct. 17, 2013, now Pat. No. 10,036,074.

(30) Foreign Application Priority Data

Oct. 17, 2012 (EP) .................................... 12306286

(51) Int. Cl.
*C12Q 1/689* (2018.01)
*C12Q 1/6883* (2018.01)

(52) U.S. Cl.
CPC .......... *C12Q 1/689* (2013.01); *C12Q 1/6883* (2013.01); *C12Q 2600/118* (2013.01); *C12Q 2600/16* (2013.01)

(58) Field of Classification Search
None
See application file for complete search history.

(56) References Cited

U.S. PATENT DOCUMENTS 6,582,908 B2 6/2003 Fodor
6,610,836 B1 * 8/2003 Breton .................. C07K 14/26 435/320.1
8,119,365 B2 * 2/2012 Blattner ............... C07K 14/245 435/252.8
8,758,764 B2 * 6/2014 Masignani ......... C07K 16/1232 424/185.1
2002/0061569 A1 5/2002 Haselbeck
2009/0142778 A1 6/2009 Hershberg
2011/0165568 A1 * 7/2011 Vatta .................... C07K 14/245 435/6.11
2014/0179726 A1 6/2014 Bajaj
2014/0377278 A1 12/2014 Elinav
2015/0267249 A1 9/2015 Le Chatelier et al.
2015/0275275 A1 10/2015 Ehrlich et al.
2015/0284779 A1 10/2015 Le Chatelier et al.

FOREIGN PATENT DOCUMENTS

WO 2012/105590 A1 9/2012
WO 2013/036290 A1 3/2013
WO 2014060537 A1 4/2014
WO 2014060538 A1 4/2014
WO 2014060542 A1 4/2014

OTHER PUBLICATIONS

Kai et al FEMS Immunology and Medical Microbiology. 2000. 29: 283-288.*
Haynes et al Electrophoresis. 1998. 19: 1862-1871.
Al-Soud, W. Abu, et al., "DNA of *Helicobacter* spp. and common gut bacteria in primary liver carcinoma," Digestive and Liver Disease, vol. 40, pp. 126-131 (2008).
Abubucker, S., et al., "Metabolic Reconstruction for Metagenomic Data and Its Application to the Human Microbiome," PLoS Comput Biol 8(6): e1002358. doi:10.1371/journal.pcbi.1002358 (2012).
Adams, L. A., et al., "Non-invasive diagnosis of nonalcoholic fatty liver and nonalcoholic steatohepatitis," Journal of Digestive Diseases 2011; 12; 10-16.
Angulo, P. "Nonalcoholic Fatty Liver Disease," N Engl J Med, vol. 346, No. 16, Apr. 18, 2002.
Anty, R., et al., "Liver fibrogenesis and metabolic factors," Clinics and Research in Hepatology and Gastroenterology (2011) 35, S10-S20.
Bajaj, J. S., "Linkage of gut microbiome with cognition in hepatic encephalopathy," Am J Physiol Gastrointest Liver Physiol 302: G168-G175, 2012.
Bergheim, I., et al., "Antibiotocs protect against fructose-induced hepatic lipid accumulation in mice: Role of endotoxin," Journal of Hepatology, 48 (2008) 983-992.
Cani, P. D., "Involvement of gut microbiota in the development of low-grade inflammation and type 2 diabetes associated with obesity," Gut Microbes 3:4, 279-288; Jul./Aug. 2012.
Li, Ding-you, et al., "Nonalcoholic fatty liver disease: For better or worse, blame the gut microbes," Journal of Parenteral and Enteral Nutrition, vol. 37, No. 6, 787-793 (2013).
Dumas, M-E, et al., "Metabolic profiling reveals a contribution of gut microbiota to fatty liver phenotype in insulin-resistant mice," PNAS, vol. 103, No. 33, pp. 12511-12516 (2006).
Elinav, E., et al., "NLRP6 inflammasome is a regulator of colonic microbial ecology and risk for colitis," Cell. May 27, 2011; 145(5): 745-757.

(Continued)

*Primary Examiner* — Carla J Myers
(74) *Attorney, Agent, or Firm* — Arrigo, Lee, Guttman & Mouta-Bellum LLP

(57) ABSTRACT

This invention is related to the area of characterization of inflammation in relation with the gut microbiota, in metabolic and autoimmune disorders. In particular, it relates to the identification of gene signatures which can be used as a marker predictive of inflammation associated diseases, such as liver-related metabolic disorders, in particular to the evolution of benign steatosis towards its most severe forms (steatohepatitis and cirrhosis) or autoimmune disorders, in particular inflammatory bowel diseases (Crohn's and Ulcerative Colitis). These gene signatures can therefore be used as a means of diagnosis, prognosis, stratification for drug studies, for monitoring patient and for assigning an appropriate treatment.

20 Claims, 17 Drawing Sheets

Figure 1A:
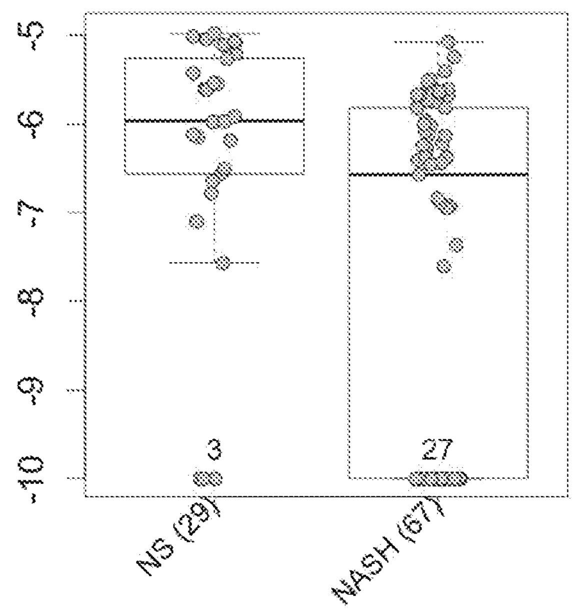

Specification includes a Sequence Listing.

(56) References Cited

OTHER PUBLICATIONS

Godon, J-J, "Molecular Microbial Diversity of an Anaerobic Digestor as Determined by Small-Subunit rDNA Sequence Analysis," Applied and Environmental Microbiology, Jul. 1997, vol. 63, No. 7, p. 2802-2813.

Heid, C. A., "Real Time Quantitative PCR," Genome Res. 1996 6: 986-994.

Henao-Mejia, J., "Inflammasome-mediated dysbiosis regulates progression of NAFLD and obesity," Nature. ; 482 (7384): 179-185 (2012).

Iacono, A., "Probiotics as an emerging therapeutic strategy to treat NAFLD: focus on molecular and biochemical mechanisms," Journal of Nutritional Biochemistry 22 (2011) 699-711.

Morgan, X. C., "Chapter 12: Human Microbiome Analysis," PLOS Computational Biology, Dec. 2012, vol. 8, Issue 12, e1002808.

Musso, G., "Gut microbiota as a regulator of energy homeostasis and ectopic fat deposition: mechanisms and implications for metabolic disorders," Current opinion in Lipidology, 2010, 21: 76-83.

Parker, R. M. C., "mRNA Detection by In Situ and Northern Hybridization," Methods in Molecular Biology, vol. 106, pp. 247-283.

Parnell, J. A., "The potential role of prebiotic fibre for treatment and management of non-alcoholic fatty liver disease and associated obesity and insulin resistance," Liver International, 32(5):701-11 (2012).

Qin, J., "A metagenome-wide association study of gut microbiota in type 2 diabetes," Nature, vol. 490, pp. 55-60 (2012).

Sokol, H., et al., "*Faecalibacterium prausnitzii* is an anti-inflammatory commensal bacterium identified by gut microbiota analysis of Crohn disease patients," PNAS, vol. 105, No. 43, pp. 16731-16736 (2008).

Sokol, H., et al., "Low Counts of *Faecalibacterium prausnitzii* in Colitis Microbiota," Inflammatory Bowel Diseases, (2009); 15(8):1183-9.

Spencer, M. D., et al., "Association between composition of the human gastrointestinal microbiome and development of fatty liver with choline deficiency," Gastroenterology. Mar. 2011 ; 140(3): 976-986.

Wang, B., et al., "Microbiomic profiles delineate potential role for gut microbiota in nonalcohonic fatty liver disease," Journal of Hepatology 2012 vol. 56, S513.

Willing, B. P., et al., "The role of the immune system in regulating the microbiota," Gut Microbes 1:4, 213-223; Jul./ Aug. 2010.

Ken-ichi Ikejima et al., Role of intestinal bacteria in liver pathophysiology, Steps in Medicine, 2006, vol. 216, pp. 281-285.

Takayuki Ezaki et al., Identification of Intestinal Flora: DNA Probe and Primers, Journal of Intestinal Microbiology, 2006, vol. 20, pp. 245-258.

Takahiro Matsuki et al., Molecular Methods in the Analysis of Human Intestinal Flora, Journal of Intestinal Microbiology, 2006, vol. 20, pp. 25-33.

English translation of Office Action dated Nov. 5, 2018, in Japanese Application No. 2015-537267.

* cited by examiner

SEQUENCE LISTING

```
<160> NUMBER OF SEQ ID NOS: 155

<210> SEQ ID NO 1
<211> LENGTH: 1344
<212> TYPE: DNA
<213> ORGANISM: unknown
<220> FEATURE:
<223> OTHER INFORMATION: Representative gene for Cluster 1

<400> SEQUENCE: 1

atgaatagag atttaacaaa aggttcagtt ttaaagtcaa tgcttctttt ttcaattcca     60

atgattttag gtgatttact tcaacaatgt tataacattg ttgatacatt gattgttggt    120

caatttctcg gtaaaaatgc tctagcaagt gttggctcat cgtttacctt aatgacattt    180

ataacatcta taatccttgg tttatgtatg ggaagtggag cgttgttttc aattagatat    240

ggacaaaaag atgaaaaagg attacgagaa gatgtatgtg catcattttt ctttattgca    300

ctcatcacgt ttatactaac agtaatatcc tatatttttc ttaatcagct ttctgttttt    360

ttacatgttc cgcatgaagt gtggggagat atgaaaggct atcttattgt tatttttata    420

ggaataccag ctattttttt atataactat tttgcttctt atttaagagc gattggtaat    480

tcaatgattc cacttatatt tttagctatt tcggcaatac ttaatattgt attagattta    540

ttttttgtaa ttgtattaaa attaggagtt gaaggtgcag ctattgctac gatgatttcc    600

caatatcttt caggtattgg catcagtatt tactcactta taaaaaatat acaagtacga    660

gcaattatga aattacaata ttttcattta aagagggttc ataaagtgat ttcgttttca    720

gttcttacat gtattcaaca atcagtaatg aatttaggta ttttaatggt acaagggtta    780

gtgaatagtt ttggaactgt agttatggca gcatttgctg ctgctgttaa aatagatgct    840

tttgcatata tgccagtaca agattttgga aatgcatttt ctacttttat tgctcaaaac    900

tatggtgcaa aagaaaaaat gcgtattcaa tcaggattaa aatcagcagt ttgtctttct    960

atgggatttt gcataattat ttcaactatt gtatgtattt ttgctaaaga tttaatgact   1020

atttttatag atgcaaaaga aacagaaatt attatggaag gtgtcaagta tttaaaaatt   1080

gaaggtgcct tttattgtgg aattggttgt ttgtttttgt tgtatggttt gtatcgtgct   1140

ttaggtaaac ctggtatgag tgtcgttctt acaatatttt ctttagggac acgtgttgtg   1200

ttagcttatg ttttatcagc aattccagcg attggtgtta ctggtatttg gtggtctgtt   1260

cctattggat gggcacttgc agatttaata ggattaattt attataggtg taaaaaaaag   1320

gaattgcttt cttttaatat ttag                                          1344


<210> SEQ ID NO 2
<211> LENGTH: 555
<212> TYPE: DNA
<213> ORGANISM: unknown
<220> FEATURE:
<223> OTHER INFORMATION: Equivalent gene for Cluster 1

<400> SEQUENCE: 2

atgtcagtag aagcaatcaa tgcgaaaaaa gtcgttgttg aagaaatcac tggtaaattt     60

aatgattcac aatctgctgt agtagtagaa tatcgtggat tatcagtagc agaagtcact    120
```

```
gaattacgta aagcattacg tgaagaagat gttgaattca aagtttacaa aaacaaatta    180

gttcaaagag ctactgaaag cgctggatat gctgaaatca atgataaatt agtaggtcca    240

aacgctattg cattcggtca tagtgatgcc gttgcacctg caagagtttt agctaacttt    300

gctaaagatc atgaagcttt agtaatcaaa gctggaattg ttgaaggaaa agtattagaa    360

gtagaagaaa ttaatgaaat tgctaaatta cctggacgtg aaggaatgta ctcaatgtta    420

cttggtatgt tacaagcacc agttagcaaa ttcgctagag ttgtaaaagc tgtagcagat    480

gcaagagaag aaaatggtgg agaagcacca gttgaagcac ctgctgaaga aaaagtagaa    540

gaagctgctg aataa                                                     555
```

<210> SEQ ID NO 3
<211> LENGTH: 1182
<212> TYPE: DNA
<213> ORGANISM: unknown
<220> FEATURE:
<223> OTHER INFORMATION: Equivalent gene for Cluster 1

<400> SEQUENCE: 3

```
atgtttattc ataatctaaa gtatacagtt aaaatacttt ttaaaaataa agttcttatt     60

ttttggatgt ttgcttttcc tattatttta ggtatttttct ttcacatggc ttttgaaaat    120

attgaaaaag acgaagcttt acaagttttt gatattgcag ttattgacaa taaggaatat    180

caaaaccaaa caatttatca agaaaccttt aaagagcttt ctgataaaaa aaataaggat    240

cagttatttc gtattcattt tgtaaataaa aaagaggcgg aacagctttt agaagataat    300

gaaatagaag gatatgttct ctttaataaa caagaaccac aaattgtgat taaagaaaat    360

ggtatggaac aaacaatctt gcaatttgtt atggatgaaa ttaaacaaaa taagaggatg    420

atagaagatc taacaaagaa acaaattgaa gatgaaatac aacaaggaaa ctacaatttt    480

aatgttcaac aaattgtaca tgatattctt caaaagctca ataaccaaga agtatcttta    540

aaagacacat caagtagtca tttaagttat atgcaaattg aatattatac cttaattgcc    600

atggcttgta tgtatggtgg gatgttgggc ttaacagcta ttaataatca attggcgaat    660

atgtccgcta aagggaaaag agtttctgtt tcaccaaata aaaaaggaat acttgtctta    720

tcttcagcac taggttctta tttagtaagc cttgttggtt tagcaattct tttaatcttt    780

ttaaaatttg gtttaaatgt tgaatttggt agtcaatggc tttatataat cattctttct    840

ttagttggtg atttagcagg tatttcgatg ggaatattta ttgcttctgt ttttagagtt    900

tctgaacaag caaaaacagg aattaatatt gcgatttcta tgtttttctc ggttctatct    960

gggatgatgg gtgttacttt aaaatatgtt attgataaaa atatacctat tgttaatctt   1020

atcaatccta ataatttgat taccgatggt ttttatgctt tatattatta caatacattt   1080

aatcgatata tcagagatat ttgttgttta ggagtattta ttattgtatg tttatttatt   1140

tcttttaggg ctttaaggag ggaacaatat gattatattt ag                       1182
```

<210> SEQ ID NO 4
<211> LENGTH: 774
<212> TYPE: DNA
<213> ORGANISM: unknown
<220> FEATURE:
<223> OTHER INFORMATION: Equivalent gene for Cluster 1

<400> SEQUENCE: 4

```
ttggaaacaa atattttatt tattattctt gtaacctttt ttgctggaat gggagcaggt     60

ctaggaacag gttttgcagg aatgtcagcg gctgctgtta ttagcccaat gctcattgct    120
```

```
tttttgaaaa tggaccctta tatggcagta ggtattgctt tgtcatcaga tgtccttgcc    180

agtgcggttt cagcttatac ttatggaaaa aataaaaatt tagatattag aaatggttta    240

ttgatgatgg taagtgtact tatttttacg gtagtaggta gttatgcggc aagtctttta    300

ccatcttcaa caatgggaag tttttcagtt tttatgactt ttattttagg agttaaattt    360

attgttagac cagtaatgac aacgaaagaa gcgatgaata atgtttcttc taaaaaaaga    420

gcaatccaat ctataatttg tggaacttgc ataggtttta tttgtggttt tgttggagct    480

ggtggaggca tgatgatgct tcttatctta acaacagtca tgggatatga acttaaaacg    540

gcagtaggta cgagtgtttt tattatgacc tttacagccc ttactggagc tatttcacat    600

tttatgattg gtgggtttcc taatttaaca gtatggattt tatgtattct ctttactctt    660

atttgggcaa gaattgctgc tttatttgcg aataaagcaa ctcctaaaac cttaaataga    720

gcaacaggaa ttgttcttgt tgttctagga attgttatct ttttattttc ataa          774
```

```
<210> SEQ ID NO 5
<211> LENGTH: 945
<212> TYPE: DNA
<213> ORGANISM: unknown
<220> FEATURE:
<223> OTHER INFORMATION: Equivalent gene for Cluster 1

<400> SEQUENCE: 5

atgacaaatg tatttgtatc attattagtt cttattgttg gttttatttt attaatgaaa     60

ggagcggatt tctttgtaga aggaagttct tctattgcca caagatttca tattccttca    120

ttaatcatcg gtttaacaat tgtggctatg ggaacaagtt tacctgaatg tgctgtcagt    180

attacagcat caatggatgg aaataatgct ttagcggtgg caaatgccgt aggttctaat    240

atttttaatt taatggttgt ttgtggtata tctgctttat ttgtaccgat tgcagtacaa    300

gtaaatacgc ttaaaagaga atttccattt tctgttttat gtgctatttt attaatgatc    360

ttaggttatt ttgggatgat cttaggacat attgatggaa ttgttctttt gattttattt    420

gtaggatata ttgtttacat gattgtttcg gctaaaaaag ccatgaatac atatcaagag    480

gaagaagaaa ttaaagttat ttcaatggga ttaagcttgg tttatattgt tggtggagca    540

atcgctatta aatttggtgg agattttgta gtagatagtg cttccaatat tgctttatct    600

ttaggaatgt cacaaaactt agtcggtctt accattgttg ctcttggaac ttctttacca    660

gaacttgtta cttcaatagt agctgctaaa aaaggtgaag tagatatggc tcttggaaat    720

gttattggtt caaatgtttt taatatttta tttgttttag gtattgcagc aacaattagt    780

ccaattactt ttatctttga aaatattatt gatattctta ttttaacaat tttttcttta    840

atagttttat attttggatt tacgaaacat aaaattgatc gtaaagaagg aattattatg    900

cttcttcttt atgtcgctta cttagcctat atcattatac gttag                    945
```

```
<210> SEQ ID NO 6
<211> LENGTH: 480
<212> TYPE: DNA
<213> ORGANISM: unknown
<220> FEATURE:
<223> OTHER INFORMATION: Representative gene for Cluster 2

<400> SEQUENCE: 6

atgagttata aaatgcatat cctcgtttgt ggtggaacgg gatgtagagc atctgccagt     60

caccagatta ttaccagact ggaagaatgt ttaaaagaga aaaacctaga agacgaagtt    120
```

caggtcatcg caaccggttg tttcggtttc tgtgaaaaag gaccgatcgt gaaagtcatg 180
cctgacaaca ccttctacgt acaggttaag ccggatgacg ccgaggaaat tgtaaatgaa 240
catgttatca aaggacgtaa agtcgaaaga ttattatata aagatccgga aaagaaagaa 300
gcagtaagcg actcgaaaca catgggtttc tacaagaaac aactgcggat cgccttgcgt 360
aactgcggat tcattgaccc ggaaaatatt gaagaataca tcgcacgtga aggatattcc 420
gcgttagcga aatgtatcac cgagatgaaa ccggaagaag tgatcaacga gatcaaatta 480

<210> SEQ ID NO 7
<211> LENGTH: 531
<212> TYPE: DNA
<213> ORGANISM: unknown
<220> FEATURE:
<223> OTHER INFORMATION: Equivalent gene for Cluster 2

<400> SEQUENCE: 7
atgaatttag agggtaaaca acagatatgg aaagattatc agaaagagat agccgatgat 60
cactattttt acgcgagaag ttgtatccgc cagactttct tcccgggttc ggaatgggct 120
tacttggata tcatgaaaaa taaactggcg aaagatgtta ttgatgatcc gcgacacacg 180
acttgcactg ggatcggtta tcattcggac atcgttccgg cagaaacaat catgacagta 240
gtcgcccggc attttgccct tatgaccgag gccgggtacg aaaatatgac tccctcctgc 300
atcacttctt tcggtattta taccgagatt ctggagacat ggcaccatca cccggaagta 360
gaagaaaaaa tcagggaatt cctttggaaa gccaccaaac gggaatttaa aaaacctaga 420
aatcttgctc acacatcaga cataatctat aagttcagaa acgagatcgc tgcccaggca 480
aaatacaagc tggtagacgt tcacaccgga agacctcttc gaggggtaga t 531

<210> SEQ ID NO 8
<211> LENGTH: 288
<212> TYPE: DNA
<213> ORGANISM: unknown
<220> FEATURE:
<223> OTHER INFORMATION: Equivalent gene for Cluster 2

<400> SEQUENCE: 8
atggatccaa aagtaagtat tatcatgggt agcacgtcag acctgcccgt catggaaaaa 60
gccgcaaaag tgttaaacga tttttgcata cctttcgaaa tcaatgccct ctccgctcac 120
cgcacaccgg cagaagtgga gtcttttgcc aaaaacgcac agaaacgggg tattgaagtt 180
atcatcgccg gagccggaat ggccgcacac ctaccgggtg ttatcgctgc catgacacca 240
attcccgtga tcggtgttcc catcaacgct tctcttgacg ggatggac 288

<210> SEQ ID NO 9
<211> LENGTH: 351
<212> TYPE: DNA
<213> ORGANISM: unknown
<220> FEATURE:
<223> OTHER INFORMATION: Equivalent gene for Cluster 2

<400> SEQUENCE: 9
atggacgaga aggtatattt ggaaaaactg gaaaagcggg agatcaagcc gacggccatg 60
cggctgttga ttctgaaggc gatgactcgt tttacccggg cgtttagcct actggatcta 120
gagacggaat tggataccgt ggataaatcg acgatattcc ggacgattaa tctgtttttg 180
gatcatcact tgattcacgt gattgatgac ggttccggtt cgttgaaata ttcggtatgc 240
agtaatgaat gtacctgttc tatcgatgat cttcacgctc atttctattg ccggaattgc 300
cacaagactt tttgtttaag aaaaattcac gtgcccacgg tggccttgcc c 351

<210> SEQ ID NO 10
<211> LENGTH: 498
<212> TYPE: DNA
<213> ORGANISM: unknown
<220> FEATURE:
<223> OTHER INFORMATION: Equivalent gene for Cluster 2

<400> SEQUENCE: 10
caatttattt acgaactttt aaagttaaga ggaatgtata ttacagaagt tatcggaaga 60
gaagtgttgg attcaagagg aaatccgacc gtagaagtag atgttattct ggaatgtggg 120
gcgatgggcc gtgctgcggt tccgtccgga gcgtccacgg gagaacatga agcactggaa 180
ttgcgtgatg gagacaagaa aagatatggc ggtaagggtg tgaccaaagc cgtaaataat 240
gtaaatacgg tgattgccga tgccttgttg ggaatgaacg tgaccgatca ggtagggatt 300
gaccgtgttt tattggaatt ggacggtacg ccgaccaaga gtaatttagg tgccaatgca 360
ttattaggag tgtcattggc ttgtgcgaaa gctgccgcta acgcattgga aatgccgtta 420
tatcgttaca tcggaggtgt gaatgcgaaa gtgttgccag tgccgatgat gaatattatt 480
aacgggggat ctcattct 498

<210> SEQ ID NO 11
<211> LENGTH: 504
<212> TYPE: DNA
<213> ORGANISM: unknown
<220> FEATURE:
<223> OTHER INFORMATION: Representative gene for Cluster 3

<400> SEQUENCE: 11
agtatcatgg tttccgtgat gccaatccct ggaaaatacg acgaaaactt cttgaatacc 60
tttgaaaaca cgaaagaagt gatcgccgga atccgcacga ttcgcaagca aaacaacatt 120
gccttcaaag atgcgatttc tttaagagtg aaaagtaatg accgctaccc gctacaattc 180
gagagcatta tctgtaaaat gggtaatatc caagatgtag aaatgatcaa cgacacggta 240
aaaggagcat ggagctttat ctgcgacacg gttgaatact tcatccccgc tgtcggagag 300
gtcaacacag aagaagtcag agccaaactg caagctgatc tatcttacgc ccaaggcttc 360
ttggcatccg tgatgaaaaa actctcgaac gagaagtttg tcagtggagc cccagcacaa 420
gttgtcgaga acgaacgtaa gaaacaagct gatgccgaag caaaaatcaa agccattgaa 480
caacaattgg cagaattgaa ctaa 504

<210> SEQ ID NO 12
<211> LENGTH: 531
<212> TYPE: DNA
<213> ORGANISM: unknown
<220> FEATURE:
<223> OTHER INFORMATION: Equivalent gene for Cluster 3

<400> SEQUENCE: 12
aaggatgtct atgttgcagt tcgagcctta ttggaaaaag aaattatcgg aatcaaggag 60
tcggtagatg atctgttcaa gcctaaaatt gaacgtttgg tgagatggaa acgaaagttc 120
acaagtgagg aactggacga gattcttgat agcttaaaac gggcgagggc tcaatacaaa 180
atgctgtgtg attgggtgta ttatagcgac gagcatcgag tcgaggggtt gcctagaacg 240
gagtttattc agaaaatcgg tagttcagcc tcagccttga aaggattgtg tgaacggggc 300

```
gtgttggaaa ttgttgtgca ggaagtcagc cgtttagagg tatctaaaga ggaagtggag    360

gatgtacacg ctttgtcggg ggcgcaagaa aaggtttttg gcgacattca agggtattac    420

aaggagaagg attgtgtctt gttgcagggc gtaacttctt cgggtaagac tgaaatatat    480

attcatctga tacaagagac gctaaggcaa ggaaaacagg tgttgtactt g             531
```

```
<210> SEQ ID NO 13
<211> LENGTH: 681
<212> TYPE: DNA
<213> ORGANISM: unknown
<220> FEATURE:
<223> OTHER INFORMATION: Equivalent gene for Cluster 3

<400> SEQUENCE: 13

gggaaagcga tacatgatta taatttaata gaggacgggg accggatttt ggtaggagtt     60

tcgggcggga aggattcatt ggccttgttg gaagtgttgg ccatgcgcgc caaggacccg    120

aaacaaaatt acacggtcat agcggctcat attgcggtgg aggatgtcgc ttacgaagtg    180

gacagcgatt acttgcgagc gttttgtgaa cgtttggggg tggagtatgt ttaccggacg    240

attcgggtcg acacgacggt gaatcccaag aaaccggctt gtttcgtgtg ttcatggcat    300

cggcgcaaga tgcttttcga tattgccaaa gagtatgatt gtaagaaact ggccttgggc    360

catcaccggg atgatgccgt ggaaagtctt ttgatgagca tgatgttcaa cggaacgatt    420

tgcagtatgc ctgcccggtt ggaaatgttc aagaatacgt tcacgcttat tcgtccatta    480

atctatcttt cgaatgacga gacttcacga tatgccgaaa tgcggcagtt taaaaagcaa    540

aaaaagcatt gcccccatga aaaggcaacg aaccgggatg ccgtgagtaa gttgcttgac    600

cagatggaaa tgatttctcc ccatgcccgg agcaatttgt ttgcagcgat gcaaaatatc    660

cgggaagatt acttgccttg a                                              681
```

```
<210> SEQ ID NO 14
<211> LENGTH: 711
<212> TYPE: DNA
<213> ORGANISM: unknown
<220> FEATURE:
<223> OTHER INFORMATION: Equivalent gene for Cluster 3

<400> SEQUENCE: 14

atgaaggaat ttggagatat agtaagggag aatgtaaagg ggttacaggc gtattcctgc     60

gctcgtgcgg aattcgaggg gacgaatgtg acattgctgg atgcgaacga gaacccgttc    120

gcgtcggaat ataatcgtta tccagatccg tttcagcggg aattgaaacg agagatcggt    180

aggttgaagg gggtggaggt ttcccggttg gtactgggaa atgggagtga cgagttgatc    240

gatatgttga tccggacggt ttgtacgccc cggcgggata atatgctcgt tttttcaccg    300

ggctattcga tgtacgaggt aagtggacga gtgaatgacg tggaggtgag gtgtttggag    360

ttggacgggg agttccagcc ggagtggaac acgttgtttg atagcgtgga tcggtttacg    420

aaaatgattt tcttttgcac gccgaataat ccggtgggga acgtaattcc tttagaacgt    480

attcgggaag tggcgtctcg ttttgatgga attgtcgtgg tagacgaggc gtatatcgat    540

tttaccgata tgccgtcggc tgttgttttg caggaggatt gccggaatgt tgtcgtgttg    600

caaactctat ccaaggcttg gggacttgcc gggttacggg taggaatttg tatggcggac    660

ccggaactgg tgatttattt aaacaaagtg aaaccgcctt ataatatcgg t             711
```

```
<210> SEQ ID NO 15
<211> LENGTH: 1017
```

<212> TYPE: DNA
<213> ORGANISM: unknown
<220> FEATURE:
<223> OTHER INFORMATION: Equivalent gene for Cluster 3

<400> SEQUENCE: 15

```
atcgagatca aaaaatatcc ggaactcacg caaatcggga gtcaacggaa acagaccgtg      60

attggtaaaa atacgggaaa gtatgatgga actccatacg gaccctactt tttcactcag     120

gaagagatta aagaagttat tcaatatgct gccgatcggt atatcacgat tattccggaa     180

atagagcttc ccgggcatgc gcttgccgct ttggctactt atccggaatt gggttgcacg     240

ggtggacctt acgaggtatg ccagatgtgg ggagtgttcc cggaagtatt ttgccccggt     300

aacgagaaga cgtttgagtt ctgggaaggt gtgttggatg aggtggcgga attgttcccc     360

ggagagatca tccatatcgg gggagacgag tgtccgaggg atgcttggaa aaagtgtaag     420

aaatgtcagg cccggatgaa acaagaaaag atgaaggaag agggagaatt gcaaaattat     480

accgttcacc ggatcgaggc gtatttgaaa gagaagggga agagaattct cggttgggat     540

gaaatattgg aaggagatgt ttctaaaacg gcgattgtta tgtcatggag aggtaagact     600

ggcggaatca aaggagcaaa gagagggaat gaggtggtga tggttccgaa tgactacgct     660

tattttgatt actatcaatc taaggatgtt gacaaggaac cttttagtat tggtggtttt     720

gtggatgttg cgaaagtata tagtttggac ccgacagagg gattgacggc cgaggaggga     780

aagaagatta tcggggtaca agctaatttg tgggcggagt atatcacgac ttttagtcat     840

gctcaatata tgttattgcc gcgtatggct gcattggcag aggtggcatg gactccgcaa     900

gagacgagag agtattcgaa tttcttgaac cgggcgaagt tgttgactca acgttacgag     960

gctttaggtt ataattttgc aaaacatatt ctacaagagt caaagtccaa tgaataa       1017
```

<210> SEQ ID NO 16
<211> LENGTH: 780
<212> TYPE: DNA
<213> ORGANISM: unknown
<220> FEATURE:
<223> OTHER INFORMATION: Representative gene for Cluster 4

<400> SEQUENCE: 16

```
ggcacgatcc tcaagacggc gcgctgcgag gagttccgta cgcccgaggg acgcaagacg      60

gcttacgaca acatcgtcaa gcacggcatc acgtcgctcg tggtgatcgg cggcgacggc     120

tcgctgaccg gcgcgcgtat attcgccgag gagtacaatt tcccgatcgt gggccttccc     180

ggtacgatcg acaacgacct gtacggcacg gacacgacga taggctacga tacggcgctc     240

aacacgatca tgcagccggt cgacaagatc cgcgatacgg cgacttcgca cgagcggctg     300

ttctttatcg aggtcatggg gcgtgaagcg ggctttctgg ccctgaacgg cgcgatcgcg     360

tcgggagccg aggcggcgat cattccggaa atcgccatgg aggtcgacca gctcgaccag     420

ctgatcgaga acggattccg caagtcgaag aacagcagca tcgtactcgt ggccgagagc     480

gagctgaccg gcggagcgat gggactggcc gagcgcgtca agaacgagta tcctcagtac     540

gatgtgcgcg tgaccatcct cggccacatc cagcgcggcg gatcgcctac ggcgagcgac     600

cggattatgg ccagccggat gggcgaggcc gcgatcaacg cgctgctcga ggaccagcgt     660

aacgtgatga tcggcattca gaacgacgag ctcgtgtaca taccgttcag ccgggcgatc     720

aagtgtcaga agccgatcaa ccgtcagttg cttacgacgc tgcgggtgct ttccatttga     780
```

<210> SEQ ID NO 17

<211> LENGTH: 228
<212> TYPE: DNA
<213> ORGANISM: unknown
<220> FEATURE:
<223> OTHER INFORMATION: Equivalent gene for Cluster 4

<400> SEQUENCE: 17
ggccgccatc acatgctcga tcgtccctat ccggacgcct ttcttttcta tcgtggttcc 60
gcgcgaggta tcgactacgt tctccgccag cgcatcgacg aagggctgcc cttccagatc 120
gattcgacgg aaacgtattc cgcagccgga gtcggccggg ttaatagtca tcgtaacatc 180
gagccccgta tgcagtccct ttcctcggaa aacaaccgga gcctttaa 228

<210> SEQ ID NO 18
<211> LENGTH: 552
<212> TYPE: DNA
<213> ORGANISM: unknown
<220> FEATURE:
<223> OTHER INFORMATION: Equivalent gene for Cluster 4

<400> SEQUENCE: 18
atgatggaaa ggaactacaa gctgccgaag gaaggcggcc tcgaacccgg agccgacccg 60
gccgacatca tccggaaatt cgaaaaaatc tacacgaaca tttacgagaa cgaagccagc 120
ggggcggcct acgtcgcccg ggaaatcgcc gattgcatcc gcgagaaaca atctatcggc 180
gaaatgtgcg tgctgggcat caccaccggc aagtcgcccg taggcgtatt ccgggccttg 240
gtcgaactgc accgtagcga gggtctgagt ttccggaacg tcgtcgtatt cagtctcgac 300
gagtttttcc cgatcacgcc cgaagagctc caaagccgca actactcgat ccacgagagc 360
ctgctcgatc tggtggacat cgcccccgag aacatccata tcccggacgg tacgctgccg 420
caggacgaag tggccgcttt ctgccgcgag tacgagtcga agatcgagga gtacgacggc 480
atcgacctga tgattctcgg cacgggcgtt cagggacaga tcggcttcaa cgagcccggc 540
tcgtacacca at 552

<210> SEQ ID NO 19
<211> LENGTH: 609
<212> TYPE: DNA
<213> ORGANISM: unknown
<220> FEATURE:
<223> OTHER INFORMATION: Equivalent gene for Cluster 4

<400> SEQUENCE: 19
ttgacccgca gcccgaaaag tacgatcttt gcatatcgca ttcagtcatc aaagaaatcg 60
gattatgaaa aacgccacat tcaaaaacgg ggacccgatt ccgcagctcg gactgggaac 120
ctggcgatcg gaaccctcgg aagcttaccg ggccgtcaag gaggctttgc gcatcggata 180
ccgtcacatc gactgcgcgg cgatttacgg aaacgaaaaa gaagtggaca ggctctgcgc 240
gactctttcc gggaaggaat cgtccggcgg gaggaactgt tcgtcacctc gaaactgtgg 300
aacagccacc acgctcctca ggacgtcgaa ccggccatcc ggcagacctt atccgatctg 360
gggctcgact acgtcgacct gtacctgatc cattggccgc tcgccttccg gaaaggaatc 420
ggtatgccgc aaagcaagaa cgacctgatc ccgctctcgc agattccgct ctcgctgaca 480
tgggaagcga tggaaaaact ggtcgacgga aaactgacac gccacatcgg cgtatcgaac 540
ttcagcatcg aggcgatcga gaaactcaac gacggggcac gcatccggcc tgaaatgaac 600
caaatcgaa 609

<210> SEQ ID NO 20
<211> LENGTH: 666
<212> TYPE: DNA
<213> ORGANISM: unknown
<220> FEATURE:
<223> OTHER INFORMATION: Equivalent gene for Cluster 4

<400> SEQUENCE: 20
ttgactatcg gtcgtcgctc cgtgctgtcc ggtttcgtcc ggatgcgccg agatagccgt 60
ttcccgtatg cggctccgga ctttacctta cgaatgaaga aaacaatgaa aaaactgctt 120
gttcttgtat ggggcctgct cgcagaggga ccgatctttt ccaaggtgaa gctgccctcg 180
gtgctgggca gcaacatggt gctccagcgc gaatgccacg ccaatctctg ggctgggcc 240 tcgccgtcga agaaagtcac ggtcacgacc tcatgggacg gtcgcaaata tgcgactcgg 300
gccgacgccg acggcaactg gttgctgaag gtggcgactc ctgccgccgg agggccctat 360
acgatccgta tcagcgacgg cgagcctgtc gtgctcgaga acgtaatggt cggcgaggtg 420
tggatttgtt ccggccagtc gaacatgggg atgcccgtct gcggttatcc gggcgatccg 480
accgagcgga tgaacgagct gatgctcgag gctgggaaat acccttccct gagactgttc 540
catgtccgtc cggaagccgc ttccgagccg aaggacgact gcgacggcat gggaggctgg 600
caggtttcct cggcgcacag cgtgcccgga tttaccgcga cgggttatat cttcggacga 660
aagctg 666

<210> SEQ ID NO 21
<211> LENGTH: 852
<212> TYPE: DNA
<213> ORGANISM: unknown
<220> FEATURE:
<223> OTHER INFORMATION: Representative gene for Cluster 5

<400> SEQUENCE: 21
atgcaattac tcaacggccg ggaagtggcc gcatttcatc gcgaacgggt ggaacgccgc 60
ctggccgata tccaggaaga actccatatc cagccggaac tggccatcat cctcgtcggg 120
gatgatgcgc cgtcggccat gtatgccaga tccatgcaga agacggcccg ggccgtcggc 180
ttgaaggcag aaatctatca gaaaccggat tccatcagtg aagtagagct tttatcgctc 240
atcgataagc tcaacgaaca ggcttctgtc ttcggcatcc tgcccatgat gcccttgccg 300
cgccacttga acagccagcg catcatcgac tgcatcgacc cgaagaaaga cgtcgatggc 360
ctgaccgatg tcaacatcgc ccatttatat acgggacgac cggggttcgt gccctgtaca 420
ccgcgggcag tcattgccat cctcgattat taccatattt ctctgagtgg caaggatgta 480
gccatcatcg gccgcagcaa cgtcgtcggg aaaccgctgg ctcagctctg cctgaaccgc 540
aacgccacgg tcacgcactg tcatacgcgc acgaaagacc tgaaagccgt ctgccgccgg 600
gcagacctgg tcatcgccgc tgccgggaga gccggcttag tgacaggcga tatgataaaa 660
cctggtgctg tagtcatcga cgtcggcatc aaccgcgtcg atggcaagac tgtcggcgac 720
gtcgcttttg atgaagcggc cgccgtggcc ggggccgtga cacccgtgcc gggcggtgtt 780
ggcgccgtga cgacgatgat ggtactggaa aacgtcgtct gcggcatcgc ccggacagaa 840
actattttat aa 852

<210> SEQ ID NO 22
<211> LENGTH: 579
<212> TYPE: DNA
<213> ORGANISM: unknown
<220> FEATURE:

<223> OTHER INFORMATION: Equivalent gene for Cluster 5

<400> SEQUENCE: 22
atgaaaaaac ttattatcgc agcgacactg gccgccctgg ccatgacttc ggctgccatg 60
gcagcgccca tccgcgatcc tcagcccggt gacttgaagg ccaacgccaa ctatggcttc 120
gaccagaaag aaggcggccg cagtgccaag agccgtctga ctggcggcga cgtcacctac 180
gtcctgagca accactggga tatccagtac gtcaacaact acaccaaggg cgacaacgac 240
aacaagatca acgaaaacta tctcgtcggc aattaccgct ttacgccgta tctgtcggcc 300
tttgccggcg gctcctacgt caagacggaa acgtataata cgaccaagtc ctacggctat 360
caggtcggcc tcaaaggcca gattcccctg gcagcccgct ggcagggctt tgcgtccgtc 420
ggtgtcggcg atgacgtcaa tacctatgaa gtcggtgtcg gctacgacat tacgccgaac 480
tgggatgccc acgtaaaata ccgcagcagc agcgtcgacg tcgataacta cgacgacgat 540
gtcaaaggct ggcaggtcgg catgggctat aagttctga 579

<210> SEQ ID NO 23
<211> LENGTH: 747
<212> TYPE: DNA
<213> ORGANISM: unknown
<220> FEATURE:
<223> OTHER INFORMATION: Equivalent gene for Cluster 5

<400> SEQUENCE: 23
atggaacaat atctttccct cattgaaacg tcgccgctct tccacggcgt cgccgaagcc 60
gatgtcctgc cgctcttgca gcgcttgaag gtacgcaaga aaaaatatga gaaaggggaa 120
ttcctctttt attccggcga tgccgtcccc tatatcggac tggtcctgga aggggcggtc 180
cacatcatcc aggaagatta ctgggggaac cgcaatatcc tgtcccagat cccggcaggc 240
ttctttttcg gcgaagcctt tgcctgtctg cctgacgcgc cggcgacggt cgacgtcgtc 300
gccgcctcgg atgcggtcat catgcaggtc tatgtcggca acatcctcca tgccggtcag 360
gtcctgacgc cggaccaggc tcgttttaca ggcaatctcc tggctctgat ggccgaaaag 420
aaccgcctcc ttacggaaaa gatacgctac ctgacccagc gctcgacgcg ccagaaaatc 480
atgctctacc tgtccgacat ggcccggaaa aaagagaagg ccaccttcgt cctgcctttc 540
aaccgccagc agatggccga cttcctctcc gtcgaccgca gcgccttatc ggccgaactg 600
agcaagatga aaaaaagaag gcctcatcga ttaccacaag gacaaattca ccttgcggca 660
ggaacattaa ggaaatcggc gggccgccag ctaagctgtc cattctggca gctaccctat 720
cggtacctgg tgggccagaa aggcttt 747

<210> SEQ ID NO 24
<211> LENGTH: 1035
<212> TYPE: DNA
<213> ORGANISM: unknown
<220> FEATURE:
<223> OTHER INFORMATION: Equivalent gene for Cluster 5

<400> SEQUENCE: 24
atgaaaggtt tatggaaata tatttcaccc tttgcaccgg acgactccgg cgcggcggcc 60
gtcctctacg gactgaacgg catcgtcgtc atttgcgatg ccggcggctg tgccggcaac 120
atctgcggtt tcgatgaacc gcgctggttc agtgggaaaa agagtgccgt cttcagtgcc 180
ggcctgcgcg atatggacgc catcctcggc cgcgacgacc gcctggtcga taaactctgc 240
caggctgccg aaacgattga tgccgacttt gccgccatcg tcgggacgcc ggtcccgtcg 300

```
gtcatcggca cagactataa ggccttgaag cacatggctg aaaagaagct gtccatccca    360

gtcgtcacag tcgatacgac gggcatggat tactacgaca agggcatcga aaaggcctac    420

gacgccttat tcccggtcct ggccgactcg tcgcagcagg ccgaagccga tacagtcggc    480

gtcctcggcg ctgttcccct ggaactgatg caccctggcg atatcgaatg gatcagccag    540

tccctggtcg aagacggctg gcagcagatt ctcttgttcg atgaaatcga cgattaccgc    600

aaggccggca aggcctccct caatctggtc ctttcgccgg ccggcctgaa ggccgctcaa    660

tatctgcaga agaccttcgg gacaccttat gagctccatt acttcggcct cgatgccgtc    720

gtcgattttg acgacaatct cttttctggc aagaacgtcc tcatcatcca tcaggctgtc    780

gctgcctcgg ctatggccgc catggccgaa gaagccggtg ccgcttacgt gacgacggct    840

tcgtggttca tggggctccc tgagccgcag gggacggact gcgtccggct ccgtgaagaa    900

gacgacctgc gccgcctggc cgacaacgac cagttcgaca tcatcctcgg cgatgcctat    960

ttccgccggg ccctgccgaa cttccatggc caatacgttg attttccgca ttttgccgtg   1020

tccgggaggg gataa                                                    1035
```

<210> SEQ ID NO 25
<211> LENGTH: 936
<212> TYPE: DNA
<213> ORGANISM: unknown
<220> FEATURE:
<223> OTHER INFORMATION: Equivalent gene for Cluster 5

<400> SEQUENCE: 25

```
atggataagt tacgtatcgt attcatgggg acgccggact tttccgtccc gtccctggaa     60

aaattggccc aggccggcta tgatatcgct gccgtctaca gccagcccga taaacagcgg    120

ggacgcggca agaaggtgac tttctcgccg gtcaaggaaa aggccctgga actgggcatc    180

cccgtcttcc agcctgattc catgcgcagt gacgacgtca tcgaacagct ccgcagcctg    240

gcgccggacg tcatcatcgt catcgcttac ggtaagattt tgccgaaagc tgtcctggac    300

atcccgaaat acggctgcct caacgtccac ggctcgctgc tgccgaagta tcgcggcgcc    360

gcccccatcc agtacgccat caaagacggc gaagccgaaa gcggcgtgac catcatgctt    420

ctcgacgaag gcatggatac ggggaagatg ctgaaaaaag cggctattcc cctggatgcc    480

aaggaaacga cggggaccct cttcgataaa ttgtccatcc tcggggccca gaccctgctc    540

gacgtcctga ccgacctgga tggctatgaa agccgcgccg tcgcccagga tgaaagccag    600

gcgacgtata cggccaagat taccaaggaa gaagcccgca tcgactggtc ccaggatgcg    660

gccgtattgg aacggctcat ccggacgctg gatccccatc cgggtgccta taccatctgc    720

cacgatagca agcgcctgaa gatatgggca gccgacgtcg tcgaagggac acaggctgcg    780

ccggggaccg tgttatcggt gactaagaaa caattcaccg tccagaccgg gaaaggggct    840

ttgcgcatct gtgaagtcca gcccgaaagc cgcaaacgca tggctgctgc ccaatatctg    900

caaagcgcag ccttgacggc tggtgaatta ttataa                              936
```

<210> SEQ ID NO 26
<211> LENGTH: 1395
<212> TYPE: DNA
<213> ORGANISM: unknown
<220> FEATURE:
<223> OTHER INFORMATION: Representative gene for Cluster 6

<400> SEQUENCE: 26

```
atggaaacct tcgtcatgga gaagttcaac ggtggcgtcg tgcgtgacga tcttgcaggc     60
gtcaactctc gcttgcagca ggagagcggc tatgaaatcg acgcaattgc ttatttgcga    120
gatatggatc attacgctgc gggccaatgc aatctcgcgt tgcacaaggt ctggcttgag    180
cgatcgggcg agaccatcga ctggtacgaa aacgttctct cctcttacgg tatcgcgctt    240
tggcatgagg ctgccgagga aaagcatgaa gtcaactacc gacattgggc tacagggcat    300
tctcccgcct ggccagtcga tggatcgctc gacgggttca ctgtgctgac tgactacgca    360
gagaagacgg gccatgtaac gttccgctac caaacgccca tggtgagcct caccgtcgaa    420
aacgatcgcg tgaccggtgc tatagggcag ggcgctgacg gctacattcg tgtcaacgca    480
agcaagggcg ttcttgtatg cacaggcggt tacgccgcga atctcgacct tcttaagcag    540
ctccagcctc acacgaccag catttacgct tataactcag cgcagccggg ctgtgaggga    600
gacggcataa aggcgtgcct tcgcgttggg gcaaaaatgg acgaaacaca ctctagcatg    660
cttttcgacc gagcaagcgt tcccgccgac tccttgggag gcgccgactg cggtactgcc    720
atggtattct ggatgggaag ccaaccctgg ctgaaagtca atctcaatgg cgagcgcttc    780
tgcaacgagt ccggcaccta tgacttcatc ctgcacgccg atgcatcgca accaggaaat    840
atccacgtgt gcctctggga tgcagactgg cagacctacg ctcaacagtt cgacatgcat    900
ggctgctcgc gcatgttccc ctttgataat ggagcggctc cgaacctacc gatcgaagtg    960
gtgacggcca tgaacgagga ggcacttaaa gccggacaca ttcagcaagc cgacaccatc   1020
gaggagctcg ccgaaaagct tggtcttcct gcagaagccc tcgcgaaaac ggtggaacga   1080
aacaaccaga attacgacaa ccagcgcgat gacgacttcg gcaaggagcc attccggctt   1140
tcccctgtac gcaaacctcc cttcttcggc gtacgtacca caggcgctct gctgtgcacc   1200
atggacggca tcgtgataaa cacccagggt caagccctgc gcgaagatgg aagcgccatt   1260
gagggcctat atgtcacagg caacgattcc ggaggatact attccatgac ttatccgaac   1320
ctgtcgaccg gcaacgcttg cggcaggaca gtaactttcg cacgaatgat tgctcagaat   1380
ctggctgccc agtag                                                    1395
```

```
<210> SEQ ID NO 27
<211> LENGTH: 1932
<212> TYPE: DNA
<213> ORGANISM: unknown
<220> FEATURE:
<223> OTHER INFORMATION: Equivalent gene for Cluster 6

<400> SEQUENCE: 27
```

```
atgggacacg gaaagaacca cgtcatcgat cgcagacggt ttgtgcaagc aagctcggtc     60
gcagcggcag ctctggcctt aggcgcgacg ggatgcgctt cgtcacaccc cgtcgcagag    120
acgggcggca cgacaactca atttgtcgca ggaacctacc aggccacggc actcggcaag    180
aagagcgata tcaccgtcga ggtcgtcttc tccgacactg ccatcgacag cgtccgcgtc    240
gtcgatcacg gagaaaccga acgcatcgcc gcaccggcgt ttgagaagat ccctgagatc    300
atcgtagcat cacaatcact cgccgtcgac gcggtgacag gagcgacgct ttcatccctc    360
gcgctgctct cggccgtaga agactgcgcg cgtcaagccg atggcgacgt gagcgctttg    420
aagcgtgcgg aggttcccaa agagcagcca accgacgagg agatcgaatg cgacctcgcc    480
gtcataggcg ccggcatttc tggaatggca tctgcactag cagctgctca gcagggagcg    540
aaggtcgtcg tgttcgagaa gtcctcgagc atgggcggca acgccctcgt gagtggcggt    600
ttcatcgagt atgccaacgc acccgaaaaa ttacgcgtcg aagtgaacga cggctacctg    660
```

```
aagatcttcc aagaagttct tcagttcaat cgagacgccg ggcttgacgc ctctctggta    720

gatgaggtgc agcaacaatg ggacgactac tacgcaaacg ggaacaccaa actctttagc    780

tcgcccgaat tccttgcgct gcaactctgc atgcttgagg gcaacaccta cgacttccaa    840

cacacttatg caacggatgt ggaggggggc acggcatggc tcgacaccat gcagtttccc    900

tggatgccac tcgtcgcaat tcccggttat tcttgggcgc atttctcggg ttcctcagaa    960

gacgtgaatg gagaaggcta tttcaacgtg ttcgaacgag agatggaagg actcgatctt   1020

cgcatcctgt tcgccacgcc ggcaaccgag ctcatcactg aaagcggtcg cgtgactggc   1080

gtcattggca gcagcgcaaa cggcagcacg tacaccgtgc gcgctaaaga cggtgtcgtt   1140

atcgcctctg gaggctatgc cgacaaccag gatatgctga aagagcacga caagatgtgg   1200

aactggaaag atctcgacac cttccactgc gacaacaact acggacacac tggagacggc   1260

atccgcatgg ccacagaagc aggcgccgcc ttcgccgaat tgccctttaa ccagatggtc   1320

ttccccttcg tggacaccgt gctctacgcc accgaaacaa ccgtcggaac caccaatgag   1380

agcatctacg tgaacaaggc cggcaaacgc ttctgcgacg agggcggcat tcgaactgtc   1440

atgacgatcg ccctgatgga gcaggatggg ggtgtgggtt tccaggtggt cgaccacgac   1500

agctccatga tcacggacgg caagacccac acaggcatgg acgtcgagta cgccattgag   1560

cggggcatcc tctaccgcgc cgacacactt gaagaactgg cgggcctcat gggcgtcgac   1620

gaggcgacat tcctgaaaac tgtcgacgat tacaacgaga tgactcgtac tttcaacgac   1680

ccagaattcg gccgatccag cttcgggccc aatgcccccc tggataatcc tccattctat   1740

gcatcacccc gcacctgggc gatgcatatc acgatggacg gcatctcgac cgactcatct   1800

caccgcgcgc tcgatgcggc cggaaatgtt gtaccgggac tctacgttgt gggcgaagca   1860

gcttgcggcg gccgcggtgt cggatcgctc ggcgcaggct atgcggtggc gcaatcaatc   1920

tacaacgtct aa                                                       1932
```

<210> SEQ ID NO 28
<211> LENGTH: 2427
<212> TYPE: DNA
<213> ORGANISM: unknown
<220> FEATURE:
<223> OTHER INFORMATION: Equivalent gene for Cluster 6

<400> SEQUENCE: 28

```
atgactgaaa cccaatccac cctgtcgcgc cgcaccttcg tcaaaggctc gctcgcgggc     60

ctggctgcca cgggagccgc gggtaccgca ctcttcggat gcgcacccca atctggcacc    120

ggagccgggg aggagcccat ggccgccacc ggagaggaga ctgcgcccga cgagatccac    180

tggagtcagt gcaacgtcaa ctgcggcggc aactgcgtct tccagtggca ctcccgcgat    240

ggcaaagtgc tctacatgga gaccgataac acaggagata ccgacttgca ggcccgcgcc    300

tgtctacgcg gccgctccat gcgacgctgg ctcaacagcc ccgaccgtct gctgtacccc    360

atgaagcgtg cgggcaaacg cggcgaagga aagttcgagc agattacctg ggacgaggct    420

atcgacacca tcgccagcga gctgaaacgc gtcatcgaca cctatggcaa tgaggccatc    480

tacgtcaact acgccacagg catgtactcg aaaacaggca accccaccgc ccgattgctc    540

aacctgctcg gcggctacct aaaccgttcc tatgactatt cggcccacat gatcgaggcc    600

gtcgcgccct acatgtacgg tacgtcgctc gacggctctt ctctgactga ggcaaccgag    660

cattctgatc tcatcgtcat gttcggcaac agccccgccg aaactcgcat gggcggtgcc    720
```

```
aatgcctcat gggatttcgc ccgccttcgc gaagccattc agaaccgcgg cggcaaaatt     780

atctctatcg acccgcgcat gaacgagacg gtctccggcc accctgacga atggcttccc     840

attcgccctg gtaccgacgc ggccctctgc gcggccatcg ctcatgaatg gatcgtcgaa     900

ggcaaagtgg acaaggaatc cctcgatact tactgcctcg gctacgacga ggacaccatg     960

cccgaatccg ccaaaggtca gaacaaatcc tacaaggatt acattatggg cactggctgg    1020

gacatggtgg agaagacgcc cgagtgggcc gcccccatca ctcagattcc tgcctccagc    1080

atccgcgaac tagccaacac catcgctgct gctaaggcac ccttcatcac ccagggatgg    1140

ggcccccagc gccacacaaa tggcgaggac gcctgccgct ctatttacat gctgccgctc    1200

ctcctaggca agtggggact tccgggcacc aacaacgggg agcgtgaatc catggcgctc    1260

acaagtctcg ttcccggctt gccagcaggc gaaaaccccg tcacgctttc cattcccgct    1320

tatcagtggg ttaacgccgt ggatcacggc cataccatga ccgccacaaa ttccggtctt    1380

gtcggaggcg atgaacttgg taccgatatc aagttcatct ggaactacgc cggcaactgt    1440

ctgaccaacc agcatggcga tatcaacatg acccatgaga ttctcgtcga cgaatcgaaa    1500

tgcgagttca tcctcgtctg ggacacggtc atgaccgact cggcgaaata cgctgacatt    1560

ctgctgcccg atgccatgcg ctcagaacaa atgaacctgc agacccaggg atacaccgaa    1620

tggtacgcgg gcgtagttct gggtactccc gctcaagaag cacccggcga gtgtcgctcg    1680

agctatgacg tcatggccga cattgccgat aagttcggcg tgcgtgatgc gttcaccgaa    1740

ggccgcactc atgacgaatg ggtaaagttc ctctatgagc aggggggcga agaagatggc    1800

tccatgccga cctgggagga aatgctcgag cagggcgtat acaagcgacc cgttgaaccc    1860

tacatcgcct tcgaggcgtt ccgcaacgat ccctccgcca acccactggg caccccctcc    1920

ggaaaaatcg agatcttctc cgaagcgctg gacgagatgt cacgtacctg ggatcttgaa    1980

gagggcgagg taatttaccc catccccgtc ttccaagcag gatttcacgg atacggttcc    2040

gtcaccgagg aattccccct ctactgctgc ggtttccatc acaagagccg cacccattca    2100

tcgttcggct tcatccccga gcttgaagcc gtggcccgtc agcagctgtg ggtaaacccc    2160

gctgatgccg agagccgctc aattgaagac ggcgacctga ttgccgtgac aagtccggtt    2220

ggcgagattc gcatcgaggc gaaggtgacg ccccgcgtca tccccggaac tgtaatgatt    2280

ccgcagggcg cctggcacaa ggccaacatg aatggcgaca aggtggacga gggcggctgc    2340

gtgaacacgc tcacgcagta caaaccaacg ccgatggcca agggcaacgg cactcactcc    2400

atgatcgtcc agattgcgaa ggcctaa                                        2427
```

<210> SEQ ID NO 29
<211> LENGTH: 2109
<212> TYPE: DNA
<213> ORGANISM: unknown
<220> FEATURE:
<223> OTHER INFORMATION: Equivalent gene for Cluster 6

<400> SEQUENCE: 29

```
ttgagtgaga agcagacgat cctcatcgtt gatgactcga tgctgaatcg cgcattgctt      60

gccgacatgc tcggcgaagc ctaccgcatc atcgaggcgg aggacggcaa gcaggccgtg     120

gcggcgttgc agaaagaggg cgcgggcata tcgctcgtgc tgctcgacta cgtcatgccg     180

cagatgaacg gcttcgacgt gctggaggtc atgaacaaaa acggctggat caaggacatc     240

ccggtcatca tggtgtccgc cgagtccgac gccgcctata tcgaacgcgc ctacgagctg     300

ggcgtgaccg acttcatcaa ccgcccctac gacgtgaaca tcgtccgccg ccgcgtcatg     360
```

```
aacacgctca tgctgtacca gaagcagcgc acgctcatgg gcatggtggc cgaccaggtg    420

tacgagcgcg agaagtccaa caacctcatg gtgtacatct tgtcgcacat cgtggagttc    480

cgcaacggcg aaagcggcat gcacgtgctg aatgtgcagg ccatgaccga gatgatcttg    540

acgcagctca tgcgcctgac cgatcagtac ccgctgacca ccgaggacat ctcgctcatc    600

acgatggcct ccagtctgca cgacatcggc aagatcgcca tccccgagga gatcctgaac    660

aagccgggcc gtttcaccga cgaagagttc gccatcatga agacccactc cgccgtgggc    720

tccgatatgc tggacgacct ggagctgtac aaggacgaga agctggtgaa ggtcgcgcgg    780

gacatctgcc gctggcacca tgagcgctgg gacggccggg ggtaccccga tggcctcgtg    840

ggcgacgaca ttcccatatc ggcccaggta gttgccctgg ccgatgtgta cgacgccctt    900

acgagccgcc gcgtttacaa gccgccgttc agccacgaag aggccctgcg catgattcgc    960

gaaggggagt gtggcgcgtt caatcctctt attctggaat gcctgacggc agtggcgggc   1020

gatttggaga agcgcctgaa ccacggcatc acgggccgcg agatttcgat tgactcgctg   1080

catttgtccg aggcgacgct ggataacggc gacgccgagg cctcgagccg cactctcgag   1140

ctgctcgact acgagcgcat gaaataccac ttcttcgctt ccatgagcaa tgaggtgcag   1200

ttcgagttca ccgaagagcc gccgatgatc gtgctgtccg actggagcga ccacaagctc   1260

gatctgcccg aaatcatcat ggatccctac aacgacgagg ccttctgcgc gacgttcggc   1320

aaggagaacc tggagaagct cagccgtctt ctgcgcgcca ccaccattga tgatccggtg   1380

atcgatatgg agatggaagc caccgtgggc gacgagctgc gttggttcca tgttctggcc   1440

cgcgcgctgt ggtcggggcc gtccgatccg gtttacctgg gctctatcgg caaactcgtt   1500

gatatcgacg atcgccaggc cgagctgatc gacctgcagt tcaaggccta tcacgacccg   1560

ctgacggaag tggtcaacgg cgccttcgct cgcaaggtca tcgccgagcg cttgggctcg   1620

ggggaggcgt gcgaccgtca tcgcgaccgc catgtgctgg cgctgtgcga cctggatttc   1680

ttcaagcagg ccaacgacac ctacggccac cagtttggcg atcgcgtgct gaagcacttc   1740

gcggagcgtc tgcaggaaag cgtgcgcggc gaggatgtcg tggcccgtgt gggggcgat    1800

gagttcctct tgtgcatgga atgccccgtc gatccgcgtc cgctgatcga ccgcatccat   1860

cggtcgctcg agggcgactt cgagggcttc ccgctgtcgg tttccatggg cgtggccatt   1920

gccggcagcg atgtgcgcga ctacgatgag ctgttccgcc gggccgatgt ggcgctatac   1980

cacaagaagc gcggcggccg cagcgggtac gtgttttaca gcgatttaga cgaagaagag   2040

cgagatttgt tgcttgaagg ggcgcatacg gcgctctcgg gcatcgacag agacgaatcc   2100

gaccagtag                                                           2109
```

<210> SEQ ID NO 30
<211> LENGTH: 2970
<212> TYPE: DNA
<213> ORGANISM: unknown
<220> FEATURE:
<223> OTHER INFORMATION: Equivalent gene for Cluster 6

<400> SEQUENCE: 30

```
atgtcacgtg acaccacccc cctcgaaaga cagctgaaga actttatcag cgacggaacg     60

ccgccggaga ttatcgcgcg ctacgagtcg ctgcccgaac gggcccaaaa gagcgatttc    120

ggccggttcg ataataatgt cgttgttttg gatacggaaa caacgggatt ctctctcgcc    180

catgatgagt tgacgcagat tgcagcggcg cgggtggaaa acggcgagat cgtcgactgg    240
```

```
ttcgttacct tcgtgaaccc gggaaagccc attcctgagg atgttgccca tctcaccgat    300
attcacgatg aggatgtggc tgacgctccc tcggcgtccg aagctctagc cgatctggcc    360
gctttcgtag gagacgccgt cgtcgtggcc cataatgccg agttcgaccg caatttcacg    420
acgaagcatc cgacgggcta tccgctgctc gagaacactt gggtcgattc cctcgatttg    480
tcccgcatcg cgctgccccg catgaaatcc catcgactca tcgatctcgt gaaggccttc    540
ggtgctcctc ggtcaacgca tcgggctgat gaagatgtgg cggcgacctg tgccctcctg    600
cgtattctgc ttgctgctgt ggaagccatg ccgactatgt tgctgcggga aatcgcctct    660
atggaggaac cgaacgattg gccgacggtt gtggtgttcg aatattttgc cgagcgcgcg    720
ggtgagacga gcgaggagaa accgcttcct ttctcgctgc gcaccctgcg tcgcgaacgt    780
gtaggaaaaa ccgatctaag accgctcgtg gatgccgatg aaatcgccgc cgatccaggg    840
cgatccttct tactccccac ggccgatgct gtggcccaag cgttcaccgc tgagggcgta    900
gtaggttccc tgtacgaaga gtacgagcag cgcggcgagc aagtggctat ggccgaggca    960
gtgcgcaatg cgtttgcccg atcgcgcaat cttatggtgg aggcagggac aggcgtgggc   1020
aaatccatgg cctatctttt gccggcggcc atcattgccc gagataacgg tattaatgtc   1080
ggcgtagcta ctaagacgaa cgctctcctc gaccaactgg tctatcatga gcttcccgct   1140
ctttcggagg agctcggtgc cgacctcacc tatgctgctc tcaaggggtt ctcccattat   1200
ccctgtctgc acaaggtgga gcgcctcgtt gtggaaggcc ccggcatgcg caccgtgggg   1260
aaggagcaaa aacctcaggc tccggccctt gccgccttgc tttccttcat tgagcagacg   1320
gcttacgacg acatcgacgg cctgaagatc gactaccgca cgctgccgcg ctggatgatc   1380
accaccacga gccacgattg cctgcgtcgc aaatgcccgt tcttcggcac gtcctgcttc   1440
gtccacggtt cgcgccgcaa ggccgaggcc gccaatatcg tcgttaccaa ccatagcctc   1500
ctgttctgcg atcttgtcgc cgacggaggc ttgctcccgc ccatccgcta ttgggtggtg   1560
gatgaggccc acagcgccga aagcgaggca cggcgcgcat ttttcccttga gttggcagag   1620
gaagacattc tctccctcgc gcgccgcgta gcttccgagg aatctcggcg caacgtcttc   1680
gtgcgggcgg agcgcaccgt tgtcatgccg ggcaatgaat cctcgacgac gctgttctat   1740
gggctcacgg ggaaggcgcg ccgtgcgggc gctgaattcg gcgaagtggc ccaggcgttc   1800
tgcaaggcgc tgcccgacct gttcttctat gacaccaata agcgctcgaa gggctacgag   1860
acggtggatc tttggttgaa tgacgagatt cgccacggct ccctcttcca aaacattgcc   1920
cgtcttggtc gcgccatggc cgagcgcgcc gagaagatgg tgacggtttg ccaggagctt   1980
gtaggctatt tggaggatat tgaaggcgcc gccgtcattc agcgcgaaat tgcctccatt   2040
gcgatggaga tgaaggagat cattcagaac gtcgaggtca tctgcacgca atgtcccgag   2100
cgctatgtgt atgcggcgag cttaagtcgc aagatcgatc gtccgcagaa caagctggag   2160
gccttgctcg tatcggtggg ggagacgctg aacgagacct tgtatgcgcg gaaccattcg   2220
gtggtctata cgtcggccac gctgaccgtt gacggcagct tcaacagctt ctcccaggcc   2280
atggggctga acgagagcga gttttccgtt gccgacgagc tgctgcttgc ctcaagctac   2340
gacttcgaca atcagatggt tgtctatgtt gtcaacgata tgcccgaacc caatgatccg   2400
agttatctcg gtgctctgca gcgcctgctc atcgacgctc accgtgccca gaacgggtcg   2460
atgctcaccc tgttcacgaa tcgccgcgaa atggagaagt gcttcgaaga ggtgcagccg   2520
gctctgaagg gagacgattt gcgcgtcgtg tgccagaagt ggggtgtgtc ggtgaagggc   2580
ctgcgcgatg acttcctcgc cgacgagcat ttgtcccttt tcgctctgaa gagcttctgg   2640
```

```
gaagggttcg acgcgccggg cgccacgctg aagggcgtcg tgataccgaa attgcccttc   2700

tcgaagccga cggatcccct ttcttgcgaa cgggccgctc gtgacgatgc cgcctggcgg   2760

cgctatgtcc tgccagcggc ggtgttggaa acgaagcagg cagcaggccg tcttattcgc   2820

aaagctgatg accggggcat tctgatcctt gcggacaagc gtcttattac gaagggctac   2880

ggcaagacgt tcctgagatc acttcccagc cagaatatcc gattcctatc ggcggctcag   2940

atcgtcgacg agatagcagc gcgccgctag                                  2970
```

<210> SEQ ID NO 31
<211> LENGTH: 1776
<212> TYPE: DNA
<213> ORGANISM: unknown
<220> FEATURE:
<223> OTHER INFORMATION: Representative gene for Cluster 7

<400> SEQUENCE: 31

```
aacgtcataa ccaaagagcc ccgccataag tatgaagtca cggcttcgct gcgatacggc     60

acgccctacc agcgcaacgg cggcgactcg ctggcgggaa acgcgtcggc gagcgactcg    120

cgcgagtatc gcaacaagct cgatctgccg aacctgaatg ccgacatgac gttcggggtc    180

aatctgggca agttccgctc gctgaccgcc gtggcctatc gcacgagcga cgcctacagg    240

ctggtcggca cgcgcgacga ggtgcgccat tacaaggagc tgaatatcat gcgcccgaaa    300

atgaacggct cgcgtccgga gatggaccct tcgaccggca tgcccgtgtt cgtcatcggg    360

cggaccgtcg ccgatacgac gatcagcgtg ggacccgatt cccggggact gagcgtcagc    420

ggttggcgcg acctgaacct tagccagcgg ttcgactacg agctgtccga ccagttccgg    480

ttccagcttt cgggaagcta tttcggcaag aagcggttcg acttcaacgg tagcattctc    540

gacgagaatc cgctgtcgaa caacagcaag ccgtggacct acgagtccta cagcgggtac    600

aacgtcaagg cgctgatgga gcactcgccc aacgagcgca acaagattta cctctcctac    660

gtccgggacg agtatttccg cgatctggac agcctgtcgg gagtcacggt ccccaagcag    720

cgccacacct acaacgtgcc ccggctgctg tggacgctcg acgcgggcag cgcgaaccgg    780

ctgacgacgg gcttggagtg ggtcaacgag cagcttcggt tcgacatgaa cccgtccggg    840

tacgacgacc gcaagagcat gaataccggc tcgctctacg tgcaggacga gattctgagc    900

ggccggccgc tcagcttcgt cgtcggcgtg agaggcgatt acaacaatca tttcggctgg    960

agcgtaaccc cgaagctctc ggccaagtac gcttaccgcg atttctcgct tcgggccaac   1020

tacgccagcg gctacaggac tccctcgctc aaggagatgt atatggactt caccgttccg   1080

attccgggcc agacttccgt catccggggt aacgaccggc tgcgtagcga gagcaaccat   1140

tacgtttcgc tgacggccga gtacaaccgc agcgggttga acctgtcggc tacggtctac   1200

aacagttatt tccgcaacaa gatcgatgtg cgcgggcaca tggaagggac gacgaccgtt   1260

ctgcagtacg agaacatccg gcgcagcgag ttcagcggtc tcgagttgat gggtacgctg   1320

cgggtgacga ccggcctgtt cgtgagagcc aactacaact atgtctacca aagcgacgac   1380

gcgcccgaaa gctcgacgca atacatattc ccgagccctc atacggccgt gtttcaggtc   1440

gaatacggct tcgacgtgcg caggtaccgc atcggcatcg acgcgacggt ccgctacgtg   1500

ggagccaaga cttacgaaga tttcatgccg atcgtgaatc tcgacttcca gtcgatgcag   1560

aacatgaagt attggagcgg gacctatacg gcccgtcata agggatacgc cgtgtgcaac   1620

gcggcggtca atgcgtctct gcccgagggt atgacgctga ccctcggcgt ggataatatc   1680
```

ttcgaccatc gtccctcggt cgtcaacttc aactccgaca tcacggcccg ccgcaacctg 1740
ttcgtccggc tcgcctacgc gttcgggtgc gattga 1776

<210> SEQ ID NO 32
<211> LENGTH: 1077
<212> TYPE: DNA
<213> ORGANISM: unknown
<220> FEATURE:
<223> OTHER INFORMATION: Equivalent gene for Cluster 7

<400> SEQUENCE: 32
catatgggct acgtccgcga ccagtacggc gtttcgcggg cgctgctcgc gttgggcgag 60
tgggagcgcg cgcggatgat actcgacttc tactggcggg tgtggcagcg cagcggcctg 120
atccataacg ctcaggcgat cggctacccc ggcattttcc accggcacga gaatgacgag 180
acggagatta cgggctattt ggtcgtgcag gcgttcgact actaccgcaa gacgcgcgat 240
acggctttcc tgcgcgagat catgccgatg ctcgagtggg cgaccgaggc ccagcagcgg 300
aacctgatcg acggcatgct gccgttcaac ggcgacgaga cctatatcgc cgggggcgtg 360
gttccccgcc aggtgatgta tcacggctcg gccgaggcga cgctgctgtt cgtcgaggga 420
agccgccggc tgatccgctt cgtccgcgag ccggggctgt ggagcgctgc acggatcgga 480
gccttggagc gcgacgcgga cgagtgcagc gagcggttcc gcgataattt ctgccgcgac 540
gggcatctgt acgtcaacaa tccccggcgg gagcggaaag tcgcttatcc gccgacccgg 600
cccggcgtct gcctgtatcc cgggcatttc gactattttc ccgagacgta ccatttcaag 660
cgatgcctct atttttgcaa agattgcatg accaaggacc atgcggccgt cgagcttccc 720
gaaccggaac ttttcagtat tccgtcggcc aatctgtttc ccatttatat cggctcggaa 780
cttttctcgg agagcgagaa gcgggcgttc ctgaacgacg tggtggcgct ctacgagcgg 840
accgggagag tttcggggca ggatcgcata ctgggctacg acttcggcat gttcctctac 900
gcgttgtgcg agacggggca tccgctgcgg gacgaggtgt acgaccggat gatgagcctg 960
cgcgacggcg ccggagcatg ggtcgagtat tatgtcgacg gccggccgag cggttgcggc 1020
tgccgcccgt gggagagcgg catcaatatc gaggcggcga tccgttatgc ccgataa 1077

<210> SEQ ID NO 33
<211> LENGTH: 351
<212> TYPE: DNA
<213> ORGANISM: unknown
<220> FEATURE:
<223> OTHER INFORMATION: Equivalent gene for Cluster 7

<400> SEQUENCE: 33
atgttctatc cttcggacta tacggccacc gctttctatt taggctatcg ccccctcttt 60
ccctttccac gccgcgtccc cgtaaaagcg tttagaaaac gccatacgga acggattccc 120
gaaaaacgag cgcatcggga caaccctgcc gacggcatgg agccggccga cgcacattcc 180
atgcaaacac gacatcccga aatacagcgc cgatcccgcc gagcgcattc ttactacgaa 240
acgggaaatt cggatatccg ccggccgacg gactttccgc ttcaaccggc ataccgccat 300
cgcggcaggg aaacgccgga caaggagaac cccggctgcc gcgacggctg a 351

<210> SEQ ID NO 34
<211> LENGTH: 834
<212> TYPE: DNA
<213> ORGANISM: unknown
<220> FEATURE:
<223> OTHER INFORMATION: Equivalent gene for Cluster 7

<400> SEQUENCE: 34

```
gacggacggc cgatttcgat cggccggtcg gctttgaatt cggagcaaaa tgaatacctt     60
tactacctaa ttgttgaaaa aatgcgcgag aaaatagagc agttgagaag acagatcaac    120
gagcataatt accggtacta cgtgctgaac gatccgctga tcggagacta tgagttcgac    180
gccctgctgc gcgagttgca ggagctggag gcggcccatc ccgagttcga cgatcccaac    240
tcgccgaccc ggcgcgtggg gagcgactcc accaacgaat tcgctacggt cgagcaccgc    300
tatccgatgc tgtcgctttc caacacctac tcgctcgacg agatcaggga gttcgacgcg    360
cgggttcgca aggaggtcgg cgaggccgag tatgtatgcg aactgaagtt cgacggaacc    420
gcaatcagcc tgacttacga gaacggccgt ctgttgcggg ccggggcgcg cggcgacggt    480
acgcgcgggg atgaggtgac ggccaatgtc cggacgatac gttccgttcc gttgcagttg    540
cggggggcgg gctatcctgc ctatttcgag atccggggcg agatattgat gcccttccgt    600
tcgttcgagc gactgaatcg cgagcgggag gatataggcg agacgccttt cgccaatccc    660
cgcaatgcgg ccgccggttc gctcaagcag cagagctcgg ccgagacggc ccggcgcgag    720
ctcgactgta cgctctattc gctcgtcggc gccgccttgc cgttcggaac gcattacgac    780
agcctgatgg cggcccgtga gtggggattt aaaatctcgg accagatcgc cctg          834
```

<210> SEQ ID NO 35
<211> LENGTH: 1125
<212> TYPE: DNA
<213> ORGANISM: unknown
<220> FEATURE:
<223> OTHER INFORMATION: Equivalent gene for Cluster 7

<400> SEQUENCE: 35

```
atgaaaaagc tttctttgtt tccgtttctc accctaaccg ttttcggcat gagtagctgt     60
gcgagcggaa cagacgaccg cgcttctctc gagtacgaga agtaccggct gcccaacggt    120
ctcgaggtcg tattgcacca ggatacctcc gatccggtcg tttccgtggc tatccagtac    180
catgtgggca gcaaccgcga gaaaccgggc aaaacgggtt tcgcgcactt tttcgagcac    240
atgctcttcc agcgttccga gaacctgccg cgcaacgcct tttccagaa aatagacgca    300
cttggcggca cgatcaccgg cggcacgagc aacgacggta ccgtctattt cgagaccgtg    360
ccgcgcgatg cgctggagaa ggtgctgtgg atggagtccg accgtatggg ctatttcatc    420
aacacggtga ccgagggcgg gctcaagcgc gagatcgacg tcgtgtcgaa cgagaagcgt    480
cagggcgaga acgtgcctta cggtctggca tgggacctga cgttcaagaa cctgtttccg    540
cagggacatc cgtacagctg gaccgtgatc ggagagattc ccgatctgcg cagcgcgacg    600
gtcgatgacg tcaaggagtt ttacgacaaa tattacacga ccagcaacgc gacgctcgtc    660
gtagcgggcg atttcgacaa agccgaggcc aaaaaactga tcgaaaagta tttcggcgaa    720
atacccgacc gaggcaagcc cgaggctccg caggtgcaga acgtgacgct cgactcgacg    780
aagaaaattt cgtacgagga tgttttctgc aacgcgccga tgctgttgct tgcctatccc    840
ggggtcgaaa cctataatga agacggctat gcgctcgatt ttctcacgaa cctgctggcc    900
ggcgacaaga agtcgccgct gtacaaggtg ctcgtcgaag agcgcaaact cgcgcccgag    960
gtcgagatgt tcagctacca gctggaagtg gcggggctga tcgttttcga tgccaaaacc   1020
ttccccggcg tgaagctcga cgacgtgcag gccgccttcg acgaggcgct cgcccgcttc   1080
gagaaggagg ggatcgatcc gaaggacctc gagcgttaca agaat                   1125
```

<210> SEQ ID NO 36
<211> LENGTH: 2358
<212> TYPE: DNA
<213> ORGANISM: unknown
<220> FEATURE:
<223> OTHER INFORMATION: Representative gene for Cluster 8

<400> SEQUENCE: 36

```
atgagcgaat tgggtgttac gtctggtaaa ccattcaaaa agtcagcgag aatcgtcgga     60
gaggtactcg gaaagtacca ccctcatggt gatagctcgg tttacatggc gatggtacgt    120
atggcccaaa gttggtcttt gcgttatccg ctggttgacg ggcaaggaaa cttcggttcc    180
gtggatggag atagccctgc ggcaatgcgt tatactgagg ctcgtttgat gaaggtaacc    240
gaggacacct tggtggattt ggataaggat accgtggaca tgattccgaa cttcgacgaa    300
tcattaaaag aacccagcgt tctacccacc agaatcccct tgctgctcgt gaatggagca    360
tcaggtattg ccgtgggtat ggcgacgaat atgcctcctc ataatctaag cgatacggta    420
gacgcgattt gtgcttatat cgatgatccg gatatagaga tagacgattt gatccggatc    480
ataaaagccc ccgatttccc cacgggagga acaatttacg ggtatgccgg ggtgaaggaa    540
gcatatcata cgggaagagg ccgcgtggtt gttcgttcga aacatctgt  ggaaacaact    600
cctcacggac gggaaaaact gatcgttcac gaaatacctt atatggtcaa caaggcggaa    660
ttgatttctc gcattgcaga tttggtaaac gagaaaaaaa tagatggaat ctctaatatc    720
aatgacgaat cagaccgtag tggtatgcgt atcgtgattg atttgaaaaa agatgccatt    780
gccaatgtcg tactgaatac attattaaaa catacggctc ttcaaacttc tttcggggta    840
aacaacatcg cactcgttgg aggtagacct cgtttgttga atttgaagga cttgatccgg    900
ttattcgtag aacatcgtca cgatgtcatt acacgccgga cgcgatttga attgaaacaa    960
gcggaagatc gagctcatat tttggaaggt ttaatcattg ccagtgatca tattgacgaa   1020
gtgatccgaa ttatccgggc atctaaaact ccggatgaag cgaaaaacaa tttgattgaa   1080
cgcttctcct tgacagaaat tcaggctcgg gcgattgtgg aaatgagatt gcgtcaactg   1140
accggtctgg agcaagacaa gctaagagcc gagtatgacg acatcatgaa actgatcgag   1200
catttgaagg aaattttggc tagtttggaa ttaagaatgc aaattatcaa ggaagaactg   1260
cttcaagtaa aagctcaata tagcgatgaa cgtaaaaccg atattgttta tgcatccgaa   1320
gaattcaacc cggaagattt ttatgccgat gaagaaatgg tgatcaccat ttctcacatg   1380
ggatatatca aacggacacc attatctgaa tacaaagttc aaaaccgcgg gggagtaggt   1440
tcgaaagggt cggccacgag agatgaagat ttccttgaac acatgatcat ggccacgatg   1500
cataatacca tgttattctt cacggaaaaa ggaaaatgtt tctggctgaa agtatgggaa   1560
atcccggaag gcaccaaaca atccaaaggt agagctatcc agaatctgtt aaatatcgag   1620
ccggatgata aggtgaaagc ttacatcaac atcctcaatc tgaaagacga agagtatatt   1680
aataataact atatcgtatt atgctctaaa caaggtattg tgaaaaagac gaccttggaa   1740
gcctattctc gtccgagagc aaatggtgta aatgccatta caattaaaga aggagatcaa   1800
ttactggatg caaaaatgac caatggcaaa tgtgacatca tgattgcaat caaatccggt   1860
aaagccatcc gtttcccgga agaaaaagtt cgtcccatgg gtagaacggc atctggggtg   1920
aaaggtatct cgctagataa cgaaggagac gaggtaatcg gtatgatttg catcgaatcc   1980
ggtaaatccg acgtgttggt tgtttctgaa aatggatatg gaaaacgctc cagtatagag   2040
gattatcgta tcaccaatag aggtggtaag ggggttaaga cgatcaacat gacggaaaag   2100
```

```
acaggaaatc tgatagcctt acttgacgtt acggatgaag ataacttgat gattattaac   2160

aagtctggat tgacgataag actggatgtc agcactttga gagttatggg acgtaacacg   2220

cagggagtga gattaattaa tttgagaaat gatgatgcta ttgccgctgt agcgaaagta   2280

tccgcttcga aagaagagaa tcttccggaa gaagggcagg agggaacgga aatagcagag   2340

tcaaacgatg aagaataa                                                 2358
```

```
<210> SEQ ID NO 37
<211> LENGTH: 1548
<212> TYPE: DNA
<213> ORGANISM: unknown
<220> FEATURE:
<223> OTHER INFORMATION: Equivalent gene for Cluster 8

<400> SEQUENCE: 37

atggaaaaag tgtttagtcc gaaattattc ggattaatta aagacggttc ggtaaagaag     60

aatttgtcga aggatattct tgccggaatt gtggtaggta tcgtggcctt accgttggca    120

attgcttttg ccgtggcctc aggtgtttcc cctgaaaagg ggattataac ggctatcgtg    180

gccggatttc tcatctcgtt ctttggtggt agccgggtac agattggggg acccacggga    240

gcttttatca ttattgtcta cgggattgta aatgattacg gtctggacgg gatgattatt    300

tcaacgatat ttgccggggt gatcatgatc gggttcggaa tgttgcggtt agggactttg    360

ctgaagttta ttcctcaccc gttgattgtc ggttttactt ccggtatcgc cttgacgatt    420

ttctccacgc agatatccag tgcgttggga ttgacgctga cggatgtgcc ggggagtttt    480

atcggtaagt ggggcgctta tttcggggga atagatacgg tgaactggta tgccgtggga    540

atcacgatcg tgaccgtgtt gatcgcggtg tatatgccga aatcacgag ccgggtgccg     600

ggttcgtttg tggctatact ggtggtgacg cctatcgtgg ctttcttttt gccggaaggt    660

gcggtgacga cgatcggttc cgagttcggg gagattaaat gtaatttgac tccggtgttt    720

ccatcaatcg agtgggggca gttgtcacat tacctgcagc ctgccatgac aatcgctatt    780

ttaggtgcaa tcgagtcgtt gttgtccgcg gtggtggctg acggtatgat tagtgggcac    840

catcgttcga atacagagtt gatcgcccag ggaattgcta atattgcctc tcctttgttt    900

ggcggtattc ctgccacggg tgccattgcc cgtacggcaa ccaacgtgaa gaacgggggg    960

cgtactccgg ttgccggaat cacccatgcc gtggtgttgt tgctgatcat gttgttcttt   1020

ggaaaatggg catctttgat tccgatgtca tgtctggcgg gtatcttgat cgtggtatct   1080

tataatatga gtgaatggcg gtcgttccgt tctattttgc gggcatctat gtccgacgtg   1140

gtgattttgc tggtgacttt cttcttgacc gtgctggtcg atctgaccgt ggctattgaa   1200

atcggagttg tgttggctgc cctgttgttt atgaaacgta tggcggataa cgctccgaaa   1260

gagatgatcg gtgccacgaa tatggatagt gatgtgcttg agaattataa ggatctgccg   1320

aaaggtttgg gtatatacga gattagcggg ccgttttttt tcgggtcggc aaagacatat   1380

tgtgaaacaa ttcgtaactt aggcgtgaat tatgatgtgc tgattattcg tatgcgtcat   1440

gttcctttcg tggatactac cgggttgaaa aatctgagag agacgattct ccaattgaag   1500

aatgagggta cgtatatcgt tttatcggga gtgagcgaat cggtgaag                1548
```

```
<210> SEQ ID NO 38
<211> LENGTH: 1950
<212> TYPE: DNA
<213> ORGANISM: unknown
<220> FEATURE:
```

<223> OTHER INFORMATION: Equivalent gene for Cluster 8

<400> SEQUENCE: 38

```
ttcaactttc cccctgtcgg tgggaaaaac aataaaggcc cgaaattcgg cggctactgg      60
tcgtttatca tcatcgccgc tttcattatc gggattcaat ttttcagtat gccctcgaat     120
ccggaacgga tttcttggca gaaattcaaa acagatcttt tagcgaaagg tgaggtaaaa     180
gatatttaca tcgtcagaaa tggcggtaaa gccgaaatca ccttaaaacc agagaaagtg     240
gaaacccaca gcgacctagt ggcaaaagga tttaaccaga aaagtgtagg tccgcaatac     300
tacgtgcctt tcggaacact ggagcaattc gaaaagaatt tacaagacgc gcaaaaagaa     360
tacccggaag aggcatccaa cgtgtttgtc gattataaag acgattttaa ctggtgggga     420
gaagtcatca cactattcct gcccatcgct attttcgtgg gaatctggat attcttcatg     480
cgacgcatga gcaagggagc cggtggcggt ggtggcggtg gcattttttaa tgtcgggaaa     540
tccaaagcaa aattgtttga caaagaatcc aatataaaaa ttacgttcaa agatgttgcc     600
ggattagccg aagctaaaca agaggtggaa gagatcgtat ctttcctcaa atccccggat     660
aaatacacca aattaggagg aaaaattcca aagggagcct tgttagtagg gcctccggga     720
accggtaaaa ccttgatggc aaaagccatg gctggggagg ctaacgtacc gttcttctcc     780
atgtcgggat cggacttcgt ggaaatgttc gtcggagtgg gggcttcccg tgtacgagac     840
ttgttcaaac aggccaaaga aaaagctcct tgtatcatct ttattgacga gattgacgcc     900
atcggtcggg caagaggcaa aaacccgaac atgggagcca atgatgaacg agaaaacaca     960
ttgaaccagt tactgaccga aatggatggt ttcgaaacaa actcgggagt catcatactg    1020
gcagccacga acagggctga catcttggac agcgccttgt tgcgtgccgg acgtttcgac    1080
cgccagatat acgtggatct tccggaatta aaagaccggg aagagatttt caaggttcac    1140
ttgaaaccat taaaactcgc cgaagacatt gactacgcct tttggcaaa acaaaccccg     1200
ggattctccg gcgcagacat cgccaacgtg gcaaacgaag ccgcactaat tgcagcccga    1260
aaaaataaat cggccgtgga aaaacaggat ttcctggatt caattgaccg tatcgtgggc    1320
ggacttgaaa accgcagcaa agtcatcaaa ccaagtgaaa agaaagcgat tgcttatcac    1380
gaagccggac acgccaccgt atcgtggtta ctacaacacg cccatccact attgaaagta    1440
accatcgtac cacgagggaa agccttggga gccgcttggt acttgccgca ggaacgccaa    1500
attaccacga aagaccaatt gcttgaccag atgtgttccg tgctgggtgg acgagctgcc    1560
gaggaaatcg tgttcgggga aatatccacg ggggcacaaa atgacttgga acgtgcaaca    1620
aaacaggctt acgccatggt atccatttac gggatgagcg acaaagtagg catgttgagt    1680
tattatgatt ccacaggtca gagcgatttc agtttcacca agccctattc agagaaaaca    1740
gcagaattga ttgatgccga ggtaaaagat atggttactg ccgcttatga acgggcaaag    1800
caactattaa acgatcacag ggaacaacat cgtcaagtgg cagaattgct gattgaacgg    1860
gaagtgatct ttagtgatga cttggagaat attctcggga aacgtccgtg gacagaggaa    1920
gaagaaactc aacagccgga agagttgtaa                                     1950
```

<210> SEQ ID NO 39
<211> LENGTH: 1965
<212> TYPE: DNA
<213> ORGANISM: unknown
<220> FEATURE:
<223> OTHER INFORMATION: Equivalent gene for Cluster 8

<400> SEQUENCE: 39

```
atcgatgtgt cgaaatataa tgacgggtta cgcgggggag tggtgaaaat tcgggccaag      60
atagagaaag acgccggaaa taaaatattg cggatcacgg agatcccttt cgggcggacg     120
acttctgcct tgatagattc gatcttgaaa gcgaacgaga aaggaaaaat caaaatcaag     180
aaaattgatg acaatacggc ggcaacagct gaaatcttag tgtatctggc ggccggagtc     240
tcttccgata agacgcttga tgctttgtat gcctgcacgg attgcgaatt gtcgatttct     300
cccaattctt gtgtcatcga gaacgataaa cccatcttca tgccgattac cgatattttg     360
cgcaagtcgg tggatgaaac cgtagccttg ttgttgttgg agctgaaaat caagctggga     420
gagctggaaa cggattggca atattcatcg ttggaaaaaa tattcataga agaacgtatt     480
tataaggata aagaattcga ggagagcgag acgatcgatc aagtggtggt tcacgtgcgg     540
aaacgtttgg aaccgttttt gccggaattg attcgtccgg tgacggatga cgatataaaa     600
cttttgctgg agatcaagat gaaacgtatc ttgaaattca actcggaaca ggcagagaat     660
tatatcaagg agttggaaaa ggagattgcc cgggtgaaat ttgacatcga acgtatcatc     720
ccttactcga ttaactatta cgagaatatc aagaaaaagt acggtaaagg ccgggaacgc     780
ctcacggaga ttcggaattt cgagaatatc gaggccacga aagtggtggt ggcaaacgaa     840
aagttgtaca tcaaccggga ggaaggtttc atcgggacag ccttgaagaa ggacgaattc     900
atctgcgagt gttcggacat tgacgacgtg atcgtgttcc ggaaggacgg tacgtattac     960
gtgaccaaag tggccgataa actgttcgtg ggaaaagagg tgctgtacgt gaacgtgttc    1020
aagaaaaatg acaagcgtac gatatacaac gtggcttacc gggatggcaa agtgggaccg    1080
tcttacgtga aacgtttctt cgtgacggga acgacgcgcg ataagcaata caacctgacg    1140
aaaggtacgc cgggatcgcg ggtgctgtat ttcagtgcga acccgaacgg ggaggccgag    1200
gtcatcaagg tgtgcctgaa accgaaaccg gggatgaaaa aactggtatt cgagtatgat    1260
tttgccggtt tggcaatcaa gggacgcgac tcgctgggaa acgtgttgag taaaaatgat    1320
attcataaag tttccttggt acagaaaggg gcttccacgc tgggcggtcg gaagatatgg    1380
atcgacgagg atgtgttgcg cttgaatacg gacgaacgcg gccgttacct gggagaattc    1440
caggggggacg atcggatttt ggtggtaaat aaaaatggta cttactacac gacggattac    1500
gatttgagta atcactacga ggaggaattc ttggtgatcg agaaatatga gcccgagaaa    1560
gtctggtcgg ccgtattctt tgacgcggag cagcaattct attatctgaa gcgtttccgt    1620
ttcgagaacg tggcgcgtca cacgctgttt atcggggaaa cggaagggtc gtatctggtt    1680
gccttgagtg gcgaaaaacg cccccggttc gagatcgtgt ttggcggacg ttacgagggg    1740
cgtccggccg aggtgatcgt tgcggatgaa tttattgccg agaaatcgta caaggctcgc    1800
ggaaagcgga tgaccactta cgaggtgaag caaattaatg aaatcgaacc tttggatagc    1860
ggggaagggg aaagcgagga aacaccttcg aacgatgtcg atttcgagat cacgaacccg    1920
gatatgctga atgacgagac gcagatgaag ttggattttg aataa                    1965
```

<210> SEQ ID NO 40
<211> LENGTH: 1239
<212> TYPE: DNA
<213> ORGANISM: unknown
<220> FEATURE:
<223> OTHER INFORMATION: Equivalent gene for Cluster 8

<400> SEQUENCE: 40

```
atgagaaaat tgacattgct attgttgatc gccatctctt gtggattcta cacgggggta      60
```

-continued cgagcgcaag tcaacgtgac ttccgtttca gaaaaaaatg acgcggataa cctttacaaa 120
atgatgaaag aggcattccc gttatcattc aacgacccgg catccccaag attcgtgttt 180
ttcaacaaga ataaaaactt tgttttcggc gtggggggat atgtgcaagt acagggaatt 240
tacgacttta acggggttcc caatgacaat tattttacca cgaacaccat cgctctcaaa 300
ggagatcaac ccggaggtag gtatggaatt tcagtcgggc aatcccgttt attcttcaag 360
ttaatcgggg atacggatgt cggcagactg gtgacttaca tggaaatgga attcgagggg 420
aaccagagta ccccgattct aagacaagct tttatcaaat tcaaaggatt cacgatcggt 480
aagacttgga gtaccttttg cgatattgcc gcaggaccgg ccacgataga cgaggaaggc 540
ccttccagcg aagtagcgtt acgccaacca cagattcgtt acacgtatga ttttactgac 600
aacctggaag catccttggc cttggaatac gtggagccat cctacacgga aggagaattt 660
accaagtaca tcaaccaacg gattcctgac atcccgatga acgtgaagta tagtttcaaa 720
aacgggagtc acctgcaagc gggagccgtg ttgagaaata tgtactataa agataacatc 780
gaggaaaaag accggatcgt taccggcttc ggagtttcat tgagtggtat ttggcaattt 840
gccgaaaata catccctctg cttccaaggc gtgtacggga aaggcatctc caactacata 900
caggatatct ccggatcagg acttgacctc gttccctgtg ccacggcaga agggaaatta 960
aaagcaattc gtgcatgggg tggctacatc ggattttctc acaactggtg caaagccctg 1020
acatcaaaca tcatgtacag ctacgcccga gtccttgacc gttacgggat gcctgcaaca 1080
tcatacaaat acgcgcaata tgccgccgcc aacctattct gggatttcag tgaatacggt 1140
tcctgtgcca tagagtacgt gttcggccgc cggaatgact tcaacaaaga ttacggcaac 1200
gccagtcgta tcaacacgat gatacagtac cggttctaa 1239

<210> SEQ ID NO 41
<211> LENGTH: 555
<212> TYPE: DNA
<213> ORGANISM: unknown
<220> FEATURE:
<223> OTHER INFORMATION: Representative gene for Cluster 9

<400> SEQUENCE: 41
gcctgtttac gcactaagga gcggagcatg gctgataacg caaaatggta tgtcatccac 60
acctattccg gctatgaaaa tgcggtgaag gcggccattg aaaagtccgt ggtgaaccgc 120
aatatgtccg acatggtcct gaagatggag atccctatgg agaccgtcac cgaggtcacc 180
gagtcgggtg tcatgaagga agtggagcgc aaggtattcc ccggttacgt cctcattaag 240
atgatcttga cagatgacac ctggcatctg atccgcaaca tccgtggcgt caccggcttc 300
gtaggagagg ccaacaaggc catccccctg acggaggagg aggtcgctgc actgggcgtg 360
gaaaagcacg agatcgtggt cctgtacaac gtgggcgata ccgtgaagat cacggacggc 420
cctctggcca gcttcatggg taccgtggag gagatcgacg ccgacaagaa caaggttcgt 480
gtggtggtct ccatgttcgg gagagagact cccgtagagc tggagctcga tcaggtcgag 540
gtcgtccagc cctga 555

<210> SEQ ID NO 42
<211> LENGTH: 873
<212> TYPE: DNA
<213> ORGANISM: unknown
<220> FEATURE:
<223> OTHER INFORMATION: Equivalent gene for Cluster 9

<400> SEQUENCE: 42

```
cccccccccc cccccgccga gcctcaggcc gaggctcgtc tgctgatgct gtcggccaac     60

aacctgctgc gtccccagga cggcggcccc gtcaccgtgc ctacgcagga tatggtgctg    120

ggctcctact acctgacctt cgagcggttt gaaaacggta tgtgccagat gactaatgac    180

cagttctggc ccgagggcat cgactttgcg ctggccggta agagctacga cgagctcacc    240

gacgaggaga aggagcagaa ccgcctcaac gtctaccggg acgaggacga ggtgctgatg    300

gcctacaacg agcacatcat cggcatccac cagcccgtgt gggtgcgggt ggagaagaaa    360

ctgggcgacg agacgctgcg ccatgtggtg cgggctactc ccggccggat catcttcaac    420

cgcaacatcc cccaggatct gggctttgtc aagcgcttca acgaggacgg tacgccctcc    480

gataagttct ttgactatga gatcaccgag acctgcggca agaagctgct gggcaagatc    540

gtggaccgca ccatcaagca gtatggcttt accatcgccg ccgaggtgct ggacaacatc    600

aaggccaccg gctataagta ctccacccgt ggctccatca ccatctccat tgcggatatg    660

acggtgcctg agaagaagta ttccctcatt gccgagacgg agcagcgagt ggtggatatc    720

gaggaccagt acaacatggg cttcatcacc gacgaggagc gctacaagct ggtggtgcgt    780

gagtgggaaa agaccaccaa cgatgttacc gacgcactga ccgccagtct ggataagtat    840

aatcccatct tcatgatggc cgactccggc gcc                                 873
```

<210> SEQ ID NO 43
<211> LENGTH: 1251
<212> TYPE: DNA
<213> ORGANISM: unknown
<220> FEATURE:
<223> OTHER INFORMATION: Equivalent gene for Cluster 9

<400> SEQUENCE: 43

```
atgaagactc gcaatggtct gttcgctgac gttcccgaaa atctgtggaa tgactggcat     60

tggcaggtcg ccaatcgtgc tgagacgatt gaggatctga agaagtacat gaacctgacc    120

cccgatgagg aggccggtgt tgccaagacg ctgggcaagc tgcgtatggc agttactcct    180

tattacctgt ccctgatcga tctgaacgac ccgttcgatc ccatccgtaa gatggctatc    240

ccccgtgctg aggagctgga gtatgccgat tacgaggatg ccgatcccct gcacgaggat    300

accgactccc ccaccccccgg cctgacccac cgctatcccg accgtgtgct gctgctgatc    360

accgaccagt gctccatgta ctgccgtcac tgcacccgtc gtcgtttcgc cggccagaat    420

gactgcgagg tgccgatggc tcagatcgac aagtgcatcg actacgtggc cgctcatcct    480

gaggtccgtg acgtgctgct gtccggcggt gactccctga tggtctccga cgagacgctg    540

gagtacatca tcaagcgtgt gcgtgccatt cctcacgtgg agatcgtccg tctgggctcc    600

cgcacccccg tggtgtgccc ccagcgtatc actcctgagc tgtgtgccat gctgaagaag    660

tatcatcctg tgtggctgaa cactcacttc aacacgccca aggagttcac tcccgaagcc    720

gccaaggcct gcgccatgct ggctgatgcc ggtattcctc tgggcaacca gtccgtgctg    780

ctggccggtg tcaacgactg ctcccacgtc atgatggagc tggttcacgg tctggtcaag    840

atgcgtgtac gtccttacta catctacgct tgcgatcctt ccctgggtct gagccacttc    900

cgtactcccg tgtccaaggg catcgagatc atggaagctc tgcgtggtca tacctccggc    960

tattgcgtgc ccaccttcgt ggtggatgct cccggcggcg gcggcaagac tcctgtcatg   1020

cccaactacc tgatctccga gactccccgc aaggttatcc tgcgtaactt cgagggcgtt   1080

atcacctcct acactcagcc tgagcactat gttcaggatt gccactgcga tgtctgcatg   1140
```

ggcaagaaga aggctgagaa gaccggtgtg gcatgggtcg ccgagggtac caagcagcgt 1200
tatctggagc ccaccaagct actgcgtaac gagcgtcacg tcaagaaata a 1251

<210> SEQ ID NO 44
<211> LENGTH: 1341
<212> TYPE: DNA
<213> ORGANISM: unknown
<220> FEATURE:
<223> OTHER INFORMATION: Equivalent gene for Cluster 9

<400> SEQUENCE: 44
aacggctatg accgggtgga ccagcagacg ctggacgcca tggaggccta ttgccgggac 60
tacaagagct ttttggacca cagcaagacc gagcgggagt gcacggccca caccgtggcg 120
ctggcggagg cggcgggctt tatcccctat gagcggggca tggccctgca gcccggcgac 180
cgggtgtacc gggtgaaccg gaagaagagc gtgatgctgg ccgtgatcgg ccgggagagc 240
ctgtccgagg gcgcacagat cgtggcctgc cacatcgact ctccccgtct ggacctgaag 300
ccccatccca tttatgagga cagcgagctg gcctacggca agacccatta ctacggcggc 360
gtccgtaagt accagtgggt ggcgatcccc ctgcagctgc ggggtgtggt agccctgaag 420
gacggcacgg cggtgtccgt ggtgctgggc gagggcgacg agcccaagtt cgtcatcaat 480
gatctgctgc cccatctggg cggtgagcag gggaagaagc ccctcaacga ggccattgcc 540
ggtgagacgc tgaacatcct catgggcagc cgtcccttgg gcgacagcga ggacagcgac 600
cgtgtgaagc tgcgggtgct ggatctgctc cacgagaagt acggcatctg cgaggatgac 660
ctgacatccg ccgagctgga ggtggtcccg gcctttaatg ccacggatat cggtctggac 720
ggcagcctca tcggcgccta cggccacgat gaccgggtgt gcagctatgc ggccctgaag 780
gctctgctgg agctggagac ccccaccaag accgccgttt gtatgctggc ggacaaggag 840
gagatcggct ctatgggcgt caccggtatg cagtccgcct tcttcgatac ctttatggag 900
gatctgtgcg agagtcaggg cgttgccctg cgggtgtgct atgagagcgc cttctgcctg 960
tcctccgacg tgacggcggc ctatgaccct aacttcgccg aggtgtatga gaagcgcaac 1020
gacgctcagg tgaaccacgg tctggggctg tgcaagtaca cgggcgcccg tggcaagggc 1080
ggctcctccg atgccgacgc cgagacggtg gcttatgtcc gccgggtgat ggacgaggcc 1140
ggcgtggtgt ggcagatcgg tcagatgggc aagatcgacg ccggcggcgg cggtacggtg 1200
gcccagtaca tggccaaccg caacatcacc accattgatg ccggtgtgcc ggtgctgagt 1260
atgcacgctc ccttcgagac ggtgggcaag ctggattgct acatgaacta tctgggctgc 1320
aaggccgtct atctggcgta a 1341

<210> SEQ ID NO 45
<211> LENGTH: 237
<212> TYPE: DNA
<213> ORGANISM: unknown
<220> FEATURE:
<223> OTHER INFORMATION: Equivalent gene for Cluster 9

<400> SEQUENCE: 45
atgcttgtga atcaagcgga agttagtcac agcaaggagg tgcaacggat ggctaagtgc 60
gaattttgcg acaagggcgt gaccttcggc atcaaggtct ctcactccca ccggcgttcc 120
aatcgtccct ggaagcccaa tgtcaagcgt gttaaggcgg ttatcaatgg cacgcctcgc 180
catgtgtatg tttgtacccg gtgcctgcgt tccggcaagg ttacccgtgc gatctga 237

<210> SEQ ID NO 46
<211> LENGTH: 465
<212> TYPE: DNA
<213> ORGANISM: unknown
<220> FEATURE:
<223> OTHER INFORMATION: Representative gene for Cluster 10

<400> SEQUENCE: 46
atgcaaattg acaagcgcct gaaaatcgtc attgccgctg tcatcgtagc tgcctgtgcc 60
tttggcggct ataaatacta tgaatcccag caagccgcaa aacaatccaa ggccatcgaa 120
acagccgatg tcgtccgcaa agacctgcgt tcgaccgttt ccgccacagg gaccatcagc 180
cctgtcgatt ccgtcgaagt ctcgccgaag atcacggccc gcatcagcca ggtcctggtc 240
aaagaaaatg accgggtcac agccggccag accgtagccg tcctcgacgg caaagattat 300
gaagccaaac gcgaccaggc ccagtataag gtcaccaaca ccaaagtcga atacgaccgg 360
gcccagcagc tctatgacct cggtgccggc accaaacagg ccctggatac ggcgaaattc 420
aactatgaca ctgccgtcag tactttgacg gaagccgaat cggac 465

<210> SEQ ID NO 47
<211> LENGTH: 873
<212> TYPE: DNA
<213> ORGANISM: unknown
<220> FEATURE:
<223> OTHER INFORMATION: Equivalent gene for Cluster 10

<400> SEQUENCE: 47
atgcaagaaa ataaaggaag tcttatggtg aaaaaaatat gctcatggat cgtcggcgtc 60
ctgcttaccg tcctggtcct cctcatcgga gtctttgctt tttggtattt cgggtcgacg 120
aactatcatc tcacaggcgt ccccgtcctg aattatcatc aagtcaataa taaattcaac 180
accgtgctga ccatgaagcc agccaatttt gacgaacaga tgaaatatct gcacgacaac 240
gactaccatt ccattacctt ggaacaattc gatgcctaca tgcgcggcga aggcgattta 300
ccagatcgtc cgatcctcat cacctttgat gacggctacg tcgacaatta tgaaaatgcc 360
tatcctatcc tgaagaaata caacatgcgt ggcacgattt tcctgatcat caacctcatg 420
gacacgccgg gctacctgac ttgggaccaa gtcaaggaaa tggctgctga cggcatggaa 480
tttggttccc ataccatcag ccataagccg ctgaccagct tcgaccgggc cggagtgcgt 540
cacgaactgc aagactctaa ggacatcatc gaaaagatga ctggcaagcc ttgtcacttc 600
atcgccttcc cagaaggcaa atataacgat atggtcatgg aagaaacaaa aggcgctggc 660
tatcgctacg cctttaccgt agatacaggc cgcgacttcc cttgggacga tccatacgat 720
ttggaccgcg tccccatgtt tgaaggccct ataagcttca aacacttccg gttccgcctg 780
accttcagcg ccttcagcgc gcttctgtgg aagacccata aatactttga acacatagaa 840
atgaccaaag acttggccca acatatccca cag 873

<210> SEQ ID NO 48
<211> LENGTH: 738
<212> TYPE: DNA
<213> ORGANISM: unknown
<220> FEATURE:
<223> OTHER INFORMATION: Equivalent gene for Cluster 10

<400> SEQUENCE: 48
atgagaatcg acattatctc actctttccg gagttcatcg aagctttttt ccagcacagc 60
atcatcgggc gggcccgggc agccggtctg ttggatctgg atgtgaccaa tccccgtaat 120

```
ttcacgtatg accgtcatca tatggtcgat gataccatct atggcggcgg ctgtggcatg    180

ctcatgaaaa cagcgcccct ctatgccgct gtcgaagctg tgcggcgcca ggtgccgcgg    240

cggcgtatca tcttcatggg gcccgcaggg cagaccttta cgcaggccaa agcacgcgag    300

ctggcgacat acgaccagct tattttatta tgcggccatt acgaaggtgt cgattaccgc    360

gttgagcagg atttggccga tgaaactatt tccgtcggcg attacgtcct tactggcggt    420

gaactgccgg ctatgaccgt taccgatgcc gtggcccgca tgattcccgg agtcctcggc    480

gcagttgccg gggccgctga cgattctttc tattcgtcgc tcctggaata tccgcagtac    540

actaagcctg ccgtctttcg cggcatggcc gtaccggaag tcctgcgaaa cggcgatcac    600

gccaaaatcg atgcctggcg ccgggaggcg tcgctagcgc ggaccttgga attacggcca    660

gatcttttgc agcactgcga tttgtcgcca gctgaccaaa agatactggc aaaactgaaa    720

ggggcgaaaa aaggatga                                                  738
```

<210> SEQ ID NO 49
<211> LENGTH: 822
<212> TYPE: DNA
<213> ORGANISM: unknown
<220> FEATURE:
<223> OTHER INFORMATION: Equivalent gene for Cluster 10

<400> SEQUENCE: 49

```
atgaagaagc agcgcaaccg cgggattttc cagatccagc gcggcctgga atgtagccgg     60

gaagaagcgg aactcatcat gaccgaagtc ttccgcaacc tcggccagtc gctcatggaa    120

atcctctata cgcccaatct gaaccccggg aatatccgcg actatgtcac cctggaacat    180

ccggaacgcc tcgatgaggc cgtgaaggaa gggaagggcg tcatcgtcct gacggcccat    240

atgggcaact gggaatggct cggcgccctg gccatgtacg gctatccggc gtcgaccatc    300

gtcaagaatc aggccaacga cgccgtcacg cgcctgctca acgaaaaccg tgaaggcatg    360

gggctggaag tctttgcccg cggcggcaat gaaatgatta tcgccgcccg tgccctgaag    420

cgcaagaagc tcctgggctt cctggccgac caggacggcg gcttccacgg cgttcctcag    480

ccgttcttgg gcaagatgag ctcgacgcct aaggggccgg ccatgtttgc ccagaaattc    540

cattccccca tcgtgccggt ctttcccgtc catgacgaaa accatcggac ccatttgatg    600

atcggcgagg tcatgcactt tgaagatacg gggaataaag aagaagatat tgcccgcatg    660

acccgcaaga tggctgtggt cacagagcaa ttcatcaaag aacatccgac agaatggctg    720

tggttccagc accgctggag tacagaaccg gaagaaatca tagcgttgca gcagaaaccg    780

gaggcgcata ccgatgatag cagaaaagct gaaaaagaat aa                       822
```

<210> SEQ ID NO 50
<211> LENGTH: 831
<212> TYPE: DNA
<213> ORGANISM: unknown
<220> FEATURE:
<223> OTHER INFORMATION: Equivalent gene for Cluster 10

<400> SEQUENCE: 50

```
gtgcttatga aagctaagga attgcgggtc attgacagtc atttccattt ctgtgactat     60

atcggcttca atcagattgc tattgctgcc ggttatacca atactgaaga atgtctgcac    120

aaggcctttc aagacaacaa tatcgtccac ggcgtcgtca tgggcaacaa gaccctggac    180

ccggccggcc atcactatcc cgattacatg agttactgca tcggcctgga cagcaacgtt    240

ttttatgaca atatggacct catggtggaa caggtcgaag agaacctcaa gcgcaagcag    300
```

```
tgctgcggca tcaagctcta tccgggctat aaccacgtct acgtctatga tgaactctac    360

gacccgatct acgaattggc ccggaagtac aataagcccg tcgccatcca cacgggcctg    420

acggcgacgg ccaatgccct tttgaagtac agccatccca tgaccctcga tgaagcggcc    480

gtcaaatatc ccgacgtcca gttcgtcatg tgccacatcg gcaatccttt cctgcaggat    540

gccattgccg tcctggaaaa gaaccacaac gtcgccgtcg atttgtcagg ccttttggaa    600

ggcaagattc ccgacatggt caccttcctg cgggacaaac aggggtatat ctccatgctc    660

cgggactggc tgaactatct aggttcttac gaccgggtca tgttcgggac cgactggccc    720

ctggccaatt tcgccgatta tattaccttt gtcaaagatt tcatccccga aacgtattgg    780

gatgacgtct tcttcaacaa tgccaaccgc atctaccagc ttggcttata g             831
```

```
<210> SEQ ID NO 51
<211> LENGTH: 1446
<212> TYPE: DNA
<213> ORGANISM: Bifidobacterium
<220> FEATURE:
<221> NAME/KEY: misc_feature
<223> OTHER INFORMATION: Representative gene for Cluster 11

<400> SEQUENCE: 51
```

```
atgcgtgtga gcgtgcccat agactcttcc gacgccaaag ccaccagttc cggcgatact     60

acacgccgcg atggcttcgg caccccgcat gccggcgcaa acacaaacgt cagcaacggc    120

ccgaccgacg cccgctccac caaccgccgg atcatggcgc tggccctgcc gaccttcggc    180

cagctcatcg ccgaaccgac cttcatcctt atcgacacag ccatcgtcgg ccatatcggg    240

gatgcggcgt tggccggcct gtcaatcggc tccaccatca tcctcacggc agtcggacta    300

tgcatattcc tggcctactc gaccactgcg caggtggcac atctgctggg agcgggtcgt    360

cgtcgcgagg gactgcaggc aggcattgat ggcctgtggc tggccttgag catcggcacc    420

gtactgggat tgggattgtt cgcggctgcc gagccattat gccgggcact gggcggtcag    480

ggcgaagtat tggaacaagc cgtgacctat acgcgcgcaa tcgtgctggg tgcgccaggc    540

atgctgatgg tatatgcggc gaacggcatt ttccgaggat tgcagaaggt tcgtatcacg    600

ctgatcgctg cggtgggcgg cgcggtggtg aacacggtgc ttgatgtgtt gttcgttatt    660

gtgctgaatt ggggcattgc cggctccgga gtggcgacgc tggtagctca gtggttcatg    720

gggctgttcc tggtaatccc cgccattctg tggtcccggg cggatggtgc gagtctgcgg    780

cctcgtttgg ccggtattgc ggcagccggg ggcgacggac tgccattgtt cattcgcaca    840

ttggcgattc gtgcggccat ggtgactacg gtcgcctgtg ccgcgcgcat gggtactgcc    900

gtgttggccg ggtttcaggc cgtgaactcc tcttggaatt ttgcgatgaa catgctggat    960

tccgtgggca tcgccggcca gacgctggtg gccacagcgc tgggcgctgg cagcgtgcag   1020

caggcgcggc ggctgacgcg ggcgaccggg cgtgcgggac tggtcaccgg cgcggtaatc   1080

ggcacggctt ttgcggtagt cggcctgttc gccgggcact tcttctcccc tacgccacat   1140

attcagacgc tgatcgccgt gggcatggtg acgatgggca tcttcttccc actgcaaggc   1200

tggatgatgg caatcgacgg cattcttatc ggcgcgcgcg actaccgcta tctggccgtc   1260

acatgcacgc tgaccgccgt ggtgtatgtg acgctcatac tcatactggc caatatggtg   1320

acgccggcgc tgacgagcga cctgatgcgt accgccgtac tctgggccgc gttcaacgtg   1380

gtgctcatgg gtgggcgcgg tctgtccaac ggactacgcg tgcgctcgga cgcatggatg   1440

aggtag                                                              1446
```

<210> SEQ ID NO 52
<211> LENGTH: 1791
<212> TYPE: DNA
<213> ORGANISM: Bifidobacterium
<220> FEATURE:
<221> NAME/KEY: misc_feature
<223> OTHER INFORMATION: Equivalent gene for Cluster 11

<400> SEQUENCE: 52

```
atggatatga gccagccgga tgacgacggc gtctaccgga atggtgcgac caagcgcaaa     60

gcccgcacgg aactggccat gcaatgcctc actgagctgt ggaatgcggc ctgcaaggat    120

gtctctttcc ccgtgcccga ctccggcatc ggcttcgccg cggtaggctc gctggcacgt    180

ggccaactgg gccccagctc cgacctcgac ctggtcatca tctacgagcc tcgcacgttg    240

aacgaccagc agctcaacga gttggccaac aaactctggt acccgctatg ggacagcggt    300

ctggacctcg accactccat ccgcacgcgc gcccaatgcg aggaagtcac cgaccatgac    360

cttcccgccg ccatgggctg gctggacgtg aagcccatcg ccggcgacac cgctctgatc    420

accaccaccg ccacgtccat cctcgaacgc tggcgcaagg ccgcccgcaa gcgcctgccc    480

gaactgctcg actccgccaa agcccgactc gacgaattcg gccggctcca atacgtcaat    540

cagcccgaca tcaaagaggc ccgtgggggg ttgcgcgatt cggtgctcgt ctccgcgctc    600

gccgcctcat ggctggccga ccgcccgcac ggcatttacg acgaagctgt ggaacgtctg    660

ctcgacgtac gcgactgcat ccatctggtg gccggcaagg ataccaacct gatgctgacg    720

ccctatcagg ccaaagtggc tgccatgctt ggccttgccg atccgacttg gcccgaaaac    780

gagcgtgccg cctactcgat cgacgatctg cagacactgc ttgcccgtat cggtcggcgc    840

atctccttct cgcttgattc caccgcttcc cgcgccgaac attcgctgac ccacgaaaag    900

ccgcgattcg cgttcttcca gatgttctct cagcgctctg gtggcaagcg cgaagccccg    960

caattcgacg tggtggctcc cggcgtggcc aagcacgaag gcgaattggt gttggcgccc   1020

ggtgccgagc ctgccaagga tgccaagctg gcgttgcgta tggccgtggc ggccggcgaa   1080

ttcggtcttc ccatcaaccc gtctaccttg gttaatctga agcgctgccc gattcacgac   1140

aaccagtggg atgacgaatc gcgcgagctg tttatccgtc tgcttgcgtg cggatcgaat   1200

cttatggaag tgtgggagag catcgatttc gtggacattc cgggtcgatg gatgccggaa   1260

tggctcggcg tccgcaaccg tccgtccgcc tcggccgccc accggtacac catcgatcgg   1320

catatggtgg aggtcacgtc gcgtctgggt cgtgagacac cgtccggtgg acggtacgat   1380

gacgatcatt tcaaggcatt gctgttggcc ggtatcaccc acgacatcgg caagcgcgcg   1440

ttcgtggccg atcacgccgc cgagggtgcc cgccatgtgc cggcgattct caagcgtatg   1500

ggctacgcgc cggacatcgt cgactgggct accgtgctgg tgcgtgagca tttgacgcta   1560

tccgaatttg ccacgggtaa ggacccctat gatccggccg tggcggagga gttggccgac   1620

cgcttgcacc acgacaagat gctgctggat atgctgttcg acctgacccg ggccgacggc   1680

tcctcgctcg gtgccaccgc cggtgagacc atcaccaagc aatacggctg gtccaagtgg   1740

cgcgaacaaa tcgtccgcgg catgtattcc gccgcccgcg ccgctatgta a            1791
```

<210> SEQ ID NO 53
<211> LENGTH: 1278
<212> TYPE: DNA
<213> ORGANISM: Bifidobacterium
<220> FEATURE:
<221> NAME/KEY: misc_feature
<223> OTHER INFORMATION: Equivalent gene for Cluster 11

<400> SEQUENCE: 53

```
atggatatga atactgtgct cgccgttctt ggcgtgattg tggcggcggt tatcgtaatc     60
gccctgagca tctggttggg caagtcccgc aagcgcgatt tggatcgtgc gatgggcaag    120
gttgcccccg acaacaagaa gacccgcgac gccaaggccg ccgccgacgc tcggctggcc    180
gccgaagccg aggaagctaa ggctgcgact gccgccgagc cggccaagtc agccgaatcg    240
gccaaagccg agcctgcgcc agccgcgcag gccgaacccg aaccggcagc tgcgcccaag    300
cccgagtccc aacctgcctc caagcccact cccgccaaac ctgaaacccc cgaatcggtc    360
ggctctcgac tgacccgact caaggcaaaa cttgccaagt ccggcaaccc gttcggcaag    420
gccctgttcg acatcctcgc caaagacaat ctctccgagg ccgattggga agacgtcgaa    480
gacacactgc tgcttgccga cgtcggtgcg gatgcttccg cccaactggt cgatgacctg    540
agaaccgacg cccgcatcac tggtaaagcc gacccagccg aagtacgcgc cacgctcaag    600
gagaagctgc tcgatctggt cggtcgagat acggaccgcc gcctcaatgc cgaaaagccg    660
ggtgccgcca agcccagcgt catcatcatg gtcggcgtca acggcaccgg caagaccacc    720
actgccggca aactggctcg actgttcgtg gccgaaaaca agcaggtcat gatgggcgcg    780
gccgacacct tccgcgcggc cgccgccgac cagctcgaaa cctggggcgc acgcgtcaat    840
gtgcccgtcg tccgctccga caaggacggt gccgacccgg catccgtcgc ctttgaggca    900
tccgccaagg ccaaggaagc gaacgcggac gtgctcatca tcgatactgc cggccgactg    960
cagaacaagt cgaacctgat ggacgagctc ggcaagattc gccgtgttac cgaaaagaac   1020
ctgccggtgg atgaagtgct gcttgtgctc gacgccacca ccggccaaaa cggcatggcc   1080
caggccaagg tgttcgccga agccatcggc attaccggtg tggtgctctc caagcttgac   1140
ggttccgcca agggcggcat cgtggtcagc gtgcagaagg agctcggcgt gccggtcaag   1200
ctcgtcggtc ttggtgaagg tccggacgat ttggcacctt tcgatcccga aggtttcgtg   1260
gacggcattc tcgcgtag                                                 1278
```

<210> SEQ ID NO 54
<211> LENGTH: 822
<212> TYPE: DNA
<213> ORGANISM: Bifidobacterium
<220> FEATURE:
<221> NAME/KEY: misc_feature
<223> OTHER INFORMATION: Equivalent gene for Cluster 11

<400> SEQUENCE: 54

```
atgacgtcgc tgcagcgccg cgagcagctg attgaagtcg gacgctcgct attcgccgcc     60
aaaggcttcg aagcggtaag cgtggaggaa atcgccgcgc acgccaaagt ctccaagccg    120
attgtgtatg agcatttcgg cggcaaagag ggcctgtatg ccgtcattgt ggatcgtgag    180
atgcgcgcgc tgaccggtac gctgaccgcc gcgctcgacg atccgaccgt gcacccgcgc    240
cagattgtgg aacgcacggc gcttgcgctc ctcacctata tcgaagagaa tgccgagggg    300
ttccaggtac tggtacgcga ctcgccgagc accgacccgt ccggctcatt cagctcgctg    360
atgggagaca tcgccgtacg cgttgaagac attctttccg aaacattcaa acggcagaag    420
ctgtctgcca agggcgtgcc gtactacgcg cagatgctgg tgggcatgac cgtattcacc    480
gggcagtact gggccgaccg gccaaaggtg agcaaggagc agctggctgc atacattgtg    540
gatttggcct ggcatggcct gagccggctt gactccaagc cccagttgtt ctttgagggc    600
```

gccaaggcgc ggaaggaggc cgagcgccga gccaagcgcg agtccgattc cggcagcccg 660
gattcagacc agacgagttc tgcccaatcg gatcccgagc acgccaccgg ggaagattca 720
gggttgcaga acatgcgttc aggggcacag gttacgcaac actctgccga gtcgggaggc 780
gaagtgctac ggtttgaaca ggaaactgaa cataacgact aa 822

<210> SEQ ID NO 55
<211> LENGTH: 1035
<212> TYPE: DNA
<213> ORGANISM: Bifidobacterium
<220> FEATURE:
<221> NAME/KEY: misc_feature
<223> OTHER INFORMATION: Equivalent gene for Cluster 11

<400> SEQUENCE: 55
atggccagca cggcaaagac gctcaccttt gtgatccccg catacaatat ggagtcctac 60
cttgaccgtt gcgtgaactc gctgctttcg gcaagcgaca tcagcgacct cgaggtgctg 120
attgtggacg acggttcgaa agacggcacg ctggagtacg cgcgcaaact ggaacgcacc 180
aatccaggtg tcgtacgcgc gattcaccag gagaacaaag gccacggcgg cgcggtgaac 240
accggtatca cggcggcgac cggcatgtat gtcaaggtgg tggatgcgga tgattgggtc 300
gacccgcagg ccatcgacac ggttctggcc acgttgcgtg cacagcatga caccgacgaa 360
ccgattgaca tgctggtgac caattacgtg tatgacaagg tggccaagcg tcacaagacc 420
gtagtgaact tccgccgtgt aatggaggcc ggccgcgtgc tcggctggga tgacctgggc 480
aagttcggtc tggcgcagta catcatcatg catgcgctca ccttccgcac gcaggtggtg 540
cgcgattccg ggctgaagct gccggagcac acgttctacg tcgatttcta ttactcgtac 600
cagccgttcc cgtgggtgaa gcgcatccag tacctcgatg tgccgttcta ccactacttc 660
atcgggcgcg agggtcagag cgtgcagacc gacgtgatga ttaagcgtgt ggaccagttg 720
cggctcgtca atcggctgat gaccgaggcc acgcccgaac gcggtacggt gccggagggg 780
ctgtaccggt acatgattca cttcctggcg atcgaatcgt gcgttacctc gacgttcctg 840
attctctcgc gcgatccggc caactacgtt aagaaaaccg agctgtggga tgcgattgac 900
gcctattcgc cggccatcgg caaggatgtg cgctcgcagc tgatgtcccg cgcgctcaat 960
ctgcccggca aaaccggccg ctggatcgtg cgcaacggct atctcatcgc caaacgcatc 1020
gtcggcttta actga 1035

<210> SEQ ID NO 56
<211> LENGTH: 429
<212> TYPE: DNA
<213> ORGANISM: unknown
<220> FEATURE:
<223> OTHER INFORMATION: Representative gene for Cluster 12

<400> SEQUENCE: 56
tccttcgtac cccagttcga tacggtacct tcggtcaacc aggtcgaatt tcatccctac 60
ttccagcaga aagaaatcag agccatcatg gccaaagata aggtctatct cgaagcctgg 120
gcgcccctcg gacagggcaa cccgcagctc ttcagtgaac caatcattac taagattgct 180
gaagctcacg gcaaagatgc cggccaagtc attctgcgct ttgaatacca ggacggagcc 240
atcatcttcc cgaagacgac caaaccggcc cgcatgaaga gcaacatgga catcttcgac 300
ttcgccttga ccgacgaaga aatggccgct atgcgcgccc tcgatacggg taagggaaag 360
cacgatcccg atgcccccgg cgttgccgaa aggcttctcg gtgcctttga cgttcatgcg 420
aacgattaa 429

<210> SEQ ID NO 57
<211> LENGTH: 342
<212> TYPE: DNA
<213> ORGANISM: unknown
<220> FEATURE:
<223> OTHER INFORMATION: Equivalent gene for Cluster 12

<400> SEQUENCE: 57
atgaacatac aaatcttcgg cacgaccaaa tgcttcgata ccaaaaaagc cttgcgctac 60
ttcaaagaac gaaaaatccc cgtccaattc gtcaacctga aagaaaaagg actgagtaaa 120
ggcgaatata ataaagtcaa acaagccgta ggcggcctcg atgccatgct cgacacaaac 180
tgtaaggaca aagatacctt ggccttaatc caatacgccg tagacagcga aaaagacgcc 240
aagatcttag aaaaccagca agtcctaaaa acacctatcg taagaaacgg tgccaaagca 300
accataggct acgtgccgga cgtttggaaa acctgggact ga 342

<210> SEQ ID NO 58
<211> LENGTH: 441
<212> TYPE: DNA
<213> ORGANISM: unknown
<220> FEATURE:
<223> OTHER INFORMATION: Equivalent gene for Cluster 12

<400> SEQUENCE: 58
atgactacct ccccgtctct gcctgcggaa aaaatctatc aacaggcctt gctttccggc 60
tacgacgact gcggcatcat cgccatcgac gagatggatg aatatctgga acgcttccaa 120
gagcgactgc aaaaggaacc gacgagccgc cccttttatg aacgcatcgc acccggtatg 180
aaaacgaaac agcggtgtcc ctgcgccaaa tcggtcatca tctgtacgtg gtggctcggc 240
cgctaccagc tcccccccttc cctcgaagga aaatacgccc gggccttctt tctcgccccg 300
caagtatccc tcgacgatga aggactccgg aagaaagacg cctttaccga ctggctgacg 360
gcagaaggca tccgctggaa aggcggcgaa aaaagctccc accttcaaat cggcggcctt 420
cgccatgccg ccatgaaggc c 441

<210> SEQ ID NO 59
<211> LENGTH: 156
<212> TYPE: DNA
<213> ORGANISM: unknown
<220> FEATURE:
<223> OTHER INFORMATION: Equivalent gene for Cluster 12

<400> SEQUENCE: 59
gtcatgatgg aaggccactc ccagcgcttg gccgtcgtcc tctttgccat ggccatcgtc 60
tacggcggct tatggtactg gaaacggcgt caagacgcca aaaaagttct ccataaaatc 120
gaagaagatc tcgaaaaaaa ggctgaccgg ccctga 156

<210> SEQ ID NO 60
<211> LENGTH: 150
<212> TYPE: DNA
<213> ORGANISM: unknown
<220> FEATURE:
<223> OTHER INFORMATION: Equivalent gene for Cluster 12

<400> SEQUENCE: 60
cccgaaagct acctcgatgc cgacggcctt gcctggttgg aagatttcct gcccagcctg 60
aaagcagccg gaaaaaccct catcgtagcg acccaccacg ccggtatcat cgaaaagatt 120
atcgataaag acatatcact gaagtcataa 150

<210> SEQ ID NO 61
<211> LENGTH: 780
<212> TYPE: DNA
<213> ORGANISM: unknown
<220> FEATURE:
<223> OTHER INFORMATION: Representative gene for Cluster 13

<400> SEQUENCE: 61
atgagcaaaa cggcatttat cacgggagct tcctcgggca taggagccgc caccgcacgg 60
gcgctggccg aactgggtta cgatctggtc atcaccggtc gtcggacgga ccggctgcaa 120
gccctcaacg accgcttgga aaaggaattc ggcgtcaagg cgctggtcct cggattcgac 180
gtgcgcgacc gtttccagac cgagagcgcg atcgacgcgc tgcccggcca tttccgcacg 240
atcgacgtac tggtcaacaa cgccggactg gcttccgggt tcgagcatat cgacgagggc 300
gacccgatgg actgggacaa gatgatcgac acgaacgtca agggtctgct ctacgtcacg 360
cgcgccgtct cgcggatgat gatcgagaac gggcaagggg gccatatcgt caacatcggc 420
tcaatcgccg gcacgcagcc ctatgagaac ggagccgtct actgcgcgtc gaaacatgcc 480
gtgcatgcgc tctctcaagg catgcgaatg gacctgctga gccacgggat caaagtgacc 540
gagatacggc ccggcatggt cgacaccgag ttctcgaccg tccgattcca cggcgaccgc 600
gagcgggccc gcgaagtcta tcggggcatc gaaccgctca cgggcgacga catcgcgcgg 660
atcgtcgcat ggatcgtctc gctcccggcc catgtcaaca tcaacgacat cgaagtcatg 720
ccggcccggc aggccaacgc ttacctgacc tgccgcaaac ccgtcgcggc aaagcaataa 780

<210> SEQ ID NO 62
<211> LENGTH: 672
<212> TYPE: DNA
<213> ORGANISM: unknown
<220> FEATURE:
<223> OTHER INFORMATION: Equivalent gene for Cluster 13

<400> SEQUENCE: 62
tcggaggacc ggctcgtcgc cacgaccgag cggccgctgg cgacggtcgg acaggccgcc 60
tttctggaag cggtcgacaa gaccgtgcac ggggcctttc tcgactgggg gattccggcc 120
aagcacctgt tcctgccgaa ccgcaaccag cagggacgca tcgagatcgg caagaaatac 180
gtcgtctacg tctactcgga caacatcacc ggccgggccg tcgcaacgac ctacctgaaa 240
tcgttcgtcg acaatgcgga accgagcgtc gctccccgcg acgaaacgga cattctggtc 300
gcgctcgaaa gcccgatcgg tttccgcgtc gtagtcaacg accgccactg gggcatgatc 360
taccgcaatc agattttccg tcccgtacac gtaggcgatc ggatgaaagc ctatgtcacg 420
cgaatcaccg aagacaaccg gatcgacctg agcctgcaga agcagggata cgacgaggtg 480
aaggagtcgg ccgagcgatt gctggaactg ctgcgcaaag ccggaggcac gctcccgctc 540
ggcgacgaca gcgcccccga cgcgatacac aagcacaccg gcatgagcaa gaaaacgttc 600
aagcgcagcg caggccgact gttcaagcag ggaatcgtca tactcgaaaa ggaacggatt 660
acgctgaaat aa 672

<210> SEQ ID NO 63
<211> LENGTH: 1281
<212> TYPE: DNA
<213> ORGANISM: unknown
<220> FEATURE:

<223> OTHER INFORMATION: Equivalent gene for Cluster 13

<400> SEQUENCE: 63

```
agcccgtggg ccggaggcgt ggtgctgatc ttgtttacgg tgctggcgct cgtgctggcc     60
aatcttccgt ggaccgcgtc cgcttatcac catctgctcg aagcccgtct gcggatcggt    120
ttcgacggtt tctccctcga cgagccgctc gaggcgtggg tcaacgacgg gctgatggcc    180
gttttcttct tttacgtcgg gctggagatc aaacgggaag tgatcgccgg ccgtctgtcg    240
ggcctccggc aggccgcgct tcctttggcc gctgcgccgg gcggtatggt ctttcccgcg    300
ctgatctact tcgcgatcaa tccgtcgggg ccgtatgccg cgggatgggg cgtgccgacg    360
gcgacggaca tcgccttcgc gctcggcgtg ctgtcgctgt tcggtccccg cgtgcccgtt    420
tcgctgaaag tgttcctgac ggcgctggcc atcgtcgacg atctgggggc gatcgtgctg    480
atcgccgttt tctattcgac ggggatcgat tacggcctgc tggcggcggc cggaggggta    540
ttcgccctgc tgctcgtgct gaaccggctg aatgtctacc ggatgtgcct gtacctgatt    600
ccgagtatcc tgctgtgggt gcttttcctg cattcgggcg tccatgcgac gattgcgggc    660
gtgctgatcg cgatgacgat tcctgcgacg cctcgctatt ccaagcgcta tttcggctac    720
aagagccgtc attgcatgga cgacttccgc cggcacgacc gggaggggac cgaggtgttg    780
tccaaccgcg cgcagatgga ggacctggag cggctgagcc gggtggccct ccagtcgatc    840
agtccgtctc agcggctgga gcacgggctg catcatacgg tcgcgttttt catcatgccg    900
gtctttgcgc tggcgaatgc cggcgtgacg gtagacgggc tgggcgattg gcgggtgctg    960
gcttccggac agggactggg cattttttctg ggtctggtgc tcggcaagcc gctgggcatt   1020
ttcctgttaa gccgtctgtg cgtgcggctc ggatggggag cgctgcccga aggggctacg   1080
tggcgtggcc tgctggccgt ctcgtgtctg ggcggaatcg ggttcacgat gtcgattttc   1140
atcaatacgc tgcctttcgg cgatccggtc tacgtggcgt cgggaaagat cgccgtgctg   1200
gcggcgtcgt tctccgcgat cggagtcagc ttgttgggca tgaggtttct gatgagggga   1260
aaagcttcgg agacggagta a                                               1281
```

<210> SEQ ID NO 64
<211> LENGTH: 1605
<212> TYPE: DNA
<213> ORGANISM: unknown
<220> FEATURE:
<223> OTHER INFORMATION: Equivalent gene for Cluster 13

<400> SEQUENCE: 64

```
gtgctgatcg aggcgggtat ctcgcagcgg ggcgaaatgg cgcggctcga acggatgatc     60
cgccccgatc tgggcatcgt cacgaacata ggcgacgcgc atcaggaaaa tttcgactcg    120
ccccggcaga aggccgacga gaagctaacg ctgttcgagc atacgccgac gatcgtctac    180
aacgcggccg acccgctgct cgcccgcctc gtcccggaac gctacgatga ccggaagctg    240
atcggcgtcg agccggcaga acgcgagctg gacggactac cgttcgacga tccggcctcg    300
cgcgcgaacg ccgcgctcgc gctcgcgctg tacggcgcgc tgggcttcga cacggagccg    360
atccggaagc ggctgccccg gctgcaaagc gtcgccatgc ggctcgagct caaggacggc    420
ataaacggtt gcaaaatcgt caacgacacg tacaactcgg atatcaactc gctcgaaatc    480
gcgctgcaat acctgtcggc aacgagcgga aaccgcgata aggtactgat cctctcggac    540
atcgaccaga gcggactgcc gtcggacgag ctgtatgccc gcgtggcgga gctcgttcgc    600
gcgaacggca tatcggagct gatcggcatc ggcgaagaga tattccgcca tgccgcgttg    660
```

```
ttcgactgcc ggaaggaatt ctatctgtcg accgacaatt tcctgaaggc cggcgagcgg    720

gcacgcttcg tccgaaaaag cattctgctc aagggcggac gacggttccg gttcgagcgg    780

atcggccgcg tgctcgagaa caagattcac acgaccgtgc tggaggtcga tctcgaccgc    840

atgcagcaca acctgaacta tttcagggga ctgctgcgtc ccggcgaacg gatgatggcc    900

atggtcaagg ccgcaggata cggcagcggc acgttcgagg tggcgaacct gctcgagcgg    960

caaggcgtcg actttctggc cgtcgctttc gccgacgagg gcgtcacgct gcgcgaggcg   1020

ggcatcacga tgccgatcgt cgtgctgaac gccgattcgg acagtttcga cctgatgctc   1080

gactaccggc tcgagcccga gatatacagc cgctcgtcgc tgcgctcgtt caccgaggcg   1140

gtccgccgtc acggagccgg ccgcagtccg atccatatca agctcgacac aggcatgcac   1200

cggctcggat tcgagcgtgc cgacatcgaa ccgctgatcg acacgttgcg cgagaccccc   1260

gaagtgtatg tccggacggt cttcacgcat ctggcaggca gcgacgaggc acgccacgac   1320

gatttcacgc gctcgcagat cgcgctgttc cgcgagctga gcgaccggat cgcagccgct   1380

tttcccgaac tgcacattct gcgtcacatc gataacagcg cgggcatcga gcgctttccg   1440

gaagcgcagt tcgacatggt ccggctcggc atcgggctgt acggaatcgg cttcgtgcat   1500

caggaaaacc tgctgcccgt cagcacgctg cgcagccgga tcgtgcagat caaggagatt   1560

cccgtcggcg acacggtcgg atacggacgc cacggcgtgg cgaaa                   1605
```

<210> SEQ ID NO 65
<211> LENGTH: 882
<212> TYPE: DNA
<213> ORGANISM: unknown
<220> FEATURE:
<223> OTHER INFORMATION: Equivalent gene for Cluster 13

<400> SEQUENCE: 65

```
atggcgacga cgaataacga cggcaagacg ctcgtcgtgc tgctcggcgc gacagccacg     60

ggcaaaaccg acgtcggcat cgcgctggct cgggcgttcg gatcggaaat cgtatcgtcc    120

gactcgaggc agatttaccg cgagatgagc atcggaacgg ccaagccgac cgaagaggag    180

ctctcggccg ttccgcacca cctgatcggc acgcgcagcg tccgcgagga ctattcggca    240

ggccggtacg agcaggatgc gctccgggtg ctggaggaac gtttccgcga acacgatatc    300

ctgtttctgg tcggcgggtc gggcctgtac atcgacgcgg tctgctacgg catggacgag    360

cttccggccg tcgatccgca tttgcggaaa acactcgtcc gcagggcgca gaccgaagga    420

ctcgagtcgc tgttcgaaga actgcggaag ctcgatccgg cgcattgcga agtcatggac    480

cgcagcaacc ctcaacgagt gatccgcgca ttggaagtat gcctgcagag cggccgaccg    540

tacagcagcc tgcggaaagg cgaaccgaaa acgcgccctt ttcgtatcct gcgcgtcggg    600

ctccgaatgt cccgcgacgt actctacgac cggatcgacc ggcgggtcga ccgcatgata    660

gccgacggcc tcgaacggga ggcccgggaa ttgtatcctc tccgggaata caatgcgctg    720

caaacggtcg gctacaggga gttgttcgcc tatttcgaag gcgagacgag ccgggagcgg    780

gccatcgaac tgatcaagcg caacagtcgc cgctacgcga aacggcaaac gacctggttc    840

gcaaggaata cggacacgcg atggttcgaa gcagaagaag gg                       882
```

<210> SEQ ID NO 66
<211> LENGTH: 609
<212> TYPE: DNA
<213> ORGANISM: unknown
<220> FEATURE:

<223> OTHER INFORMATION: Representative gene for Cluster 14

<400> SEQUENCE: 66

```
atgattatct tgcagtacga agcgaatcgt ccgcatatcg ttcacttaat tccgaatgcc     60

atgaaaacca aaatgctcgt cctgttcgcg cttgccctgc tcggaacggc cgaaaaggca    120

acggctcagg ccgcagacaa gaaagccgca cgcaaggaga aaaaagagct caggcaatcg    180

atcgaccgcg caaggcacca gcaggcactg gacgcgatcc tcgacagcgc gttcgttttg    240

caggcgaacg ccgtgcttct ggagaactac ccgagacagc aggtcgactt tcatcggaac    300

ttcgtctcga tggagggcgg ccatttcagc attcagatga gcggcatcgc ggccaatccc    360

gtcctcaaga cgggaggcga ggtgtcccgc atgcggatca ggaccgacaa aaaaggcttc    420

gtccggtgca gaatagacct ctcgggcatc gtgatgactt cttcgaccgt atatctgacg    480

ctgtaccccg acagcaacga ggcgaccgca acggtccgtt cgctccgggg aggccggggc    540

gtcacgctcg aaggcgtcat cgtgccggcg gccgatgccg aggtgctccg gaatatctcg    600

acttactga                                                            609
```

<210> SEQ ID NO 67
<211> LENGTH: 1212
<212> TYPE: DNA
<213> ORGANISM: unknown
<220> FEATURE:
<223> OTHER INFORMATION: Equivalent gene for Cluster 14

<400> SEQUENCE: 67

```
gaggccatcg atatcaatta tatcgacgag accgagtacc cgcgcgtggc cgtaatggcc     60

gcccgctgca tcaacatcat ggccaatctg tggcactctc ccgagcaggc caaatggaaa    120

gccggggcgc tggctatcgg ttcttcggaa gcctgcatgt tgggcggcgt ggccgcgtgg    180

cttcgctggc gcgcgaagcg caaagcgcag ggcaagccgt acgacaagcc gaatttcgtg    240

atttcgaccg gtttccaggt cgtgtgggaa aagttcgcgc agctgtggca gatcgagatg    300

cgaacggttc ccctgacgct cgagaagacg acgctcgatc cgcagctggc tctctcgatg    360

tgcgacgaaa atacgatctg cgtcgtgccg atcgaaggcg tgacgtggac gggtctgaac    420

gacgacgtcg aggcgctcga ccgggcgctg gaggattaca atgctcggac cggctacgat    480

attccgattc atgtggatgc cgcctcgggc ggctatatcc tgccgtttct ggacccggac    540

aagaaatggg atttccggct gaagtgggtg ctctccatca gcacttcggg gcataagttc    600

gggctcgtat atccgggcct cggctgggtc gtatggaagg acaaaaaata cctgcccgac    660

gaaatgtcgt tcagcgtcaa ctacctgggg gcgaacatta cgcaggtcgg actgaatttc    720

tcgcgtccgg ccgcgcagat tctcggacag tattaccagt ttatccgcct gggcttcgaa    780

ggctacaagg agattcagtc caacagcatg gacatcgccc gttacgctca cgagcagatc    840

ggcaagatgg ctccgttcga gaactacagc gacgacgtcg tgaatccgtt gttcatttgg    900

tacatgaagc ccgaatacga ccgtacggcc aagtggacgc tttacgattt gcaggcggct    960

cttcagcaga acggctggat ggtacctgcc tacacgctgc ctaacaatct tcagaactat   1020

gtcgtgatgc gcatcgtgtt ccgtcagggc atgagccgcg atatgaccga catgctgctt   1080

acggacatgc agaatgcgat caccgagttc gagaaactcg agtatcctac gcaaactcgc   1140

gtagcccaga acaagcagca gagggtggtc ggcaaggtct tcacgcatac ccatgtcaag   1200

gcaagtcgtt ag                                                       1212
```

<210> SEQ ID NO 68
<211> LENGTH: 930
<212> TYPE: DNA
<213> ORGANISM: unknown
<220> FEATURE:
<223> OTHER INFORMATION: Equivalent gene for Cluster 14

<400> SEQUENCE: 68

```
cagacgttct gcaccgagca tctcataccc ctcgaatccg ttccgatcca aaatacgcat     60

tcgtccgttt ccgacaagga gaaaaaagca aaccggcacg agaccggccc ggaccggttc    120

atcgaaagaa tcgcggaagg gaacatcgac gagcaactgt tcgcccatta tacgcataac    180

atctgccgtt accggctcgg agacttccgc atccgcatcg aggtatgcta ccgcgcgggc    240

gaggaccgcg aatcgccgcc caccacggca ctgctcgagg gccgggtaca cgtgtgggcc    300

gccgtctttt tcaaccggac cgttcagatt tcctaccgct tcatcgtacc gaaaatcccg    360

agaaacgagt cggacgagcc gggacgggcc gacgagcggt acgacggact ggaccctgcg    420

gaattctgcg cgacgggcca tccgttcgac acctaccagc tgatctcggt ggcgggtatc    480

gcacagcacg tagagcattg ggtctataac gagaaactgg accggcaaga gatcgacggt    540

tcgctggaca aggtggagat cagcgacttc aagctcgaca aagactccgt attccgtccg    600

gaaggcaccg gcgaaggaaa cctgaccttc gacgaggtgc agcgcagata ccgcaactat    660

ttcgacaaga ccccgcaagc ggaattccgg gccccggatc accgctatat ctatatcgac    720

gtctgggagg atatcgccca tacgggcgac acggacttcg ggaaaatggc cgaggacgaa    780

atcatcgagc acatcgaaac ggcccaccgg gcggaactgg tcggactgat gacgctctat    840

ccgatggaat ggccctaccg catggattcg agctacgagg acgtgtgcgg acgaaatatc    900

gcgatcgata cggacgatct ggtgctggcg                                     930
```

<210> SEQ ID NO 69
<211> LENGTH: 1128
<212> TYPE: DNA
<213> ORGANISM: unknown
<220> FEATURE:
<223> OTHER INFORMATION: Equivalent gene for Cluster 14

<400> SEQUENCE: 69

```
atgaaattcg tcgtatcctc caccgcactg ctgaacgtgc tgcagacctc caacaaggtg     60

gtcagcaaca agaacacgct gcccattctc gacaacttcc tgttcgagct caaggacggc    120

gtgctgaaga tcaccgcttc ggacctcgag accacgatga tcggcacgct gaaagtcgac    180

agcatggagc aggaaggcgt gatcgccgct ccggtcaaac tgatgatcga ttcgctgaaa    240

gagttctcgg agcaaccgct gacgatcgag gccaacgagt cgacgtggga aatccagatc    300

agctggaaaa cgggcaagct ggccattccc ggcacttccg gactgagcta cccgacgcag    360

cccgcgctcg acgaagagac gaaacaggaa atctccgtcg acacgaacct gctgcttacg    420

ggcatcaaca aaacgatttt cgcgacggcc gacgacgagc tccgcccggt gatgaacggc    480

gtgtacgtca acatcgaacc gcaggcgatc acgttcgtgg cgaccgacgc ccacaagctg    540

gtcaagtacg ccgcctcggc cgaaaccggt acgaccgcct ctttcatcct gcccaaaaag    600

ccggctaacc tgctccgggg cgtactgggg aaggaagacg ccgacatccg gatggaattc    660

gacgacaaaa acgtcgtctt ccacctgaaa aaccatacgc tcgtctgccg gctgatcgag    720

ggcaactatc ccaattacaa cgccgtgatt ccggccaaca acccgaacaa ggtgctcgtg    780

gaccgcacgg agctcctgaa cggtatccgc cgcgtggccg tctgctcgaa tcaggccacg    840
```

```
aacctgatca agttcgagat cgagcccaat acgatcaacc tgaccgctca ggacctcgat    900

ttctcggtgt cggctcagga gtcgctcacg tgcgactacg agggcgaggc gatcgagatc    960

ggcttccggt cgaccttcct tgtcgagata ctctcgaaca tcgagacgca gaacgtatcg   1020

gtcgagctgg ccgactcgac gcgcgccggc gtgttcaagc ccgtctacga cgaggctccg   1080

gacaccgaga cgctgatgct gctcatgccg atgatgatca acgcataa                1128


<210> SEQ ID NO 70
<211> LENGTH: 1935
<212> TYPE: DNA
<213> ORGANISM: unknown
<220> FEATURE:
<223> OTHER INFORMATION: Equivalent gene for Cluster 14

<400> SEQUENCE: 70

atgaaatcag ggagactctt tacccgaacg tgctgcctgc tgggcttctt actgtcgacg     60

gcgtgcgggt cccggacgga gaaggccagc ccggactatc ccgagttcaa gatgatcgtg    120

cggctgtggc ccgatcatca caaggacagc gcgctcagag aagagctgct tcaggcgctg    180

aagaagtatc cggacttttg cgacgaagtc tggctctgca tggaattcga gactttctcg    240

aaagaagcgc acaaagaatc cgcgcgggcc atggctgtag cggccgaacg gctgcggaat    300

gcgggcatcg gcgtgtcgat acagggaata acgctcggtc acggggacga tttcgaatcg    360

ggagcggcgc ggccccaccc ggagctcaca tggggcaata tcgtcgacgc gcggaatgtc    420

cggaccgtca cttcgagctg tccccgccag caggctttcc acgactacct cggagaaacc    480

tatgccctgt acgccgggct atgccggccg tcctgcgtat ggctggacga cgacttgcgc    540

gttacctatc acgctccggc gcggcagctc tgtttctgcg atacctgcct cagcctgttc    600

aaccggcagc acggggagca ctggacccgg gaaacgctgg tcgaggcgct ggacaggaac    660

gaaggggaag gccggctgcg gcggcaatgg atatcgttct gcaagcagag cctcgccgag    720

gtagcccgga ctgtcgcgcg agccgtccac gaggtttcgc ccggcacccg gatgggcttg    780

cagcatgcca attttcaccg cgaactcatg gaaggacggg actggaaccc gacgctcgac    840

gcgctggagg aagagacagg actggccccg gcttcccggc cgggaaacgg attctacgac    900

gatcacgccc ccagaggcat gctgctcaag ggatacgaca tggcccgcca gatccgccgt    960

ctgaagccgt ccgtgcgcga aatagccgcc gaggtggaag gatacagaca ccgcgcgacc   1020

ggcaaatccc ctcacggcct gtgcgtggag tctatgttct acctggccat gggagcgact   1080

cagctctcgt acgcgatcat ctgcgccgct tcggagccga tgcagtggta tgcggacaac   1140

tatttcaagt cgctgagcgc ctggcgcccg ttctacgagc aatacgtcgc cttcaaccga   1200

gggacggaac cgggcggaat cgatccttat atcggtcccg accatgcgtt gcgcgatacg   1260

gaggcgggcg aaccctcttt cgcatggagc gttgcgggat ccggcgatat gatctacgat   1320

atggcgacac tcggcctgcc cttctgcccc gacgggaacc attcgtcggc actcatcatg   1380

gacgcttcgg ccgtgcaggg actggcccga gacgaggccg cccggctttt cggcacccgg   1440

ggcatcctgc tcgaccgggc ggcatgggaa caggcacggc agcgcagact cgatacgctg   1500

cttacggacg ttccggttcc cgacggactc gccggagtcg agtgcatgat ctccgggaac   1560

ggaggcagga cggcagtcgt tccttcgttc agcgccgacg tcaacaatgc cggaagactg   1620

aatctgctgc gcatcgccga ctggctttcg gacgggaagc ttccggcgat catggagacg   1680

atggctcagg ccgccgtcgt gccccggatc gactcggcgc agaacctgcg ttccgtcatg   1740

ctgctcaact gcagtatctc gaaacaggat tcgatccggc tccgcctgcg cggatgtccg   1800
```

```
ccggaggcga aacgcacttt cgtctggaaa aaagcgggac aaccggacga aatcctgcgt   1860

ccccggtacg aaggcacgga tgcggtcgtc cggattcccg ctctggaagg ctggaatgtc   1920

ggctggctgg ccgtc                                                    1935


<210> SEQ ID NO 71
<211> LENGTH: 3708
<212> TYPE: DNA
<213> ORGANISM: Bifidobacterium
<220> FEATURE:
<221> NAME/KEY: misc_feature
<223> OTHER INFORMATION: Representative gene for Cluster 15

<400> SEQUENCE: 71

atgagtttcc atgtatccgc gcaatcggtt cgcgcggtgg ccggtggact cgtcgccgca     60

gcgacattgc tgtcaggcct tgcccttgcg ccgaccgcaa tggccgccga ttcagccacc    120

gctgacaacg cgcccagcgt tgccggtcac gcgtataacg aactgccgta taacaatcct    180

gatgtcaccg tcacccaaat cgacaatagc gcactgccca gctacatgcg caaccccatc    240

gggcagaacg agggtattga caccccgaac gatctttcgc agaactacta ctctgcagat    300

gcatccgcgc tgagctatga cggcaaactc ttcgtcttca ccggtcacga tgaggcttcg    360

cccgactacg gctccttcaa catgaaggac tggggcgtat acgtcaccga tgaagacggc    420

ctgaatcaag gcaaatggac acattacaag accatcgcca aggcagacct gttcagctgg    480

gccaccggcg atggcgcgta cgccggccaa gtcgtagccg acgataacgg caccccgagc    540

gacacttccg atgattggtt ctactactac gtgccggtga aggacaaggc ttctgaggcg    600

gctggacagg acccgttcgc catcggcgtg gccaagtcga agagtccgct cggcccgtgg    660

aaggatgcca tcggcaagcc gctgctcacc acatcgcaaa cccagattga aaccatcgat    720

ccggcattct ttgtggacga ggatggcacc ggatatttgc actttggtac gttcggcact    780

cagctcgcca tcaagatgaa gaaggacgcc acaaccggcc gcacctcata caccgaggtg    840

gaaaccaagg ctgatggcac cacgccgaac ctccacacca tgaaggacgc ggacagcaac    900

gcgaacggcc cgaagggatt cttcgaggcg gcgtgggtgt tccgtaaggg cgatacctat    960

tacaacgtgt acgacggcgg taagcccggt tcgggcacgg ccacctgcgt ggaatcgaac   1020

tatcaagctt gcatccagta ctccacttcc gacagcccgc tcggcccatg gaagtaccaa   1080

ggcgtaatcg tgccttctgg ctcggccacc acgatgcacc cctcggtgct ccagttcggc   1140

gacaaatggt atgtgaccta tcacaccggc gacaaggaag gcggcaccga tttccgccgt   1200

gccgtgtgca ttgatgaagt cgattggacc gccgacggcc agatggtttc caccgcccat   1260

ccaaccaagg ccgagaaaac gcagccctcc accaacgtgg ctccgtacgc aaaggtgagc   1320

gccacgttca ctgaaacgcc tgcttggaag ggttcggtga acgacggccg tgtgttgcaa   1380

accgctgtgg tcccgccgaa tcactggacc aactaccgtt ctatcccgca atcgcagtcc   1440

ggcgattctc tggtctacca atgggatggc actgtgcgcg tcaactcgtc taaggtttgg   1500

ttcgacgtgg attccaacgc tctgcgcgcg cccgcctcgt ggaagattca gtacttggac   1560

gcggacggca catggaagga tgtcaccaac ccgagtgcct atacaacgac cacaggcaag   1620

gccaacccca acgccgtcac cttcgatgcg gtgaccacta ctgccttaaa gctcgacatg   1680

accggtcaag ctgtggatgg cggctatgcc tccgtggccg ttgctgaatg ggaagtcggc   1740

tccgactcca gcgaatcgcc ggcaatcact gcgccgaaga gcgtgaccac cgccaccggt   1800

actgcgccta ctctgccggc cacagtggat gtgaagtacg ggaacccaac cgttgcctcc   1860
```

```
ccagtaattt ggcgtccagt tgatgcttcc tcgtatgcca aggtcggttc gtttacggcc   1920

tacggcgtgg tcgccggcgt gcccggtgag gcaagcgagc agggcaatgt gtcggtaaat   1980

gtcaccgtgc aggacggcta ccagcctgcc gctgatacca cgaagccgac tgtaaccgtt   2040

gccgttactg ctaacgcagg caatagcgag tggctcacca ccgctccgtt cgccaccgtg   2100

caggccacgg acgacaccgc acctatcgcc aagctggaga tttccgctga tcaaggcaag   2160

agctggacca ccatcgccgc gaatgcaaac gcggccattg ccacgctttc ccagcagggc   2220

gatgtcgaag tgtgggctcg cgccaccgat caggccggca acgtttccga cgtggccaag   2280

gccggcggca aggtggactc cgccgcgcca accgtgactg ccgccgccga taagggggag   2340

cgcacgctga ccttgaccgc tgatgacggc accggttccg gtgtcgcatc aattgaatac   2400

cgcattggca cagacggtca atgggccacg tacagcaagc cgattgctgc accgagcgcg   2460

tcgcgcgcca ccgtgtacta ccgcgccacc gataaggccg gcaacgtgtc cgcttcggcg   2520

aaaaccgaca ttccatccga cacttccgtg ccgctgaccg gctacattga gggcgatgcc   2580

accgccaccg atgtggacgg caaggcatcc ggctgggtca agggtgccgc cgcgttgaac   2640

gacggcaaga tcattcccga tatcaccatt gccaacgagg atgtctgggg cacttggccc   2700

aacaccggtg agatgcgcct cgactacgag tgggaccgtg aagtgactat cgactctagc   2760

cgcgtgcaat tcacctcgga tgatggcgga ttgggtattc cggcatcgtg ggaattgcag   2820

tactgggacg ccttggcgaa caacggtgcc ggcaacttcg tggatatttc cgacgccacc   2880

tacagtgtgc ccgccaattc accgtctgct ggctgggcca ccggcgatgc caaggggtgg   2940

tctgatggca cgtggaacac tccggtcaag actaccaagt tgcgtatggt tatcacgtcc   3000

ggctcggctt ctccggctgt tgccgaatgg caggttcatg ccattgacga cagtacgcct   3060

gagcccacac cgatcgacaa gaccgagctc aagcaggcgc tcgctgactc gcctaaggct   3120

gacgatgcct ccaagtacac cgagacttca tgggcggagt acgcggcggt attggattcg   3180

gcgcagcagg tgtacaaggc tgaggatgcc accgaagctg tggtggcgga tgccgcaacc   3240

cagctgaagc gggcagcgaa gaagctggtg cttgtagcta cggtgcaaga tcgtgccgtg   3300

ctgagcgctc agctcgatgc cgctgctgcc gtggatcgga cgaagtggac cgatgaatca   3360

ctggccgtgc tggattccgc aattgctacg gcgaatgcgc tgattggtga cgatcgggcc   3420

acgcagtctg atgtgaaggc cgcgactgag gcaatcagcg atgccattgc gggtctggtt   3480

gagaagagca ccacgaagcc tggccagggt ggcgataagc ccggttccgg cacggacaag   3540

cccaaccaag gcaacgattc caaccagaac aagggtgata ccgactccgg caagcacaag   3600

aagatacctg acaccggtgc agccgtgctt ggtgttggca tcctcgccgt ggtacttgcg   3660

gttgcgggtg taatcatcct caagcgccgc aagtccggta cctgctag               3708
```

<210> SEQ ID NO 72
<211> LENGTH: 1227
<212> TYPE: DNA
<213> ORGANISM: Bifidobacterium
<220> FEATURE:
<221> NAME/KEY: misc_feature
<223> OTHER INFORMATION: Equivalent gene for Cluster 15

<400> SEQUENCE: 72

```
atgggtcagg atcaatcatc cgtttttgat ctcgcagcgg tagccgccgc gtccaatggg     60

gggaacaacg acccgctgct gcctccggcg cgattcattg gcgatccgca gaagccgagt    120

cgtatgccgt acaacaagta cgtcgcatat gataagcagg tgccgtttga tttcccggag    180
```

```
cgtacgtggc cgggcaagcg actgcagcgc gcgccgcgct ggtgctccgt cgatcttcgc    240

gacggcaatc aggccctcgt caacccgatg gattccgagc gcaagctgcg tttctggaac    300

ctgctcgtct ccatgggatt caaggagatc gaggtgggct tcccgtccgc ttccgagacc    360

gatttcgact tcatccgtat gctcatcgag cgtgagctga ttccggacga cgtgaccatc    420

gtggtactca cccagtgccg cgagcacctc atccgccgca cttacgaggc gctcaagggt    480

gccaagcgcg ccatcgtgca cttctacaac tccgtgtctg tgttgcagcg cgaggtcgtg    540

ttccgcaaga acaaggaaga gatcaagaag ctcgccaccg acgccgccga actgtgcaag    600

gacctcgaga acgaggccaa gggcatcgac ctgtactacg agtactcgcc ggaatccttc    660

accggcaccg agccggagta cgccgtcgag gtgtgcaacg ccgtgatcgg tgttatcaag    720

ccgactcccg agcacccgat gatcatcaac ctgcccgcca ccgtggaaat gaccacgccg    780

aacgtgttcg ccgacgaagt ggagtacgtc tccacccacc tcgacgaccg tgactccgtg    840

gtgctctccc tccacccgca caacgacgaa ggcatgggcg tggccgccac cgagctggcc    900

gtgctggccg gcgccgaccg cgtggaaggc tgcctgctgg gcaacggcga gcgtaccggc    960

aacgtcgact tggtcacgct gggccacaac cggctcaccc aaggcatcga cccgcagctt   1020

gacctgtcca acgtgcccga gattcgcaag acggttgagt actgcaacca gatcaagatg   1080

tccgagcgtc acccgtacgc cggcaacttc gtgttcactg cgttctccgg ctcgcatcag   1140

gacgccatca agaagggtct cgaggctcgt caggtggccg ccgagcgtgc tggcgccgat   1200

ctcgacagct tcgtgtggct tgtgccg                                       1227
```

<210> SEQ ID NO 73
<211> LENGTH: 846
<212> TYPE: DNA
<213> ORGANISM: Bifidobacterium
<220> FEATURE:
<221> NAME/KEY: misc_feature
<223> OTHER INFORMATION: Equivalent gene for Cluster 15

<400> SEQUENCE: 73

```
cgcatagcca cgaccgcggg cggcatcctg ctcgcggcct gcgtcacggt cgccggcatg     60

tccgcgtgga gatcgcatga atccgccacg gccgcacgcg agctggaaca ggcgacggcg    120

gactgcgcca ccgcccacgc tgcggcgaag aaagccgaac agaagctggt cgaatatctc    180

gacggcgacc ggctcgcaca ggcgaaagcg gtcacggccg acaagctcgc cgacccggaa    240

accctggaaa ccctcgacaa gctggccgaa caatattccg agggcgagcg aatccccgca    300

tgtgccgcca cggacacgga aacggccaac gccaccacat ccaagctgca agccatcgaa    360

aagaagcaca cgggaaatct ctcgcggctg aagaaggcgg cgggcgcggt gttctcctca    420

cggctggccc ataccgtcga acagggcgaa cgattgtatt cctcctccga aggcaaggtg    480

gccgacgaat attctcgcgc cctgctgcgc gcctccatcg acaagcgcga cgagaaggcc    540

atcaccgacg ccatggacaa ggtgaacgcc tccatcgacg cgaagaccaa ggccgacgag    600

gaaaggaaag cgcaggagga ggccgcagcg gctgcggcgg cgcaggcgca gagcacgccg    660

gcaccgcaac agtactcgta cacgccctcc ggctccgctt cgggcccggg ttccggcccg    720

acgggcggcg gataccattc ctccggcggt tccgccggct cgaccggcgg ttccgcgtct    780

ccgggctggt cggtgcccgc gaacccggac ccctcgcaac tgcccggcac cgacccgagc    840

ctatga                                                               846
```

```
<210> SEQ ID NO 74
<211> LENGTH: 960
<212> TYPE: DNA
<213> ORGANISM: Bifidobacterium
<220> FEATURE:
<221> NAME/KEY: misc_feature
<223> OTHER INFORMATION: Equivalent gene for Cluster 15

<400> SEQUENCE: 74

ttgaaccggc cggaaccgcg tccgctgccg aaaccgctgc gcgtcctgtg cctgttcgtc     60

gccgcgctcc tcgtgtgctc gctgggcgtc atcgtcgcca accaccagcc gtcaacggcc    120

ggcgacgacc acggttccgc gacggacgcg aaacaggagt ccacgggcaa aaggaaaacg    180

gattcgggcc cgcgacggta cgccggcctg gaggcggcgg gaatcccggt tcccggcgac    240

tggtctcagc gcaccaccgc gttccccgtt gacacccaca aggacggcac ccgcacgctc    300

tccgaaaacg cggacggcat cacgctgcac aatggttccg gcccgatcga caccgcattg    360

gaaacggtgg acgcgctgct cgatccaaac ggcagcgacg acgaatggcg caagaacgtg    420

ttcgcgctgc tcggcgacga cggtgccggg gagagccatc cggtctccga cgcgccgcgc    480

tggtggtgga cccagcgccg cttccacgcc ggatccgtat gctcgggcca atacgatgac    540

aagtacgtca actacgccta cacctgcacc tccgacggca aatgggaggg ctcggatacg    600

gatgccatcc agtcccagcc gttctggacg acgaaggaaa ccagcttccc gatcccggaa    660

ggcggcggac cgtcatccac gacggatccg cagcagaccg tcagccaggc gtacaacacc    720

gtgctcttgc cgatggacga cggcaactgg cacgtcaccg tctactgccc ggccgcgctc    780

gacgcgtcat tgctggacaa ggatgccaac gagctcgacc ccgatcaggt gaaggccggc    840

gacgaggcgt acacggtgat ctccgccacc ggatacggca cggtccagca tccctgccgg    900

accgtggagg tcgtggtcgg cgggcagaag cccttctggt cgctgaggaa cacgcaatga    960


<210> SEQ ID NO 75
<211> LENGTH: 1449
<212> TYPE: DNA
<213> ORGANISM: Bifidobacterium
<220> FEATURE:
<221> NAME/KEY: misc_feature
<223> OTHER INFORMATION: Equivalent gene for Cluster 15

<400> SEQUENCE: 75

atgccgggag gcatccgcaa catcggcata ccgttgacga tagcgggcat gggcgtattg     60

acctgcacgc tgctggtcag catggcgagc gtggtcgcgg ccatcgcgat cctcgtggtc    120

ggcatgggcg tcatcctcgt gctggcgatc agggaccgcg agcaccgcaa aatggtggac    180

cgcgccgtgg agaaacgcac gtggagggcc gcgcagcgta ccggcgcaaa cctgtaccgt    240

tccggcctgc tcgcgccgat cgacggcggc aaggccatgc tgccgggcat cctctccagg    300

ggggtcctga cctcggcgct ggacggcttg ggccgtgagt tctgcctggt caggcacgcg    360

cacaccggcg aatactcgct gctcctgtca tgccagccgc agggcgcgag cctcgccgac    420

gacgacgggg aggactcgta cgtggcctcg tgggccgggc tcatggaatc gctcgcctcc    480

gagaccggcg tcacccaact ggccgtgacc gtggacacgg cacccgattc cggcgtgcgt    540

ttccgccgca cgctgagcaa acgcatcgtg gaggacgctc ccgagctcgc ggcgcgcgcc    600

atggcgcaga tcatggacca gtacgcagcc ggcggcgctt ccaacgacgt gacgctcacc    660

ttgactttcc gctacaccga ccgtgacggc aaatacctgg aggccgggga ggccgcgcgt    720

cgcataagcc tgctgctgcc ctcgatccgc gagcagatag cgcaggcggg aggcggtgcc    780
```

```
gcgagggccc tgggcatgga ggagatcact cgcatggtcc gcgtcgccta cgatccggcc    840

gcgcaggaga ccatcgagga atccgacgag cccccgtaca tcgcatggga ggattgcggg    900

ccgctcatgc acgaggccgg ctggagccat tattcgcacg attccgggct gagccgcaca    960

tgggagatgg tggacccgcc gcaaagcaac gtgaccgccg acacgctcac ccgactgctc   1020

agcccattgg cggactgcga ccgcaagcgc gtccccgtgc tctaccggat gctgccgccc   1080

gacaagacca tgttcatggc cgaacagaac cggcagaagg cagccaacca ggtcagccag   1140

gagaaacgcg ccacggtgag gtccatgagc cagataggca aggccaaccg ccaggccgtc   1200

gaaacgaacc agggcgcggt catggtgttc ttcgggatgc tcgtcaccgt caccgtgtcc   1260

aggggcgaac aggaaagcca acgactcgaa gccgcgtcac gcgccgtgga acaggccgca   1320

ggcggcgcga agatcgacct gcgcccctgc tacggggcac aggacacggg attcgccgca   1380

agcctgcccc ttggattgaa cgtcagatca tacactccag ccggccccct cggccggctc   1440

ctgtcctga                                                           1449
```

<210> SEQ ID NO 76
<211> LENGTH: 1440
<212> TYPE: DNA
<213> ORGANISM: unknown
<220> FEATURE:
<223> OTHER INFORMATION: Representative gene for Cluster 16

<400> SEQUENCE: 76

```
atgaagaagt tcctctctct tctcatggcg ctgaccatgc tgatggcctg cactgcttgc     60

ttcggttctg ctgaatccgc aagcgatccc gctgcttacg acggcagcga ggtgaacatc    120

accttctaca acacgatggg ctccaacctg accccctgtgc tggataccta catcgaagag   180

tttaacaagc tctacccgaa catccatgtc agctacacct ccgttggcgg ctacgatgat    240

gtccgcgacc agatttccaa ggaaatcacc gtcggcggcc agcccaacat cgcttactgc    300

tacccggacc acgttgccct gtacaacctc gcgcgtgcgg tgcagccgct ggatgcttac    360

attgacagca cggcgaccgt cacccgcgcc gacggcacga ccgaaacctt cggcctgacg    420

caggagcaga aggacgactt catttccgcg tactacgagg aaggccgtca gttcggcgat    480

ggcaagatgt acacgctgcc gatgagcaag tccaccgaag tgctgtacta caacaagacg    540

ttcttcgacg cgaacggcct gaccccgccc accacttggg acgagatgga agcgctgtgc    600

aacaagatcg tcgaaatcga cccgtacagc atcccgctgg gctatgactc cgagaacaac    660

tggttcatca ccatgacgga gcagctcaag accccctaca ccagcgccac cggcgagccc    720

ttcctgttca acacgcccga aaaccgcgcg ttcgtgaagc gtttcgcaac gtggtacaat    780

caggggcttg tgacgaccca gaccatctac ggcagctaca cctccggtct gttcgtctct    840

gactccggca tcaagagcta catgtccatc ggctcctccg ccggcgcgac gcatcaacgt    900

ccgaccaagg gtgcggacgg cacctatccc tttgaagtgg gcatcacgac catcccgcag    960

gtggatgcca gcaacgcgaa ggtcatttct cagggcccga gcctgtgcat cttcaagaag   1020

tccaatgcgc aggaagtggc cgcttcctgg ctgttcgtca agtacctgac caccacggtt   1080

gatttccagg ctgaattctc catggcgtcc ggctatgtgc cagtcatcaa gtccgttgcg   1140

aacaacgaag tctatgcgga attcgttgcg ggcgcggacg gcggcgacaa cgtggcggcg   1200

ctggcggcga aggtctgcct ggagcaggtt gacgcttact acacctctcc tgcgttcccc   1260

ggctcttccg aagcacgcag ccgcgttggc gaactgatgg cgggctgcat gacggatgct   1320

gcggcactgg gcgacctgac caagccggaa aacgatgcga agctggacga gctcatccag   1380
```

aagcgcttcg acgaagctat caccaagtgc gaacagtcca tcgcgggctt tggtatctaa 1440

<210> SEQ ID NO 77
<211> LENGTH: 558
<212> TYPE: DNA
<213> ORGANISM: unknown
<220> FEATURE:
<223> OTHER INFORMATION: Equivalent gene for Cluster 16

<400> SEQUENCE: 77
gcggacaacc tgacgaagca caccgccgcg ggccgcacgg tgtccagtac cttccattac 60
ggcgacacgg aagcggagca aaagaagcat ctgctgctga aaagcattgc gccgctgggc 120
agtgtcggca cgttcactta cgatgcgttc gggaatccgc tgacgagtca ggtgcagaat 180
gcggatacga atccgagcta cttcatccgc ggcgaaactt cgtacacgaa tgatggcaac 240
tatgtcacgg agcagaagga cgcgcgcggc aagattgtgc gcacggaaat cgatccggag 300
cgcggcacga cgacgagcgt gaccgacgcg aaggggcaga cggtgacgta tgaatacgac 360
aatctgcgtc gaattgtaaa aacttctgca aacgtgggcg cagaagaagg aattccgaca 420
gtacataacg aatataccta tgacgagcag cgcggaaatc tggtcgaaat ccgtcacaat 480
acggacggga acgccgcgaa cgacgtggtg tatactttcg agcaggacgc gctgggtcgt 540
cagacggcgg tcaaggtc 558

<210> SEQ ID NO 78
<211> LENGTH: 1377
<212> TYPE: DNA
<213> ORGANISM: unknown
<220> FEATURE:
<223> OTHER INFORMATION: Equivalent gene for Cluster 16

<400> SEQUENCE: 78
atgacacgcg cacgcggcag ggatgccgac atgacacaag gcaatattct gcggcaatat 60
attgatttcg cgctgccgct gaccgtcggg ctgctcttcc agcagctgta cagcgcgggg 120
gacagcatcg tggtaggcaa tttcgttggg gaaacggcgc tgggggcagt cggttcaacg 180
ggcaacatta ttaacatgct catcggcgta tgcaacggtc tgtcgcttgg cgccggggca 240
gtcatcagtc aggcgtacgg cgcgaaaaac catgagcgca tcagcaaagc ggtacatacg 300
acgatgctga tgacgttcct gctgtgcatc gtggcgacgg tggtcggcgt ggcaattgta 360
aagccaagtt tgcagctgat gcgcacaccg gattccatgc tggtggaagc aaccgagtac 420
ctgaccatct actttgcggg cattgcggga ctactgattt acaacatggg cagcgcgatt 480
ctgcgcgccg tgggcgactc gcggcgaccg ctgtattttc tcgttttctc cgcggtcgtc 540
aacaccgtgc tggacctgct gttcgtcatc tgcttccaca tgggtgtggc aggtgtggcg 600
tatgcgacga ttatcgcaca ggcggcaagc gcggtgctcg tgctgtatgt gctgacgaag 660
gagaacgcgt ccttcgggct gcggtggagc aagctgcaca tcgacgggcg gacgatgaag 720
gaaatcctgc tgattggcct gcccgcgagc atccagcagg gtctgacctc gttctcgaac 780
gtgttcgtac aggcgtacat caacgacctt ggcgacctga gcgcatcggg ctgggcggcg 840
tacaaccgca tcgacatgtt cctgatggtg cccacgacgg caattgggca ggcctcgacg 900
acattcgtgg cgcagaactg gggcgcgcag cagccggagc gcgcgcgcaa aggcgttcgc 960
acaggcatcc tgctgtcgct ggggtgcatg ggcgtgtgcg ctgtcggcgt gatactgctg 1020
gcgcgcccgc tgctgtcgat tatttccccg tcggaggcgg tcatttcctt cggggcgcgc 1080

```
ttcctgtata tcatcacgcc cttctacctt gtcatttcgt tcaatcagat gtacgcgggc   1140

gcactgcgcg gcatcggcga atcggtggtt ccgacggtta tcatgctgtt ctcgttcgtc   1200

gtattccgcc aaatctacct ttatctcgcc acaacgatga ttgcggatga acagctgcgc   1260

ttcgtcattg ttgcgctggc gtacccggta ggatggatgc tctgttcggc gctggaggcg   1320

attgcgtacc accgcagccg gctgttccat ccggcgctga agaaggcgga agcgtaa      1377
```

<210> SEQ ID NO 79
<211> LENGTH: 891
<212> TYPE: DNA
<213> ORGANISM: unknown
<220> FEATURE:
<223> OTHER INFORMATION: Equivalent gene for Cluster 16

<400> SEQUENCE: 79

```
atggctgtct ttttgcaggt tatcaccctg tttctgctga ttttctgcgg cttcttctcg     60

gcgaagggga agctcgttga cgaaaaacggc atttccacgc tcaacaaaat tgttctctac   120

ttcgccctcc ccgccctgac gctctacggc ttgcagaagg acgccagtcc tgagctgatt   180

catgacctga ttctcgtgtt cttcatcagc cttgccatca tgattctgag cgggctgatt   240

gcctacttcc tctaccgcag cgagccgaac gagcgccgca gcgtgctgac gaacctgtcc   300

atgctgtcca acagcgccta catgggctac ccggtcgtca ttgcgacgct gggcgaggat   360

atgctgattt atgccgtcgt gtttgtcggc gcgttcaacc tgatgtgctg gacgttcggc   420

tcgttcttct tcggcggcat cagtgcgatt cagcccaaga agctgctgac aaacccgtcg   480

ctgattgcgg tgattgttgg tcttgtgctg ttcctgacgg gctggcggct gccgggtttc   540

atcaacgacg cgctgtcgat gatgggcaat gtgacgacgc cgcttgccat gttcgtcatc   600

ggggcgcggc tgattgatct tcgcttcgca cacctgcagg actggaagct gctgctggcg   660

tgtgcgctgc ggctgattat cttcccggcg gcggtgctgc tgctgcgctt cacgggtctg   720

cccgcggcgg tggtgagcgt actgtacatc tgcaccgcta tgccctgcgc ggcgacgacg   780

gccatgcaga gtgaaatgta ccactgcgac aattcgctgg cttcgcgcgg agtggcgctg   840

tcaacagcat tctcgatttt gacgctgccg ctgatgctgc tgctggcgta a            891
```

<210> SEQ ID NO 80
<211> LENGTH: 1602
<212> TYPE: DNA
<213> ORGANISM: unknown
<220> FEATURE:
<223> OTHER INFORMATION: Equivalent gene for Cluster 16

<400> SEQUENCE: 80

```
atgatgaaat atgtatttgt gaccggcggc gttgtttctt cgctgggcaa gggcacgacg     60

gcagcatccc tgggacggct gctgaaggcg cgcggctaca aggttgccat gcagaaatgc   120

gacacctact ataacttcaa tccggcgctg ctgtcccctt tgcagcacgg cgaaaatttc   180

attacggagg acggcgtggc ggctgacctt gacttagggc actacgagcg ctttatcgac   240

gagtcgctca agggtgaagc aagcatcacc accggcaaga ttcacactgc cctggtggag   300

cgcgagctgc gcggcgaata ccacggcgcg acgattacag tcgtgccgca tgtgacgaac   360

gaaatcaagc accgcatcat cacagcggca gaaaactccg gcgcggacat tgcgattatc   420

gaaatcggcg gtgtggcggg cgatatcgag tcctccccgt atctggaggc gattcgtcag   480

ttgaaatggg agcttggcgc gggcaacaca tgcttcatcc atgtggcgct gatgccgtat   540

ttgtccgttg cgggcgaaat gaaaacgaag ccgacgcagc actctgtcaa ggccctgcgc   600
```

```
gccatcggca ttcagccgga tgttatcgtc tgccgcacag aggtgaacat cagccagtcc    660

gcgaaggata aaattgcgct gttctgcaat gtgccggtgg gtaacgttgt gcagaaccgg    720

gatgcgtcca cactgtttga agtgccgctg aatctggaaa aagagggatt ggcgggcatg    780

gtgctgaaaa cgctgaagct tgacaatccc ccggcggatt tgaccgagtg gacgaacatg    840

gtcgcccgct atgacgcgcc gacgcaggaa gtgcatatcg cgctggtcgg caagtacgtt    900

gccgtgcatg atgcatacct gtctgtgcac gaagcgcttg tccatgcagg catcgcaaac    960

ctcgcggcgg tgtatgtgga ctatatctcc tcggacgagc tgacggaagc gaacgccgcg   1020

gaacggctgg gcagctatca cggcatcatc ctccccggcg gcttcgggca ccgtggcgcg   1080

gaggggatga tggcggcggc gaacttcgcg cgcacgaagg gtatcccctg cctgatgatt   1140

ggctacggaa tgcagcttgg cgtggtggaa gcagttcggt cgcttttgtc gctgccagac   1200

gcgaactcga cggaagtcaa tcggctggcg aacccggcgg tggtggcgat tccgcgcgac   1260

cgtgtggacg agaacgacgg ccggcagaat gcgcgcatgg gcggcatgga cgtcgtgctg   1320

accgagggca gccgcaccgc ggccatctac ggtctgacga tggtgcacga gcgccacggc   1380

aaccgttacg aggtggatga tgcgttcctt gcgccgctgc acgaggtcgg cgtggatttc   1440

gtcggcttca gcgcggacgg aaattacccg gaggtattcg agattccggc gcatccgttc   1500

tatatcggca caatttatca tccggagttc ctttcccgcc ccaacaaggc gcatccgctg   1560

ttcgcagcgt tcatcggcgc agcggcggcg catcaggcat aa                       1602
```

<210> SEQ ID NO 81
<211> LENGTH: 3039
<212> TYPE: DNA
<213> ORGANISM: Bacteroides
<220> FEATURE:
<221> NAME/KEY: misc_feature
<223> OTHER INFORMATION: Representative gene for Cluster 17

<400> SEQUENCE: 81

```
atggcgcagg aaaacctgaa agtttccggg caggtgacag acaataaagg agaagccatt     60

atcggagcct cagtgaaagt actgaaaacg ggtacgggga ctatttctga tatagatggt    120

aagtttacta tccaggttcc tgtgggagcg gaactggaga taggatatgt cggctataat    180

ccgaagagag tgaaagtggt gaataaaaac ttcgtaacgg tagtccttga ggagaatgtg    240

gtagcattgg gcgatgtagt tgttgtcgga tatggcattc agaaaaagga aagtctgaca    300

ggagctatcg gaaacctgaa agtagatgat atagtaaaga ccaaggcacc tagtttggca    360

caggccattc agggaaaagt tgccggtctg cggatcagac aggaaaatgg agagccgggt    420

aagtttagtt ccaatatcaa tgtccgtggc ttcggaactc ctttgtttgt gattgacgga    480

gtggtgagag acggttccag cgaatttcaa cggctgaatc cggaagatat tgaaagcata    540

tcttttctga aagatgctac tgcctctatc tatggtatga attcggcgaa tggtgccgtg    600

attgttacca ccaagaaagg ggctacaggc aaaccgcgta ttacgttgaa cgccaatgtc    660

ggcattactt ctcctaccaa tgtgccggag atggccaacg ccggacaata tatgaccatg    720

cgaaatgagg cggaaatcaa tgcaggcaga ccggcttata tcacaaagga cgaattgacc    780

aaatggcagc aaggtgctcc cggttatgag agtgtagact tgtatgatgc cgttttcaat    840

aagcacgcca cacagttcca gacgactctg tccctggaag gtggtaccga caaagtaagt    900

tattacggta gtttcggtta tgccaccgat aacagcttgt tgaagaataa cgcattgact    960

tatgataaat atacattccg ttccaatgtc agtctgaaga ttacaaaaga cctgacagcc   1020
```

```
agtatcaatc ttggcgggcg ttatgatacc accaaccgtc cctggtttcc tttctatgat   1080

atatttaaga gtacgcgtgt aaatccgcct actacttcta tctatgccaa tgacaatccg   1140

gattattata ataacttctc ttatgtccct aatccggcag ctatgatcga tgccgattat   1200

accggcagcg ctaaagagcg gaataagaac ttgcagacac agtttgcatt agagtataat   1260

attccttatg taaaggggct gaaggtgaaa ggtactttta tctacgatta caataactac   1320

ggatataagg ctacgcggaa aggttttaag acatatacct atggcgaata tacgggcgag   1380

tatacggcgg cagatgccaa ttatccggct ttgcttcagg ataatcgcag agaatcggaa   1440

cgggtggata tgcagttcca gacaaactat aacagaacgt tcggcaacca taccatcgga   1500

gctacttatg tcttcgaaag acgcgaagag aaagcaaact ggatgaatgg tgagcgcaag   1560

tttgactttt tcacaatcgg tgaactggac aatgcacgcg aatctgacca gaaagtatcc   1620

ggttcctcgg aacaccaggc ttatctttct catatcgggc gtctgaccta tgattataaa   1680

ggcaaatatc tggcagagct tgcttgcaga tacgacggtt cttatcgata tgctccgggc   1740

agcagatggg cattctttcc gtccgcttcc gtaggatgga gaatttcgga agagagcttt   1800

atcaaagaca acttcaagtt tgtcgataat ctgaaacttc gtttctctgc cggtcgttcg   1860

gggcaagatg ccggtgatcc gttccaatac ttctccggtt acacgttgaa cagtggcgga   1920

tatgtattca gtcagggaaa ttataccaat ggggtggctt ctcctgtgat gatcaataag   1980

aatctgacct ggattaaagt gaatatgtat aatattggta ttgacttttc aatctttaac   2040

cggctgatcg cagtagagtt tgatatttat cagcgtgacc gcagcggcct gttagccgac   2100

cgttacggtt ctcttcccaa tacgttcggt tccaagttgc cacaggaaaa cctgaacggc   2160

gaccgtacga ggggtattga atttacattg actcatacca acaaaatcgg tgatttccac   2220

tacagtgtat ccggtaactt taacttggcg cgtacccaac gccgttatat agagagcggt   2280

ccttacaaga gcagtatgga aagatggaga aaccaggcat ccaaccgctg gggagatttt   2340

atctgggggt atcagacgga cggacgtttc cagaactttg acgagattaa tacatatccg   2400

attcagaatg ggataacgg aaattccaag gaacttcccg gtgactacat cctgaaagac   2460

gtaaacggtg acggagtggt gaatgatctg gacaagaccc ctttattctg gtccggcagc   2520

ccattgattc actatggttt caatgtggaa gcgtcctgga agaacttcga cttctatgct   2580

ctttttcaag gttctgccct gtacacggtg cagtttgacg aggtatacgc aaagatgctc   2640

tgtttcaagg gtggcaatac ccccgaatac ttctacgacc gttggcatct gtccgacccg   2700

tatgatgcga acagtgaatg gataccggga gaatggccgg ccatccgtct ggagcaggac   2760

atgggatcgt tctatacgag ggattcgcag atatggcgta agaacgcttc ttatctgaga   2820

ctgaaaacaa ttgagatcgg ctacaccttc agtccccgac tgatgcataa actgggtatc   2880

ggtagtttaa gaatctatgc gaacggaaat aacctgttta ctatctgtga cccgtttgta   2940

aaggcattcg atccggaaaa gattgaagga gactatagtg ccggcttgaa ttatcctctg   3000

aataagagct ttaactttgg attgaccttg aacttttaa                         3039
```

```
<210> SEQ ID NO 82
<211> LENGTH: 1938
<212> TYPE: DNA
<213> ORGANISM: Bacteroides
<220> FEATURE:
<221> NAME/KEY: misc_feature
<223> OTHER INFORMATION: Equivalent gene for Cluster 17

<400> SEQUENCE: 82
```

```
atgattatga aaatatatag ttatttatta ttgggagcta tgttcctgct gggcggatgt     60
agcgatttgc ttgatatcga tccgaagaat aaaattccgg cggatgaatt gttctctact    120
ccggaaggag tacaggcaca tatggccaat ctgtacggtc gtttgcctat cgaagatttt    180
acctattcac cgaatcgcgg cttcaatgtg ggagtcggta cggatgtgaa taatgccggt    240
tttatggctg ctcatttctg tgatgaggct atccatccgg agtacaatga ctttggagaa    300
gagtggttcg attattggga agacggttat aaactcattc gtgatttaaa cagtctgttg    360
gttactattc ctacattgac cagtattacc gaacagcaaa agaatgagat caatgcggaa    420
actcatttcc tgagagctta tacctatttt gccttagcca aagatacgg tggggtacct     480
atcattaaag aaccgcagga gtataacggt aatatcgaag aactgcgtgt ccctagaaat    540
acggagaaag atacttggga ctttgtcttg gaagaatgtg accaggcagt atcgcttttt    600
ggagatgcga atgaaaatga tgtgctgaga gcgaacaaat gggtagcatt ggcactgaag    660
tcaagagcag ctctgtatgc agcttccgtt gccaagttta ctcatcagcc ttatgtctct    720
ttctctggtc cggctgttga ccagaagctg gtaggtatag aagttatatc ggctgatcat    780
tattatgatg aatgtatatc agcttcacag gaaatcatga atagtggtaa gttcggtctt    840
tacaaacctt cccccgctac tccggaagaa gcgacaacca actatcaaaa gttatttgaa    900
caacctttcc aatgtctgga cggattgaaa gagcctatct tcatgaaggc ctatgctgca    960
aataccattc tggcacataa ctatgatgtc tggttcagcc cccgtcagat gatcctcgac   1020
ccgaatctct atcccggtcg tatgaatccg acactggatt ttgtcgactc tttcgaagat   1080
tatacggatg acggaaccgg aacacccaag ccgatcagca ctcgtgtgga tggaaatgaa   1140
agtgattata atggatttaa cttatccacc cgatacctgt ctttcccgat agataaacct   1200
taccaggcat ttgccggtcg tgatgcccgt ttgagtgcca tggtgttatt cccgggacag   1260
aacttcggaa gtacgaagat cattatccag ggtggtctgg tgaaagctga cggttccggt   1320
tatcattata ggactcaggc ttcggagaag ggacaggatg gtctgatcta ttatacttac   1380
ggagcggaga aagcacggaa atattcagga ttcgatccga ctttgggaca ctatacccgc   1440
agcggattcc tgtttaagaa gttcttgcag atagaaaatc cggttgagca ggcatggagt   1500
aaaggtacac agccttggat cgatttccgt tatggggaaa ttcttctcaa ctatgcagaa   1560
gccgttatcg aaaagacaac ctctacttct gctgaaaaac aggctgcaca agacgctttg   1620
aatgcggtcc gcaaaagagc ggctcacaaa gatgacattg cattgactca ggcgaatgtt   1680
cgcaaagaac gttttgtcga gctggcattt gaaaacaagc gcagatggga tttgtcgcgc   1740
tggagaactt tccataagga atttgaaaac cgggtgagaa agggacttgt acctttcctt   1800
gacctgcgga caaatcctgc gcattatgta tttgtacgtg tcaatccgtt gggcattgaa   1860
tcaaagacct ttgattatag ctggtattat aagagtattc cgggtacggg ggctaatggt   1920
ctggtacaga atccttaa                                                  1938
```

<210> SEQ ID NO 83
<211> LENGTH: 1149
<212> TYPE: DNA
<213> ORGANISM: Bacteroides
<220> FEATURE:
<221> NAME/KEY: misc_feature
<223> OTHER INFORMATION: Equivalent gene for Cluster 17

<400> SEQUENCE: 83

```
atgaggaaag aacttgtttt tgttttattg gcattatttc tgtgtgccgg ctgtaacggt     60
```

aacaaaaaga aaatgaacgg tgaacacgat ttggatgcgg caaacattac gttggatgac 120
catacgatca gtttttatta taattggtat ggaaatccgt cagtggatgg agaaatgaag 180
cactggatgc acccgatagc ccttgctccg ggacattcgg gagatgtcgg tgccatatcc 240
ggacttaatg atgacatcgc ctgtaatttt tatccggagc tcggaacgta cagcagcaat 300
gatcctgaaa tcattcggaa acatatccgg atgcatataa aagcgaatgt cggtgtactg 360
tctgtcactt ggtggggaga aagcgattat ggcaaccaaa gtgtgtctct cctgctggat 420
gaggctgcaa aagtaggggc aaaggtgtgc tttcatatag agccttttaa tggacgcagc 480
ccgcaaacgg taagggagaa tattcaatat atagtggata cttatggtga tcatccggct 540
ttttaccgta cgcacggcaa acctcttttc tttatctatg attcttatct gatcaaacct 600
gccgagtggg cgaagttgtt tgctgccggg ggagagataa gtgtgcgtaa taccaagtac 660
gacggtcttt ttattggtct gacattgaag gaaagcgagt tgcccgacat tgagacagcg 720
tgcatggatg gcttttacac ttactttgcc gcaacaggtt tcacaaatgc ttctactccg 780
gccaactgga aatccatgca gcaatgggca aaggcacata ataaattgtt tattccgagt 840
gtcggtccgg gatatattga tacccggatt cgtccttgga acggaagtac cacccgagac 900
cgtgagaatg gaaaatatta cgatgatatg tataaagctg ccatagaaag cggtgcttct 960
tatatttcga ttacgtcttt caatgaatgg catgaaggaa ctcagataga gccggctgtc 1020
tcaaagaagt gcgctgcttt tgaatatttg gattataaac cattggctga tgattactat 1080
ttgataagaa ctgcctattg ggtagatgaa ttccggaaag caagatctgc ttcggaagat 1140
gttcaataa 1149

<210> SEQ ID NO 84
<211> LENGTH: 702
<212> TYPE: DNA
<213> ORGANISM: Bacteroides
<220> FEATURE:
<221> NAME/KEY: misc_feature
<223> OTHER INFORMATION: Equivalent gene for Cluster 17

<400> SEQUENCE: 84
atggagaact atttaagaat cccaagaatt atccaccaaa catggaaaag aaaagatata 60
ccttttcctc ttgaccaact accacaaaca tggaaagaat atcttccgaa ttgggaatat 120
gtcctatgga cagatgaaat gaacagggaa tttgtccaca aacatttccc tgattttttg 180
gagaagtatg atgcatatcc ttgtaacata caaagagcag acgctatacg ctatcttctc 240
ttgaaagttt atggaggatt gtacgtagac atggatttcg agtgcctcga aaatattgag 300
tttttactag aaggatcgga ttttatcgta ggtaaggaac ccgactggca tgctaaacgc 360
tttggttttg aatatatcat ttgcaacgct ttcatggcct caacacccga taatgatttt 420
atcaactttg tatgccaaag gttaatcaat cattccggtg ggaaagttgt taataacgga 480
tttgatatac tggattccac aggccctttc ttgctaacgc atgcattcaa cgcatttcca 540
cataaagaag acatacgtat cctcgaatca aagacaatat atcctatcgg acaatgggag 600
gtagagaaaa taaaaaacaa ccagattcct gaagaaatgg aagagcgtat caatcaggct 660
catgccatac actatttctt tggtacctgg tttggtaagt aa 702

<210> SEQ ID NO 85
<211> LENGTH: 2220
<212> TYPE: DNA
<213> ORGANISM: Bacteroides
<220> FEATURE:
<221> NAME/KEY: misc_feature
<223> OTHER INFORMATION: Equivalent gene for Cluster 17

<400> SEQUENCE: 85

```
atggcgatgg cgttttttc gtgtacccat acggatcaga cgcccgcaaa agactttgtc     60
gattatgtaa atccatatat cggcaatatc agccatctgc tggtgcctac ttacccaacc    120
gtacatctgc cgaactcgat gcttagggtc tatccggaaa ggggagacta tacatcggac    180
agggtaaacg gccttccggt ggtggtgacc agtcataggg gcagctcggc ttttaacctg    240
agcccggtgc agggagaggt atcccgaccg attgtatctt actcctatga tttggagaat    300
attacccccct atagttattc cgtatacctg gatgaggctg atatacaggt tgagtatgcc    360
ccttcacatc aggctggtat ttatcatatc agttttggga cggaaggtga taatgctttg    420
gtggtgaata cgaagaacgg aaagctggtc gctgaagaaa aaggagtcag tggctatcag    480
gttattgaca acactcctac caaaatctat ctgtatctcg aaaccagtca gctaccttta    540
cgtaaagggg tactggcaga tggaaaagtt gatatggaaa gtaaggaagg cagtgccatc    600
gctttgtttt atggaagcga gaagaacctg aatctacgtt acggaatttc ttttatcagt    660
gccgagcagg caaagaagaa tctgcaacgt gacatcacca cctatgatgt aaaggcggtg    720
gcggatgccg gacgcaggat atggaacgag acattgggca agattgtgat agaaggcggt    780
tcggaagacg aaaaagaaat cttctacact tccctttatc gtacctacga acgcatgatc    840
aatctttcgg aggacgggaa atattacagt gctttcgatg gcaagattca tgaagatggc    900
ggagtacctt tttatacaga tgactggata tgggatactt accgggctac acatccgttg    960
cgtatcttga tagaaccgca gaaggaactc gatatgattc gttcatatat acggatggca   1020
gaacagtcgg acagaagatg gatgcctacc ttccccgagg tgaccggaga cagtcaccgg   1080
atgaatggca atcatgcagt ggcggttatc tgggatgctt attgcaaagg attgaaagac   1140
tttgatctgg aggctgctta tgaagcctgc aaaggagcga ttacagagaa aacgttgttg   1200
ccctggctga gatgtccgtt gacggagctc gataagttct atcaggaaaa aggatttttc   1260
cctgcactga accctggcga agaagagact tgcaaggctg ttcattcgtt cgagagacga   1320
caagcggttg cggttatgtt gggtaactgt tacgataatt ggtgtctggc acagatagcc   1380
agaacattaa acaagaccga tgactataag aagtttatga ggatgtctta tacgtaccgg   1440
aatgtttata atgcggaaac gggtttcttt catcccaaga acaaggacgg aaagtttatc   1500
gaaccgtttg actatcgata ttcgggagga cagggggcac gtggctatta tggtgaaaac   1560
aacggttgga tctatcgttg ggatgtgcag cacaatccgg cggatttgat tgccttgatg   1620
ggtggacagg cttcatttat cgagagattg aatcagacat tcaatgaacc gttggggcgg   1680
agcaagtttg atttctatca tcagttgccg gaccataccg gcaatgttgg ccagttctct   1740
atggcaaatg agccttgtct gcatattcct tatttgtata actatgccgg tcagccgtgg   1800
atgacacaaa aaaggattcg cgttttgctg aaccagtggt tccgtaatga cttgatgggc   1860
gttcccggtg atgaagacgg agggggaatg actgcatttg tggtattctc catgatgggc   1920
ttttatccgg taactcccgg ttctccaact tataatatcg gcagtccggt attccaatcc   1980
gcaaagatgg aggtaggtga cggacattat tttgagatca tagcggagaa ttatgcgccg   2040
gaccataagt acatccagtc ggctaccttg aatggaaagc cgtggaataa gccgtggttc   2100
agccagtcgg atattcaaaa cggcggacgt ctggttttgc agatgggaga taagcccaat   2160
aagaagtggg ggatagcttc ggatgccgtg ccgccctctt cagagagttt gccggaataa   2220
```

<210> SEQ ID NO 86
<211> LENGTH: 864
<212> TYPE: DNA
<213> ORGANISM: Bacteroides
<220> FEATURE:
<221> NAME/KEY: misc_feature
<223> OTHER INFORMATION: Representative gene for Cluster 18

<400> SEQUENCE: 86

```
atgaatatat tagtaaccgg tgccaacgga caacttggta atgagatgcg ggcgctttcc     60

gctgagaatg ggcagcacac ctactttttt acggatgttc aggaactgga tatatgtgac    120

gaacaggcca tacgcgcatt tgtgtccggc aaccgggtgg atgtcattgt gaactgtgca    180

gcctatacgg cggtagacaa ggcggaggat aatccggagc tctgcgacaa gctgaaccat    240

atagctcccg gctatctggc tgcagcggct gaagcctgtg gcgctgccat gatacaggtg    300

tctacggact atgttttcga tggaaccggg catattcctt atacggaaga cattgctcct    360

tgtcccaact ccgtctatgg ttccacaaag ctggcaggcg agcaagcggt cggggagaaa    420

tgcagtcgtg ccatgattat ccgcactgca tggttatatt ccatttatgg caataatttt    480

gtaaagacaa tgatccgctt gggcaatgag cgtgagaaac tgggagttgt tttcgaccag    540

atcggcacgc cgacctatgc caacgatttg gcccgcgcca tctttgcggc tatcaatcag    600

ggcattgttc ccggtgtata tcatttcagt gacgaaggtg tctgttcctg gtatgatttt    660

acggtggcta ttcatcgcat ggcgggtatc acctcatgca aagtcagtcc gctgcatacg    720

gatgaatatc cggctaaggc tccgcgtccc caatattccg tattggataa gacgaagatt    780

aaaaagactt tcggcattga gattcctcat tgggaggaga gtctgcaggt ctgcattgat    840

aagctggcac agcaggcaga ctga                                           864
```

<210> SEQ ID NO 87
<211> LENGTH: 1167
<212> TYPE: DNA
<213> ORGANISM: Bacteroides
<220> FEATURE:
<221> NAME/KEY: misc_feature
<223> OTHER INFORMATION: Equivalent gene for Cluster 18

<400> SEQUENCE: 87

```
atgagtctgt tgaaacaaat gcagcaagag ctgctacaac tggaagagca tagtaatctg     60

cgccacttac ccaaaatgac acatgacgga cgggaagtta tcgtaaacaa taaacgcatg    120

ctgaacctat cttccaacga ctatctggga ctggcatcag acagggcatt gcgtgaagag    180

tttctccgca cacttacccc ggatacgttc ctgccttctt cttcctcttc ccgactgctg    240

acaggtaatt ttacagtcta cgaagaactg gaagctgagc tatcacacct tttcggtacg    300

gaagctgcct tggtcttcaa cagcggttat catgccaaca caggtattct acccgctgtc    360

agcgatgcac acaccctgat acttgccgac aaacttgttc acgccagctt gattgacggt    420

atccgccttt cggcagccaa atgcatccga taccgccaca atgacctgac gcaactggaa    480

agactgttgg aggaacatca tactgtccat caccgggtca tcatcgtcac cgaaagtatc    540

ttcagtatgg atggtgacca agctgattta cagaaactaa cagaactaaa gcgcaagtat    600

gacaatgtcc tgctctacgt agatgaagca cacgccttcg gtgtacgcgg caggcaagga    660

ctcggttgtg ccgaagaatt ccattgcatt cacgacattg acttccttgt cggtacattc    720

ggtaaagcgg ctgcatctgt cggcgcctac attgtatgca aaaaggtaat acgggaatat    780
```

```
ctcgtaaacc gtatgcgcac cctcatcttc accaccgggc tgccaccggt aaacattgca    840

tggaccttgt ttatcgtacg ccgtttggct gacatgcagg aacggcgcaa acatttggca    900

catatcagcc ggacgcttcg cgaagcttta caggtacgag ggtatacatg ccccagcgtc    960

agccatatcg tcccaatgat aatcggcccg agcgcagaca cagtcctaca ggcggaagca   1020

ttgcaacggc atggatttta cgccctgcca gtccgtccgc cgacagtacc ggagggcatg   1080

tcgcgcatcc gcttttcgct gacagcggaa atcagaaagg aagaaataga agagctgagt   1140

aataacatca gcgcctatac cgactaa                                       1167
```

<210> SEQ ID NO 88
<211> LENGTH: 831
<212> TYPE: DNA
<213> ORGANISM: Bacteroides
<220> FEATURE:
<221> NAME/KEY: misc_feature
<223> OTHER INFORMATION: Equivalent gene for Cluster 18

<400> SEQUENCE: 88

```
atggaaaact ccttgtaccg cggcgagcgt attctggtaa ataaatggag ctatgggttg     60

cggcttcctt tcatgggctt atggggatat caccgctggg cggaaaggcc cgtacacaag    120

gaagatattc ttgtattcaa caaccctgcc aatcttctcc aagctacaat cgaccggaaa    180

gaagtattta tcagccgctg tttaggagta ccgggagaca cgctgttagt cgattcccct    240

ttctccgtaa tcccctcgga gaaaaatgcc cccgaccaaa agttccttta tacctaccct    300

caaaaaaaag aaaaacagtt ggattcgtta cttactattc tttccatccg tcccaacgca    360

ttgttaggac aagatacggt gaataacgta cgcagtttca gcaggtatga atattattta    420

ttagaacagg ctttaggtaa caacaactgg ataaagccaa tcgacaagga agactccgta    480

gaagtgctga aaccgctcat catccccggt aaggggaaag cggtacgcgt gtatccctgg    540

aacatgacgt tgctgcgcaa cacattggta ttgcacgaaa aaaaacgggc tgaaatcaaa    600

aacgatacgt tgtacataga agggaagccc gcacagcact gctatttcac aaaagactac    660

tactgggtgg gagccaacaa ccccattaac ctgtcggatt cacgcttgtt cggccttgta    720

cccaaagacc atgtcattgg aaaagcaacc gtaatctggt tttccaagga gcaagggaca    780

gggcttttcg gcggctaccg ctggaacagg atgtggaaag aggtcaaata a             831
```

<210> SEQ ID NO 89
<211> LENGTH: 699
<212> TYPE: DNA
<213> ORGANISM: Bacteroides
<220> FEATURE:
<221> NAME/KEY: misc_feature
<223> OTHER INFORMATION: Equivalent gene for Cluster 18

<400> SEQUENCE: 89

```
atgggaactt tcgacgggcc gggtctccgg ctcgtcgttt tccttcaagg gtgtcctttc     60

cgctgccttt attgcgccaa ccccgacacc atagactcca aaggcggcat ccccactcct    120

gccgatgaaa tcctgcaaat ggcggtcagc cagaaagcat tcttcggaaa gaaaggggga    180

attacatttt ccggtggaga gcccacattg caggcagaag ccttgatacc tttgttcaaa    240

gggttgaaag ccaacggcat tcacacctgc cttgacacca acggcggcat ctggaacgaa    300

aaggtggaag aactgctaag cctgacggac ttggtactgc ttgacatcaa agagttcaat    360

cccgaacgcc accgcgccct caccggacgc agcaacgagc agaccctgcg tacggccgcc    420

tggctggaac aacagggaca tccgttttgg ttgcgttatg tgttagtgcc gggatacagc    480
```

gattttgaag aagacatacg cagcatgggc gcacagcttg gcaaatacca aagcatacaa 540
cgggtggaga tactccctta ccaccgtctg ggagtgcaca aatacgaagc gatgggctgg 600
gactaccaac tgaaagaggt cgtagagaat acgcctgaac aattgcagcg agccgagcga 660
ctgttcaaag aatactttcc cacagtggtg gtaaattag 699

<210> SEQ ID NO 90
<211> LENGTH: 1224
<212> TYPE: DNA
<213> ORGANISM: Bacteroides
<220> FEATURE:
<221> NAME/KEY: misc_feature
<223> OTHER INFORMATION: Equivalent gene for Cluster 18

<400> SEQUENCE: 90
atgaaacagt atttagtctt tttattatcc ctattgacct gcctgccttg ctcctccacc 60
gccaccgcac atacggaacg ggcggcaaag gcctccccta cggcggattc catacgcatc 120
agcctgctga catgcgcttc gggagaggag atatattccc ttttcggaca taccgccata 180
cgatacgaga actacacacg cggcatcgac gccgtattca attacggcat attcaatttc 240
aatgcaccaa acttcatcct ccgtttcgct ttaggtgaaa cggactacca actgggagcc 300
ggcgattatg aacgcttcgc ggcggaatat tattatttgg agcgcgatgt ctggcagcaa 360
gaactgaacc tcaccccggc ggaaaaaaag aagctggtcg ccctgcttga agaaaactac 420
cgtcccgaaa accgggtgta ccgctacaac ttcttctacg acaactgcgc cacacgtccg 480
cgcgacttaa tagaaaaatc cattgacggc acactgcaat atgccgacaa catgaccgac 540
acaaacaccg gaacctcttt ccgcgaccta ttgcacaaat acagcaaagg ccatccatgg 600
tcacgtttcg gcatggattt gtgcatgggc agccaagccg acaagcccat cagccgcaga 660
ctgatgatgt tcgtcccgtt ctacgtgcag gattacttca acacagcccg gatcatcggc 720
agcgacaagc aagtgcgccc cctggtactg aacgaagaga aaatcataac aaccggaatg 780
gaagagacgg gacagccgtc cgaaggattc accccgttgc aggccgcctt gttgctgttt 840
atactgaccg cagccaccac cctttacggc atacgccgaa agaaaacgct ttggggaata 900
gacctcgtgc tgttctttgc cgcaggaatg gcgggatgca tcctgacatt cctcgtcctg 960
ttctcccagc acccggccgt cagccccaac tatctgctgt ttgtgttcca tcctctccac 1020
ctcctctgcc tgccatgcat gctgaacagg gtgcgaaaaa ggagaagaag ccgttatatg 1080
ctggcgaact tcctggtttt aacacttttt atattgcttt ggctcataat accgcaaaga 1140
tttccgtcag ctgtattacc tttggcactt tgtttgctga tacgttctgc gagcaaccta 1200
attctcacat acgataagaa ataa 1224

<210> SEQ ID NO 91
<211> LENGTH: 504
<212> TYPE: DNA
<213> ORGANISM: Escherichia
<220> FEATURE:
<221> NAME/KEY: misc_feature
<223> OTHER INFORMATION: Representative gene for Cluster 19

<400> SEQUENCE: 91
atgtcgtgtg aacctcaact gactaaacgt ttgggtgttc accaacgtgt aacttattat 60
ttgggtaagc ttttaatgaa aacttttaca gctaaaccag aaaccgtaaa acgcgactgg 120
tatgttgttg acgcgaccgg taaaactctg ggccgtctgg ctactgaact ggctcgtcgc 180

```
ctgcgcggta agcacaaagc ggaatacact ccgcacgttg ataccggtga ttacatcatc    240

gttctgaacg cagaaaaagt tgctgttacc ggcaacaagc gcgaagacaa aatgtactac    300

caccacaccg gccacatcgg tggtatcaaa gaagcgacct ttgaagagat gattgcccgc    360

cgtcctgagc gtgtgattga aatcgcggtt aaaggcatgc tgccaaaagg cccgctgggt    420

cgtgctatgt accgtaaact gaaagtttac gcgggtaacg agcacaacca cgcggcacag    480

caaccgcaag ttcttgacat ctaa                                           504
```

<210> SEQ ID NO 92
<211> LENGTH: 1332
<212> TYPE: DNA
<213> ORGANISM: Escherichia
<220> FEATURE:
<221> NAME/KEY: misc_feature
<223> OTHER INFORMATION: Equivalent gene for Cluster 19

<400> SEQUENCE: 92

```
atggctaaac aaccgggatt agattttcaa agtgccaaag gtggccttgg cgaactgaaa     60

cgcagacttc tgtttgtggt cggtgcgctg atagtgttcc gtattggctc ttttattccg    120

atccctggta ttgatgccgc tgtacttgcc aaactgcttg agcaacagcg aggcaccatc    180

attgaaatgt tcaacatgtt ctctggtggt gctctcagcc gtgcttctat ctttgcgctg    240

gggattatgc cgtacatttc ggcatcgatc atcgtgcagc tgctgacggt ggtttatcaa    300

ccgctggcgg aactgaagaa agaaggggag tctggtcgtc gtaagatcag ccagtacacc    360

cgctacggta ctctggtgct ggcgatattc cagtcgatcg gtattgctac cggtctgccg    420

aatatgcctg gtatgcaagg cctggtgatt aatccaggct ttgcattcta tttcaccgct    480

gttgtcagtc tggtcacagg gactatgttc ctgatgtggc tcggcgaaca gatcactgaa    540

cgtggtatcg gtaacggtat ctcgatcatt atcttcgccg gtatcgttgc gggactcccg    600

ccggccatcg cccatactat cgagcaagcg cgtcaaggcg acctgcactt cctcctgttg    660

ctgttggttg cagtattagt atttgcagtg accttctttg ttgtattcgt tgagcgtggt    720

caacgccgca ttgtggtaaa ctacgcgaaa cgtcaacagg gtcgtcgtgt ctatgctgca    780

cagagcacac atttaccgct gaaagtgaat atggcggggg taatcccggc aatcttcgct    840

tccagtatta tactgttccc ggcaaccatc acgtcatggt tcgggggtgg tactggttgg    900

aactggctga caacaatttc gctgtatttg cagcctgggc aaccgcttta tgtgttactc    960

tatgcgtctg caatcatctt cttctgtttc ttctacacgg cgttggtttt caacccgcgt   1020

gaaacagcag ataacctgaa gaagtccggt gcatttgtac caggaattcg tccgggagag   1080

caaacggcga agtatatcga taaagtgatg actcgcctga ctctggttgg tgcgttgtac   1140

attactttta tctgcctgat cccggagttc atgcgtgacg cgatgaaagt gccgttctac   1200

ttcggtggga cctcgctgct tatcgttgtt gtcgtgatta tggactttat ggctcaagtg   1260

caaactctga tgatgtccag tcagtatgag tctgcattga agaaggcgaa cctgaaaggc   1320

tacggccgtt aa                                                       1332
```

<210> SEQ ID NO 93
<211> LENGTH: 360
<212> TYPE: DNA
<213> ORGANISM: Escherichia
<220> FEATURE:
<221> NAME/KEY: misc_feature
<223> OTHER INFORMATION: Equivalent gene for Cluster 19

<400> SEQUENCE: 93

```
aacactatgg ataagaaatc tgctcgtatc cgtcgtgcga cccgcgcacg ccgcaagctc      60

caggagctgg gcgcaactcg cctggtggta catcgtaccc cgcgtcacat ttacgcacag     120

gtaattgcac cgaatggttc tgaagttctg gtagctgctt ctactgtaga aaaagctatc     180

gctgaacaac tgaagtacac cggtaacaaa gacgctgcag cagctgtggg taaagctgtc     240

gctgaacgcg ctctggaaaa aggcatcaaa gatgtttcct ttgaccgttc cgggttccaa     300

tatcatggtc gtgtccaggc actggcagat gctgcccgtg aagctggcct tcagttctaa     360


<210> SEQ ID NO 94
<211> LENGTH: 711
<212> TYPE: DNA
<213> ORGANISM: Escherichia
<220> FEATURE:
<221> NAME/KEY: misc_feature
<223> OTHER INFORMATION: Equivalent gene for Cluster 19

<400> SEQUENCE: 94

acacatcagg agagaggaat gaaaacaatt ggtttgctgg gaggaatgag ctgggaatcc      60

actattcctt actatcgtct gataaatgaa ggcattaaac agcggcttgg tgggcttcac     120

tctgcgcaag tgctgctaca tagcgtcgat tttcatgaaa tagaagagtg ccagcgtcgc     180

ggtgagtggg acaaaaccgg ggatattctg gctgaggcgg cgcttggctt acagcgggcg     240

ggcgcagaag gcattgtgtt atgtaccaat acgatgcaca aagtggcgga tgccattgag     300

tctcgttgct ctctgccttt cttacatata gcggatgcca ctggacgtgc aattaccggg     360

gcaggaatga ctcgtgtggc gctgctgggt acgcgttaca ccatggaaca ggatttttat     420

cgcgggcggc tgacggaaca attttccatc aactgtctta ttcctgaagc ggatgaacgg     480

gcgaaaatta atcagattat ttttgaagaa ctgtgtctgg ggcaatttac cgaagcatca     540

cgcgcttatt atgcgcaagt gattgctcgc cttgcagaac agggcgcaca gggcgtcatt     600

tttggctgca cagaaattgg tttactggtg ccagaagagc gcagtgttct gcctgtgttt     660

gataccgcgg cgatccatgc cgaggatgct gtcgctttta tgctgtcgta g              711


<210> SEQ ID NO 95
<211> LENGTH: 360
<212> TYPE: DNA
<213> ORGANISM: Escherichia
<220> FEATURE:
<221> NAME/KEY: misc_feature
<223> OTHER INFORMATION: Equivalent gene for Cluster 19

<400> SEQUENCE: 95

gtgtctggct tacagataat cgtcgatgag ggcagtttta tggaaaagaa acacatttat      60

ctgttttgtt ctgcgggcat gtctacctct ttactggtat caaaaatgcg cgcacaggca     120

gaaaaatatg aagttccggt cattattgaa gcatttccgg aaacactggc tggtgaaaaa     180

ggtcagaatg ccgatgtcgt gttattaggg ccgcagattg cttatatgtt gcccgaaatc     240

cagcgtttgt tacccaacaa accggtcgaa gtaattgact cgctgcttta tggcaaagtc     300

gatggtttag gcgtgcttaa ggctgcggtt gcagcgatta aaaaagccgc agcaaattaa     360


<210> SEQ ID NO 96
<211> LENGTH: 414
<212> TYPE: DNA
<213> ORGANISM: Paraprevotella
<220> FEATURE:
<221> NAME/KEY: misc_feature
<223> OTHER INFORMATION: Representative gene for Cluster 20
```

<400> SEQUENCE: 96

```
tcatacaaga aaaaactacg gatgaagagg ctgaataaga ttcaaaatat agtattcata     60

accggagctg tgctgttgtt gattggggca gccacttttt ttaccggttg gctttatgct    120

ttttatcttt atacggtggg ggcttgcgct tttgctgcga tgcagttgcg tgccgggtac    180

gaaggggata atttcgttat ccgccggttg cggggacaac aagtcatcgg tgcgcttttg    240

ttggtttgta cagccttttt tatggctatg cgtatttttg atttcggttt tgcccgcgga    300

caggaatggg tggtatgcct ggcagtcgct tgcgtgctgg aattgtacac cgcttttcgt    360

attccggccg aattggagaa ggaaaagtca cgaaaaaaca acaataagtt ttaa          414
```

<210> SEQ ID NO 97
<211> LENGTH: 1023
<212> TYPE: DNA
<213> ORGANISM: Paraprevotella
<220> FEATURE:
<221> NAME/KEY: misc_feature
<223> OTHER INFORMATION: Equivalent gene for Cluster 20

<400> SEQUENCE: 97

```
atgaaacaaa tatctatttt agccttgagc atactgcttg ctctccctgc cgtagccgac     60

gaggggaaag aaggaaaagc caaaacggat taccgaccgg tcgtccacgg tacgctacgt    120

ggcaaatacg agtaccaacc ggaagaaaag gccggacgct ttcaagtgcg caccgcccga    180

gtcagcatcg aaggaaaagt cgcacctgta gtggcctata aagccgaaat cgacttgtct    240

gacgaaggca aaatcaaaat gctggatgcc tacacccggc ttagcccgct gaaaggcttc    300

gatttcacca tcggacagat gcgcgtcccg ttcaccatcg atgcccaccg ttcaccccac    360

cagcaatact ttgccaaccg ttcattcata gccaagcaag tgggtaacgt gcgcgatgtg    420

ggagccacgc tgggctacaa gataggaggt ccgctgcccc tcaccctgca agcgggaatg    480

ttcaacggtt cgggcctgac cgaccagaaa gatttctgga ccaacaacat caactattcc    540

gccaaggcac aatggcaact gcccaaaggc ttttccgtca cgctgagcgc acagaaaatc    600

agaccggaac acatttcggt caacatgtac gacggcggca ttacttacca ggccggaaga    660

tggatgatag aagcggaata cttgtataaa cactacacca aagatgcctt tcaggacgtg    720

aacgccttcg acgggttcat ttgctatgac ctgccactga aaaaagtatt cagcaaaatc    780

tcattcctcg gacgcttcga ttacatgggc gaccatagcg acggtacggc caacgagaac    840

ggacacctca cactgaccga tgccgaacgc aaacgtatca ccggcggcat caccctgagc    900

atcgccaaac cgttcatttc ggacatccgt atcaattatg agaaatattt ctacaacgag    960

gatgccaccc ccaaggtttc cgagcaggac aaattcgtca tcgagttcat gactcgtttt   1020

tag                                                                 1023
```

<210> SEQ ID NO 98
<211> LENGTH: 1458
<212> TYPE: DNA
<213> ORGANISM: Paraprevotella
<220> FEATURE:
<221> NAME/KEY: misc_feature
<223> OTHER INFORMATION: Equivalent gene for Cluster 20

<400> SEQUENCE: 98

```
atgcaggtca gggccgtgat gataggcacg cacaacatgt gtgaggagac tttgtttgag     60

aacgagctgt tccgccgcga gatgaaagag gccggtgtgg cattgatatg gattaccccc    120
```

```
ggatgggacc agcagtggaa agcggattcg ggaagcccgg aagcttattg gcagatgttg    180
gacgatttgg cggagaccag cggatatggt gagttgaaat ttactcccat catcccgata    240
gggcattccg ccatggcgac ctacccgtgg aattttgcgg cctggcatcc ggagcgcacc    300
ttggccgtgg tatcttacca tggggatgcg ccgcgtacga acctgaccgg ttacggacga    360
gagaatctgg agtggggacg gacgcgtaac atcgacggta ttcccggcct gatggtagaa    420
ggggaatatg aatggtggga ggctcgggtg aatcctgcat tggcattccg tatgatgtac    480
cccgagagtt gcatttcttt tctctgcgat gcggggcgag gccattttga cgtgtcggac    540
cgtacggcgg aatatatcgc cttgtttgtg aagaaggcct tgcaggcacg tctgcccgat    600
acggtggcgc aagaccgtcc cgtggctttg cggaaagtac gcccacagga cggatggttg    660
gcagaacgct ggcatcccgt gcaaccccgc agggcgaagc ccgcacctta cgcgaagtat    720
aaaggtgacg tgcacgatgc tttctggtac ttcgaccgtg agatggctga gacaacggag    780
gagcgttatg cccgggagag agggaaagaa atgctgtatc tgggggtgaa acaggagggg    840
cggttggcac cttacaatcc ccggtcgcat gttaaggtca atgtgccctt ccgtccggaa    900
gccgatggcg tgacgttccg cttgaaagcc gtcttcacgg acagccttcg tgcgtcggta    960
gcgtcgcccc gtgtggaagg ccgtcccgtc atcacccgca tctgcggtcc ggtgaagaag   1020
ttggacgaca cgacattcgt ggtcgatttc taccgtatgg gactgggtaa ttcgcggcgt   1080
gtgtcggata tgtgcctgtt ggccagttac gacggtgacg accgttacaa gagcgtggtg   1140
caggaactga acgtccgcct tccttatcct ctcacggagg ggcgcaggca atatttgctt   1200
tttcccggca tcgcggatgt gacggagggg acggagactg ttccgcttca cgccacgtcg   1260
gattgcggtt tgccggtgcg ttattacgtg aaagaaggtc cggccgaggt ggaagggaca   1320
aatttgcgcc tgacgcggat tccgccccgt accaagtttc ctgtgaaagt gacggttgtg   1380
gcctggcaat acgggttggc cggacgggta cagacggctg aacccgtgga gcggagtttt   1440
tatatcgtcc gggagtag                                                 1458
```

<210> SEQ ID NO 99
<211> LENGTH: 1095
<212> TYPE: DNA
<213> ORGANISM: Paraprevotella
<220> FEATURE:
<221> NAME/KEY: misc_feature
<223> OTHER INFORMATION: Equivalent gene for Cluster 20

<400> SEQUENCE: 99

```
atggatatgt tgacagctac acgtagggaa tggaacgaat tatatgtgtt tttcaacctc     60
ttggctcaag gagggatagt cttgggcaat gaagaggggc taccttccgg tcgtgtgttg    120
cctatttttc aggtaacgcg gcaggaacat gacggagagc gtcgttacac ggtagaagag    180
accgacatcc atgtcgaagg ggaacagatg gacgaacgtt ttccgcgtga agacttcggc    240
acagtggcgg ctatgattct cgatacgttg aaacgggaac ggaacgaaga ggtggaggca    300
cccgaagggg tggagggctt tctcgatgca ctgaagattt atgacatgga agcccggacg    360
gatgaccgta ccgatttcta cattactttt catgacagca gtttcccacc cgtgggattc    420
cgcatctatt cccgtctttg cgccatgatg cccttgttgg atggcggacg gacggccaat    480
ctgaaattcg agcagggagg tatccgtttc tcccaaccgg cggtcaacaa aatcaattat    540
acggacgacc cggacaatcc gaacgaggtg gcacgccgca tgctttacat cgagagtatg    600
ggcggcgtgt tgaaatacaa tgacgtggcc gataaagtgt tccgcagtaa cctttgcatg    660
```

atagacctca acttacctcg cgtgttggcc gagatggtac gtctgatgca tttggacaac 720
ataagccggg tggacgaact gacggaactc atagaggagc ggaacccgtt gaaaataaaa 780
gaagagttga ttcgcaaaca caggtattac cgctacaaga tgaaagagtt cctgttggct 840
ttggcgttag gcatgcgtcc ggccaagcag tataacggga cggattcggc tgtggccggt 900
ttcgtgatgg tggatgcgga gggacgtatg gtggcctatc gtaagacgga gcgtcaggtc 960
tttgccgatt ttctgttcaa gcatacccgt ttggagaaag gacatccgga aaaagacaag 1020
tatggttatt tggagcgtga aaatcgtgct tactatttga agttgaactt aaagataagt 1080
tttgtgaaaa gatga 1095

<210> SEQ ID NO 100
<211> LENGTH: 672
<212> TYPE: DNA
<213> ORGANISM: Paraprevotella
<220> FEATURE:
<221> NAME/KEY: misc_feature
<223> OTHER INFORMATION: Equivalent gene for Cluster 20

<400> SEQUENCE: 100
atgatagaag tcaggaatat aaggaaaagt ttcggttcgc ttgaagtgct caaaggaatc 60
gacctcgata tccgtaaggg cgaggtggtg agcatcgtgg ggccgagcgg tgccggaaag 120
accacgttat tgcagattat ggggacgttg gacaagccgg acagcggaag cgtccggctc 180
gacggggttg ccatggaaag cctaagccgc aaggagatgg cggatttccg taaccggcgc 240
atcgggttcg tgtttcagtt ccatcagtta ttgcccgagt tcacggcact cgaaaatgtg 300
atgattccgg cgtacatcgg gcatgcttcc acaagtgagg ccaaggcgcg ggcacaagag 360
ttgctagatt tcatgggact gtccgacagg gcttcgcata agcctaacga actttcggga 420
ggagaaaagc agcgggtggc tgtggcacgc gctttggtca accatccctc cgtagtgttt 480
gccgacgagc cttcggggag tctggatacg aaaaacaagg gagaactgca tcagttgttc 540
ttcgatttac gggaccggtt cgggcaaacg ttcgtcattg tgacccacga tgatgagttg 600
gcacgtttga cagaccgtac cattcacatg aaagacggtt tgataaccga tgataaaaat 660
ataaccttat ga 672

<210> SEQ ID NO 101
<211> LENGTH: 450
<212> TYPE: DNA
<213> ORGANISM: unknown
<220> FEATURE:
<223> OTHER INFORMATION: Representative gene for Cluster 21

<400> SEQUENCE: 101
atgacgtttc aaatcgacgt caaaggcaaa tatccgcagt tttccaattg gttggcgatg 60 agctttttttg caccggttcc gtgggaggcc gaagcgtttt acgccaacga aaaactcaaa 120
gaaggcaata tcacgctcgc atcctggccc gtgggcacgg ggccctatta catggccgtc 180
tcgcgccaaa accgcgaaca cgtgttaaag aaaaatccgc attttcatac ggctctgtat 240
ccgtgcgaag gcgatcaaaa cgatgagaaa gagggctttt taaaagactg cggaaaaaag 300
ctgccgctca cggaccgcat tgtgctcacg attgaaaaag aatcggtccc gacaacttct 360
aagttcttac agggctttta cgatagcccg gaaattacgc gacttgatgt cgggcagggg 420
tttatgacgg cggccttaga taacccggaa 450

<210> SEQ ID NO 102

<211> LENGTH: 357
<212> TYPE: DNA
<213> ORGANISM: unknown
<220> FEATURE:
<223> OTHER INFORMATION: Equivalent gene for Cluster 21

<400> SEQUENCE: 102
gaagtcaaga aaaagaaggg atacacaccg gaacttacgt ttgacgaacg gcgcgaaatt 60
ctcctcgcga tgcgcgacgt gaaagaggtc gtttcctgcc cgtggctcat taccaatgag 120
tttttggaac agcaccattg cgattttctg gtgcacgggg cggacaactc caatcagctt 180
ccgccggaaa aactcaagat tttcccgcgc accgaaggca tcagcagttc cttgctgcgc 240
gagcgcgtgc tcgacagcct catggaaatg aatctcgata aaaattccaa gagcgtttcc 300
gataagctcg cgatgtattt gattgaaacc gtcaaaaagg aatttcgtct cgaatga 357

<210> SEQ ID NO 103
<211> LENGTH: 318
<212> TYPE: DNA
<213> ORGANISM: unknown
<220> FEATURE:
<223> OTHER INFORMATION: Equivalent gene for Cluster 21

<400> SEQUENCE: 103
atgcgtttaa tcctcattgg gccgcccggt gcgggaaaag gaacccaagc tgcttttatt 60
aaagagaagt tcggcattcc tcagatttcc accggcgaca tgttgcgcgc tgccgtaaaa 120
gccggaaccg agctcggcag agccgccaag gtcatcatgg accaaggtaa gctcgtgagc 180
gacgacatca tcatcggcct tgtgaaagaa cgcctgacgg ccgacgattg caagaacggc 240
ttcctgtttg acggtttccc gcgcacgatt ccgcaggccc aggccttgct cgatgccaag 300
gttcccgttg atttcgtt 318

<210> SEQ ID NO 104
<211> LENGTH: 195
<212> TYPE: DNA
<213> ORGANISM: unknown
<220> FEATURE:
<223> OTHER INFORMATION: Equivalent gene for Cluster 21

<400> SEQUENCE: 104
atgcttcgca acatgatgtg ctctcttttg cgccacgagg ctattaagac cacactaccc 60
aaggccaagg aactgcgccg tgtcgtcgaa ccgatgatta cgttagccaa gaacccgacg 120
gttgccaatc gtcgtttggc tttcaatcgg ttgcgcgatc gtgaagtcgt caccaagctc 180
tttgacgaaa tcggt 195

<210> SEQ ID NO 105
<211> LENGTH: 234
<212> TYPE: DNA
<213> ORGANISM: unknown
<220> FEATURE:
<223> OTHER INFORMATION: Equivalent gene for Cluster 21

<400> SEQUENCE: 105
gtggagacaa tcgtttcgat actcggggcc atcagcggat ttgtctgggg accgattatg 60
ttgtttttcc ttatcggtac cggtatttat ttgaccgtcg gtttgcgcgg atatacgttc 120
cgcaacatcc cgacggcttt tcgtatgttg tttacgagga ccggtgaagg taagggcggt 180
aaaggagaaa tctcggcatt taccgctttg atgacggcta tggcaggcac tgtc 234

<210> SEQ ID NO 106
<211> LENGTH: 780
<212> TYPE: DNA
<213> ORGANISM: Haemophilus
<220> FEATURE:
<221> NAME/KEY: misc_feature
<223> OTHER INFORMATION: Representative gene for Cluster 22

<400> SEQUENCE: 106
gaaacggtca aagtgactta cgatccaaac aaaatttcgt tagataaatt actacaatat 60
tatttccgcg ttatcgatcc aaccagtatt aacaagcaag gcaatgatcg tggcagacaa 120
tatcgcaccg gcatttatta tcaaaacgag caagataaag tggttattga ggcagcgttg 180
aaagccttac aaagtaaata tcaagaaccg attcaaattg aagtagagcc actgaaaaat 240
tatgtggagg cggaagagta tcatcaggat tatctcaaga aaaacccgaa tggttattgc 300
catattgaca tcaaaaaagc cgatgagcca ttaattgatg ataaaaaata ccccaaacca 360
agtgatgcag aattaaagca aaaattgacc gcacttcaat atgacgtgac gcaaggtaaa 420
cacaccgaac gctcttttag caacgaatat tgggataatt tcgcgcctgg tatttatgtg 480
gatatcacta cgggagagcc gttattttct tctaaagata aatttgaatc aggttgcggc 540
tggccaagtt ttaccaaacc gattgccgct gaagtggcgg agtatcaaag agataatagc 600
tttaatatga ctcgtattga ggtgttaagt cgcagtggtc atgcccattt aggccatgta 660
tttgatgatg gtccacgtga taaaggtggt ttacgttatt gcatcaacag cgcatcgatt 720
aagtttattc cattggatga aatggaaaaa caaggttatg gtgatttgat ttcttttgtg 780

<210> SEQ ID NO 107
<211> LENGTH: 588
<212> TYPE: DNA
<213> ORGANISM: Haemophilus
<220> FEATURE:
<221> NAME/KEY: misc_feature
<223> OTHER INFORMATION: Equivalent gene for Cluster 22

<400> SEQUENCE: 107
aaaaatgtag gcgtaaattt aaacgtacct gtttctgtga ttgcgaatcg tcctgatgtg 60
aaaggctatc aatatcgctt aagcagtgca ttcaaaaatg caaaagcaac tgaaaaaggt 120
tggttccctg aagtgacttt aggtggcagc ttaacatcaa gtggcactaa ggtcggtaac 180
gcattacaca atcctgttgg tacaggttta atcggaatta gcctaccatt cctcaactgg 240
aatacggtga aatggaacgt gaaaatctct gaagctgatt atgaaaccgc acgtttaaac 300
tatgagcaaa gcatcactaa agccttgaat gatgtagata ccaactactt cgcctataca 360
caagcacaaa gtgcctttgc taacttgcaa aaaacacaca gctataacca acgtatcacc 420
aaatactatc gagatcgtta caatgcgggt gtatctgaat tacgtgaatg gcttgctgca 480
gcaaacacag agaaaagctc tcaactttct atcttgaatg caaaatacaa catcattcag 540
gcagaaaatg ccgtatatag ttcaatggca ggttattact ctcgttaa 588

<210> SEQ ID NO 108
<211> LENGTH: 786
<212> TYPE: DNA
<213> ORGANISM: Haemophilus
<220> FEATURE:
<221> NAME/KEY: misc_feature
<223> OTHER INFORMATION: Equivalent gene for Cluster 22

<400> SEQUENCE: 108
atgaatttaa aaaaattctt ttctgcacca accaatgaac cgatccgcga taaaaaagcg 60
gaacggaact tgtttgcacg tcgaacattg gtagcattca tcggtatttt agccctaagt 120
ggtgtgctat ttgctaatat ttaccatctc caagtggtga attacgacat gtaccaaact 180
cgctcaaatg gtaaccgtat taaattactt ccgcttcctc ctactcgcgg attaatttac 240
gaccgttacg gcgaattact ggcagaaaac ctcacctttt tcggtttata tatcgtgccg 300
gaaaaaacgg aaaatttaga ccgcactttt gaagaattgc gctatgttgt aggactcact 360
gatgaagaca ttgagcattt caaaaaagag cgccgtcgtg gtacacgcta tacgccgatt 420
ttactcaaac caagcttaac ggaagaacaa attgcccgtt ttgcagtaaa ccagtataaa 480
tatccaagcc ttgatgtacg tccttatttc aaacgaaatt acctatatgg cgaagccatg 540
acacatatat tgggttatgt tggacgcatt aatgaccgag atgttgagcg cctaaaaaaa 600
gaagaaaaat ttgctaacta ttccggttct acggacatgg ggaaactggg tattgaacgt 660
tattacgaag aacaactcca tggtacaacc ggtttcgaag aggttgaaat taataaccgt 720
ggtaaagtta ttcgtaaact acgtgaacaa ccagccaccg cgggtaaaag tattcatctg 780
actatc 786

<210> SEQ ID NO 109
<211> LENGTH: 525
<212> TYPE: DNA
<213> ORGANISM: Haemophilus
<220> FEATURE:
<221> NAME/KEY: misc_feature
<223> OTHER INFORMATION: Equivalent gene for Cluster 22

<400> SEQUENCE: 109
attggtggcg tgattggaat taccataggc gtattaattt gggcaacggc tgctgtttta 60
ggtcttgcca ttatttttac cacgatgcca attattcaag gcattgtgat gatgcttggt 120
ggatcgtatt tagtttatct cggcattaag atggcaaaag taaaaaccaa tgcggtcttt 180
gatgaaaagc agaatgcaaa tacatcaaat caatcgactt taacgagcat tatgaaaggc 240
ttattggtca atttgtctaa tgctaaagtg gtgatttatt tcagcagtgt gatgtcattg 300
gttttagtga atattaccga aacatcacaa attttgaccg cacttgccgt gattaccgta 360
gaaacctttt tatatttcta cgtcatttcg gtgctttttt cgcgttctgt tgcaaaacag 420
ttttatagcc aatatagtcg ctatattgat aatgcagcag ggctgatttt tattttattc 480
ggaatctatt taatttatag tggtgttcaa cacgctttaa tttga 525

<210> SEQ ID NO 110
<211> LENGTH: 372
<212> TYPE: DNA
<213> ORGANISM: Haemophilus
<220> FEATURE:
<221> NAME/KEY: misc_feature
<223> OTHER INFORMATION: Equivalent gene for Cluster 22

<400> SEQUENCE: 110
gtccccactg aaagtattga agtgctgaat caactgaaag atcgctaccc gcttagcgtg 60
attaccaatg gtaatgtgat tgcaacacgt attggatttg aacattttca actgagttta 120
cgtggtggag aacaaggcag agcgaaacct catcaagatt tgttccacca aaccgcccat 180
tattttggcg taaaaccgag tgaaatttta catattggtg ataacttaac cacggatgtt 240
caaggcgcca ttcaagccag ctgccaagct gtatggatta atttatcagg caaagatctc 300
aattcattta ctgaagcaag tgttttgcct acattagaaa tcaatcattt aactgaatta 360

```
ttaacacttt aa                                                          372


<210> SEQ ID NO 111
<211> LENGTH: 1605
<212> TYPE: DNA
<213> ORGANISM: Sutterella
<220> FEATURE:
<221> NAME/KEY: misc_feature
<223> OTHER INFORMATION: Representative gene for Cluster 23

<400> SEQUENCE: 111

ttgctgacag cgagtgctta cttctgcggc gtcaatgcta aacgcgccct gcagcatgcc      60

gtctttatcg ttccgtttat tgcgctctgg ctgctatctt tgcccgcccg aagcaacaag     120

tcacgaagcg gctggcaaaa agtgtgtctc gctgcagccg ttgtcggact gctgcttact     180

tttatcgacg ctgctctacg ggcattcctc tatcaaacgt actcggccga acccatgtcg     240

actttcgtat tggaatcagc agccaatacc aatcttgacg aagctctagg ctttttggct     300

accgaatgga ccggggcgct cttggggacg ttactctgtc tcgccgcgtt aactgccgcc     360

ctattcgtca tgtatttggc gagcaagacg tcttcagaca acgcgatggc ttccggttgg     420

gggcagtggc tttggcgatt ctggatgctg ctttttgcgt ccgtctgtat cctcagctgg     480

gccaaaccct cctggcgaat tcactatccc cctatttttt ggtctaaatg gatggaatcc     540

gtcgctggga tgcaatcgat ctggatgaaa gccgaccaac atgaagccgc agaaattacc     600

gaagccagat cggttttgct ggatgcttca tcagctccac gcacaatcgt cttggtcatc     660

ggcgaaagca ctactcggga cgactggagt ctttatgggt actcacgtga taccacgccg     720

aagcttaaag ccctcgaatc aacagattca aatttaggca ccttcaggca ggcttggtcc     780

gtagacacct cgaccatcgc agccttccgt tccatgttca cctttcctgt tccgcagtct     840

gcgggtgacg gccgcatcaa tctctttgcg ctctttagcg ccgctggatg gacagtgcat     900

tggatcagta atcaggacga catagccatt caaacgcaat atgccgtctt tgcctctgaa     960

gcgcagttca tcaaccgcat gaccggacgt tcaagcgcat cgatggatct gaatgttttg    1020

ccaaccttta aacaggcact tgctgatccg gctccgagga aactgatcgt tgtccatctg    1080

atcggagcgc atccacacta cgcgctgagg ttccgcgatt cagacgaaat tgactgggga    1140

cacgaccagg tgatgcagaa tctgaatcat ctcgaccgat ccccatgggt ggttgccgcc    1200

cgcaatcaat atgactgggc tatgcgctat caggacgagg tgctgtcgga actctttcac    1260

ctctctaaaa atgctcaggc ctcagccaag tctccgttag actggatttt tctatccgac    1320

cacggtcagg agctgggaga tacagcaaac cgggcgggtc actcacaaac agcgccatca    1380

agctaccgca ttccgtttct gatctggagc tccgagcgaa gcttcaatcc atatgaaaat    1440

cgtccgttcc gcgctgattt tttaagtccg ctcatgcttg agcttgctgg tatcaactgg    1500

aaaggcgaag atcctcggca agtcctcatt gccgacgact atagttggat gaagcctcat    1560

ttacctatcc aagatccgca gatgccgtca tcagacaccc catga                   1605


<210> SEQ ID NO 112
<211> LENGTH: 2226
<212> TYPE: DNA
<213> ORGANISM: Sutterella
<220> FEATURE:
<221> NAME/KEY: misc_feature
<223> OTHER INFORMATION: Equivalent gene for Cluster 23

<400> SEQUENCE: 112

ttggcggcgc ttgcctgctg tgaccttttc gtcggcgttt ccaatgacgc ttcgaatttc      60
```

```
cttaattctg ccgttggttc cagaacggct ccgttctggg tcattctcgc cgtggcaagt    120

gtcggcgtga ttttaggggc aaccttcagc tccgggatga tggagatagc caagacgggc    180

gtgtttgttc cggaaatgct gtccttcaag gaagtgatgg tgattttttg tgcagtgatg    240

gtgacggacg tcttgctgct caatactttc aactctctag ggctgcccac ctctactacc    300

gtttccatcg tttttgaact cctcggcggc accattgcgg tggcctgctg gaagatttgg    360

gcaaacggtt atccgctcac tgaccttggc ctatacgtca attcgggcaa ggcgcttgca    420

atgattatgg gcattctggc atccgtgatc attgcatttt ttacggggct tatcctgcag    480

tacttccttc gactgctgtt tactttcaac tacgagaaaa tttaccggtg gctgggcggc    540

acgttgggcg gcattgcact cacctccatt ctttacttcc tggtagtgaa gggcgcacgc    600

ggtgcaagct tcatgcagcc ggaatggatt gagtggattg aaacgcacac gagcatcatt    660

ctgatctctt catttgcgtt ttttacggtt atttttcagg ctctgattct cttctttcga    720

atgaacatct ttcccgtgat catcctcgcg ggaacatttg cactggcctt tgcttttgcc    780

ggcaacgact tggtgaattt tgtgggtgtt ccggtagcgg ccatggacag cgtgatgctc    840

tggaaggccc aacccggcat ggatcccggc atgatgatgg gcggactgcg cgatgtgaaa    900

gtcacgccta cagtcattct cggtgcttcc ggcctcatta tgtgcttaac gctttggttc    960

tctaagaagg ctcaccgtgt tattcagacg gcggtgaatc tctcgtcagc cactcgcggc   1020

ggcaaggagc agtttggttc gtcgctcccg gcgcgcttga tcgttcgcag tgccattcag   1080

atgaatgaag ttattcatca gatgctgccg aagtctgttt tcagtgctat agactcacgc   1140

tttgtgaagc gtaaacttcc gcctggagaa gttgaacctc catttgatga actgcgggcg   1200

agcgtgaatc ttgttttagc cgccattctg atttcaacag ctacgagcat gaagctcccg   1260

ctctcgacca cttacgttac gtttatggtc gcaatgggat cttctttggc tgatcgtgct   1320

tgggatcgtg aaagtgcggt ttaccgtatt tcgggtgtgc tgaccgtcat ttccggatgg   1380

ttcatgacgg ctttctctgc ggctacggcc tgcggtttcg tcgctacttt gatgtgctgg   1440

ctcggcagcc cgatgatgat ccttggcatg atcactgctt ttgcgatcat tgtgcgcacc   1500

aatttattga gcaagcagcc tgaggcggta gtggaggaag ccaagcatgt ctataaaggc   1560

gatcagaatt cgatacgaga attgctgaca acttcggtta accacaatct ggacctgaca   1620

ctcacgcttt attccgaagg tcttgaagcc ttcctgcggg aggactatga gcgtttgggt   1680

gaactgaaaa atcaagccgt aacgctttac gacgaaatca tgcttcggcg cggcgattat   1740

tacagtatgg ctttgcaggg gggcggcgct aaacgcgact atgacgcgcg aaacttctat   1800

taccgcgcct ttacaagcat gaaggaagtg gggcatgcat taagagatca gctgggcgtg   1860

gcggaaaatt atgttgccaa cagccattct cctttccgcg ggcagatgcg tgagaacacc   1920

attcttttgg caaaggatct gcagcttgtg cgtgacaact ttaccccgca agcctgcaca   1980

cgcattctgg gtatgcttga cgaagctcag cagagcttcc tcgtgcaaat cggcacggaa   2040

cagatctcac ttcgtaagag cgagctttat ttgggctatc tgctttttgc ccgtgaagtg   2100

cttaaccgct acatgatggt gaagcttctg cagacggagc tggaagctgc tgcggcgaag   2160

actgctgcag tagaggcggc aaatgccaaa ctggccgatc gagcgctcga agaaggccgc   2220

aagtag                                                               2226
```

<210> SEQ ID NO 113
<211> LENGTH: 3102
<212> TYPE: DNA

<213> ORGANISM: Sutterella
<220> FEATURE:
<221> NAME/KEY: misc_feature
<223> OTHER INFORMATION: Equivalent gene for Cluster 23

<400> SEQUENCE: 113

```
atgctgagtc aattctgtat tcgccgtccg atttttgcga cggttctctc gctcttcatt     60
gttctttccg ggctcatcgc gctgagggtg ctgccgcttt cacagtaccc caacatcact    120
ccgccctcag tacgcgtctc ggctacctat gacggcgccg atgccgaaac aattgcccgc    180
acggtagcgc agcctattga agatcagctc tcagggattg aggggctact ttacttcacc    240
accagtatcc gctcaagcgg cgacatggcc attcaatgcg tctttgatgt cggcaccaat    300
ccgaatgacg ccatgcttga gatcaacaac cgcgtacgta cggccgagcg tcggcttccc    360
gcaaaagttc gcgaccaggg cgtctctgta agaaagcgaa gcgaagatga gctcctcatg    420
atggcgctct attcgcctga taaatccatg acggcgtcgg acatggccga ctacgccaat    480
ctcaatattg tcgatgaatt aaaacgcctt tctggcatcg gtgacgtttc cgtgttcggc    540
aacgttcagt cggccatgcg catttggctt gatccggatc ggatgagcaa gcttggcgtc    600
acggtcaaag acgtcgacaa cgccgtgaca gcgcagaacg cccagcatgc cgtcggtcgc    660
gtcggcacct ctcccacgct gcccgaacaa cagctcttct acaaaattac cactccagga    720
cagctcctca caccggatca gtttgccggc atcgttgtca aaagcgacgg ccccaatgga    780
ctggttcgtc tgcgcgatat cgctactacg gaagttggca aacgcagtta tgaattccgt    840
gttgatatga atgggcagcc aggcgtcaat atcggcgtct accttcagac gggtgcaaac    900
gccatggcgg ctgcttcagt agttaaagcc cgcatcaccg aactcgccca gcaattcccg    960
aagggacacc tcgactacac catcacgaac gacacgacag tcttcgtcgg cgcatcgctc   1020
aatgaggtgt accgcacgct catggaagcg ggcattctcg ttctgctcgt ggttttcgtc   1080
ttcctgcaga gttggcgcgc cacgttgatc ccaatgctgg ctgttccggt gagcctggtt   1140
ggtacgatgg ccggactctg gctctgcggc ttttcgctca atacgctcac gctctttgcc   1200
atgacgcttg ctatcggcat tgtggttgac gatgccattg tggttcttga gaacgttgag   1260
cgtttaatgc gcaccgaaaa gctctcaccc tacgatgcgt ccattaaggc catgaaggaa   1320
gtatccggcg cgctcgtcgc aatcgttctg gtgctctctg ccgtcttcat tcctgtggca   1380
tttctcggcg gcattgcggg cgaactgtat cgacagttct ccgtgaccgt tgccatctcc   1440
gtggtgatct ctggatttgt tgcactgacg ctcacgcctg cgctctgcgc cattctttta   1500
aaacctaccg gcgataagcc tgtctctaag cctttccgac tcttcaatca gggacttgct   1560
gccttcacga tggcttttct gcaggtcgtg cgcgcagcac tgaagcacag aattgcatct   1620
gcattgatcc tcatagccgt ttgcataggc gggtggcagc ttctgcagat tacaccgaca   1680
tctttcattc ctaaggaaga ccagggcgtc gtgcgtatgg cggtgcaact ccctgaaggt   1740
tctgctttcc cgcgcacgga agaagttgca gaaggatttc taaagaagat tcaatcgctc   1800
gacggcgtac aaaacgtcgt taccatgatg ggttttgaca cgctcggcag tgacatcaag   1860
gccaatgcag cgacattcat tcttcagctc aagcactgga atgaacgtca gcagaccgcc   1920
gacgactacc agcagcagct tacgaaatgg ctgcgcgaaa gtcctgatgc ccgcggcatt   1980
gccgtgctgc cggctccgat tcccggactt ggcagctcta acggcttctc gggctacctg   2040
acctcccacg gctcggacaa tccgctggtg ctgcagggaa ttgctgaggg cttcatcgcc   2100
gaactttcca agcgcccgga acttaccggt ctgcgcacat cgcttactgc cgacagcccg   2160
```

```
cagctgctgc ttacggtcga cagagaccgt gcctacgcgc tgggcgtgga cgttgatgat   2220
gtctatgaaa ccatctccgc catgatgggg agctcttaca tcaatgactt cacccgcaac   2280
ggcaaaacct accgcgtggt catgcaggct gaagcgaaat atcgctcgct gccgtccgat   2340
attggccgcg cgagcgtacg cgcctcatca ggagaaatgg ttccaatatc aaccctcgtc   2400
acctgggagc gcgtttcagg accagactct ctcacccgca tgaacggata tcttggttct   2460
cagatcatgg gagccgctat ccaaggcgtt tcctcaggcg aagcgatccg aatcgtagaa   2520
gaaactgccc gcgactacct gccgccaggc tatcaggttg aatggatcgg tcaggcctac   2580
cacgaaaagc gtatcggcgc atcgtcagcg acagccttcg gtttcggtct gctcgtgatg   2640
ttcctgattc ttgcagcgct ttatgaacgt tggtcgctcc caatcgccgt ggtgctggct   2700
gtgccgtatg cattccttgg tgccatgacg gccgtctggc tgcgcggaac ggcaaacgac   2760
atctacttcc aaatcggtct gctcgttctg gttggactca ctgcgaagaa tgcaattttg   2820
atcgtagagt acgccgaaca gaaaatggag gaagacggta aagggccgtt tgatgccgct   2880
attgaagctg ccgggctgcg gctgcggccc attttgatga cttcgctcgc cttcattttg   2940
ggcgtcaccc cgatgcttct agccacggga gcaggttctg ctgcccgcca ctcgatgggt   3000
acgggtgttt tcggcggcat gcttgctgca acctttattt caaccatctt cgtgccggtc   3060
ttcttcactt ggtttgcgaa gaagcgcaag gcaaagcgat ga                      3102
```

<210> SEQ ID NO 114
<211> LENGTH: 1065
<212> TYPE: DNA
<213> ORGANISM: Sutterella
<220> FEATURE:
<221> NAME/KEY: misc_feature
<223> OTHER INFORMATION: Equivalent gene for Cluster 23

<400> SEQUENCE: 114

```
atgaacttcg gggtatcttt tgacgtcgac cgcaaagctc ggtgcctcga agaagtaaat     60
cgggaaattg agaacccgga cctctggaat gatcccaaac acgcccagga agtaagcaaa    120
gaaaagaaga tgctcgacga tatcgtcggc agcttcaacc gtcttacgca gggcatcgcc    180
gatgcgggcg aactctttga actttctctg gccgaagagg atttcgattc cctcgaagtc    240
atcggagagg acgtggaccg catcgagcac gaagttgctc agctcgaatt caagcgcatg    300
ttcaaccagc cgatggactc ggccaactgc tatctggaaa ttcagtccgg tgcgggcggc    360
acggaagctc aggactgggc cagcatgctc gagcgcatgt atatgcgcta cgccgaacgc    420
aagggcttta aggtcaccct cgaagaagaa acaccgggtg aagtcgccgg catcaagtcc    480
tgcacgctct ttattgaggg cgaatgggcg tacggcacgc tgcgcaccga gaccggcatt    540
catcgtctgg tgcgtaagag ccccttttgac gccaatgcgc gccgtcacac ctccttcacc    600
tcggtctacg tctatccgga agtggatgat tccatcgaca ttgaaatcaa tcctgccgat    660
ctttccatcg acgtcttccg cgcttcgggc gcaggcggtc agcacatcca gaagaccgaa    720
tcagccgtcc gaattcacca caagcccacc ggcatcatta cgatttgtca ggatgaccgc    780
tcgcagcacc gcaaccgcga aaaagccatg cagcagctca aagccaagct ctatgagctg    840
gaaatgcgca aacgcatgga agcgcagacg aagctcgaag agtcgaagtc tgacatcggc    900
tggggtcacc agatccgcag ctacgtgctt gatcagtcgc gcgtgaagga cctgcgtacc    960
ggcgttgaaa ccggcaacac gggcggcgtg ctcgacggtg atcttgacca attcatcgaa   1020
gcgagcttga agggcggcgt aaatgccgtt ccggcggccg aataa                   1065
```

<210> SEQ ID NO 115
<211> LENGTH: 2673
<212> TYPE: DNA
<213> ORGANISM: Sutterella
<220> FEATURE:
<221> NAME/KEY: misc_feature
<223> OTHER INFORMATION: Equivalent gene for Cluster 23

<400> SEQUENCE: 115

```
atggcgcttg gcattcctgt cacctcaact gcagctgcag aagcggccaa acttgacaat      60
gacattgctt ggcacaaggg cgtctgccgc ttttgcggca ccggctgcgg cttgcaagta     120
ggcgtccgaa atggccgcgt tgttgctacc aagggcgatc ccgacgcacc tgtcaacaga     180
ggcctcaact gtgtcaaggg ctacttcaac gccaaaatcc tttatggcaa ggaccgcctc     240
actcgccctc tgatgcgcat gaaggatgga aagttcgaca agaatggccg tttcgaagct     300
gtgtcttggg aaaccgcctt gaccgaaatg accaaacaaa tgaagcgcgc ctacaaggac     360
aaggggccgg cgggcatttc aatcattggc tctggtcaat acaccatccc cgaagcctac     420
acggcgagca agttcatgaa gggcggtctc cgctccaata acattgatcc caatgcgcgt     480
ttgtgtatgg catccgcggt ggttggcttc tatcagactt tcggcgttga cgagccggca     540
aactgctatg ccgatattga gaaagcagac ctgttcctcc tctgggggaa caatatggcc     600
gaagctcacc ctgtgctttg gtcgcgtgtt gccaatcgcc gtttgacgca ccaagccacc     660
cgtatcgtac agctcacaac tcatcgttca agcacgtcga atctgtcgga tctggtcatc     720
atctttaaac cgaacacgga cctcgccatt ctgaatttcg tcattcgcga aattattcac     780
cgcgggaaag tcaatcagga attcgtcgac gcacactgta ttttctgtgc cggcgttacc     840
gatatcggat acggactccg ccaaactgac aaatatgcct ggcccgctga aaaggacatc     900
atggccaagc agctttccat caaactcgat aaatgggaag ccattggcca gggccgtaag     960
gaaggcgaag ttgttccgca aaagaatacc ggtgcaactg ctggcaaaca ttggcgcatt    1020
agttttgagg atttcaagaa aggcgttgaa ccttactcgc tcgactttgt tgctgaactt    1080
gccaaaggcg ataacgccga gtctcttgct gatttcaaga aaaaactcat ggaactcgcc    1140
gactatgtct gcgatgacag ccgtaacatc atgagttact ggtgcatggg cgtaaatcag    1200
caccaacgcg gcgtttgggt gaacgagcag atttatgacc tgcatttgct ccttgggaaa    1260
catgctctgc ccggtaacgg cgctttctcg ctgacaggac agccttcagc ctgcggttcc    1320
gcccgtgagg tgggtgcttt cagtcaccgc ctccctgctg acatgcttgt cgccaatccg    1380
aagcaccgcg aaaaaacaga aaaaatctgg aatcttcctg cgggaacgct gaacccgaag    1440
gttggagccg atttaatggc cattctgcgt ggcgttgaag ataaatccat cgatttcctc    1500
tggacgcagg tcgtgaatat cattcaatct gcgccgaata acacccattg gatagaagcc    1560
tgccgtcgtc cggacgcttt cgttgtagtg tccgatattt atccgacttt ctccgctcgc    1620
tgtgctgacc tgattctccc tgttgccggc catttcgaaa aatggggact ctacggcaac    1680
gccgaacgcc gtactcaagg ctggcaccag ttggttcagg cgcctgggga agctcgtact    1740
gatgtctgga cgctgatgga gcttgccaag cgcttcacaa ttggtgaaac ctggtgtgaa    1800
caaacactaa aaggcgttcc cggcgacaaa ctcccaaatg ttctggataa ggccgctgaa    1860
ttgggttaca agcctacaga taccctttttt gacgtcctat ttgccccaac tggcaaacgt    1920
gctgaagctg tgtggccgga tccgctctac ccgaatgagc tcaacgctac tggtgatgca    1980
ctaggtctga agtatttccc agagaaagcc cttttcaacg aatatcgcca attcaccgtt    2040
```

```
ggcaacggcc atgatcttgc ggacttcgac acctatcaat ctgccaagtg ccgcggtctc   2100

atttggccag tagtaaacgg caaagaaacg ctttatcgtt tcaatcttga gtacgatcct   2160

tacgctaagg ctgacaatct tttctacggc atgctgatga agcctgtagc taccggcgat   2220

ctttacggtg ttaccaatcc ggaagcaaaa gcatacaaag gcacggcaaa gatctttttc   2280

cgtccatatg cagcacccgt cgaacaacct gacggtcagt acgatctctg gctttgtacc   2340

ggccgcattc ttgagcactg gcataccggc tctatgacag gacgtgtgcc cgagcttcac   2400

cgtgccgcac cgagtgccct gctttacatg aatcctgacg acgcgcaaaa acgtggtctg   2460

aaacgcggtg atttagcgct cgtgacgagt cgccacggag aatgcaaagc agttgttgag   2520

acgcaggttc gaaacatcat gcctgcggga tctacgtggc tcgccttctt tgacgagaag   2580

gtgagaacga atgccgtggt gattgattcc acagacccga tctcgctcga gccagacttc   2640

aaaaagactg ctgttcgtgt aaccagagca taa                                2673
```

<210> SEQ ID NO 116
<211> LENGTH: 1089
<212> TYPE: DNA
<213> ORGANISM: Acidaminococcus
<220> FEATURE:
<221> NAME/KEY: misc_feature
<223> OTHER INFORMATION: Representative gene for Cluster 24

<400> SEQUENCE: 116

```
agagaaaaga ttcgcatgaa aacaaagaaa ttcctggaaa cccttcttgc gggcttgact     60

tgtctttcat tctggtccgg gaccggagag gcggccgatg cacgctggga tgacggggtt    120

ccccgctata cagaggcaaa ggtcatcatc cacgaggatg ggcctaacct tcttttttcg    180

gatagtccgg aaatggttca aaaatgcggt gtcatgtacc gcgatacggt caagggcaag    240

ttccgtcttt ttttccacca tgtcaatgat acggacagca gcaagcggct tgccatcgtc    300

ctgcgccgaa ccgggattcg tccggccctc gtgcagctgg gaagaaatgg catttcagat    360

cctaaccgtg actggctgga agccggaaaa gaggcccaga tccgctacta tggcaagcaa    420

aaggaaacag atcccttgag gataagccgg atgactgact tgcttgggct ccaaaaaccg    480

accatcatcc gtccccagga actagtgacg ggcattgtca acctagagtc ggaccggcct    540

gtagaagttt ccgtcatgat gattcctgta aagaccgatc tggggcttgc ccttgacgca    600

tatggcatcc tgcctcctga tgaaggggat catgtcctgc gcgggacctt ccctgcgtcc    660

gatgtccatg ttcggcttca agaggcgtac ccatcgaata aactggaaac ctggggcatc    720

aaacttgctg acgacgtcct caatccctat gtgcggggaa aagacgcgac aacgggtaag    780

aaggttgtca attatggcaa ttatggggtc atgtatgatg tcatccttcc gaccaaagga    840

aagcgggaca cggtcctgcg ctttaatcca tatggcggac cttatgccgg cgcgggcctt    900

ctttccatga atggcgaaga ggctaaggaa ataaagattc ctggacatgg actggccttt    960

ggctggtccc atgacggtga gaccatggtt cttggaacca ttccggaaaa cggggaggcg   1020

accttgcatt tttcaccgcc tggatcttcc aatctgccaa ttcgcctttt tctttctcct   1080

aaatcctaa                                                           1089
```

<210> SEQ ID NO 117
<211> LENGTH: 630
<212> TYPE: DNA
<213> ORGANISM: Acidaminococcus
<220> FEATURE:
<221> NAME/KEY: misc_feature
<223> OTHER INFORMATION: Equivalent gene for Cluster 24

<400> SEQUENCE: 117

```
atggatattg cacgaactgc caaaaaaaga aaggtcgtgt tcatcatgac gcgtaaagag      60
caagaaaccc tttttgaaaa atgccggacc tatcggcgct ttttgcagaa accgcttccc     120
gaaggacttc tttcctattt ggtgggaatt gcccataaaa ggagctgcgg ccggaatgga     180
caggtgctgt cctttatgc agcggtttct tcaaaggccc ttgccgctct tttgccccat      240
cttcattggg ctgcggccct gcctaaggaa atcggtacgc ctcaaaaaga ggaggaaccg     300
gtggccctca ttttttggt acgccccaag gacgcttccc ccatcagctt gatcgatgca      360
ggcattgctg ttgattctat ggcgtactgt gctatgtgtg aaggcgtcgg gtcggcaatc     420
ctcgctgccc ttgatcgggc agctatccag gggattctgg gccttgaaaa ggatcaggag     480
gtctttcttt gtcttgccct tggctatcca gcccacaaga gcaccgtggt ccctgtaccg     540
gaaagcggaa cccttgatta ttatgtggat gaaaaaagga attattttgt tcccaaaaag     600
aacctgtccg atgtcatgac ggttctttag                                      630
```

<210> SEQ ID NO 118
<211> LENGTH: 1974
<212> TYPE: DNA
<213> ORGANISM: Acidaminococcus
<220> FEATURE:
<221> NAME/KEY: misc_feature
<223> OTHER INFORMATION: Equivalent gene for Cluster 24

<400> SEQUENCE: 118

```
atgtcggaag aattgaagaa ccagcccgct gtggatacgg gcgctgctga agaagtcagc      60
gaacaagtcg ctgtccgtat ggacaagatg cataagctgg aagaaaaggg tatcttgcct     120
tttggtcatg cctataaggt gacccatcat aataaagaag tccatgacaa ggtcaaggaa     180
ctggaagaaa agggcgctga agtccgtttt gccggacggt ttacgtctag ccgcggtcac     240
ggcaagaccg cttttatgga ccttctcgat aagtctggta agattcagct atatgtccgc     300
aaggatgagt tgggagaaga taattacagt gtggtcaaac tcctggacat tggggatatc     360
gtcggcgtag aaggcgaagt cttcacgacc catatgggtg aaccatccat tcgcgtgaaa     420
aagctcgaat tcctttctaa ggccctgaaa ccgctgccgg aaaaatggca cggcctcaag     480
gacaaggaaa tccgttatcg tcagcgctat gtggatctca ttgtaaaccc cgaagtccgc     540
gacacatttg tcaaacgtac ggaaatcatc aaaagtatcc gcaatatcct cgataatgaa     600
ggctaccttg aagtggaaac gccggtcctc aatactattt ccggcggggc tacggcccgt     660
ccttttgtga cccaccataa tgcccttgat atcgatttgt acctgcgcat tgcgacggaa     720
ttgaacctga agcgccttat tgtagggggt ctggaacggg tttatgaaat tggccgcatt     780
ttccgcaatg aagggatgga tatcaagcat aacccggaat ttacgtccat cgagctttat     840
gaagcatatg gtgactatca aaccatgatg gatattacgg aaaaactcgt gtcagaaacg     900
gcgcagcgcg tcttgggcac catgaaaatc acctatcagg gcaaggaaat cgacttgact     960
ccgccttggc ctcgtatgac catggttgaa gccgttaaga aattcagcgg ttatgacttt    1020
acgggtgtcc gcgatgttga aacggcccgc aagctggctg ctgatgccaa cgtcgaaatc    1080
cagccgacct tcggccctgg caagattctg gaagccttct ttgatgaatt cgttgaaaag    1140
aacctcattc agccgacctt catcatgggt catcctaaag aaatctcgcc gcttgctaag    1200
agcagccttg ctgatccaga agtcacggat cgttttgaag gcttcatcaa cggttctgaa    1260
atctgcaatg gttttacgga actcaacgat ccaatcgacc agaaggaacg ctttgaaaaa    1320
```

```
caggtggaag aacgcaataa cggcgatgat gaagccggta tgatggacga agacttcatc   1380
aatgccctca tgcacggcct gcctccgacg ggcggtctgg gtattggaat tgaccgtctt   1440
gtcatgctgc ttaccaattc ggcttccatc cgcgatgtcc tgctcttccc gaccatgaag   1500
cccctgggac tcgaaaagaa agacgaatct gtggcagctg ctccagccgc gcccgctgaa   1560
acggtggatg ctccgcagac cgtggcgctg gaaaagattg atttttccaa tgtgaccatt   1620
gaagcgctct tcaaggattt cgttgatttt gatcagtttg ctggctgcga cttccgggta   1680
gtgaaagtca aggactgttt tgaagtgcct aagagcaaga aacttctcca gttcacactc   1740
gatgacggaa cgggtacgga ccggaccatc ctgtcgggca tcaaggcata ctatcaggcg   1800
gaggatctta tcggcaggac cctcgttgcc attgtcaact tgccgccgcg caagatgatg   1860
ggcatcgaat cctgtgggat gctgttaagc gccgaacata atgaagggga agaacgcaaa   1920
ctgaaccttc tcatgcttga tccccatatt ccggctgggg ccaagctctg ctaa         1974
```

<210> SEQ ID NO 119
<211> LENGTH: 1113
<212> TYPE: DNA
<213> ORGANISM: Acidaminococcus
<220> FEATURE:
<221> NAME/KEY: misc_feature
<223> OTHER INFORMATION: Equivalent gene for Cluster 24

<400> SEQUENCE: 119

```
atgcgtcatt cctttaaaaa gtattttcgg aacgtggata aggttctttt tgtgagcgtc     60
atgctgctca ttgccattgg ccttgttctg attgccagtg ccacccatgc caatattccc    120
ggtccccatc gctaccgctt tgtttttcgg caggcccttt ttgtcatcgt gaacctcatt    180
ttgggcggtt acctgatgcg ttttgattac cgcatcttaa aacatgttgc caaacccctg    240
tatattttta acctggttat gctggttgcc gttatggctg ttgggaaaag tgcgttgggt    300
gcgcagcgct ggctccaatt gggccccatc agcattcagc ccagtgagtt ttccaaagct    360
atcatgattg tctgtctgtc ctcttttgtg gaatcgcggc tgccgacgtt aacggacttt    420
cgcagttgga tccctgtttt tctctatgtc tttgttcctt ttctcctggt tatgcgtcag    480
cctgacctag gaacaagcct cgtctttatg gcgattctct taggtacaat gatcatctgc    540
ggcttcagga tccgttattt tctcatcatg ggcggtttgg gtcttgcttc agcacctctt    600
atctggcaca tgcttcatga gtaccagaaa aaccggatcc gcgtcttcct caatcccgga    660
cttgaaccgt acgggagtgg ttaccatgtc attcagtcca tgattgctat tggttccggt    720
cttttttttg gccgtggtct ttttaatgga acccagagcc agcttaactt tcttcctgaa    780
aatcacacgg actttatttt cgccgtggcc ggcgaagagt ttgggtttgt tggggtgaca    840
ctgatcctga ttctctactt gattgtcatc gtcaggggca tcacgattgc ccttcatgca    900
agcgatgatt ttggaaccct gcttgctgtt gggattgttt ctatgtttac ctttcatatc    960
ctggtcaatg tgggcatgac gagcaatgtt atgcccgtaa caggggttcc gctgcccttt   1020
atgagctatg gtgtcagttc ccttacgacc aatatgctca tggtggctct tttaatgaat   1080
atccatgctc atcccaagac cttgagattt tag                                1113
```

<210> SEQ ID NO 120
<211> LENGTH: 1743
<212> TYPE: DNA
<213> ORGANISM: Acidaminococcus
<220> FEATURE:
<221> NAME/KEY: misc_feature
<223> OTHER INFORMATION: Equivalent gene for Cluster 24

<400> SEQUENCE: 120

```
atggtaacac tcaccattga caatcaaacc gtccgcgttg cggaaggaac gaccatcctt     60
gaagaagcca aatcagcagg aagcatcatc ccccatctgt tctaccgcaa tgagctcaac    120
gaaattgccg cctgccgcgt ctgttccgtt gaagtagaag gggaaacggc tatggttacg    180
gcctgcaaca gttctgttgt cgagggcatg gtcgtccata ccaattcgcc gcgggcccgg    240
gaaacacgcc gcatcaatgt ggagctcatc ttaagccagc atgactgtct gtgcgccacc    300
tgtgtaagaa gcggcagctg ccagctccag cgtctggcaa actcccttgg catcatttcc    360
cttccctacg aacgggaact gcctaaaggc gcgcgaggag cctggaccac aacctaccct    420
ctctaccgag attatcaaaa atgcatcaaa tgtatgcgct gcatccaggt ctgtgacaag    480
atgcagaccg tccatatttg ggacgttgat ggcaccggat caaggaccac ggtcgatgta    540
tcccataacc gcgtcatcaa ggactcggac tgcaccctct gcgggcagtg catcacccac    600
tgccctacgg caggccttcg ggaacgggat gacacggata aagtctacag tgcccttgcc    660
aatcctgagc tcattcccat tgtccaaatc gcgccggcgg tccgcacagc cctatgtgaa    720
gcctacggag tttcccccca ggaagcaccg atgggaaaac tggccgctgc cctgcgccgt    780
atgggctttc gctatgttta tgatacgtgc tttggggccg accttaccat catggaagaa    840
gccaacgaat ttctcgagaa atttaagaac ggtaagacaa agaaattccc cctatttaca    900
agctgctgcc ccggctgggt gcgctttctc aaaggaaagt tcccggaact gacagaccgc    960
ctgtcaacct ccaagtcccc gcagcagatg tttggcgcca tcgcaaagac ctggcttgca   1020
aaaaaactgg gaacggagcc ggaaaaactc tttctcgttt ccatcatgcc ctgccttgcc   1080
aaaaaagcag aatgcgacct tcccacgatg cagacccagc atggtaagga cgtggactgc   1140
gtccttacga cacgggaatt tatccgtatg ctgaacgcgg atcgtatcta tccccacctg   1200
ctcaaggaag aacccctcga tgatcccatg ggaacccata caggggctgg caccatcttc   1260
ggtgtgacag gcggcgtcat ggaagcagcc ctgcggacag cctattatga agtcacagga   1320
aaagatcccg atccggacct gtttgccgac atccgcaccg gtccggccct cagggaaaag   1380
acctacacct tgggcggtgc cgacgtgcac tgcgctgttg taagcggtct tggcaacgcg   1440
cggcacctgt tggaagccat caaagcagga aaagtccatt atgacttcgt ggaagtgatg   1500
gcctgccccg gcggctgcag cggcggtggt ggccagccga tttccatcga tgatgaagag   1560
cgagccgaag cgcgcggtca aagtctctat gcccttgacc aaaaaatggc cctgcgcctc   1620
agtcatcgca atcctcaaat cgaagccctc tatgcggaat ttctcggcag ccccctcagt   1680
gaaaaagcag aggaactgct ccataccgat caggggggcgt gggaagtgac ggagtgttat   1740
taa                                                                 1743
```

<210> SEQ ID NO 121
<211> LENGTH: 423
<212> TYPE: DNA
<213> ORGANISM: unknown
<220> FEATURE:
<223> OTHER INFORMATION: Representative gene for Cluster 25

<400> SEQUENCE: 121

```
atggctacca tgaaagtaat caccaataag gatcaagctc ctgtctacta cgcaactggc     60
cgcagaaaat ctgcagtcgc tcgtactttc gttaagactg gttctggaaa gatcaccatc    120
aatggtgagg atcctgagaa atacttccct aacaagtatc ttctcatcga tcttaagaga    180
```

```
cctttggatc ttaccggtat gactggaaga ttcgatatca acatcactgt caatggtggt    240

ggatattccg ctcaagagaa tgcagctcgt ttgggaatct ctcgtgcttt gactcttgtc    300

aatgctgatt tccgtaaggt cttgaaggct aacggactta tcacagtcga ctccagagtt    360

gtcgagcgta agaaatacgg tcttcacaag gctcgtaagg ctccccaatt ctccaagcgt    420

taa                                                                  423
```

```
<210> SEQ ID NO 122
<211> LENGTH: 750
<212> TYPE: DNA
<213> ORGANISM: unknown
<220> FEATURE:
<223> OTHER INFORMATION: Equivalent gene for Cluster 25

<400> SEQUENCE: 122

atgacctcaa ctaatgaaat gccaatttta gcagtaagga atttatcgaa aagatttgat     60

gatttgcaag ttcttaacaa cgtgtcatta gatgtttatc ccaaggatgt tattgctgtt    120

ttaggtcaat ctggaggagg taaatcaact ttccttagat gtttgaatct gttggaagaa    180

ccggatgatg gaagtattta ttttcacggc tatgacttgg tacatgataa gataaaactt    240

aataagctaa gagcaaagat gggaatggtt ttccaatcgt tcaatttgtt caacaacatg    300

aatgttctcg aaaatgttat gtacgcacaa ataaatgtat tgcatagaac acgtgaagaa    360

gctttgaaaa gagcacagca agctttggac gaagtcggat tattggatca tgctgactat    420

agagtgaaca acttgtctgg tgggcagaaa caaagagttg ctatcgcaag atccttagtc    480

atggatccag acattatgct atttgacgaa cctacttctg ctttggatcc tttgatggtt    540

ggagaagttt taaaagtaat gcaaagactt gccaagaacg gaatgactat gattgtcgtg    600

acccacgaaa tgtcatttgc aaagaatgtt tcaaatagaa tagtcttctt cgatggcgga    660

aaaatagttg aagaaagctc aaatcctata gagttcttta gttcacctaa aactgaacaa    720

gccagaaaat tcttaggggc cgaaaaataa                                     750
```

```
<210> SEQ ID NO 123
<211> LENGTH: 483
<212> TYPE: DNA
<213> ORGANISM: unknown
<220> FEATURE:
<223> OTHER INFORMATION: Equivalent gene for Cluster 25

<400> SEQUENCE: 123

atgaaaactg cattatatgc cggttcattc gacccattca ccaacggtca tttagaagtc     60

gttgaaaaag ctttaaaagt attcgataaa attgtaattc tagtagctaa taacaatgct    120

aaaaaataca ctttttcact agatgaaaga gtagcaatca taaaagaatg cttcaagaat    180

aattctaaag tagaagtcga atccacatcg ggaattacag ttagaaaagc taaatcttta    240

aacatcaatg tcatgattag aggtcttaga gatgttcaag attttgaaat ggagcagaga    300

ctttatatag tcaatcgagc tttagataaa gacatagaaa cattctatgt catggctagc    360

ccagctaaaa tattcatatc ttcaacaaac ttaaaattaa tgtttaaggc gggagaagat    420

atatcagatt atgtcccaaa acctgtatta aatgcattag agaaagtaaa agataggatt    480

taa                                                                  483
```

```
<210> SEQ ID NO 124
<211> LENGTH: 228
<212> TYPE: DNA
```

<213> ORGANISM: unknown
<220> FEATURE:
<223> OTHER INFORMATION: Equivalent gene for Cluster 25

<400> SEQUENCE: 124
atgccaagca aaaagataac cgatcgatat gggagaatca tcggatatac tgaagagaat 60
gctaccggta acgtctatgc aagagacaga tttggtagat tgcttggaat gtataatcct 120
aattcaggga tcacaactga tcgattcggt aagacagtag ctagaggaga tattactggc 180
gggcttgtat ggaacagcca ggacaactac aagaagaaca agaagtag 228

<210> SEQ ID NO 125
<211> LENGTH: 696
<212> TYPE: DNA
<213> ORGANISM: unknown
<220> FEATURE:
<223> OTHER INFORMATION: Equivalent gene for Cluster 25

<400> SEQUENCE: 125
atgaaaaatg aggaagcaaa agatttagct aaaagatttc atagattgag taaatccaag 60
actgactggg tcaaagaaca ttccgattca atggtcgagt ctgatggaag agctcatgta 120
aaagttgatc ttagaaagac aaatgcgtta aatctatatt ctggtggaac aagaattcat 180
ccagatattt tagaattcat agaagatgag gctatttata ctgaagtaga aaagccatta 240
tctattgatt tctatgttga agagaaagac gctaagtttg ataagttgct ggctaaagaa 300
gtaaagaatc attatttgtt taagttttca gaaactaaga agcaaaaaag tgatgtggtc 360
aagaaaagct ggaatttatt gctagcaggt attttctttg taattgtata tattttgatg 420
agttatttct ctaaaaacag tgataaatatg tcgagaaatg cttcgctatg gctctcgatt 480
ttctcggaag ttatcgatat tgtttattgg gttttcattt gggaggccgt tgataaattc 540
ttcttcgagc aaagagaagt tcaaaggcaa ttgttccgtc ttactcaatt agccactgct 600
gatataaact ttatcgccaa aggtaaatgg gaagaggaaa agaagaaatt ccattccatt 660
gaagaagata acaaggaaga agctgaaatc gactaa 696

<210> SEQ ID NO 126
<211> LENGTH: 771
<212> TYPE: DNA
<213> ORGANISM: unknown
<220> FEATURE:
<223> OTHER INFORMATION: Representative gene for Cluster 26

<400> SEQUENCE: 126
atgcatggga aatatccttt cccagaggca acggcaacca cggaagtttt ggtttccggt 60
gaaaagaaag gtaatcaagc taaactattg gccgtgagtg gtctgattgg ggggctttat 120
gatttctgcg tgagtacctt cggttggtgg gcagaaggaa tctctactcg tatcatggga 180
tggggagaag tgcttgccga caagatgaaa gtggtattta aagtgaatac gggtgcggca 240
ggacttggtt taggatatat tattgggttg aaatatgcgg cgattatttg tgccggttct 300
ttcaccgtgt ggtttgtgct gattcctttt atcagccatt tcgccgacgg acaaacgtta 360
gccgtgggag aggggatctc ggtgttattg cgggatatga ccccagagca aatattctca 420
aattatgctc gtcatatcgg tataggtggt atcgctatgg ccggagttat cggtattatt 480
cgttcttcca gtattatcaa gcaggcttta ggattggccg ttagtgaatt gggtggaaag 540
aaaaaaggcg aaggtgcggt agaacgtaca caacgtgata tttccatgaa gttcattttg 600
tcaggaatca tttccatatt gattgctact tttgtgttct tccaatttgg agtgttgggt 660

```
aatttgacac acacgatcat tgctactttg attgtattcg tcatctcgtt cctattcacg    720

actgtggctg caaacgctat tgctatcgtg ggttcgaatc ctgtatccgg a             771
```

<210> SEQ ID NO 127
<211> LENGTH: 1098
<212> TYPE: DNA
<213> ORGANISM: unknown
<220> FEATURE:
<223> OTHER INFORMATION: Equivalent gene for Cluster 26

<400> SEQUENCE: 127

```
atgaaattaa ttgatacgaa tgattttttg cttggctctc atgggttgaa ccgttttcga     60

gaaagcttgg tatccaagtt ggtgatgtat atcttgcggt tgcataaact ggataagttg    120

aatgtgaagg taaatgatga tgatccggaa gtccttttgg atagtttgat cgaggctttg    180

ggggtgacta tcgaggtgag taaggaggat ttggaaaaaa ttcctaaaaa cggtactttt    240

atcacggttt ccaatcaccc gttcggggga ctggatggta tcgtcctggt gcgtttgcta    300

tgtaaattac gtccggatta taaaatcatg tctaattttc tgttgaagaa aattgttccg    360

ttacaggatt atatattggg gctggacccg gaggagggca agaaagattc aaatatgcga    420

gtaattaaag aggcgatacg tcatgtcgtt gacgggaaac ccttgggaat attccctgcc    480

ggagaggttt cttcttacca agcagactcg aatcatgtgg aggataagga gtgggattct    540

tcggttttga agttggtgaa aatggcgaaa gtgcctgtta ttccgatata ttttaaaggt    600

tctaacagtt tgttgtttta tttactgggg atgattcatc cggtattgaa aacgattaag    660

ttgccttccg agttgttgaa caagaaaaac agggtggtga agttaaggat cgggaacccg    720

atcagtgtgg agactcagaa tacatttcat gatatagctc agtatggtaa gttcttgcgg    780

gcgaaaactt atttattggg atctgcgtta gaagtgaaga agtttttat taaatcacag     840

aaagcaatgc ctaaagcaga accgattgcg gcagagaccg agagtgcagt attgaagaaa    900

gaaatcgagg gggtagcgga agactacctg ttgtttaaca tgaagaatta cgatatatat    960

tgttcccctt ccgtgaagat tccgaacgtg ttgaacgaga ttggtcgttt gcgggaagtt   1020

actttccgtg cggtgggaga aggaacgaat cgtagtatcg atttggatga atacgatctt   1080

tattactatc acttgttt                                                 1098
```

<210> SEQ ID NO 128
<211> LENGTH: 720
<212> TYPE: DNA
<213> ORGANISM: unknown
<220> FEATURE:
<223> OTHER INFORMATION: Equivalent gene for Cluster 26

<400> SEQUENCE: 128

```
atgggatatt tatttacatc tgaatctgta tcggaaggtc accccgacaa agtggcagac     60

caaatttccg atgccgtact tgacaaaatc atcgcctttg acccggatgc caaagtagct    120

tgtgagacct tggtgaccac cggacaaacc attgttgccg gggaaatcaa aaccaaaacg    180

tacgtagacg tgcaacatat tgcccgggaa gtaatcaatc gtatcggcta cacgaaaagc    240

gaatacatgt tcgacgggaa cagttgtggg gtactgagcg ccattcatga gcaatctccc    300

gacatcaacc gcggagtcgt tcgggaagac cctatggaac agggagccgg agatcaaggc    360

atgatgttcg gttacgcctg taacgagacg gataactata tgccgctatc tcttgagtta    420

tcacatttac tattgtacga gctggcacaa atccgcaaag aaggtcaaga aatgacctac    480
```

ctgcgtccag actccaaatc gcaagtaact atcgaatacg gggaagacaa taaacccgca 540
cggattcaca ccatcgtgat ctccacccaa catgacgagt ttgtcaaagc cacggcaccc 600
accccggatg cacaactgga agccgatgct caaatggtgg atcaaatacg ctgggatatc 660
atcaatatct tgttgccaag agtgaaacgc caactgccgg aacgggtaca ggccctcttc 720

<210> SEQ ID NO 129
<211> LENGTH: 984
<212> TYPE: DNA
<213> ORGANISM: unknown
<220> FEATURE:
<223> OTHER INFORMATION: Equivalent gene for Cluster 26

<400> SEQUENCE: 129
gaccagacgt taggattgtg gggggagaag acaggtaaag gcgaggctgt gaaaaccgat 60
aaagtatcgg tagatggacg gttaaaaaaa ttatcggata tgtatgcggc atgtgacccg 120
gacttagtgg taacagcatg gcatgccacg gagaaagatt tacaagtacg ttattcctct 180
ggagatattc gggcgaaaga cggaaaattg tattttaatg atcataaaac aagagcgact 240
tgggatgttc cggaaagcgg gaagcgtaaa gtgtattttg ccgttggtaa ctgcttgatc 300
ggtaatgtta acaacacgaa agagagtatg gcaattgctt ggatgaatgg tagcaatgca 360
accacgatga ttggttatgt tgtgactaca tggcatggac gtaacggttg gggcggcttg 420
aaatactggt taactaatcc gggacgttat tctttggcag aggctgttta catgaatcaa 480
caggatttct tgtaccagca atatcaatgg tatccttctt tgattaagga gaactatcct 540
acgtttgaag gaaatgaatt ccaacttgca gggcaaaagg tggcagaagc gataaaggga 600
caaccgacgc aggatcagat cggtttttgg catgatcggg atgtgttggc ttactatggt 660
gatccattgt ggaacgttcg tttgcaggag ataccggaag agaccgattt taccgtaact 720
tcaaaggtga agggtaaaaa gtgcattatt acaatcaaga ccaaggagaa ttttagccta 780
gaacgtatga aaggagataa atttaaacag gaacatgtgc tggatttgcc tttcagttac 840
ttcttcccgg aacgcttgaa taatcctcgt ctagcagcag ggcaagattg gagagcggtc 900
gtggatgaaa acttcttgat catttataat ccagatttca aacctaatat gacgtatgag 960
gttgtattgg atatagataa atag 984

<210> SEQ ID NO 130
<211> LENGTH: 447
<212> TYPE: DNA
<213> ORGANISM: unknown
<220> FEATURE:
<223> OTHER INFORMATION: Equivalent gene for Cluster 26

<400> SEQUENCE: 130
gtgggagagg tgaacgtggt gactaagatg aaagagacga atacggtaat tggtggtgaa 60
ggaaacggtg gtgtcatcta tccggaaagc cattacgggc gtgatgcttt agtaggagta 120
ggcttattcc tttctcattt cgtggcggaa ggaaagagca tgacggtttt aaaagcaact 180
tacccgcaat attttatttc gaaaaacaag ctaacacttt ctcccgatat ggatgtcgac 240
aagatattgg agggcttgaa aaagaaatat gcttcagaag agattaccga tattgatggt 300
gtgaaaattg acttcaaaga tggctgggta catctacgta aatccaatac agaaccgatt 360
atacgaattt attccgagtc gaaagatgaa gcagcagcta atcaattggc agaagaagtt 420
ataaaggtgg cacaaagcct gtattaa 447

```
<210> SEQ ID NO 131
<211> LENGTH: 570
<212> TYPE: DNA
<213> ORGANISM: Haemophilus
<220> FEATURE:
<221> NAME/KEY: misc_feature
<223> OTHER INFORMATION: Representative gene for Cluster 27

<400> SEQUENCE: 131

ttggtgttac aagcggctag ccctcgtgcg attaaatttg tgatgtatcg tccaatttac     60

aacaaatggt atctcacttg gttcttccgt attttcaaag tcatcccaat tggtggcggt    120

tcaagccgag aatctattga aaccattcgt gaatatttag cgcgtggtga agtggtggct    180

ttattcccag agggtcatat cagctataac ggtcaaatca atgagttcca aaaaggcttt    240

gagcacgtat taaaagattt agagaatgtg acgactgttc ctttctattt acgtggatta    300

tggggtagca gcttctctcg tgcggattct ttctataaga atttaactaa acgccaaggt    360

aaacgtgaaa ttttagtagc atttggtaaa cccattcatg gctttattga tgcgacagcg    420

atgaagcaaa aagtactcga actttctttc tccgtatggg aaaaagtcat gagtaaacgt    480

aaaccgctga tgcatcattg gttgagttca gcaaaatcga atttattcaa agaagccgcg    540

gtggatgcgc aaggcactaa actgaataac                                     570


<210> SEQ ID NO 132
<211> LENGTH: 186
<212> TYPE: DNA
<213> ORGANISM: Haemophilus
<220> FEATURE:
<221> NAME/KEY: misc_feature
<223> OTHER INFORMATION: Equivalent gene for Cluster 27

<400> SEQUENCE: 132

gtcgagtttg tcgaaactgc caatgattgg gaacaagaaa ttggggtgtt aatcgatcct     60

gaggcttttg ctgaagtttg ggtcggatta gtaaatgaga aagatgaaat ggatgatgtg    120

tttgcgaaat tcttaatttc acaccgagaa gaagatcgtg aattccacgt tatttggaaa    180

aaatag                                                               186


<210> SEQ ID NO 133
<211> LENGTH: 540
<212> TYPE: DNA
<213> ORGANISM: Haemophilus
<220> FEATURE:
<221> NAME/KEY: misc_feature
<223> OTHER INFORMATION: Equivalent gene for Cluster 27

<400> SEQUENCE: 133

tttatttcca aagcaccgcg ttgggcaatt gcttataaat tccctgcaca agaagaatta     60

actcgcctaa atgatgtgga attccaagtg ggcagaacag gggcaattac cccagtggct    120

aaattggaac cggtatttgt ggctggtgtc acggtgagta acgccacatt gcataacggt    180

gatgaaatcg aacgcttgga cattgcgatt ggtgatacgg tagtgattcg ccgtgcggga    240

gatgtgatcc cacaaattat cggcgtatta cacgaccgtc gcccagcaga tgcgagaccg    300

atcattttcc ctaaaacttg tcctgtatgt gattcggcca ttgttcgtat tgaaggtgaa    360

gcggtagcgc gttgtacggg cggtttgttc tgtgcagcac agcgtaaaga agcgcttaaa    420

catttcgttt ctcgcaaagc tatggatatt gatggggtag gggggaaatt aatcgagcag    480

ttggtggatc gtgaattaat tcatacgcca gccgatttat ttaagttaga tttaaccacg    540
```

<210> SEQ ID NO 134
<211> LENGTH: 723
<212> TYPE: DNA
<213> ORGANISM: Haemophilus
<220> FEATURE:
<221> NAME/KEY: misc_feature
<223> OTHER INFORMATION: Equivalent gene for Cluster 27

<400> SEQUENCE: 134

```
ttgattgccg aaagcacaca aaacaagtat aatctcgtcg attttttttaa ctcaaacata     60

ggaaaaaata tgggtttctt aactggtaaa cgtattttag taacaggtct tgcaagcaac    120

cgttctatcg cttacgggat cgcaaaagca atgaaagaac aaggcgctga acttgctttc    180

acttatttaa acgataaatt acaaccacgc gtagaagaat ttgcaaaaga atttggttct    240

gacatcgtcc ttcctttaga cgtagcgacc gatgaaagca tccaaaattg ctttgcagaa    300

ttaagcaaac gttgggaaaa atttgatggt ttcgtacacg ctatcgcatt cgcaccaggc    360

gatcaattag atggtgatta cgtaaacgca gcaactcgtg aaggctaccg tatcgctcat    420

gacatcagtg cattcagctt tgttgctatg gcacaagcgg cacgtcctta cttaaatcca    480

aatgcagcgt tattaaccct ttcttactta ggagcagagc gcgcaattcc taactacaac    540

gtgatgtgtt tagcgaaagc gtctcttgaa gcagcaactc gcgtaatggc agctgactta    600

ggtaaagaag gtattcgtgt gaatgcgatt tctgcgggtc caatccgtac cttagcagca    660

tcaggcatta aaaacctcaa gaaaatgctt tctgcatttg agaaaaccgc agcattacgc    720

cgc                                                                   723
```

<210> SEQ ID NO 135
<211> LENGTH: 681
<212> TYPE: DNA
<213> ORGANISM: Haemophilus
<220> FEATURE:
<221> NAME/KEY: misc_feature
<223> OTHER INFORMATION: Equivalent gene for Cluster 27

<400> SEQUENCE: 135

```
aaacttaagg cggaaattat gggaaaaagt gttgttgttc ttggcgctca gtggggcgat     60

gaagggaaag gcaaaatcgt tgatttatta acagatcgcg ttaaatatgt ggtgcgttac    120

caaggtggtc acaacgcagg tcacacttta attattaatg gtgaaaaaac cgtattacgc    180

ttaattccat caggtatttt acgtgataac gtgacctgtt taatcggtaa cggtgtagtg    240

ctttctcctg ccgcattaat gcaagaaatg ggcgaattag aaagccgtgg cgtaaaagta    300

cgtgaacgtt tattaatttc agaagcttgt ccattaatcc taccttatca cgttgcaatg    360

gatcacgcac gtgaagccgc attaggtaaa aaagccattg gtacaaccgg tcgtggtatc    420

ggcccagctt atgaagataa agtagctcgt cgtggtttac gtgtgggcga tttattcaat    480

cgcgaagcct ttgctgaaaa attaaaaaat atccttgaat actataattt ccaattggtg    540

aactactaca aagtagaacc tgttgattat caaaaaacat tagacgatgt attcgcggta    600

gctgatatta ttactgccat ggtagcagat atcacaacca tcttagatac tgctcgtaaa    660

aatggtgaca acatcctgtt c                                               681
```

<210> SEQ ID NO 136
<211> LENGTH: 504
<212> TYPE: DNA
<213> ORGANISM: Desulfovibrio
<220> FEATURE:
<221> NAME/KEY: misc_feature
<223> OTHER INFORMATION: Representative gene for Cluster 28

<400> SEQUENCE: 136

```
cactccggca tgaccggcct ggcgaatgcg gtcttcaacc accacgatct gctgttggtc     60
gttctggaca acggcactac ggctatgacc ggccatcagc ccaatcccgg catgttgcag    120
gaaatgctcg gcgacatgag cgtgcatatg gatatggaag ccgtggtgcg cggcctgggc    180
gtgaccgaat gcgtcaaggt aaaggccttc aatctcaagg ccgtgaccaa ggccctggag    240
gaaatgaagg gcaagtccgg ggtgcgggtg ctcatcgccg aggagccgtg cgtgctctat    300
gcccgtcgtc gcctcaagaa agggcagccc caggtggccc aggtggtgca gcagggcgag    360
gaagccttgc gctgcctgga gcagctggcc tgtccggcct tttatcgcca gggcgacaat    420
ctggcggtgg atgaaaccct gtgttccggc tgcatgatct gcctgcagat cgctcccacg    480
gcctttaaag ccaaaaagcg ctga                                           504
```

<210> SEQ ID NO 137
<211> LENGTH: 606
<212> TYPE: DNA
<213> ORGANISM: Desulfovibrio
<220> FEATURE:
<221> NAME/KEY: misc_feature
<223> OTHER INFORMATION: Equivalent gene for Cluster 28

<400> SEQUENCE: 137

```
atgttcgcgg gcgactggga gggttgcgcc cagaacatca ggcgcattta cgccgcggtg     60
gagcgcctga aacctaaaat ggtggtggga accgagtgcg gtcatgccca tcgcggcacc    120
gtggtggaag gcccctactg ggcggacgc gccagcggcg acccgcccgt gcccttcatc    180
cattacgtgg aatgggtggc gcactgtctg cgtaccggca agctgaaaat tgatcccgcc    240
aagaagatca aaatcccctg taccctccag gatgcctgca actatgtgcg caacgacgga    300
ctgggcagat atacgcggga aatcatgagt tatatcgcgg aggacttccg cgagatgacg    360
cccaatgccg accacaactt ctgctgcggc ggcgggggcg gcctcaacgg catcggcctc    420
tatcgcaagg aacgcaatat cggcctcaaa aacaaactgg atcagatcaa ggctaccggc    480
gcgcaactgg tcgtgacccc ctgtcacaac tgttgggacg ccatcaggga tatgatggaa    540
gtctatgagg aacacaatat caaatggtca ttcctcaaac cgcttctcgt ggatattatg    600
gcggtt                                                               606
```

<210> SEQ ID NO 138
<211> LENGTH: 549
<212> TYPE: DNA
<213> ORGANISM: Desulfovibrio
<220> FEATURE:
<221> NAME/KEY: misc_feature
<223> OTHER INFORMATION: Equivalent gene for Cluster 28

<400> SEQUENCE: 138

```
gcccgcctca tgggccgcct gaccctgaac cccctgccgc atattgatcc catggggctg     60
ctggtcttcg gcctgaccag cctttccggc gcgtttgttt tcggctgggc caagcccgtg    120
cccgtaaacg cgcgctattt ccgccatccc gccagggaca tgatgctggt ggctctggcc    180
gggccgctga cgaacttcct gctggccgtg cttttcggcg tgaccctgcg cctggtgctg    240
gcctttttcc cctttgacgt ctggcaacag cacaacttct acattttcgt cctgtcttcc    300
ctccaggccg gcgtggtgat caatttcggc ctgggctggc tcaatctggt gcctattccg    360
ccgctggacg gcagcaaggt tgtggcctat tttctgcccg gcgaaacggc ctggcgctac    420
```

ctgagcatgg agcgctacgg ttttatcatt cttttgctgc tgctgttcac cggagccctg 480
ggctacgtgc tggggccgct ggtcagcggc agcgccagag ggcttctgtc cctcctgggc 540
ttattgtaa 549

<210> SEQ ID NO 139
<211> LENGTH: 1068
<212> TYPE: DNA
<213> ORGANISM: Desulfovibrio
<220> FEATURE:
<221> NAME/KEY: misc_feature
<223> OTHER INFORMATION: Equivalent gene for Cluster 28

<400> SEQUENCE: 139
atgcccaagg atgccgttgc aaccgggtcc gtcgaggttg atgaaggcca agcggggtgc 60
tgcgccgcgg cgattgaaga tctgagctgc ccggatctgt atctgaaccg cgagttgagc 120
tggctgaaat tcaacgccag ggtgcttgac caggcgctgg atccgcgttt tccgctgctg 180
gagcagttga aatttctggc tatttttcac aataacctgg atgaattttt catggtccgg 240
gtggcgggca tcgtgcagca gcacaagaac ggtctgccct gcggcacgcc ggacaagctg 300
cgcccggccc gccagctggc ggaaatccgc aagcgggttc tggtcctgca ggaaccagcc 360
tataagcact ggaaagaact ttcacgccag ttggctaaaa aaggcgtgcg cttccggcgc 420
tacagccagc tcacggaaaa acagcgtaaa tttctggatg attttttcca taccgaagtc 480
tatccggtgc tgacgcccca ggccattgat ccggcccatc cctttcccac catttccaat 540
ctgagcatca actttatcgt ccagctccgg tgcccggaca ataccatccg ttttgcccgg 600
ctgcgctgcc ccagcaatgt ttcgcgtttc gtcttcgtgc cgcgcaccaa ggcggccaag 660
gattatgtct gcctcggcct gtccagcaac ctgcgcgaca cggacgtgat tctgctggag 720
gatctgatcc gccagtatct ggaaaccctg ttttacggca acaaaattct ggcctgcggc 780
ctgttccgga tcacccgcaa tacggacctg gagcttgccg aggaagaagc cgacgacctg 840
ctggaagcta tcagggacct ggtggaccag cgccgcttcg gcgatgtggt gcgcctggag 900
ttcgccagcg gggtgaatcg catgctggtt gattttctgg cgcggcatct ggtggtgggg 960
ccgtttcaaa tctacaagat ccgggggccc ctggcttttt cccagatgtt gccgttttac 1020
ggcgtggaca ggcccggcct caagctgccg ccgcagcacc cccgtcag 1068

<210> SEQ ID NO 140
<211> LENGTH: 525
<212> TYPE: DNA
<213> ORGANISM: Desulfovibrio
<220> FEATURE:
<221> NAME/KEY: misc_feature
<223> OTHER INFORMATION: Equivalent gene for Cluster 28

<400> SEQUENCE: 140
ctgtccggcg cggcgggtgg tccgcgcgtg gaagtgagcc ggggaccctg gaacaaggtt 60
tatctgggca tttcccttcc cgcgcccggt ctgcgcgacc tgcgcgctgt ggatctggac 120
gtgctgagct atctgctcgg cggcgacggc acctcgacct tctaccgcaa gtacaagtat 180
gaaaagcaac tggtggacgg catcagcgtg gacaatatga gtctggcccg cgcgggcctg 240
ttgaccatca ccgcccagct ggacgccgac aagctggaac ctttctggca ggagctgacc 300
agggatctgg ccggattgac ggccaaggac ttcagcgccg acgccgtgcg ccgggccaag 360
ttcaatctgg aggacagcat ggaccgggcc ggggaaaccc tcaacggtct ggcatcctgg 420
aagggaacca tccagtttga tctgggcggg gagcaggggg agcgcaacat gcgtttcgcc 480
cagcgcaatg tggatgaaaa tcagttgcag aatgccgtca gccag 525

<210> SEQ ID NO 141
<211> LENGTH: 501
<212> TYPE: DNA
<213> ORGANISM: Faecalibacterium
<220> FEATURE:
<221> NAME/KEY: misc_feature
<223> OTHER INFORMATION: Representative gene for Cluster 29

<400> SEQUENCE: 141
gttcgtaacc cggcagtctt cctgctggac gagcctctgt ccaacctgga tgctaagctg 60
cgtacctcca tgcgcaccga gatcatcaag ctgcacaaga agctggctac caccttcatc 120
tacgttaccc acgaccagac cgaggctatg accatgggcg accgtatcgt ggttatgaag 180
gatggcatca tccagcaggt cgataccccg cagaacctgt acgatatgcc ctgcaatatg 240
ttcgttgcag gcttcatcgg cagcccccag atgaacttcc tggacggcac cctgatcaag 300
aagggcgagt tgtacggtgt tgatctgggc ggcgatgtga tccccctgcc caaggagaag 360
accgctgacg gcaagctgga ttcctacgtt ggcaagaaga tcaagatggg catccgtccc 420
gaggatatcg atgacgagcc cgagtttatg gcaaagcaca ccgactgcca gctggatgct 480
aaggtcgatg tttccgaaat g 501

<210> SEQ ID NO 142
<211> LENGTH: 582
<212> TYPE: DNA
<213> ORGANISM: Faecalibacterium
<220> FEATURE:
<221> NAME/KEY: misc_feature
<223> OTHER INFORMATION: Equivalent gene for Cluster 29

<400> SEQUENCE: 142
gggacgattc ttgctctcac ctttttcgct gcgtttcgca attttcacat ttcaatctgc 60
tcgcagattg ttgacaagct gcgcttgacc cgatactata aaggcaagtc gaatacacgc 120
caaggaggtg caaccatgac cgccgtaatc tacgcccgct attcatccga cagccagcga 180
gaagcgtcca ttgagggaca gctgcgcgac tgcaaggact acgccgagaa gaacggcatc 240
accgtggtcg gcacctacat tgaccgtgcc tactctgcca aaacggatga ccgcccagac 300
tttcagcgga tgatcaagga cagcggaaag aaaatcttcg acgtagttct ggtctggaag 360
ctcgaccgtt ttgcccgaaa ccgctacgat gccgtgaact acaagtacca gctggaaaag 420
aacggtgtcc atctggtgtc tgctatggaa cccatctcgc aggggcctga aggcattatg 480
gtggagagta tgctgatcgg catggcggaa tactattccg ccgagctcgc cctgaaagta 540
gcgcgcggtg agcgcgaaaa cgccctccag tgcaagtaca ac 582

<210> SEQ ID NO 143
<211> LENGTH: 453
<212> TYPE: DNA
<213> ORGANISM: Faecalibacterium
<220> FEATURE:
<221> NAME/KEY: misc_feature
<223> OTHER INFORMATION: Equivalent gene for Cluster 29

<400> SEQUENCE: 143
atgcgtcaac tcatcattgc acgaaaagat ctgcagatgt ctcccggtaa gctggcggcg 60
cagtgctgcc acgcttcgct ggcattcctc accgacccca tcggtatggg acagggcgtg 120
gaacccatcg agaaagacgg agaaattacc ggctatcggg cagaaatcat gttggagaaa 180
gcaacctatg aagaatggtt cgatggctct tttaccaaaa ctatctgcgg ggcaaagaac 240
cgcaatcaac tgctgaaagc aaagacaatt gccgaggaat tgggccttgt ggaaaacaaa 300
gacttcttcc ttatccggga tgcctgccac accgagctgg agccggaaga atttgatgaa 360
aacggagaag gcatgaccct gacctgcatc ggtttccgcc cgctgccgga tgaaattgca 420
catcagatca gccataaatt tcatttgtat tga 453

<210> SEQ ID NO 144
<211> LENGTH: 1134
<212> TYPE: DNA
<213> ORGANISM: Faecalibacterium
<220> FEATURE:
<221> NAME/KEY: misc_feature
<223> OTHER INFORMATION: Equivalent gene for Cluster 29

<400> SEQUENCE: 144
atgaaactac tcaaacaatt cattcagcag gaaacggtcc tcaccgcagc cgctgtgctg 60
gccgttgtct ccgccttctt tgttctgccg gatgcgcagt atctcggcta catcgacctg 120
cgcacgctgg cgattttgtt ttccctgatg acggtcatgg ccgggctgcg gcggcagggc 180
ttttttgatg gactgggccg ggcattgctg tcccgtaccc acagcacctt tcagctgacg 240
ctggtactgg tcgggctgtg ctttttcgga agcatgttca tcaccaacga tgtttccctg 300
ctgaccttcg ttccctttac gttcgtggtt ctgagccgtc tgggagcgga tgtccgccgc 360
tcccttctga tcccggtggt ctgtatgcag accattgcgg caaaccttgg cagtatgctg 420
acccccatcg gcaacccgca gaacctctat ctttacggaa aaagcggcat gagcatcggg 480
ggatttgttc ttcttatgct gccctacacc ctggtctctc tgctcctgct gctggcttgg 540
gcagcgctgg tctgccggaa agcctctgcc gccctctccg tggacgagct tgtttcttct 600
tctgcatctc agggagatca gaagatcatc ctgctgtatc tggttctgtt tgcaatctgc 660
ctgctggccg tgatccgggt actgccctat ggcattgcct ttgccgctgt actcgtctgc 720
gttctttttg cagacccgca caccttacgg gcagtggact attccctgct tttgaccttt 780
gtggcttttt tcatcttcat tggcaatctg gggcgcattc cggccttttc cggctggctg 840
caggagtttc tgaccggccg ggaagttctg gtggcggttc ttgcttcgca ggtcaccagt 900
aatgttcccg ccgccctgct gctgtccggg ttcacggcag agacacaagc cctcatcatc 960
ggcaccaatc tgggaggtct tggcactttg atcgcatcca tggccagtct tatttcctac 1020
cgacagatcg cacgggagct gccacagggg aagaagcagt attttgggct gttcaccctg 1080
tccaacctga tttttcttgc gatcctgctg ggtgtgtggt ttttgctccg ctga 1134

<210> SEQ ID NO 145
<211> LENGTH: 471
<212> TYPE: DNA
<213> ORGANISM: Faecalibacterium
<220> FEATURE:
<221> NAME/KEY: misc_feature
<223> OTHER INFORMATION: Equivalent gene for Cluster 29

<400> SEQUENCE: 145
atgcctagaa gaggtaacat tgctaagcgc gatgtcttag ctgatcctat ttacaattcc 60
aagatggtca cccgcctggt caacagcgtc atgctggatg gcaagaaggg cgtcgctcag 120
aagatcgttt acgaagcttt ctccatgatt caggaaaaga ccggcaacga tcctctggag 180
actttcgaga aggcgatgga gaacatcatg cccagcctcg agtgcaagac ccgccgtgtt 240

```
ggtggcgcta actaccaggt tcccctggag gtcagccccg ctcgccgcga gactctgggt    300

ctgcgctggc tgactgccta cagccgcacc cgtggtgaga agaccatggc acagcgtctg    360

gctgctgaga tcatggatgc tgccaacaac actggtaacg ccgtgaagaa gcgtgaggat    420

actcacaaga tggcagaggc taacaaggct ttcgctcatt tccgttattg a             471


<210> SEQ ID NO 146
<211> LENGTH: 672
<212> TYPE: DNA
<213> ORGANISM: Escherichia
<220> FEATURE:
<221> NAME/KEY: misc_feature
<223> OTHER INFORMATION: Representative gene for Cluster 30

<400> SEQUENCE: 146

gtggataagg ttttagattc agccatcctt tcttcggcaa ataaaagaaa gggtatcctt     60

gctattggcg cacatcctga tgatatagaa ttgggctgtg gcgcgtcgct tgctcgtctt    120

gcgcaaaaag gaatttatat cgcagccgtg gtgatgacta ccggcaactc tggcacagat    180

ggaataatcg atcgccatga agaatcgcgc aacgccctaa agatattagg gtgccaccaa    240

actattcatc ttaattttgc tgacacccgc gcgcatttac agctcaatga tatgatttcc    300

gccctggaag atatcattaa aaatcaaatt ccttctgatg ttgaaatcat gcgggtatat    360

accatgcatg atgccgaccg ccatcaggat catctcgctg tttatcaagc ttcaatggtt    420

gcctgccgca ctattccaca aattctcggc tacgaaaccc cgagtacctg gctttcattt    480

atgcctcagg tttttgaatc cgttaaagaa gaatatttca cagtcaaact tgctgcatta    540

aaaaaacata aaagccagga acgacgcgat tatatgcgtc atgatcgcct gcgtgcagtt    600

gcacaatttc gcgggcaaca ggtcaatagc gatctgggtg aaggctttgt aattcataaa    660

atgattcttt ga                                                        672


<210> SEQ ID NO 147
<211> LENGTH: 558
<212> TYPE: DNA
<213> ORGANISM: Escherichia
<220> FEATURE:
<221> NAME/KEY: misc_feature
<223> OTHER INFORMATION: Equivalent gene for Cluster 30

<400> SEQUENCE: 147

atgagtgatg agggactggc gccaggaaaa cgcttgtcgg aaatccgcca gcagcagggg     60

ctttcacaac gtcgtgccgc cgaactctcc gggctgactc acagtgctat cagtacgata    120

gaacaagata aagtcagccc tgccatcagt acgctgcaaa agctgctgaa ggtgtatggt    180

ctgtcactct cggaattctt ttccgagccg gaaaaacctg atgagccgca ggtcgtcatt    240

aatcaggacg acttaattga gatgggcagt cagggtgtgt caatgaagct ggttcataac    300

ggtaacccga atcgcacgct ggcgatgatc tttgaaactt accagccggg cacaaccact    360

ggggaaagaa ttaagcatca gggtgaggaa ataggcactg tactggaagg tgaaattgtt    420

ctgacgatta atggtcagga ttaccacctc gtcgcggggc aaagttatgc cattaatacc    480

ggcatcccgc acagtttcag taatacgtcg gcaggtattt gccgaattat cagcgcccat    540

acgcccacca cgttttaa                                                  558


<210> SEQ ID NO 148
<211> LENGTH: 2019
<212> TYPE: DNA
<213> ORGANISM: Escherichia
```

<220> FEATURE:
<221> NAME/KEY: misc_feature
<223> OTHER INFORMATION: Equivalent gene for Cluster 30

<400> SEQUENCE: 148

```
atggatgccc tgcaattatt aacctggtca ctgatcctct atctgtttgc cagtctggct     60
tcgctgtttt tactcggtct ggacagactg gctattaagc tttccggcat cacatcgctg    120
gtgggtggcg tgattggcat catcagcgga attacgcaat tacatgcagg cgtaactttta    180
gtcgcccgtt ttgccacgcc ttttgacttt gccgatttaa cactgcgaat ggatagcctc    240
tcggcattta tggtgatggt tatctccttg ctggtggtgg tttgttcgct ctattcattg    300
acttatatgc gcgaatacga gggtaaaggc gcggcggcga tgggcttctt tatgaatctt    360
ttcatcgcat cgatggttgc cctgctggtg atggacaacg ctttttggtt catcgtgctg    420
tttgaaatga tgtcgctgtc ttcctggttt ctggtcattg ccaggcagga taaaacgtcg    480
atcaacgctg gcatgctcta ctttttatc gcccacgccg gatcggtgct gattatgatc    540
gccttcttgc tgatggggcg cgaaagcggc agcctcgatt ttgccagttt ccgcacgctt    600
tcactttctc cggggctggc gtcggcggtg ttcctgctgg ccttttcgg ttttggcgcg    660
aaagccggga tgatgccgtt gcacagctgg ttgccacgcg ctcaccctgc cgcaccatcg    720
cacgcttcgg cgttgatgtc tggcgtaatg gtcaaaatcg gtattttcgg catcctgaaa    780
gtagcgattg atctgctggc gcaaacgggt ttgccgctgt ggtggggcat tctggtgatg    840
gcgatcggcg caatctccgc gctcctgggc gtgctgtatg cgctggcgga acaggatatc    900
aaacggctgc tggcctggag caccgtcgaa aacgtcggca ttattttgct ggcggtcggt    960
gtggcgatgg tcggtctgtc actgcacgac ccgctgctca ccgttgttgg actgctcggc   1020
gcgctgtttc atctgctcaa ccatgcgctg ttcaaagggc tgctgtttct cggcgcgggt   1080
gcgattattt cgcgtttgca tacccacgac atggaaaaaa tgggggcact ggcgaaacgg   1140
atgccgtgga cagccgcagc atgcctgatt ggttgcctcg cgatatcagc cattcctccg   1200
ctgaatggtt ttatcagcga atggtacacc tggcagtcgc tgttctcact aagtcgtgtg   1260
gaagccgtag cgctacaact tgcgggtcct attgctatgg tgatgctggc agtcactggt   1320
gggctggcag taatgtgctt cgtcaaaatg tacggtatta ctttctgtgg cgcgccgcgc   1380
agtacacacg ctgaagaggc acaggaagtg ccaaatacga tgatcgtcgc catgctactg   1440
ctcgcggcac tctgcgtatt cattgcgctt agtgccagtt ggctggcacc gaagataatg   1500
cacattgccc atgcgtttac caatacccct cccgtcactg tcaccagcgg aatagcactt   1560
gtacccggca cgtttcatac acgggtcact ccctcattac tgttgctgtt actactggcg   1620
atgcctttgc tgcctggcct ttactggctg tggtgtcgtt cgcgccgcgc agcgtttcgt   1680
cgcactggag atgcctgggc atgcggctac ggctgggaac atgcgatggc cccgtcaggc   1740
aatggcgtga tgcagccgct gcgtgtggtc ttttgtgcgc tatttcgtct acgacaacag   1800
ctcgacccta cgctgaggct gaacaaaggt cttgcgcacg tcaccgccag ggctcagagc   1860
acagaaccct tctgggatga gcgggtgatc cgcccccatcg tgagcgccac ccaacggctg   1920
gccaaagaaa tacagcatct gcaaagtggc gactttcgtc tctattgcct gtatgtggtc   1980
gccgcactgg ttgtgctgct aatcgctatt gccgtctaa                         2019
```

<210> SEQ ID NO 149
<211> LENGTH: 438
<212> TYPE: DNA
<213> ORGANISM: Escherichia
<220> FEATURE:
<221> NAME/KEY: misc_feature
<223> OTHER INFORMATION: Equivalent gene for Cluster 30

<400> SEQUENCE: 149
atggacaaca aaatatcaac ctattctccg gcattcagta ttgtgtcatg gatagctctc 60
gttggtggta tcgttaccta tctgttaggg ctatggaatg cagagatgca gttaaatgaa 120
aaaggatatt attttgccgt actggtatta ggactgtttt ctgcggcgtc ttatcaaaag 180
accgttcggg acaagtatga aggcataccg accacctcca tttattatat gacctgcctg 240
actgtcttta ttatctctgt tgcgttactg atggtaggtc tgtggaatgc gacgttatta 300
ctcagcgaga aaggttttta tggactggct ttcttcttaa gcttgtttgg tgcagtagcg 360
gtgcagaaga atattcgtga tgccggaata aacccaccaa aagaaacaca gattacccag 420
gaagaataca gcgaataa 438

<210> SEQ ID NO 150
<211> LENGTH: 666
<212> TYPE: DNA
<213> ORGANISM: Escherichia
<220> FEATURE:
<221> NAME/KEY: misc_feature
<223> OTHER INFORMATION: Equivalent gene for Cluster 30

<400> SEQUENCE: 150
atgcctggaa cggaaaaaat gaaacatgtc agtttgactc tgcagcttga gaatgacctg 60
aaacatcagc ttagtattgg cgcactaaaa cctggcgcac gcctgattac taaaaatctg 120
gcggagcaat taggtatgag tattacacct gtgcgtgaag cattattacg tctggtttcg 180
gtgaatgcgc tttctgtcgc accagcgcaa gcatttacag ttccggaagt ggggaaacgt 240
caattagacg aaatcaatcg gatccgctac gagctggaat taatggcagt tactctggct 300
gttgaaaacc tcaccccgca agacctggcg gaactcgagg aattgctcga gaaattacag 360
caggcgcaag aaaagggcga catggaacaa atcattaatg cgaacaggct atttcgctta 420
gcaatttatc atcgttcaaa tatgcccatc ctgtgtgaga tgattgagca actgtgggtc 480
aggatgggac ctggtttaca ttatctttat gaagcgatta atccagcgga attacgggag 540
cgtatagaaa actatcgtct attactcgcc gcgttaaaag caaaagacaa agagggatgc 600
agacattgtc ttgctgaaat tatgcaacaa aatattgcta ttctatacca gcaatacaat 660
cgttaa 666

<210> SEQ ID NO 151
<211> LENGTH: 981
<212> TYPE: DNA
<213> ORGANISM: unknown
<220> FEATURE:
<223> OTHER INFORMATION: Representative gene for Cluster 31

<400> SEQUENCE: 151
atggaatgca cgctagcaca taaaagctcc cttgaactat ggtcacatat ggccgaaacc 60
aatgctgcgc ccacatgcta cgaccggacg ctcaagtcca agaagggcgc cgtcggcgtt 120
gcggcgaagg acgttgattt ctggctgaat cgaggaagct tcttcaccga accgcttcac 180
attgccgtcg ggtctccatc cgagcgctgc cgcgtcttgc gctgcgtttc ccacatcgat 240
cgccaactcg gcaacaaagg cacggtatgg ggaattgccc ctaagcttgc cacagtttca 300
ccggcaatgt gcctggcgca gttcgccggc gagctgcctc tcgcgcaact cactgagctc 360

```
gcatgcgccc tgagcggcaa ctaccgcttc gcctccaaac ccgaagacgt tgtcacctcg    420
gcagtaccgc tcacatcgtt gcgagagatg cgtgcgttcc ttcacgctca tcaacaaatt    480
cgtggagcat cgaaggcgct cagggccatc gatctcgcca tcgaccacct aggctccccc    540
tatgagacca ttctctacct gtttctctgc ctgccccgca agcttggagg ctacggcctc    600
cccaagcccg ttgccaacca accgatcgcg cccaagtccc gcgaagcgca ccttgtcgcc    660
cagcacaatt tctacccgga tttattctgg cccgacaagc agctcatcgt cgaatacgac    720
agcttcaagc accacagcac gccgaaaaag acagagcatg acgcccggag gcgtaacgat    780
ctcgggtcca tcggctatcg cgtcatgatc gccaatcgtt ccatcgtttc ttccgccgca    840
ctgttttccc aattcgcaga taacgtccgc cgtgaacttg gcgtgcgaag ccgtccggag    900
acggcgcatt gccgagatag ccgaatgcag cttcgcaggt tgcttcttgc acccgattcg    960
attgcggagt tctggaggta a                                              981
```

<210> SEQ ID NO 152
<211> LENGTH: 1395
<212> TYPE: DNA
<213> ORGANISM: unknown
<220> FEATURE:
<223> OTHER INFORMATION: Equivalent gene for Cluster 31

<400> SEQUENCE: 152

```
atggaaacct tcgtcatgga gaagttcaac ggtggcgtcg tgcgtgacga tcttgcaggc     60
gtcaactctc gcttgcagca ggagagcggc tatgaaatcg acgcaattgc ttatttgcga    120
gatatggatc attacgctgc gggccaatgc aatctcgcgt tgcacaaggt ctggcttgag    180
cgatcgggcg agaccatcga ctggtacgaa aacgttctct cctcttacgg tatcgcgctt    240
tggcatgagg ctgccgagga aaagcatgaa gtcaactacc gacattgggc tacagggcat    300
tctcccgcct ggccagtcga tggatcgctc gacgggttca ctgtgctgac tgactacgca    360
gagaagacgg gccatgtaac gttccgctac caaacgccca tggtgagcct caccgtcgaa    420
aacgatcgcg tgaccggtgc tatagggcag ggcgctgacg gctacattcg tgtcaacgca    480
agcaagggcg ttcttgtatg cacaggcggt tacgccgcga atctcgacct tcttaagcag    540
ctccagcctc acacgaccag catttacgct tataactcag cgcagccggg ctgtgaggga    600
gacggcataa aggcgtgcct tcgcgttggg gcaaaaatgg acgaaacaca ctctagcatg    660
cttttcgacc gagcaagcgt tcccgccgac tccttgggag gcgccgactg cggtactgcc    720
atggtattct ggatgggaag ccaaccctgg ctgaaagtca atctcaatgg cgagcgcttc    780
tgcaacgagt ccggcaccta tgacttcatc ctgcacgccg atgcatcgca accaggaaat    840
atccacgtgt gcctctggga tgcagactgg cagacctacg ctcaacagtt cgacatgcat    900
ggctgctcgc gcatgttccc ctttgataat ggagcggctc cgaacctacc gatcgaagtg    960
gtgacggcca tgaacgagga ggcacttaaa gccggacaca ttcagcaagc cgacaccatc   1020
gaggagctcg ccgaaaagct tggtcttcct gcagaagccc tcgcgaaaac ggtggaacga   1080
aacaaccaga attacgacaa ccagcgcgat gacgacttcg gcaaggagcc attccggctt   1140
tcccctgtac gcaaacctcc cttcttcggc gtacgtacca caggcgctct gctgtgcacc   1200
atggacggca tcgtgataaa cacccagggt caagccctgc gcgaagatgg aagcgccatt   1260
gagggcctat atgtcacagg caacgattcc ggaggatact attccatgac ttatccgaac   1320
ctgtcgaccg gcaacgcttg cggcaggaca gtaactttcg cacgaatgat tgctcagaat   1380
ctggctgccc agtag                                                    1395
```

<210> SEQ ID NO 153
<211> LENGTH: 1689
<212> TYPE: DNA
<213> ORGANISM: unknown
<220> FEATURE:
<223> OTHER INFORMATION: Equivalent gene for Cluster 31

<400> SEQUENCE: 153

```
ccccgccgcg acttcctcgg ccttggcgcc gtggccgccg tgggggccat gggcttggca     60
ggatgcgcgc cccagacttc ggccgagaaa gacctcggag caactggtgg cgcagccgcg    120
acgcccgaag ccgcagcggt cgcggaagac tggcttggcg cagagcccga agtcgccgag    180
agcgacatcg tcgaaaccct cgacaccgac ttcctcatca ttggcgccgg cacggccggc    240
cttgccgctg ctggcgcggc ggccgatttg ggcctcaact tcattgcctg cgataagagc    300
aaccaggttc ccgagacccg cgagtacctc ggcggcgtag acaccgctta cgccaaggcc    360
aacaacgtga ccatcgaccg gccgaagctc ttgaacgagc tgacgcgcta cgcctccggc    420
aagtgcaacc agaagctcat caagcgttgg atcgacgatt cggccgaata cattgattgg    480
gtgaccgagg taatgaaaga cgccggcaaa gaggtcatgc tggacatgcc gcccgagcac    540
gccacgggcg gtaccgacta ctatgtgccc tatgtgcagc acctgtggga gccctcttac    600
gtcccgccca cgcgcaacga cgtcatcgcc gagcgcttgt ccggccaagg tcacgacatt    660
ctgttcgagc ataagatggt gaagcttgtt cacgccgatg gcaaggtgac gggcgctatc    720
ttcgaaacca aagacggcat gaagcagatc aatgctaaaa acaccctgct cgccacgggc    780
ggctacgcgg ccaaccccgt gatgatgacc gccctgcagc cctccgctgt agcctgctgc    840
accgcctcca gcttcaatcc cacttgcaca ggcgacggca tcaaggcggg gctgtgggcc    900
ggagcctcta aagacaagga cgccgccccc atggtcttcg accgtggggc cgtggctcct    960
ggcgtggatg ccggctacga gggcgaaggc gaaggcgcca tgttccgtgg cagcatcttc   1020
caagagaaca tcggcagcca gcccttcatg aaggtgaatc gccgcggtca gcgcttcgcc   1080
aacgagtcca ccccctacga cttcatctgc ttcgccgcta cctaccagcc cggcggggtg   1140
tggtgccagg tctacgacag caacatgatg gacgatatgc tgcgcttcga aaccgtcggc   1200
tgctcgcgcg tggtgcccta catcgagatg ggcatgacct acgacgagta caccgccgct   1260
tcccaagagt ccggcatcct catgaaagcc gacaccattg aagagttggc cgacatgctc   1320
ggcttcaccg gccaggacaa ggataacttc ctcgccgagg tggagcgtta caacggcttc   1380
tacgacaacc aggtggacga ggacttcggc aaggaggcct accgcctctc cgccatccgc   1440
cagccccccct tctacggttg ctggttcggc ggctcgctgc tcaccacgat cgacggtctg   1500
cgcattaacg agaactgcca ggtgctcgat ccggagctga acgtcatcga gggcctgtat   1560
gccgctggtg acgtatccgg cagcttcttc tcgggtaact atcccgagta tgtcgtaggc   1620
gtggcctgcg gccgcagctc cgttgagggc cgtcacgtgg cgaagctgct ctccggcgcc   1680
gctcaatag                                                           1689
```

<210> SEQ ID NO 154
<211> LENGTH: 456
<212> TYPE: DNA
<213> ORGANISM: unknown
<220> FEATURE:
<223> OTHER INFORMATION: Equivalent gene for Cluster 31

<400> SEQUENCE: 154

-continued

```
gagcctcatg gcgataccgt gtggcgcgtt tgccttacgg cgctttgtcg ccatgcggat     60

gccgaggacg cgttccagaa ttcatttcta aaatacgcac tcgcagatga tgttcagttt    120

cgtgaagagg aacatcgcaa ggcgtggttg attcgcgttg cttcgaacac gtgccgcgat    180

atgcggcggg cggctgcgag taagaatgtg ccgcttgatg agacctcatt cgaatcgctc    240

gcgtcccgcg atgaggaggc tcagcccgat tcgcgtgtga aagaagtgct cgatgccatg    300

agcgacctcg atgaccctcc ccgcactccc gtgtatcttg ccctgtacga gggctacacg    360

gctccggaga tcgcctcgat gctcgacgtc cccgtgaata ccgtgtattc ctggattgcc    420

cgcggcaaaa agacgctgaa ggaggccctc tcatga                              456


<210> SEQ ID NO 155
<211> LENGTH: 510
<212> TYPE: DNA
<213> ORGANISM: unknown
<220> FEATURE:
<223> OTHER INFORMATION: Equivalent gene for Cluster 31

<400> SEQUENCE: 155

atgagcatta atcgagtgat catcagcggc aatctgaccc gtgaccccga gctgcgcagc     60

acccagtccg gcatggacgt catgagcttc ggcgtggccg tgaacgaccg tcgtcgtaac    120

ccccagacca acgagtggga ggattatccg aacttcgttg actgcaccat gttcggcaat    180

cgggctcgca gcctgcacca gtacttgtcc aagggcacca aggtggccat cgagggcaag    240

cttcgctgga gccagtggga gcgcgatggt cagaagcgca gcaagctcga agtcatcgtt    300

gacgagctcg aattcatgtc gagccgcaac ggcggcggcg ctcagtccta cggcggcgat    360

ttcggcggca accagggcta tgctccggcg gctccggcct atagtgctcc ggctcccatg    420

cccgcaccgg ctccggcgcc cgcgcccatg cccgctgcac cggttatcga cgcttcctct    480

tccgtgtacg atgatgacat tccgttttaa                                     510
```

GENE SIGNATURES OF INFLAMMATORY DISORDERS THAT RELATE TO THE LIVER

The instant application contains a Sequence Listing which has been submitted electronically in ASCII format and is hereby incorporated by reference in its entirety. Said ASCII copy, created on Apr. 13, 2015, is named Listing.txt and is 223,525 bytes in size.

SUMMARY OF THE INVENTION

This invention is related to the area of characterization of inflammation in relation with the gut microbiota, in metabolic and autoimmune disorders. In particular, it relates to the identification of gene signatures which can be used as a marker predictive of inflammation associated diseases, such as liver-related metabolic disorders, in particular to the evolution of benign steatosis towards its most severe forms (steatohepatitis and cirrhosis) or autoimmune disorders, in particular inflammatory bowel diseases (Crohn's and Ulcerative Colitis). These gene signatures can therefore be used as a means of diagnosis, prognosis, stratification for drug studies, for monitoring patient and for assigning an appropriate treatment.

BACKGROUND OF THE INVENTION

Systemic and local inflammation is a pathological feature observed in many disorders, and in particular metabolic disorders and autoimmune disorders. Low-grade inflammation is an independent risk factor of metabolic diseases and associated co-morbidities such as heart disease, stroke and diabetes. Inflammation predates the detection of insulin resistance and therefore may be a good predictor of diabetes. Chronic (persistent low-grade) and acute (high-grade) inflammation is a key characteristic feature of autoimmune disorders, such as inflammatory bowel disease.

Metabolic syndrome is also known as Syndrome X, metabolic syndrome X, cardiometabolic syndrome, insulin resistance syndrome, CHAOS or Reaven's syndrome. It is generally believed to be a combination of disorders that affect a large number of people in a clustered fashion. The symptoms and features of the syndrome include at least three of the following conditions: diabetes mellitus II, impaired glucose tolerance or insulin resistance, high blood pressure, central obesity and difficulty in losing weight, high cholesterol, combined hyperlipidemia, and fatty liver. On a physiological basis, insulin resistance appears to be responsible for the syndrome. However, insulin resistance can be defined in a myriad of different ways, including impaired glucose metabolism, inability to suppress lipolysis in the tissues, defective protein synthesis, altered cell differentiation, abnormal cell cycle control or proliferation, all of which being implicated in the liver and cardiovascular disease associated with metabolic syndrome.

Although certain bacterial associations have been examined for these conditions, the role of bacterial microbiota in their onset has not been understood yet. And there remains a need for methods for diagnosing, treating, and preventing conditions such as obesity, metabolic syndrome, insulin-deficiency or insulin-resistance related disorders, glucose intolerance, diabetes mellitus, non-alcoholic fatty liver (NAFL), abnormal lipid metabolism, atherosclerosis and related disorders.

Nonalcoholic fatty liver disease NAFLD is the hepatic manifestation of the metabolic syndrome, with insulin resistance as the main pathogenetic mechanism. Non-alcoholic fatty liver disease (NAFLD) represents a spectrum of liver diseases encompassing simple fatty infiltration in liver tissue (steatosis), fat and inflammation of the liver tissue (non-alcoholic steatohepatitis—NASH), and cirrhosis, in the absence of excessive alcohol consumption, viral diseases (HCV, HBV) or other identified etiologies (autoimmune disorders). It is the leading cause of chronic liver diseases in Western countries with a prevalence as high as 30% of the general population. Concerning NASH, studies reported an estimated prevalence of 3 to 5% of the general population. NAFLD is strongly associated with obesity (NAFLD found in more than 90% of obese patients), type 2 diabetes (NAFLD is found in 40% to 70% of T2D patients), and dyslipidaemia. NAFLD may thus be considered as the hepatic manifestation of the metabolic syndrome.

Among the spectrum of NAFLD clinical presentations, simple steatosis has not been associated with liver related morbidity, but NASH was associated with a >10 fold increase risk of liver related death and a doubling of cardiovascular risk. Consequently, NASH is considered as the second most frequent etiology for liver transplant indication, after HCV, representing 18% of patients registered in US transplants list (OPTN).

In fact, both the prevalence and natural history of NAFLD suggest that it is a very common cause of liver disease and that its subtype NASH can progress to cirrhosis. These observations stress out the significant impact of NAFLD in terms of patient health, health-related quality of life and healthcare economics.

Although most patients with NAFLD have steatosis, only a minority progress to more advanced disease, characterized by inflammation and subsequent fibrosis, cirrhosis, and hepatocellular carcinoma. Studies indicate that about 5.4% of patients with NASH develop severe complications of end stage liver disease during long term follow-up. Such progression is probably influenced by genetic and environmental factors, only some of which have been identified. Recognized independent risk factors for progression are age >45 years, presence of diabetes (or severity of insulin resistance), obesity (body mass index >30), and hypertension. The patients who do progress often present late in the natural course of the disease and have substantial liver related morbidity.

There is therefore a need to develop prognosis tests to assess the risk of liver related morbidity for these patients, in particular, to predict the risk of progression from benign fatty liver towards NASH and advanced liver diseases.

Liver biopsy is currently considered as the best tool for assessing degree of severity of the NAFLD, and in particular inflammation and of liver fibrosis. However, liver biopsy is an invasive procedure which is not appropriate or practical outside specialist hepatology practice. Furthermore, it presents drawbacks of interpretation error due to sampling error and to observer variability (Adams L. A. & Feldstein A. E., *Journal of Digestive Diseases* 2011). There is therefore a clear need to develop reliable non-invasive screening tests to efficiently differentiate the patients who have established NASH versus those who have a steatosis only, as well as patients at low risk of progression from those with more aggressive disease.

NAFLD is often asymptomatic and commonly first discovered as an incidental biochemical abnormality identified during routine blood tests. However, the characteristic biochemical changes (e.g., a relatively greater rise in alanine aminotransferase than in aspartate aminotransferase) tend to reverse, and alanine aminotransferase levels fall as hepatic fibrosis progresses. This means that steatohepatitis with advanced disease may be present even in those with relatively normal alanine aminotransferase levels in blood.

Several other methods have been proposed for non-invasive quantification of hepatic fat and inflammation, including magnetic resonance imaging or spectroscopy and blood biomarker panels. However, evidence supporting their use in wider clinical practice is still limited: routine ultrasound imaging of the liver provides a qualitative assessment of hepatic fat content, but sensitivity is limited, particularly when <33% of hepatocytes are steatotic. And, although they offer greater sensitivity for detecting milder degrees of steatosis, magnetic resonance techniques for lipid quantification are often resource intensive and are not yet widely available for routine clinical use. Furthermore, hepatic fat content tends to diminish as cirrhosis develops, and so NASH is probably consequently underdiagnosed in the setting of advanced liver disease.

Hence, no widely accepted, reliable methods are available yet for differentiating simple steatosis from steatohepatitis in routine practice, other than liver biopsy. Consequently, most NAFLD patients remain undiagnosed, and are managed at the primary care level for controlling their underlying metabolic factors (obesity, diabetes, cholesterol . . . ). Patients further progressing towards NASH are identified late in the course of their disease and develop significant liver related morbidity.

There is therefore an urgent need, beyond prognostication, for identification of patients with NAFLD so as to change patient management by (a) providing a greater impetus for modification of diet and lifestyle; (b) guiding drug selection in patients with insulin resistance or diabetes; and (c) allowing specific monitoring strategies to be instituted if cirrhosis is present.

Several therapeutic strategies have been proposed so far to handle the NAFLD patients. However, no drugs are currently approved specifically for treating liver inflammation or fibrosis, the main clinical features of NASH, and many drug candidates failed to demonstrate significant efficacy for treating NASH (reversing established inflammation and fibrosis at histological level). An emerging strategy considers that effective drug treatment should be focused on early onset of NAFLD, to control steatosis and prevent progression to inflammatory stages. This strategy requires effective triage of patients with NAFLD, so that medical care can be tailored to individual's risk of progression towards NASH.

There is therefore also a clear need to develop a screening test to diagnose and clinically differentiate NAFLD suffering patients, for being use as triage test at primary and secondary care level. This test should be additionally non-invasive, and economically acceptable.

The present Inventors identified particular gene signatures which are predictive of the evolution of Non Alcoholic Fatty Liver Disease (NAFLD) towards its most severe forms (hepatitis, cirrhosis, liver cancer). These gene signatures are advantageously assessed in stool samples of the patients. These gene signatures are therefore considered to be the first reliable and non-invasive means of diagnosis, prognosis, and stratification for drug studies of liver-related metabolic diseases. They can also be used for monitoring and assigning appropriate treatments to the thus-diagnosed patients.

Autoimmune disorders arise from an inappropriate immune response of the body against substances and tissues normally present in the body. Inflammatory bowel diseases (IBD), such as Crohn's disease or ulcerative colitis, are among the most prevalent autoimmune disorders. These diseases are detected, staged and monitored by 3 main approaches:

- Clinical evaluation, mainly using composite scores that integrate both patients data as well as patients self-report questionnaires;
- Biological markers, based on blood (ie inflammation markers such as CRP, or platelet count), or feces (ie calprotectin); and
- Imaging tools, including endoscopic exams with or without histologic analysis and magnetic resonance based exams (MRI or MR enterography).

Any of these approaches are filling the needs for new tools to monitor the disease activity and subsequently the treatment regimen in IBD. The tight control of IBD, thought accurate surveillance and treatment adjustment, is nowadays key in the management of such patients because of the recurring and remitting nature of these disorders.

Monitoring clinical symptoms alone is not reliable enough to assess disease activity. Patients self reporting low disease activity often present intestinal lesions during an endoscopic exam. Biological markers, such as fecal calprotectin, are useful, but non specific and their increase is associated with systemic/mucosal inflammation at the late onset of the flare. Endoscopy enables to detect mucosal healing, which is consider as the most robust and reliable sign of disease remission; however, routine repeated endoscopic monitoring is not feasible, because of the required bowel preparation and general anesthesia. New imaging tools, such as MRI has been shown to be effective, but it is expensive, time-consuming, and limited access precludes routine use. The MR Enterography, presented as the most promising approach, implies also bowel preparation and invasive colonoscopy.

In summary, patients and healthcare providers are actively looking for non-invasive tools enabling evaluation of disease activity and monitoring of patients care.

Here, stable patients are defined as patients for whom disease activity is stable over several weeks (patient in a "stable state"). While instable patients (or patient "in an instable state") are patients:

who had their treatment changed or intensified in the following weeks, whose blood tests showed elevated activity in the following weeks, and/or whose self-evaluation showed decreased health

FIGURE LEGENDS

FIG. 1 discloses the repartition of the gene of the cluster 1 in cohorts of the NASH1 study (A and D), NASH 2 study (B and E) or Crohn study (C and F), depending on their health status (simple steatosis (=NS) or NASH—stable or instable for Crohn). Either a global approach (A, B and C) or a threshold approach (D, E, and F) was used, as explained in the examples below.

FIG. 2 discloses the repartition of the genes of the cluster 31 in cohorts of the NASH1 study (A and D), NASH 2 study (B and E) or Crohn study (C and F), depending on their health status (simple steatosis (=NS) or NASH—stable or instable for Crohn). Either a global approach (A, B and C) or a threshold approach (D, E, and F) was used, as explained in the examples below.

FIG. 3 discloses the repartition of the genes of the cluster 19 in cohorts of the NASH1 study (A and D), NASH 2 study (B and E) or Crohn study (C and F), depending on their health status (simple steatosis (=NS) or NASH—stable or instable for Crohn). Either a global approach (A, B and C) or a threshold approach (D, E, and F) was used, as explained in the examples below.

FIG. 4 discloses the repartition of the genes of the cluster 11 in cohorts of the NASH1 study (A and C) or the NASH 2 study (B and D), depending on their health status (simple steatosis (=NS) or NASH). Either a global approach (A, B) or a threshold approach (C, D) was used, as explained in the examples below.

FIG. 5 discloses the low or high relative abundance of the genes of the two clusters 1 and 31 for the NASH1 cohort (A), the NASH2 cohort (B), and the Crohn cohort (C) (circles represent simple steatosis or Crohn-stable status whereas crosses represent NASH or Crohn-instable status).

FIG. 6 discloses the low or high relative abundance of the genes of the two clusters 1 and 19 for the NASH1 cohort (A), the NASH2 cohort (B), and the Crohn cohort (C) (circles represent simple steatosis or Crohn-stable status whereas crosses represent NASH or Crohn-instable status).

FIG. 7 discloses the low or high relative abundance of the genes of the two clusters 19 and 31 for the NASH1 cohort (A), the NASH2 cohort (B), and the Crohn cohort (C) (circles represent simple steatosis or Crohn-stable status whereas crosses represent NASH or Crohn-instable status).

DEFINITIONS

As used herein, the term "inflammatory disease" designates metabolic disorders associated with a systemic change of expression of pro- and anti-inflammatory cytokines. C-reactive protein and adipocytokines (i.e. tumor necrosis factor-alpha (TNF-α), interleukin-6 (IL-6), and adiponectin) have been often observed as the pro- and anti-inflammatory cytokines associated with metabolic disorders. C-reactive protein, fecal calprotectin and cytokines (e. tumor necrosis factor-alpha (TNF-α), interleukin-6 (IL-6), interleukin-8 (IL8) have been often observed as the pro- and anti-inflammatory cytokines associated with inflammatory bowel diseases.

In a preferred embodiment, said inflammatory disease is chosen in the group consisting of: insulin resistance, hypercholesterolemia, impaired glucose tolerance, type 2 diabetes, hypertension, cardiovascular diseases, inflammatory bowel diseases, rheumatoid disorders and liver diseases.

"Liver disease" is also referred to as "hepatic disease". It is a broad term that covers all the potential problems that cause the liver to fail to perform its designated functions. More specifically, it encompasses in the present application all the different stages of liver steatosis, non-alcoholic liver steatohepatitis, liver fibrosis, cirrhosis, liver failure, and liver cancer.

As used herein, the term "Nonalcoholic Fatty Liver Disease" (NAFLD) encompasses the entire spectrum of fatty liver disease in individuals without significant alcohol consumption, ranging from fatty liver to steatohepatitis and cirrhosis.

"Steatosis" is also often referred to as "non-alcoholic fatty liver" (NAFL). It corresponds to the presence of hepatic steatosis with no evidence of hepatocellular injury in the form of ballooning of the hepatocytes or no evidence of fibrosis. It will be also designated hereafter as "simple steatosis". On a medical point of view, steatosis occurs through several mechanisms. First, expansion and inflammation of adipose tissue results in adipose insulin resistance and increased lipolysis and thereby in an elevated flux of free fatty acids into the liver. Second, an impaired hepatic fatty acid oxidation and a decrease in proteins inducing lipid oxidation, e.g., adiponectin, results in further accumulation of fat within the liver. Third, increased hepatic de novo lipogenesis driven by hyperinsulinemia and increased carbohydrate intake elevate the hepatic fat content. Fourth, impaired VLDL (Very Low-Density Lipoprotein) secretion exacerbates this process. The overwhelming of lipid oxidation capacity eventually occurs resulting in the generation of reactive oxidative species (ROS), gut-derived signals (e.g., bacterial endotoxins, short-chain fatty acids), inflammatory cytokines, and an imbalanced release of adipokines that then may result in the advance of this condition toward more severe stages such as steatohepatitis, fibrosis, and cirrhosis.

It is interesting that, in the natural history of NAFLD, about 60% of the subjects have no change in their liver histology parameters during a follow-up period of 3.5 to 11 years and 13% even have an improvement. On the other hand, within the same period of time, 28% of the subjects have a progression to liver damage as steatohepatitis, fibrosis, or cirrhosis (Angulo, *N Engl J Med.* 2002 Apr. 18; 346(16):1221-31). This has resulted in the fields of gastroenterology and hepatology that the terms "benign" and "malignant" are being used to separate these hepatic consequences of NAFLD.

Therefore, the term "benign steatosis" will be used in the present application to designate a condition in which hepatic steatosis is present, but there is a minimal risk (if any) that this steatosis will progress into steatohepatitis, fibrosis, or cirrhosis. In other words, a patient suffering from "benign steatosis" as meant herein is predicted (or prognosed) to have no change in his liver histology parameters.

On the contrary, the term "inflammatory steatosis" will be used in the present application to designate a condition in which hepatic steatosis is present, but there is a risk that this steatosis will progress into steatohepatitis, fibrosis, or cirrhosis. In other words, a patient suffering from "inflammatory steatosis" as meant herein is predicted (or prognosed) to suffer from a liver steatohepatitis, a liver fibrosis, cirrhosis, liver failure or a liver cancer within the next months or years.

Non-alcoholic steatohepatitis (NASH) is diagnosed in the presence of hepatic steatosis and inflammation with hepatocyte injury (ballooning), with or without fibrosis. This stage can progress to cirrhosis, liver failure and rarely liver cancer. As used herein, the term "steatohepatitis" encompasses non-alcoholic steatohepatitis as well as alcoholic steatohepatitis.

NASH cirrhosis is diagnosed in the presence of cirrhosis with current or previous histological evidence of steatosis or steatohepatitis whereas cryptogenic cirrhosis is diagnosed in the presence of cirrhosis with no obvious etiology. Patients with cryptogenic cirrhosis are heavily enriched with metabolic risk factors such as obesity and metabolic syndrome.

NASH-associated fibrosis is diagnosed in the presence of hepatic steatosis and inflammation, with fibrosis. Fibrosis corresponds to the formation of excess fibrous connective tissue in a liver in a reparative or reactive process. "Scarring" designates confluent fibrosis that obliterates the architecture of the underlying organ or tissue.

Cirrhosis is a consequence of chronic liver disease characterized by replacement of liver tissue by fibrosis, scar tissue and regenerative nodules (lumps that occur as a result of a process in which damaged tissue is regenerated) leading to loss of liver function.

Liver failure designates the inability of the liver to perform its normal synthetic and metabolic function as part of normal physiology. Two forms are recognized, acute and chronic. "Acute liver failure" is defined as the rapid development of hepatocellular dysfunction, specifically coagulopathy and mental status changes (encephalopathy) in a patient without known prior liver disease, whereas "chronic liver failure" usually occurs in the context of cirrhosis.

"Liver cancer" designates a malignant tumor that grows on the surface or inside the liver. Liver cancer should not be confused with liver metastases, which are cancers that originate from organs elsewhere in the body and migrate to the liver.

The term "Inflammatory bowel diseases" herein designates in particular the Crohn disease and ulcerative colitis.

Of note, inflammatory bowel diseases or rheumatoid disorders belong to "auto-immune disorders".

As used hereafter, "diagnosing" a disease or a condition in a subject means to identify or to detect that the said subject is actually suffering from said disease or said condition. By contrast, "prognosing" a disease or a condition in a subject hereby means to predict that the said subject will suffer from said disease or condition.

In particular, it is hereby contemplated that "diagnosing steatosis" in a subject means identifying or detecting that said subject has a simple steatosis (and not a NASH). By contrast, "prognosing steatosis" in a subject means that said subject actually has a benign steatosis which will remain stable.

More particularly, it is hereby contemplated that "diagnosing steatohepatitis" in a subject means identifying or detecting that said subject suffers from steatohepatitis (with or without fibrosis). By contrast, "prognosing steatohepatitis" in a subject means that said subject is likely to develop a steatohepatitis (with or without fibrosis), for example because it has a inflammatory steatosis. In other words, the said subject has a risk of suffering from steatohepatitis (with or without fibrosis).

More particularly, it is hereby contemplated that "diagnosing fibrosis" in a subject means identifying or detecting that said subject suffers from steatohepatitis with fibrosis. By contrast, "prognosing fibrosis" in a subject means that said subject is likely to develop a liver fibrosis, for example because it has an inflammatory steatosis or an established steatohepatitis. In other words, the said subject has a risk of suffering from fibrosis.

By "the subject has a risk of suffering from a disease", it is hereby meant that the subject when harbouring gene abundance profiles associated with above-mentioned diseases or conditions has more than 50%, preferably more than 60% and more preferably more than 75% of risk of suffering from the above-mentioned diseases or conditions.

As used herein, the term "metagenome" refers to genomic material obtained directly from a subject, instead of from a cell culture. Metagenome is thus composed of microbial and host components.

As used herein, the term "gene" refers broadly to a genetic information unit. It is composed of DNA or RNA that may code for a polypeptide or for an RNA chain of a given organism. More specifically, a gene is a locatable region of genomic sequence, which is associated with regulatory regions, transcribed regions, and/or other functional sequence regions. The genes which are referred to in this invention are preferably "bacterial genes", i.e., they correspond to a locatable region of the genome of a bacterium.

In all the present description, the term "gene signature" refers to a set of information that is related to the amount of one or more gene(s) in a tested sample. This information may arise from the identification of the amount of gene copies or gene products in the tested sample. As used herein, the "gene signature of the invention" therefore encompasses either the expression level of at least one bacterial gene, preferably of at least two bacterial genes, or the abundance of these at least one or two bacterial genes.

As used herein, the "expression" of a gene is the process by which information from a gene is used in the synthesis of a functional gene product. These products are often proteins, but in non-protein coding genes such as ribosomal RNA (rRNA), transfer RNA (tRNA) or small nuclear RNA (snRNA) genes, the product is also a functional RNA. Gene expression can thus be detected by determining the presence of the corresponding rRNA, tRNA, mRNA, snRNA and/or the gene products at the protein level, by conventional means.

On another hand, "gene abundance" refers to the absolute or relative amount of the tested genes. "Absolute amount" (or "absolute abundance") of a gene designates the total number of copies of said gene in a define volume of the tested sample, whereas "relative amount" (or "relative abundance") of a gene designates the total number of copies of said gene relative to the total amount of genes or alternatively the total number of copies of said gene relative to the amount of a single reference gene or preferably a combination of reference genes present in the tested sample. Ubiquitous genes, such as genes essential for the survival of the organism like DNA polymerases or genes coding for proteins involved in glucose metabolism, are good candidates for reference genes in metagenomic studies.

The "gene signature" used in the method of the invention therefore comprises or consists of either the abundance profile and/or the expression profile (either absolute or relative) of the tested bacterial gene(s).

By "abundance profile", it is meant the absolute or relative abundance of the group of tested genes. This abundance can be determined by detecting the copies number of the tested genes at the DNA level, for example by quantitative PCR, sequencing or nucleic acid microarrays.

By "expression profile", it is meant the expression levels of the group of tested genes. These expression levels can be determined by detecting the levels of the gene products, for example the transcript levels or the protein levels corresponding to the tested genes.

In the context of the invention, two genes are held "equivalent" if the replacement of one gene by the other in the analyzed gene signature does not significantly affect the performance of the method of the invention. Such equivalent genes are concomitantly absent from the samples and their abundance vary concomitantly, in the same direction and in the same proportion in the samples where they are present. This is typically the case when "gene A" is correlated to "gene B", meaning that the expression level or abundance of "gene A" is statistically correlated to the expression level of "gene B" respectively. In the context of the invention, this correlation is rather positive (meaning that when "gene A" is upregulated in a patient, then "gene" B is also upregulated in that same patient). This correlation can be determined for example by a measure of association such as the Pearson's or Spearman's correlation coefficient. Alternatively, covariance can be used for the identification of equivalent genes.

The equivalence of two genes is expected by the man skilled in the art to be the consequence of situations such as when two genes belong to the same genome (Qin J, Li Y, Cai Z, Li S, Zhu J, Zhang F et al., *Nature,* 2012), when two genes belong to the genomes of two coupled bacteria or when the product of these two genes are involved in the same metabolic and/or signaling pathway (Abubucker S, Segata N, Goll J, Schubert A M, Izard J, et al., *PLoS Comput Biol,* 2012).

In the context of the present invention, "covariant" genes are linked with a minimum Pearson correlation of at least 0.45, more preferably 0.5, and even more preferably 0.6 to the representative genes disclosed in the present invention.

In a preferred embodiment, said equivalent gene is a covariant gene belonging to the same bacterial cluster.

As used herein, a "gene cluster" or a "cluster" refers to a list of equivalent genes The man skilled in the art is familiar with methods that can be used to identify such clusters of equivalent genes (Qin J, Li Y, Cai Z, Li S, Zhu J, Zhang F et al., *Nature,* 2012). Said cluster may contain several hundreds of bacterial genes, preferably covariant genes, as defined above. For simplification purposes, only five of these covariant genes have been identified in the present application, for each cluster. In each cluster, the gene that is significantly correlated (minimum Pearson correlation >0.7) with the most genes from the cluster has been designated as the representative gene of the cluster. These representative genes are for example SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41, SEQ ID NO: 46, SEQ ID NO: 51, SEQ ID NO: 56, SEQ ID NO: 61, SEQ ID NO: 66, SEQ ID NO: 71, SEQ ID NO: 76, SEQ ID NO: 81, SEQ ID NO: 86, SEQ ID NO: 91, SEQ ID NO: 96, SEQ ID NO: 101, SEQ ID NO: 106, SEQ ID NO: 111, SEQ ID NO: 116, SEQ ID NO: 121, SEQ ID NO: 126, SEQ ID NO: 131, SEQ ID NO: 136, SEQ ID NO: 141, SEQ ID NO: 146, and SEQ ID NO: 151. All the other genes in each cluster are "equivalent" to these representative genes. Therefore, a cluster contains one representative gene and hundreds of equivalent genes, all of them being considered as covariant genes.

As used herein, an "equivalent gene signature" is a gene signature containing, in addition to or in replacement of representative genes, equivalent genes which confer the same performance to the method of the invention. These equivalent genes have been described above. In a preferred embodiment, the equivalent gene signature contains at least two genes that belong to two different clusters. In another preferred embodiment, the equivalent gene signature contains at least two different genes that belong to only one cluster. An equivalent gene signature may contain a mix of representative genes (SEQ ID NO: 1, 6, 11, 16, etc.) and equivalent(s) thereof, or only equivalent genes. It may also contain all the equivalent genes of a cluster. Alternatively, it may contain the arithmetic or geometric mean of the signals associated with several or all the equivalent genes of the cluster(s).

By "comprising", it is intended to mean that the gene signature may further comprise any other genes, among which, specific genes that do not significantly affect the essential characteristics of the gene signature of the invention (therefore overlapping the meaning of the term "consisting essentially of"). In contrast, by "consisting of", it is intended to mean that no further gene is present in the gene signature which is analyzed.

A "reference signature" is a predetermined gene signature, obtained from a biological sample from a subject or several subjects, having known inflammation-associated disease. In particular embodiments, the reference signature used for comparison with the test sample have been obtained from biological samples from subjects which have been reliably and unambiguously diagnosed (for example by means of a liver biopsy) as having an inflammatory disease and in particular a liver disease such as simple steatosis ("steatosis reference sample") or NASH ("NASH reference sample"), and/or from biological samples from subjects which have been diagnosed for having NASH and fibrosis ("fibrosis reference sample") and/or from biological samples from subjects which have been diagnosed for a Crohn's disease ("Crohn reference sample") for whom the disease activity is known. The reference signature therefore comprises or consists of the expression and/or abundance of the bacterial genes which has (have) been determined on said reference samples. Preferably, these information have been obtained from a sufficient number of subjects, typically by using 96 samples of different patients for each stage of the liver disease (simple steatosis/NASH/fibrosis), using another set of 145 samples of different patients for each stage of the liver disease and using another set of 118 samples of Crohn patients with different states of the disease.

By "comparing" the gene signature of a tested subject with a reference signature, it is meant to collect a biological sample from the tested subject, extract its genomic content, either RNA or DNA, with the appropriate method, estimate the expression or relative abundance of each gene respectively, and compare either the expression and/or abundance of each gene of the signature separately with the expression and/or abundance of the same gene in the reference signature (which is not preferred), or to affect a diagnosis or prognosis outcome to the test sample using an algorithm which is calibrated based on reference samples or signatures. In particular embodiments, depending on the selected algorithm, the algorithm may issue a value, which is then compared to a predetermined reference value (e.g., via logistic regression). Such comparison requires mathematical and statistical methods such as those mentioned below, in order to extract discriminative features (e.g., genes) from the reference signature that can be generalized for diagnosis or prognosis purposes.

As used herein, the term "reference value" (or "control value") refers to a specific value or dataset that can be used to identify patients associated with an outcome class (e.g., simple steatosis, NASH or NASH-associated fibrosis, stable or instable state of Crohn's disease activity). As mentioned previously, said reference or control value is obtained from the historical expression and/or abundance data for a patient or pool of patients having being diagnosed unambiguously for a define pathology. This reference or control value is a predetermined value, which can take a variety of forms. It can be a single cut-off value, such as a median or mean. It can be a single number, equally applicable to every patient individually, or it can vary, according to specific subpopulations of patients. This reference value can be easily determined by the skilled person with any of the above-mentioned calculation models.

As used herein, "a reagent for the determination of a gene signature" designates a reagent or a set of reagents which specifically allows for the determination of said gene signature, i.e., specifically intended for the specific determination of the abundance and/or expression level of the genes comprised in the gene signature. These reagents can be for example nucleic acid primers or probes that can specifically hybridize with the mRNA, DNA, or cDNA included in the gene signature. They can be alternatively antibodies or enzymes specifically recognizing the proteins produced by the genes included in the gene signature. This definition excludes generic reagents useful for the determination of the gene signature of any gene, such as Taq polymerase or an amplification buffer, although such reagents may also be included in a kit according to the invention.

In the context of the present invention, a reagent (e.g., a probe, a primer or an antibody) is "specific" for its target or "recognizes specifically" its target if it exhibits a threshold level of binding activity, and/or 2) it does not significantly cross-react with known related molecules. One skilled in the art can readily determine said binding affinity.

DETAILED DESCRIPTION OF THE INVENTION

The recent findings of Flavell and al. (*Nature,* 2012) provide evidence of a link between inflammasomes, the gut microbiota and NAFLD, based on mice studies. These results, corroborating previous publication, established that the gut microbiota dysbiosis exacerbates hepatic steatosis and governs rate of NAFLD progression.

The present inventors hypothesized that the presence of specific bacterial genes representative of a specific gut microbiota composition or alteration (so-called dysbiosis) in patient stools would be useful information and could be related to liver-associated metabolic disorders such as NASH or fibrosis.

Studies from Sokol and al. (IBD, 2009), have established that gut microbiota is in the heart of the pathogenesis of inflammatory bowel diseases (IBD). Several other studies have demonstrated that gut microbiota imbalances are associated with IBD (vs. healthy controls) and also correlated to diseases activities and diseases prognosis (Sokol 2008, Morgan 2012, Willing 2010).

The present inventors analysed by quantitative metagenomic the gene abundance of bacterial genes on a number of stool samples that have been collected from patients for which a recent liver biopsy reading was available or whose Crohn's disease activity was monitored.

In metabolic fatty liver disease, the comparison of metagenomes between groups of patients having steatosis (N=29) or steatohepatitis with (N=33) or without (N=34) fibrosis triggered them to identify metagenomic signatures for discriminating between these patients.

These discriminative gene signatures have been subsequently validated on a large number of stool samples from patients having undergone a liver biopsy, for some of them at different stages of the disease.

In IBD, the comparison of metagenomes between groups of Crohn's patients in stable low activity disease (N=20) or instable disease (N=98) triggered them to identify metagenomic signatures for discriminating between these two category of patients.

Thus, a number of genes differentially abundant between different stages of NAFLD and between different disease activity status in Crohn's patients have been identified. Importantly, the abundance of these genes could be correlated with the future evolution of the disease (e.g., into an improvement or a worsening of the liver histology).

More precisely, 14 clusters of genes have been found to be commonly associated with benign steatosis or a stable state of Crohn disease, and 7 clusters of genes have been found to be associated with more advanced liver disease (NASH, fibrosis, cirrhosis). Furthermore, 8 clusters of genes have been found to be highly associated with NASH without fibrosis, and 2 clusters of genes have been found to be associated with NASH-associated fibrosis. Several combinations of a minimum number of genes are therefore proposed as being predictive of benign steatosis, or of NASH with or without fibrosis or of Crohn's disease activity.

Moreover, 4 clusters of genes have been found to be highly associated with benign steatosis (clusters 1, 31, 19 and 11) and 3 clusters of genes have been found to be highly associated with stable Crohn disease (clusters 1, 31 and 19).

It is important to note that the method of the invention not only permits to diagnose a particular inflammatory disease stage, but also permits to prognose a positive or a negative outcome of a subject suffering from said inflammatory disease, in particular liver disease or Crohn's disease.

This can be explained as follows. The gut micro biota is acquired during infancy (between 0-3 years old). The host immune system holds a key role in the selection of a definitive core microbiota which is specific (in its composition) of each individual and remains stable over time. The core microbiota stability which has been observed over the time and throughout life, is independent of dietary changes and is resilient (i.e. recovered after iatrogenic disruption). Considering this stability and resilience, the features (composition, richness, diversity) of the core microbiota are correlated with defined inflammation-induced metabolic disturbances and will be present at the onset of the pathology and throughout the evolution of the disease. Consequently, it is possible to prognose if a fatty liver will progress to an advanced liver damage such as steatohepatitis, fibrosis, or cirrhosis, or will remain benign throughout the patient's life, by simply analyzing the gut microbiota of said patient at a point of time during the course of the disease.

Another important point is that the gut microbiota holds a key role in controlling gut barrier function and in particular its permeability. Changes in gut microbiota composition lead to gut barrier function alteration promoting bacterial translocation (presence of bacteria and their components in the blood) and metabolic endotoxemia (presence of endotoxins in the blood) that initiate the development of inflammation. Therefore, inflammation-induced disturbances such as diabetes, hypertension, hypercholesterolemia, inflammatory bowel diseases and liver diseases are initially driven by impaired gut permeability triggered by changes in the gut microbiota composition (Cani P., Gut microbes, 2012). A test based on gut microbiota analysis, which aims to diagnose, monitor or predict evolution of a liver disease might thus be as well useful for diagnosis, monitoring or prediction of any other inflammation-associated disturbances (i.e., diabetes, hypertension, hypercholesterolemia, inflammatory bowel diseases and cardiovascular diseases).

In a first aspect, the invention thus relates to a method for the in vitro diagnosis or prognosis of an inflammatory disease in a subject, comprising the following steps:

a) determining from a biological sample of said subject a gene signature comprising or consisting of one bacterial gene, preferably of at least two bacterial genes, b) comparing the obtained gene signature with at least one reference gene signature, c) determining the phenotype of said subject from said comparison.

This method is advantageous over the prior art diagnosis or prognosis method as it is non-invasive, economically acceptable, and present high sensitivity and high specificity.

In an embodiment, the method of the invention can also be used for predicting the outcome of a patient suffering from an inflammatory disease.

In a preferred embodiment, said inflammatory disease is chosen in the group consisting of: insulin resistance, hypercholesterolemia, impaired glucose tolerance, type 2 diabetes, hypertension, cardiovascular diseases, inflammatory bowel disease and liver disease.

In a more preferred embodiment, said inflammatory disease is an inflammatory bowel disease (such as the Crohn disease) or a liver disease (such as benign steatosis, NASH or NASH-associated fibrosis).

The method of the invention can be applied to any subject, either human or animal. Yet, in a preferred embodiment, it is applied to a human patient, in particular to a human suffering from overweight, obesity, liver disease, diabetes (that is, from any metabolic disorders) and/or inflammatory bowel diseases.

More generally, in metabolic disorders, the method of the invention is useful for monitoring human patients showing enhanced level of hepatic enzymes such as aminotransferases, alkaline phosphatase, gamma-glutamyl transferase, as well as markers of hepatocyte injuries, such as CK18, alpha macroglobulin, platelet volume, haptoglobin, Apolipoproteine A1, and bilirubin. In inflammatory bowel diseases, the method of the invention is useful for monitoring human patients showing enhanced level of inflammation markers such as platelet count, mean platelet volume, erythrocyte sedimentation rate (ESR), serum thrombopoietin, serum erythropoietin, C-reactive protein and orosomucoid ($\alpha_1$-acid glycoprotein), TNFalpha, Interleukins (notably IL1, IL2, IL6, IL8, IL10, IL15) as well as fecal markers of inflammation such as lactoferrin and calprotectin.

As mentioned previously, the present inventors have identified 31 clusters of bacterial genes that are differentially abundant in the stool of patients suffering from benign steatosis, NASH and/or NASH-associated fibrosis, or in samples from Crohn patients in stable or instable state. These clusters of bacterial genes are presented in Table 1 below. Each cluster of bacterial genes is thought to be representative of a bacterial entity and contains several hundreds of bacterial genes that are present/absent altogether and in the same proportion (so-called "covariant genes"). For simplification's purpose, only five of these covariant genes have been identified in the present application, for each cluster. These five genes and all the genes belonging to the same cluster are held as "equivalent".

More precisely, as disclosed in table 1 below,

- cluster 1 contains at least 425 genes among which the five genes SEQ ID NO:1-5 (Minimum Pearson correlation: 0.64),
- cluster 2 contains at least 473 genes among which the five genes SEQ ID NO:6-10 (Minimum Pearson correlation: 0.72),
- cluster 3 contains at least 486 genes among which the five genes SEQ ID NO:11-15 (Minimum Pearson correlation: 0.72),
- cluster 4 contains at least 324 genes among which the five genes SEQ ID NO:16-20 (Minimum Pearson correlation: 0.7),
- cluster 5 contains at least 515 genes among which the five genes SEQ ID NO:21-25 (Minimum Pearson correlation: 0.86),
- cluster 6 contains at least 320 genes among which the five genes SEQ ID NO:26-30 (Minimum Pearson correlation: 0.66),
- cluster 7 contains at least 456 genes among which the five genes SEQ ID NO:31-35 (Minimum Pearson correlation: 0.7),
- cluster 8 contains at least 336 genes among which the five genes SEQ ID NO:36-40 (Minimum Pearson correlation: 72),
- cluster 9 contains at least 509 genes among which the five genes SEQ ID NO:41-45 (Minimum Pearson correlation: 0.8),
- cluster 10 contains at least 275 genes among which the five genes SEQ ID NO:46-50 (Minimum Pearson correlation: 0.86),
- cluster 11 contains at least 646 genes among which the five genes SEQ ID NO:51-55 (Minimum Pearson correlation: 0.74),
- cluster 12 contains at least 320 genes among which the five genes SEQ ID NO:56-60 (Minimum Pearson correlation: 0.86),
- cluster 13 contains at least 323 genes among which the five genes SEQ ID NO:61-65 (Minimum Pearson correlation 0.7),
- cluster 14 contains at least 593 genes among which the five genes SEQ ID NO:66-70 (Minimum Pearson correlation: 0.7),
- cluster 15 contains at least 283 genes among which the five genes SEQ ID NO:71-75 (Minimum Pearson correlation: 0.74),
- cluster 16 contains at least 621 genes among which the five genes SEQ ID NO:76-80 (Minimum Pearson correlation: 0.76),
- cluster 17 contains at least 263 genes among which the five genes SEQ ID NO:81-85 (Minimum Pearson correlation: 0.82),
- cluster 18 contains at least 1039 genes among which the five genes SEQ ID NO:86-90 (Minimum Pearson correlation: 0.82),
- cluster 19 contains at least 1231 genes among which the five genes SEQ ID NO:91-95 (Minimum Pearson correlation: 0.74),
- cluster 20 contains at least 712 genes among which the five genes SEQ ID NO:96-100 (Minimum Pearson correlation: 0.8),
- cluster 21 contains at least 575 genes among which the five genes SEQ ID NO:101-105 (Minimum Pearson correlation: 0.88),
- cluster 22 contains at least 1232 genes among which the five genes SEQ ID NO:106-110 (Minimum Pearson correlation: 0.64),
- cluster 23 contains at least 298 genes among which the five genes SEQ ID NO:111-115 (Minimum Pearson correlation: 0.7),
- cluster 24 contains at least 785 genes among which the five genes SEQ ID NO:116-120 (Minimum Pearson correlation: 0.76),
- cluster 25 contains at least 780 genes among which the five genes SEQ ID NO:121-125 (Minimum Pearson correlation: 0.82),
- cluster 26 contains at least 491 genes among which the five genes SEQ ID NO:126-130 (Minimum Pearson correlation: 0.72),
- cluster 27 contains at least 827 genes among which the five genes SEQ ID NO:131-135 (Minimum Pearson correlation: 0.64),
- cluster 28 contains at least 531 genes among which the five genes SEQ ID NO:136-140 (Minimum Pearson correlation: 0.88)
- cluster 29 contains at least 289 genes among which the five genes SEQ ID NO:141-145 (Minimum Pearson correlation: 78),
- cluster 30 contains at least 320 genes among which the five genes SEQ ID NO:146-150 (Minimum Pearson correlation: 0.74),
- cluster 31 contains at least 299 genes among which the five genes SEQ ID NO:151-155 (Minimum Pearson correlation: 0.66).

In each cluster, the gene that is significantly correlated (Pearson correlation >0.7) with the most genes from the cluster has been designated as the representative gene of the cluster. The sequences of these representative genes are SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41, SEQ ID NO: 46, SEQ ID NO: 51, SEQ ID NO: 56, SEQ ID NO: 61, SEQ ID NO: 66, SEQ ID NO: 71, SEQ ID NO: 76, SEQ ID NO: 81, SEQ ID NO: 86, SEQ ID NO: 91, SEQ ID NO: 96, SEQ ID NO: 101, SEQ ID NO: 106, SEQ ID NO: 111, SEQ ID NO: 116, SEQ ID NO: 121, SEQ ID NO: 126, SEQ ID NO: 131, SEQ ID NO: 136, SEQ ID NO: 141, SEQ ID NO: 146, and SEQ ID NO: 151.

The present inventors have found that the method of the invention is highly sensitive and specific when the expression and/or the abundance of only one or two bacterial genes chosen in the above-mentioned clusters is determined and compared, directly or indirectly, to reference gene signature (see examples below). It is therefore equivalent to use a gene signature containing the representative genes (for example SEQ ID NO:1 for cluster 1) or containing any of their equivalent genes (for example SEQ ID NO:2 or 3 or 4 or 5 for cluster 1). In a preferred embodiment, the gene signature contains at least two different genes belonging to the same cluster (either a "representative" and at least one "equivalent" thereof, or at least two equivalent genes as defined above). In another preferred embodiment, the gene signature contains at least two different genes said genes belonging to at least two different clusters.

For example, the method of the invention can use the gene signature of SEQ ID NO:1 and SEQ ID NO:6, or of SEQ ID NO:2 and SEQ ID NO:6, or of SEQ ID NO:3 and SEQ ID NO:6, or of SEQ ID NO:3 and SEQ ID NO:6, or of SEQ ID NO:3 and SEQ ID NO:7, or of SEQ ID NO:1 and SEQ ID NO:9, etc.

In a preferred embodiment, the gene signature determined in the method of the invention comprises or consists of one or at least two bacterial genes, preferably at least three, preferably at least four, preferably at least five, preferably at least six, preferably at least seven, preferably at least eight, preferably at least nine, preferably at least ten, preferably at least eleven, preferably at least twelve, preferably at least thirteen, preferably at least fourteen, preferably at least fifteen, preferably at least sixteen, preferably at least seventeen, preferably at least eighteen, preferably at least nineteen, preferably at least twenty, preferably at least twenty-one, preferably at least twenty-two, preferably at least twenty-three, preferably at least twenty-four, preferably at least twenty-five, preferably at least twenty-six, preferably at least twenty-seven, preferably at least twenty-eight, preferably at least twenty-nine, preferably at least thirty, preferably at least thirty-one bacterial genes.

Preferably, said bacterial genes belong to the same cluster or to different clusters of genes as defined above.

In a more preferred embodiment, the above-mentioned bacterial genes are chosen in the group consisting of: SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41, SEQ ID NO: 46, SEQ ID NO: 51, SEQ ID NO: 56, SEQ ID NO: 61, SEQ ID NO: 66, SEQ ID NO: 71, SEQ ID NO: 76, SEQ ID NO: 81, SEQ ID NO: 86, SEQ ID NO: 91, SEQ ID NO: 96, SEQ ID NO: 101, SEQ ID NO: 106, SEQ ID NO: 111, SEQ ID NO: 116, SEQ ID NO: 121, SEQ ID NO: 126, SEQ ID NO: 131, SEQ ID NO: 136, SEQ ID NO: 141, SEQ ID NO: 146, and SEQ ID NO: 151. Alternatively, the gene signature determined in the method of the invention comprises or consists of an equivalent gene signature thereof.

In an even more preferred embodiment, the above-mentioned bacterial genes are chosen in the group consisting of: SEQ ID NO: 1, SEQ ID NO: 51, SEQ ID NO: 91, and SEQ ID NO: 151, that are highly associated with define stage of liver and bowel-related disorders.

In other words, the gene signature determined in the method of the invention comprises or consists of a bacterial gene chosen in the group consisting of: SEQ ID NO: 1, SEQ ID NO: 51, SEQ ID NO: 91, and SEQ ID NO: 151.

Alternatively, the gene signature determined in the method of the invention comprises or consists of an equivalent gene signature thereof.

In a preferred embodiment, said "equivalent gene signature" corresponds to a gene signature in which at least one so-called representative gene has been replaced by an equivalent thereof as defined above, said equivalent being preferably a covariant gene belonging to the same bacterial entity.

In a more preferred embodiment, equivalent genes of SEQ ID NO:1 are chosen in the group consisting in SEQ ID NO:2-5, equivalent genes of SEQ ID NO:6 are chosen in the group consisting in SEQ ID NO:7-10, equivalent genes of SEQ ID NO:11 are chosen in the group consisting in SEQ ID NO:12-15, equivalent genes of SEQ ID NO:16 are chosen in the group consisting in SEQ ID NO:17-20, equivalent genes of SEQ ID NO:21 are chosen in the group consisting in SEQ ID NO:22-25, equivalent genes of SEQ ID NO:26 are chosen in the group consisting in SEQ ID NO:27-30, equivalent genes of SEQ ID NO:31 are chosen in the group consisting in SEQ ID NO:32-35, equivalent genes of SEQ ID NO:36 are chosen in the group consisting in SEQ ID NO:37-40, equivalent genes of SEQ ID NO:41 are chosen in the group consisting in SEQ ID NO:42-45, equivalent genes of SEQ ID NO:46 are chosen in the group consisting in SEQ ID NO:47-50, equivalent genes of SEQ ID NO:51 are chosen in the group consisting in SEQ ID NO:52-55, equivalent genes of SEQ ID NO:56 are chosen in the group consisting in SEQ ID NO:57-60, equivalent genes of SEQ ID NO:61 are chosen in the group consisting in SEQ ID NO:62-65, equivalent genes of SEQ ID NO:66 are chosen in the group consisting in SEQ ID NO:67-70, equivalent genes of SEQ ID NO:71 are chosen in the group consisting in SEQ ID NO:72-75, equivalent genes of SEQ ID NO:76 are chosen in the group consisting in SEQ ID NO:77-80, equivalent genes of SEQ ID NO:81 are chosen in the group consisting in SEQ ID NO:82-85, equivalent genes of SEQ ID NO:86 are chosen in the group consisting in SEQ ID NO:87-90, equivalent genes of SEQ ID NO:91 are chosen in the group consisting in SEQ ID NO:92-95, equivalent genes of SEQ ID NO:96 are chosen in the group consisting in SEQ ID NO:97-100, equivalent genes of SEQ ID NO:101 are chosen in the group consisting in SEQ ID NO:102-105, equivalent genes of SEQ ID NO:106 are chosen in the group consisting in SEQ ID NO:107-110, equivalent genes of SEQ ID NO:111 are chosen in the group consisting in SEQ ID NO:112-115, equivalent genes of SEQ ID NO:116 are chosen in the group consisting in SEQ ID NO:117-120, equivalent genes of SEQ ID NO:121 are chosen in the group consisting in SEQ ID NO:122-125, equivalent genes of SEQ ID NO:126 are chosen in the group consisting in SEQ ID NO:127-130, equivalent genes of SEQ ID NO:131 are chosen in the group consisting in SEQ ID NO:132-135, equivalent genes of SEQ ID NO:136 are chosen in the group consisting in SEQ ID NO:137-140, equivalent genes of SEQ ID NO:141 are chosen in the group consisting in SEQ ID NO:142-145, equivalent genes of SEQ ID NO:146 are chosen in the group consisting in SEQ ID NO:147-150, equivalent genes of SEQ ID NO:151 are chosen in the group consisting in SEQ ID NO:152-155.

In a particular embodiment, the method of the invention uses a gene signature comprising or consisting of the bacterial gene of SEQ ID NO:1 or equivalent gene(s) thereof (for example chosen among SEQ ID NO:2-5) belonging to cluster 1. In other words, the method of the invention uses a gene signature comprising or consisting of the bacterial gene whose sequence is SEQ ID NO: 1, or an equivalent gene signature thereof. This equivalent gene signature preferably contains one or more gene(s) chosen from SEQ ID NO:2 to 5. This bacterial gene is preferably used to prognose or diagnose liver-disease or Crohn disease according to the methods of the invention.

In a particular embodiment, the method of the invention uses a gene signature comprising or consisting of the bacterial gene of SEQ ID NO:51 or equivalent gene(s) thereof (for example chosen among SEQ ID NO:52-55) belonging to cluster 11. In other words, the method of the invention uses a gene signature comprising or consisting of the bacterial gene whose sequence is SEQ ID NO: 51, or an equivalent gene signature thereof. This equivalent gene signature preferably contains one or more gene(s) chosen from SEQ ID NO:52 to 55. This bacterial gene is preferably used to prognose or diagnose liver-disease according to the methods of the invention.

In a particular embodiment, the method of the invention uses a gene signature comprising or consisting of the bacterial gene of SEQ ID NO:91 or equivalent gene(s) thereof (for example chosen among SEQ ID NO:92-95) belonging to cluster 19. In other words, the method of the invention uses a gene signature comprising or consisting of the bacterial gene whose sequence is SEQ ID NO: 91, or an equivalent gene signature thereof. This equivalent gene signature preferably contains one or more gene(s) chosen from SEQ ID NO:92 to 95. This bacterial gene is preferably used to prognose or diagnose liver-disease or Crohn disease according to the methods of the invention.

In a particular embodiment, the method of the invention uses a gene signature comprising or consisting of the bacterial gene of SEQ ID NO:151 or equivalent gene(s) thereof (for example chosen among SEQ ID NO:152-155) belonging to cluster 31. In other words, the method of the invention uses a gene signature comprising or consisting of the bacterial gene whose sequence is SEQ ID NO: 151, or an equivalent gene signature thereof. This equivalent gene signature preferably contains one or more gene(s) chosen from SEQ ID NO:152 to 155. This bacterial gene is preferably used to prognose or diagnose liver-disease or Crohn disease according to the methods of the invention.

Of note, it is possible in step a) of the method of the invention to use a gene signature comprising or consisting of at least one gene of each of the clusters identified by the inventors. In particular, it is possible to use in the method of the invention a gene signature comprising or consisting of all the so-called "representative" genes identified by the inventors, optionally along with equivalent(s) thereof. More particularly, it is possible to use a gene signature taking into account the signals of all the so-called "representative" genes along with their equivalents genes. Even more particularly, it is possible to use a gene signature taking into account the arithmetic or geometric mean of the signals associated with several or all the equivalent genes of the cluster(s) (example 1b and 2b).

A "biological sample" may be any sample that may be taken from a subject, such as a serum sample, a plasma sample, a urine sample, a blood sample, a stool sample, a lymph sample, or a biopsy. Such a sample must allow for the determination of the gene signature of the invention.

Preferred biological samples for the determination of the gene signature in the method of the invention include stool sample and gut biopsy (gut biopsy via colonoscopy is notably less invasive than a liver biopsy).

In a more preferred embodiment, the biological sample used in the method of the invention is a stool sample. Indeed, such a sample may be obtained by a completely harmless collection from the patient and thus allows for a non-invasive diagnosis of an inflammatory disease such as a liver disease or an inflammatory-bowel disease. The DNA can be extracted from said sample for example by using the extraction protocol described in Godon J J. et al, *Appl. Environ. Microbiol.* 1997. Other protocols can nevertheless be used and are well-known. Of note, the bacterial DNA and the host DNA do not need to be physically separated for subsequent metagenomic analysis.

The determination of the presence of an inflammatory disease such as in certain Crohn's patients or patients with a liver disease is carried out thanks to the comparison of the obtained gene signature with at least one reference signature, as mentioned in step (b) of the method of the invention.

The comparison of a tested subject gene signature with said reference signature, which permits diagnosis or prediction of the tested subject's clinical status and evolution based on his/her abundance or expression profile, is preferably performed by applying an algorithm on the gene signals measured in the tested sample. This calculation can be done by those skilled in the art using statistical models or machine learning technologies. The PLS (Partial Least Square) regression is particularly relevant to give prediction in the case of small reference samples. The comparison may also be performed using Recursive Partitioning, Support Vector Machines (SVM), linear regression or derivatives thereof (such as the generalized linear model abbreviated as GLM, including logistic regression), Linear Discriminant Analysis (LDA, including Diagonal Linear Discriminant Analysis (DLDA)), Diagonal quadratic discriminant analysis (DQDA), Random Forests, k-NN (Nearest Neighbour) or PAM (Predictive Analysis of Microarrays) algorithms. Cox models may also be used. Centroid models using various types of distances may also be used. For cases where the studied populations are not homogenous i.e., when several distinct set of genes can be involved in—or support—or lead to the phenotypes, other algorithms such as recursive partitioning or simple combinations of the variables identified can be considered.

The reference samples mentioned above are usually used to select and calibrate the optimal statistical algorithm that best separates patients suffering from each stage of an inflammatory disease such as liver disease or inflammatory-bowel disease. The best separation is generally the one that misclassifies as few samples as possible and that has the best chance to perform comparably well on a different dataset.

For a binary outcome such as benign/malignant diagnosis, linear regression or a generalized linear model (abbreviated as GLM), including logistic regression, may be used. Linear regression is based on the determination of a linear regression function, which general formula may be represented as:

$$f(x_1, \ldots, x_N)=\beta_0+\beta_1x_1+ \ldots +\beta_Nx_N.$$

Other representations of linear regression functions may be used (see below).

Logistic regression is based on the determination of a logistic regression function:

$$f(z)=\frac{e^z}{e^z+1}=\frac{1}{1+e^{-z}},$$

in which z is usually defined as $$z=\beta_0+\beta_1x_1+\ldots+\beta_Nx_N.$$

In the above linear or logistic regression functions, $x_1$ to $x_N$ are the expression or abundance values of the N genes in the signature, $\beta_0$ is the intercept, and $\beta_1$ to $\beta_N$ are the regression coefficients.

The values of the intercept and of the regression coefficients are determined based on a group of the reference samples as defined above. When defining the linear or logistic regression function based on these reference samples, the user associates good or bad diagnosis (e.g., a diagnosis of simple steatosis or NASH, or of stable or instable state of Crohn disease, respectively) or prognosis to define values and a particular threshold value (hereafter called "reference value") is identified. Depending if the value associated to the test signature is inferior or superior to the reference value, a test gene signature can then be classified as having a good or bad diagnosis (e.g., a diagnosis of simple steatosis or NASH, or of stable or instable state of Crohn disease, respectively) or prognosis (benign or inflammatory steatosis).

Other types of generalized linear models than logistic regression may also be used. These approaches are well known to people skilled in the art.

In summary, an algorithm (which may be selected from linear regression or derivatives thereof such as generalized linear models (GLM, including logistic regression), nearest neighbour (k-NN), decision trees, support vector machines (SVM), neural networks, linear discriminant analyses (LDA), Random forests, or Predictive Analysis of Microarrays (PAM)) is calibrated based on a group of reference samples (preferably including several reference signatures associated to benign steatosis and several reference signatures associated to NASH and NASH-associated fibrosis) and then applied to the test sample. In simple terms, a patient will be classified as good (or bad) diagnosis/prognosis based on how all the genes in his signature compare to all the genes from the reference signature(s).

The notion of whether individual genes of the gene signature are increased or decreased in a good diagnosis/prognosis versus a bad diagnosis/prognosis sample is of scientific interest. For each individual gene, the gene expression or abundance levels in the good diagnosis/prognosis group can be compared to the bad diagnosis/prognosis group by the use of Student's t-test or equivalent methods. However, such binary comparisons are generally not used for diagnosis/prognosis when a signature comprises several distinct genes.

In a preferred embodiment, the method of the invention permits to determine whether a subject is suffering from a liver disease, and, in particular, from benign steatosis, NASH or NASH-associated fibrosis.

The present invention thus relates to a method for the in vitro diagnosis and/or prognosis of a liver disease, comprising the following steps:

a) determining from a biological sample of a subject a gene signature comprising or consisting of one bacterial gene, preferably of at least two bacterial genes, b) comparing the obtained gene signature with at least one reference gene signature, c) determining the phenotype of said subject from said comparison.

In a preferred embodiment, said liver disease is chosen in the group consisting of: steatosis, non alcoholic steatohepatitis, liver fibrosis, cirrhosis, liver failure, and liver cancer.

In a preferred embodiment, the method of the present invention can be used for the diagnosis or prognosis of particular stages of a liver disease.

In particular, the method of the present invention can be used for the (good) diagnosis or prognosis of benign steatosis or for the (bad) diagnosis or prognosis of steatohepatitis.

In this embodiment, the method of the invention comprises the steps of:

a) determining from a biological sample of a subject a gene signature comprising or consisting of one or at least two bacterial genes chosen in the group consisting of: SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41, SEQ ID NO: 46, SEQ ID NO: 51, SEQ ID NO: 56, SEQ ID NO: 61, SEQ ID NO: 66, SEQ ID NO: 71, SEQ ID NO: 76, SEQ ID NO: 81, SEQ ID NO: 86, SEQ ID NO: 91, SEQ ID NO: 96, SEQ ID NO: 101 or an equivalent gene signature thereof, b) comparing the obtained gene signature with at least one reference signature, c) diagnosing from said comparison if the said subject has a benign steatosis or a steatohepatitis.

For such diagnosis or prognosis method, a benign steatosis is considered as a positive result, while steatohepatitis is considered as a negative result (considering that the patient is suffering from or will suffer from steatohepatitis).

The present inventors have indeed demonstrated that a combination of one or more bacterial genes chosen in the group consisting of: SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41, SEQ ID NO: 46, SEQ ID NO: 51, SEQ ID NO: 56, SEQ ID NO: 61, SEQ ID NO: 66, SEQ ID NO: 71, SEQ ID NO: 76, SEQ ID NO: 81, SEQ ID NO: 86, SEQ ID NO: 91, SEQ ID NO: 96, SEQ ID NO: 101 or of equivalent genes thereof, enables to discriminate efficiently between subjects suffering from steatohepatitis (that is, suffering from NASH with or without fibrosis) or more advanced liver disease (cirrhosis, liver cancer) and subjects having benign steatosis (cf. example 1 below).

More precisely, they have demonstrated that it is possible to efficiently discriminate between these subjects by analysing a gene signature consisting of two, three, four, five, six, seven, eight, nine, or ten of these bacterial genes.

It is thus possible to diagnose or prognose patient suffering from steatohepatitis by determining the expression and/or abundance of one or at least two bacterial genes, preferably at least three, preferably at least four, preferably at least five, preferably at least six, preferably at least seven, preferably at least eight, preferably at least nine, preferably at least ten, preferably at least eleven, preferably at least twelve, preferably at least thirteen, preferably at least fourteen, preferably at least fifteen, preferably at least sixteen, preferably at least seventeen, preferably at least eighteen, preferably at least nineteen, preferably at least twenty, preferably at least twenty-one bacterial genes chosen in the group consisting of: SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41, SEQ ID NO: 46, SEQ ID NO: 51, SEQ ID NO: 56, SEQ ID NO: 61, SEQ ID NO: 66, SEQ ID NO: 71, SEQ ID NO: 76, SEQ ID NO: 81, SEQ ID NO: 86, SEQ ID NO: 91, SEQ ID NO: 96, SEQ ID NO: 101, SEQ ID NO: 106, SEQ ID NO: 111, SEQ ID NO: 116, SEQ ID NO: 121, SEQ ID NO: 126, SEQ ID NO: 131, SEQ ID NO: 136, SEQ ID NO: 141, SEQ ID NO: 146, SEQ ID NO: 151, or of equivalent genes chosen in the equivalent signature.

In a preferred embodiment, benign steatosis or steatohepatitis is diagnosed by determining the gene signature consisting of the four representative genes: SEQ ID NO: 1, SEQ ID NO:81, SEQ ID NO:56 and SEQ ID NO:96, which has been shown to be highly specific and relatively sensitive (AUC: 0.83, sn: 0.62; sp: 0.9; PPV: 0.72; NPV: 0.85), or a gene signature consisting of the nine representative genes: SEQ ID NO: 1, SEQ ID NO:16, SEQ ID NO:41, SEQ ID NO: 71, SEQ ID NO:81, SEQ ID NO:21, SEQ ID NO: 46, SEQ ID NO:91, and SEQ ID NO:96, which has been shown to be highly specific and sensitive (AUC: 0.86, sn: 0.66; sp: 0.9; PPV: 0.73; NPV: 0.86), or a gene signature consisting of the ten representative genes: SEQ ID NO: 1, SEQ ID NO:6, SEQ ID NO:11, SEQ ID NO:21, SEQ ID NO: 31, SEQ ID NO:41, SEQ ID NO:51, SEQ ID NO: 61, SEQ ID NO:76, and SEQ ID NO:96, which has been shown to be highly specific and sensitive (AUC: 0.83, sn: 0.59; sp: 0.9; PPV: 0.71; NPV: 0.83).

In another preferred embodiment, benign steatosis or steatohepatitis is diagnosed by determining a gene signature consisting of all the genes of the six clusters 1, 5, 17, 10, 12 and 20 (see table 1 below), which has been shown to be highly specific and sensitive (AUC: 0.81, sn: 0.48; sp: 0.94; PPV: 0.78; NPV: 0.81), or a gene signature consisting of all the genes of the 10 clusters 2, 5, 8, 12, 13, 15, 16, 17, 18, and 21, which has been shown to be highly specific and sensitive (AUC: 0.8, sn: 0.52; sp: 0.9; PPV: 0.68; NPV: 0.81).

In another preferred embodiment, benign steatosis or steatohepatitis is diagnosed by determining a gene signature consisting of at least one gene of each of the two clusters 1 and 31 (see table 1 below for the correspondence with the targeted sequences) which has been shown to not sensitive but very specific (AUC: 0.64, sn: 0.29; sp: 0.9; PPV: 0.48; NPV: 0.8), or a gene signature consisting of at least one gene of each of the four clusters 1, 16, 13 and 14 which has been shown to be highly specific and sensitive (AUC: 0.76, sn: 0.59; sp: 0.87; PPV: 0.65; NPV: 0.83) or a gene signature consisting of at least one gene of each of the 5 clusters 12, 5, 10, 18 and 19 (AUC: 0.7, sn: 0.41; sp: 0.94; PPV: 0.75; NPV: 0.79) which has been shown to be highly specific and sensitive or a gene signature consisting of at least one gene of each of the 8 clusters 3, 16, 15, 11, 13, 14, 7 and 4 which has been shown to be highly specific and sensitive (AUC: 0.73, sn: 0.66; sp: 0.84; PPV: 0.63; NPV: 0.85).

In another embodiment, the method of the present invention can be used for the diagnosis or prognosis of subjects suffering from a steatohepatitis with fibrosis once they have been diagnosed for steatohepatitis, in particular by means of the steps a) to c) above.

In this particular embodiment, the method of the invention further comprises the steps of:

d) Determining in said biological sample a gene signature comprising or consisting of one or at least two bacterial genes chosen in the group consisting of: SEQ ID NO: 106, SEQ ID NO: 111, SEQ ID NO: 116, SEQ ID NO:121, SEQ ID NO: 126, SEQ ID NO: 131, SEQ ID NO: 136, SEQ ID NO: 141, SEQ ID NO: 146, SEQ ID NO: 151, or an equivalent gene signature thereof, e) comparing the gene signature obtained in step d) with at least one reference signature, f) determining from said comparison if said subject suffers from a steatohepatitis with fibrosis.

For such diagnosis or prognosis method, a NASH without fibrosis is considered as a "positive" result, while a more-advanced liver-related disease (NASH with fibrosis) is considered as a negative result.

The present inventors have indeed demonstrated that, once the gene signature of the subject is found to be associated to steatohepatitis as determined in step a) to c), a combination of one or more bacterial genes chosen in the group consisting of: SEQ ID NO: 106, SEQ ID NO: 111, SEQ ID NO: 116, SEQ ID NO:121, SEQ ID NO: 126, SEQ ID NO: 131, SEQ ID NO: 136, SEQ ID NO: 141, SEQ ID NO: 146, SEQ ID NO: 151 or of equivalent genes thereof, enables to discriminate efficiently between subjects suffering from "simple" steatohepatitis (that is, without fibrosis) or fibrosis-associated steatohepatitis (cf. example 2 below).

In the example 2 below, they have also demonstrated that it is possible to efficiently discriminate between these subjects by analysing a gene signature consisting of two, three, four, five, six, seven, or eight of these bacterial genes.

It is thus possible to diagnose or prognose patient suffering from fibrosis associated-steatohepatitis by determining the expression and/or abundance of one or at least two bacterial genes, preferably at least three, preferably at least four, preferably at least five, preferably at least six, preferably at least seven, preferably at least eight, preferably at least nine, preferably at least ten bacterial genes chosen in the group consisting of: SEQ ID NO: 106, SEQ ID NO: 111, SEQ ID NO: 116, SEQ ID NO:121, SEQ ID NO: 126, SEQ ID NO: 131, SEQ ID NO: 136, SEQ ID NO: 141, SEQ ID NO: 146, SEQ ID NO: 151, or of equivalent genes chosen in the equivalent signature.

In a preferred embodiment, fibrosis-associated steatohepatitis is diagnosed by determining the gene signature consisting of the seven representative genes: SEQ ID NO: 106, SEQ ID NO:111, SEQ ID NO:116, SEQ ID NO:121; SEQ ID NO:131, SEQ ID NO:136 and SEQ ID NO:151, which has been shown to be highly specific and sensitive (AUC: 0.83, sn: 0.76; sp: 0.82; PPV: 0.81; NPV: 0.78), or a gene signature consisting of the eight representative genes: SEQ ID NO: 106, SEQ ID NO:111, SEQ ID NO:116, SEQ ID NO: 121, SEQ ID NO:126, SEQ ID NO:131, SEQ ID NO: 136, and SEQ ID NO:151, which has been shown to be highly specific and sensitive (AUC: 0.81, sn: 0.82; sp: 0.79; PPV: 0.79; NPV: 0.82).

In another preferred embodiment, fibrosis-associated steatohepatitis is diagnosed by determining a gene signature consisting of all the genes of the six clusters 22, 23, 25, 27, 28 and 31 (see table 1 below for the correspondence with the targeted sequences), which has been shown to be highly specific and sensitive (AUC: 0.85, sn: 0.74; sp: 0.85; PPV: 0.83; NPV: 0.76), or a gene signature consisting of all the genes of the seven clusters 22, 23, 24, 25, 27, 28, and 31, which has been shown to be highly specific and sensitive (AUC: 0.85, sn: 0.88; sp: 0.7; PPV: 0.75; NPV: 0.85).

In another preferred embodiment, the method of the present invention can be used for the diagnosis or prognosis of particular states of Crohn patients.

In particular, the method of the present invention can be used for the diagnosis or prognosis of a Crohn patient in a stable state or for the diagnosis or prognosis of a Crohn patient in an instable state.

In this embodiment, the method of the invention comprises the steps of:

a) determining from a biological sample of a subject a gene signature comprising or consisting of one or at least two bacterial genes chosen in the group consisting of: SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41, SEQ ID NO: 46, SEQ ID NO: 51, SEQ ID NO: 56, SEQ ID NO: 61, SEQ ID NO: 66, SEQ ID NO: 71, SEQ ID NO: 76, SEQ ID NO: 81, SEQ ID NO: 86, SEQ ID NO: 91, SEQ ID NO: 96, SEQ ID NO: 101 or an equivalent gene signature thereof, b) comparing the obtained gene signature with at least one reference signature, c) diagnosing from said comparison if the said subject has a Crohn disease in a stable or instable state.

For such diagnosis or prognosis method, a "Crohn patient in a stable state" or "stable Crohn disease" is considered as a positive result, while a "Crohn patient in an instable state" or "an instable Crohn disease" is considered as a negative result.

The present inventors have indeed demonstrated that one or more bacterial genes chosen in the group consisting of: SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41, SEQ ID NO: 46, SEQ ID NO: 51, SEQ ID NO: 56, SEQ ID NO: 61, SEQ ID NO: 66, SEQ ID NO: 71, SEQ ID NO: 76, SEQ ID NO: 81, SEQ ID NO: 86, SEQ ID NO: 91, SEQ ID NO: 96, SEQ ID NO: 101 or of equivalent genes thereof, enables to discriminate efficiently between subjects suffering from stable Crohn disease or instable Crohn disease (cf. example 4 below).

In a particularly preferred embodiment, the Crohn disease is prognosed or diagnosed by determining a gene signature consisting of at least one gene of each of the 5 clusters 3, 11, 17, 10, and 18 (see table 1 below for the correspondence with the targeted sequences), which has been shown to be highly specific and sensitive (AUC: 0.73, sn: 0.4; sp: 0.99; PPV: 0.89, NPV: 0.89), or a gene signature consisting of at least one gene of each of the six clusters 2, 7, 11, 15, 17, and 18, which has been shown to be highly specific and sensitive (AUC: 0.74, sn: 0.4; sp: 0.99; PPV: 0.89; NPV: 0.89) or a gene signature consisting of at least one gene of each of the six clusters 3, 11, 13, 15, 17, and 18, which has been shown to be highly specific and sensitive (AUC: 0.74, sn: 0.4; sp: 0.99; PPV: 0.89; NPV: 0.89) or a gene signature consisting of at least one gene of each of the seven clusters 3, 11, 12, 14, 16, 17, and 18, which has been shown to be highly specific and sensitive (AUC: 0.73, sn: 0.4; sp: 0.99; PPV: 0.89; NPV: 0.89).

The gene signature may be determined by any technology known by a man skilled in the art. In particular, each gene expression or abundance may be measured at the genomic and/or nucleic and/or proteic level. In a preferred embodiment, the gene signature is determined by measuring the amount of the DNA copies of each gene. In another embodiment, the gene signature is determined by measuring the amount of nucleic acid transcripts and/or protein produced by each of the genes.

In a preferred embodiment, the gene signature of the subject in step a) and d) is determined by using methods of gene abundance profiling based on hybridization analysis of polynucleotides, sequencing of polynucleotides, and/or proteomics.

The amount of DNA copies of each gene can be measured by any technology known by a man skilled in the art. The most commonly used methods known in the art for the quantification of DNA strands in a sample include Northern blotting and in situ hybridization (Parker & Barnes, Methods in Molecular Biology 106:247-283 (1999)) and PCR-based methods, such as quantitative polymerase chain reaction (qPCR) (Held et al., Genome Research 6:986-994 (1996)).

Alternatively, antibodies may be employed that can recognize sequence-specific duplexes, including DNA duplexes or DNA-protein duplexes. Representative methods for sequencing-based analysis include chain-termination methods, shotgun sequencing methods, de novo sequencing, next generation sequencing methods (including Massively Parallel Signature Sequencing (MPSS), Polony sequencing, 454 pyrosequencing, Illumina (Solexa) sequencing, SOLiD sequencing, Ion semiconductor sequencing, DNA nanoball sequencing, Helioscope single molecule sequencing, Single molecule real time (SMRT) sequencing, RNAP sequencing, Nanopore DNA sequencing, Sequencing by hybridization and Microfluidic Sanger sequencing).

The amount of protein produced by the genes can be measured by any technology known by a man skilled in the art. In particular, the measure may be carried out by using a protein microarray, in situ fluorescent hybridization (FISH) or any technologies well-known in the art.

In a particular embodiment, the gene signature in step a) and d) of the method of the invention is determined by measuring the relative abundance of said bacterial genes. As disclosed previously, the relative abundance of a gene is assessed for example by measuring the total number of the copies of said gene and the total amount of bacterial genes present in the tested sample and by making a ratio between these two amounts. As shown in the example below, it is possible to measure the number of gene copies for example by sequencing the DNA extracted from faecal samples using high throughput sequencing technologies (Next Generation Sequencing or NGS), mapping/aligning the short reads obtained on a non-redundant reference catalogue and counting the number of reads mapped to a single reference sequence from the catalogue.

Normalizing the number of reads mapped over the length of the genes and normalizing the gene counts over the total amount of bacterial genes are the two preferred options to normalize the data.

In a preferred embodiment, the diagnosis and/or prognosis methods of the invention can be used for designing a treatment for a subject suffering from a inflammatory disease such as a liver disease or inflammatory bowel disease. In this embodiment, the methods of the invention comprise the additional step of designing a treatment for the subject, said treatment being adapted to the particular pathology which has been diagnosed (by the method of the invention).

In particular, it is possible to use the methods of the invention for testing the efficiency of a treatment in a subject suffering from an inflammatory disease such as a liver disease or Crohn disease.

For example, if the diagnosis method of the invention enables to identify that a subject is suffering from type 2 diabetes, an adapted treatment can be a pharmacological treatment chosen in the group consisting of: antidiabetic drugs, such as (but not limited to), metformin, biguanides, thiazolidinediones, sulfonylureas, meglitinides, alpha-glucosidase inhibitors, incretin mimetics (including glucagon-like peptide analogs and agonists, gastric inhibitory peptide analogs, dipeptidyl Peptidase-4 Inhibitors, amylin analogues), TGR5 activators, GPR119 ligands, Glucokinase activators, agonist of zinc transporters, IL1beta inhibitors, inhibitors of thioredoxin-interacting protein; as well as life-style interventions, such as a broad spectrum of diets of different caloric restriction intensities and macronutrient composition (low carbohydrate, low fat, saturated fat diets);

as well as bariatric surgery procedures including Gastric band, bilio-intestinal bypass, and gastric bypass, gastric sleeve surgery.

For example, if the diagnosis method of the invention enables to identify that a subject is suffering from benign steatosis, an adapted treatment can be a pharmacological treatment chosen in the group consisting of: antidiabetics drugs, such as (but not limited to) metformin, biguanides, thiazolidinediones, sulfonylureas, meglitinides, alpha-glucosidase inhibitors, incretin mimetics (including glucagon-like peptide analogs and agonists, gastric inhibitory peptide analogs, dipeptidyl Peptidase-4 Inhibitors, amylin analogues), TGR5 activators, GPR119 ligands, Glucokinase activators, agonist of zinc transporters, IL1beta inhibitors, inhibitors of thioredoxin-interacting protein, enteric lipase inhibitors; as well as peripheral cannabinoid receptor blockers or agonists, as well as antioxydants, such as (but not limited to) pentoxifylline vitamin E and vitamin D, as well as caspase inhibitors, PDE4 selective inhibitors, bile acids and their derivatives (ursodeoxycholic acid (UDCA), FXR and RXR agonists) and Polyunsaturated fatty acids such as, but not limited to, Omega-3 Fatty Acids, and conjugated Omega-3 Fatty Acids, as well as lifestyle interventions, such as a broad spectrum of diets of different caloric restriction intensities and macronutrient composition (low carbohydrate, low fat, saturated fat diets); as well as bariatric surgery procedures including (but not limited to) Gastric band, bilio-intestinal bypass, gastric bypass, and gastric sleeve surgery.

For example, if the diagnosis method of the invention enables to identify that a subject is suffering from a NASH-associated fibrosis, an adapted treatment can be a pharmacological treatment chosen in the group consisting of: antidiabetics drugs, such as (but not limited to) metformin, biguanides, thiazolidinediones, sulfonylureas, meglitinides, alpha-glucosidase inhibitors, incretin mimetics (including glucagon-like peptide analogs and agonists, gastric inhibitory peptide analogs, dipeptidyl Peptidase-4 Inhibitors, amylin analogues), TGR5 activators, GPR119 ligands, Glucokinase activators, agonist of zinc transporters, IL1beta inhibitors, inhibitors of thioredoxin-interacting protein, enteric lipase inhibitors; as well as peripheral cannabinoid receptor blockers or agonists, as well as antioxydants, such as (but not limited to) pentoxifylline vitamin E and vitamin D, as well as caspase inhibitors, PDE4 selective inhibitors, bile acids and their derivatives (ursodeoxycholic acid (UDCA), FXR and RXR agonists) and Polyunsaturated fatty acids, such as (but not limited to) Omega-3 Fatty Acids, and conjugated Omega-3 Fatty Acids, antifibrotic drugs, such as (but not limited to) colchicine, Interferon gamma, ARBs, PPAR ligands, pirfenidone; as well as lifestyle interventions, such as (but not limited to) a broad spectrum of diets of different caloric restriction intensities and macronutrient composition (low carbohydrate, low fat, saturated fat diets); as well as bariatric surgery procedures including (but not limited to) Gastric band, bilio-intestinal bypass, gastric bypass, and gastric sleeve surgery.

For example, if the diagnosis method of the invention enables to identify that a subject is suffering from a NASH without fibrosis, an adapted treatment can be a pharmacological treatment chosen in the group consisting of: antidiabetics drugs, such as (but not limited to) metformin, biguanides, thiazolidinediones, sulfonylureas, meglitinides, alpha-glucosidase inhibitors, incretin mimetics (including glucagon-like peptide analogs and agonists, gastric inhibitory peptide analogs, dipeptidyl Peptidase-4 Inhibitors, amylin analogues), TGR5 activators, GPR119 ligands, Glucokinase activators, agonist of zinc transporters, IL1beta inhibitors, inhibitors of thioredoxin-interacting protein, enteric lipase inhibitors; as well as peripheral cannabinoid receptor blockers or agonists, as well as antioxydants, such as (but not limited to) pentoxifylline vitamin E and vitamin D, as well as caspase inhibitors, PDE4 selective inhibitors, bile acids and their derivatives (ursodeoxycholic acid (UDCA), FXR and RXR agonists) and Polyunsaturated fatty acids, such as (but not limited to) Omega-3 Fatty Acids, and conjugated Omega-3 Fatty Acids, antifibrotic drugs, such as (but not limited to) colchicine, Interferon gamma, ARBs, PPAR ligands, pirfenidone; as well as lifestyle interventions, such as (but not limited to) a broad spectrum of diets of different caloric restriction intensities and macronutrient composition (low carbohydrate, low fat, saturated fat diets); as well as bariatric surgery procedures including (but not limited to) Gastric band, bilio-intestinal bypass, gastric bypass, and gastric sleeve surgery.

For example, if the diagnosis method of the invention enables to identify that the state if a subject suffering from inflammatory bowel disease, an adapted treatment can be a pharmacological treatment chosen in the group consisting of: azathioprine, mesalamine, abatacept, adalimumab, anakinra, certolizumab, etanercept, golimumab, infliximab, rituximab, tocilizumab, natalizumab, corticosteroids, cyclosporine, methotrexate, tacrolimus, Anti-JAK (tofacitinib), anti-integrins (Vedolizumab, rhuMAb Beta7, MAdCAM-1 Antagonist), or Anti IL12/IL23 (Ustekinumab, ABT874).

More preferably, in this embodiment, the invention encompasses a method for treating a subject suffering from an inflammatory disease, comprising the following steps:

i) diagnosing and/or prognosing an inflammatory disease such as a type 2 diabetes, hypercholesterolemia, hypertension, inflammatory bowel disease (e.g., Crohn disease) or liver disease in a subject according to the method of the invention, and ii) treating said subject with an appropriate treatment, said appropriate treatment being chosen in those classically attributed by the practitioner once said inflammatory disease is diagnosed.

Preferably, said appropriate treatments can be chosen in the group consisting of: antidiabetics drugs, such as (but not limited to) metformin, biguanides, thiazolidinediones, sulfonylureas, meglitinides, alpha-glucosidase inhibitors, incretin mimetics (including glucagon-like peptide analogs and agonists, gastric inhibitory peptide analogs, dipeptidyl Peptidase-4 Inhibitors, amylin analogues), TGR5 activators, GPR119 ligands, Glucokinase activators, agonist of zinc transporters, IL1beta inhibitors, inhibitors of thioredoxin-interacting protein, enteric lipase inhibitors; as well as peripheral cannabinoid receptor blockers or agonists, as well as antioxydants, such as (but not limited to) pentoxifylline vitamin E and vitamin D, as well as caspase inhibitors, PDE4 selective inhibitors, bile acids and their derivatives (ursodeoxycholic acid (UDCA), FXR and RXR agonists) and Polyunsaturated fatty acids, such as (but not limited to) Omega-3 Fatty Acids, and conjugated Omega-3 Fatty Acids, antifibrotic drugs, such as (but not limited to) colchicine, Interferon gamma, ARBs, PPAR ligands, pirfenidone.

Even more preferably, the invention encompasses a method for managing a subject suffering from an inflammatory disease, comprising the following steps:

i) diagnosing and/or prognosing an inflammatory disease such as a type 2 diabetes, hypercholesterolemia, hypertension, inflammatory bowel disease (e.g., Crohn disease) or liver disease in a subject according to the method of the invention, and ii) taking care of said subject with an appropriate treatment, said appropriate treatment being chosen in those classically attributed by the practitioner once said inflammatory disease is diagnosed.

In this particular embodiment, said appropriate treatments are preferably lifestyle interventions, for example diets of different caloric restriction intensities and macronutrient composition (low carbohydrate, low fat, saturated fat diets); and/or bariatric surgery procedures including (but not limited to) gastric band, bilio-intestinal bypass, gastric bypass, and gastric sleeve surgery.

In a preferred embodiment, the invention encompasses a method for treating a subject suffering from a liver disease, comprising the following steps:

i) diagnosing and/or prognosing benign steatosis, steatohepatitis, or fibrosis-associated steatohepatitis in a subject according to the method of the invention, and ii) treating said subject with an appropriate treatment, said appropriate treatment being chosen in those classically attributed by the practitioner once said stage of liver disease is diagnosed.

Preferably, said appropriate treatments can be chosen in the group consisting of: antidiabetics drugs, such as (but not limited to) metformin, biguanides, thiazolidinediones, sulfonylureas, meglitinides, alpha-glucosidase inhibitors, incretin mimetics (including glucagon-like peptide analogs and agonists, gastric inhibitory peptide analogs, dipeptidyl Peptidase-4 Inhibitors, amylin analogues), TGR5 activators, GPR119 ligands, Glucokinase activators, agonist of zinc transporters, IL1beta inhibitors, inhibitors of thioredoxin-interacting protein, enteric lipase inhibitors; as well as peripheral cannabinoid receptor blockers or agonists, as well as antioxydants, such as (but not limited to) pentoxifylline, vitamin E and vitamin D, as well as caspase inhibitors, PDE4 selective inhibitors, bile acids and their derivatives (ursodeoxycholic acid (UDCA), FXR and RXR agonists) and Polyunsaturated fatty acids, such as (but not limited to) Omega-3 Fatty Acids, and conjugated Omega-3 Fatty Acids, antifibrotic drugs, such as (but not limited to) colchicine, Interferon gamma, ARBs, PPAR ligands, pirfenidone.

Even more preferably, the invention encompasses a method for managing a subject suffering from a liver disease, comprising the following steps:

i) diagnosing and/or prognosing benign steatosis, steatohepatitis, or fibrosis-associated steatohepatitis in a subject according to the method of the invention, and ii) taking care of said subject with an appropriate treatment, said appropriate treatment being chosen in those classically attributed by the practitioner once said stage of liver disease is diagnosed.

In this particular embodiment, said appropriate treatments are preferably lifestyle interventions, for example diets of different caloric restriction intensities and macronutrient composition (low carbohydrate, low fat, saturated fat diets); and/or bariatric surgery procedures including (but not limited to) gastric band, bilio-intestinal bypass, gastric bypass, and gastric sleeve surgery.

In a preferred embodiment, the invention encompasses a method for treating a subject suffering from an inflammatory bowel disease such as a Crohn disease, comprising the following steps:

i) diagnosing and/or prognosing the state of the patient suffering from an inflammatory bowel disease in a subject according to the method of the invention, and ii) treating said subject with an appropriate treatment, said appropriate treatment being chosen in those classically attributed by the practitioner once said state of the inflammatory bowel disease is diagnosed.

For example, if a Crohn patient is diagnosed in an instable state, an adapted treatment can be a pharmacological treatment chosen in the group consisting of: azathioprine, mesalamine, abatacept, adalimumab, anakinra, certolizumab, etanercept, golimumab, infliximab, rituximab, tocilizumab, natalizumab, corticosteroids, cyclosporine, methotrexate, tacrolimus, Anti-JAK (tofacitinib), anti-integrins (Vedolizumab, rhuMAb Beta7, MAdCAM-1 Antagonist), or Anti IL12/IL23 (Ustekinumab, ABT874).

In another aspect, the present invention further concerns a kit for the in vitro diagnosis and/or prognosis of an inflammatory disease such as a liver disease or a Crohn disease according to the method of the invention, comprising at least one reagent for the determination of a gene signature comprising at least one or two bacterial genes chosen in the group consisting of: SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41, SEQ ID NO: 46, SEQ ID NO: 51, SEQ ID NO: 56, SEQ ID NO: 61, SEQ ID NO: 66, SEQ ID NO: 71, SEQ ID NO: 76, SEQ ID NO: 81, SEQ ID NO: 86, SEQ ID NO: 91, SEQ ID NO: 96, SEQ ID NO: 101, SEQ ID NO: 106, SEQ ID NO: 111, SEQ ID NO: 116, SEQ ID NO: 121, SEQ ID NO: 126, SEQ ID NO: 131, SEQ ID NO: 136, SEQ ID NO: 141, SEQ ID NO: 146, SEQ ID NO: 151, or an equivalent gene signature thereof.

Said kit may comprise additional reagents (e.g., primers, probes or antibodies) specific for additional genes or gene products of one or more reference gene(s). Reference genes herein designate genes having an ubiquitous level of expression and/or abundance across bacteria, that can be used to normalize the gene levels for the signature. Said kit may also contain instructions for the determination of the presence or absence of an inflammatory disease such as a liver disease or an inflammatory bowel disease.

Advantageously, the reagents included in the kit of the invention are specific for SEQ ID NO: 1, SEQ ID NO:81, SEQ ID NO:56 and SEQ ID NO:96; for SEQ ID NO: 1, SEQ ID NO:16, SEQ ID NO:41, SEQ ID NO: 71, SEQ ID NO:81, SEQ ID NO:21, SEQ ID NO: 46, SEQ ID NO:91, and SEQ ID NO:96; for SEQ ID NO: 1, SEQ ID NO:6, SEQ ID NO:11, SEQ ID NO:21, SEQ ID NO: 31, SEQ ID NO:41, SEQ ID NO:51, SEQ ID NO: 61, SEQ ID NO:76, and SEQ ID NO:96; for all the genes of the six clusters 1, 5, 17, 10, 12 and 20; or for all the genes of the 10 clusters 2, 5, 8, 12, 13, 15, 16, 17, 18, and 21 if the kit is intended to diagnose or prognose benign steatosis.

More advantageously, these reagents are specific for SEQ ID NO:1, SEQ ID NO:91, SEQ ID NO:51 and/or SEQ ID NO:151.

Advantageously, the reagents included in the kit of the invention are specific for: SEQ ID NO: 106, SEQ ID NO:111, SEQ ID NO:116, SEQ ID NO:121; SEQ ID NO:131, SEQ ID NO:136 and SEQ ID NO:151; for SEQ ID NO: 106, SEQ ID NO:111, SEQ ID NO:116, SEQ ID NO: 121, SEQ ID NO:126, SEQ ID NO:131, SEQ ID NO: 136, and SEQ ID NO:151; for all the genes of the six clusters 22, 23, 25, 27, 28 and 31; or for all the genes of the seven clusters 22, 23, 24, 25, 27, 28, and 31, if the kit is intended to diagnose or prognose fibrosis-associated steatohepatitis.

In a preferred embodiment, the kit of the invention is dedicated to the in vitro diagnosis and/or prognosis of an inflammatory disease such as liver diseases or inflammatory bowel diseases. By “dedicated”, it is meant that the reagents in the kit of the invention essentially consist of reagents for determining the abundance and/or expression level of the particular genes included in the gene signature, optionally with one or more housekeeping gene(s), and thus comprise a minimum of reagents for determining the expression and/or abundance of genes other than those mentioned in the gene signature and housekeeping genes.

In another aspect, the invention thus relates to a method for the in vitro diagnosis or prognosis of an inflammatory disease in a subject, said method using the kit of the invention, which is defined above. In a preferred embodiment, said method comprises the following steps:

a) determining from a biological sample of said subject a gene signature comprising or consisting of one bacterial gene, preferably of at least two bacterial genes, thereby using the kit of the invention as defined above, b) comparing the obtained gene signature with at least one reference gene signature, c) determining the phenotype of said subject from said comparison.

In a preferred embodiment, the said method permits to determine whether a subject is suffering or will suffer from a liver disease, and, in particular, from benign steatosis, NASH or NASH-associated fibrosis, in the conditions defined above.

In another preferred embodiment, the said method permits to determine whether a subject has a Crohn disease in a stable or instable state, in the conditions defined above.

In addition, the instructions for the determination of the presence or absence of a Crohn/liver disease phenotype preferably include at least one reference signature, or at least one reference sample for obtaining a reference signature. In a preferred embodiment, at least one reference signature is obtained from a steatosis reference sample. Alternatively, at least one reference signature is obtained from a NASH reference sample. Alternatively, at least one reference signature is obtained from a fibrosis reference sample. Alternatively, at least one reference signature is obtained from a Crohn-stable reference sample. Alternatively, at least one reference signature is obtained from a Crohn instable reference sample. More preferably, the determination of the diagnosis of the Crohn/liver disease is carried out by comparison with these reference signatures as described above.

In another aspect, the present invention also related to a nucleic acid microarray comprising or consisting of nucleic acids specific for one or at least two bacterial genes chosen in the group consisting of: SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41, SEQ ID NO: 46, SEQ ID NO: 51, SEQ ID NO: 56, SEQ ID NO: 61, SEQ ID NO: 66, SEQ ID NO: 71, SEQ ID NO: 76, SEQ ID NO: 81, SEQ ID NO: 86, SEQ ID NO: 91, SEQ ID NO: 96, SEQ ID NO: 101, SEQ ID NO: 106, SEQ ID NO: 111, SEQ ID NO: 116, SEQ ID NO: 121, SEQ ID NO: 126, SEQ ID NO: 131, SEQ ID NO: 136, SEQ ID NO: 141, SEQ ID NO: 146, SEQ ID NO: 151, or of equivalent genes thereof.

More advantageously, these microarrays comprise or consist of nucleic acids specific for at least one bacterial gene chosen in the group consisting of: for SEQ ID NO:1, SEQ ID NO:91, SEQ ID NO:51 and SEQ ID NO:151.

Even more advantageously, these microarrays comprise or consist of nucleic acids specific at least one gene of each of the clusters 1 and 31, of each of the clusters 1, 16, 13 and 14, or of each of the clusters 3, 16, 13, 15, 16, 11, 14, 7 and 4 (see table 1 below for the correspondence with the targeted sequences). They can be used for example to prognose or diagnose liver disease in patients suffering thereof.

Even more advantageously, these microarrays comprise or consist of nucleic acids specific at least one gene of each of the clusters 3, 11, 17 and 10, of each of the clusters 2, 7, 11, 15, 17 and 18, or of each of the clusters 3, 11, 13, 15, 17 and 18, or of each of the clusters 3, 11, 12, 14, 17 and 18 (see table 1 below for the correspondence with the targeted sequences). They can be used for example to prognose or diagnose evolution of Crohn disease in patients suffering thereof.

According to the invention, a “nucleic microarray” consists of different nucleic acid probes that are attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes can be nucleic acids such as cDNAs (“cDNA microarray”) or oligonucleotides (“oligonucleotide microarray”), and the oligonucleotides may be about 25 to about 60 base pairs or less in length.

In a preferred embodiment, the nucleic acid microarray of the invention is an oligonucleotide microarray carrying oligonucleotides that can specifically hybridize with one or at least two bacterial genes chosen in the group consisting of: SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41, SEQ ID NO: 46, SEQ ID NO: 51, SEQ ID NO: 56, SEQ ID NO: 61, SEQ ID NO: 66, SEQ ID NO: 71, SEQ ID NO: 76, SEQ ID NO: 81, SEQ ID NO: 86, SEQ ID NO: 91, SEQ ID NO: 96, SEQ ID NO: 101, SEQ ID NO: 106, SEQ ID NO: 111, SEQ ID NO: 116, SEQ ID NO: 121, SEQ ID NO: 126, SEQ ID NO: 131, SEQ ID NO: 136, SEQ ID NO: 141, SEQ ID NO: 146, SEQ ID NO: 151, that act as specific probes. Preferably, the oligonucleotides are about 50 bases in length.

It is acknowledged that the nucleic acid microarray of the invention encompasses the microarrays specific for the equivalent gene signature as defined above.

Advantageously, said nucleic acid microarray comprises or consists of nucleic acids specific for at least SEQ ID NO: 1, SEQ ID NO:81, SEQ ID NO:56 and SEQ ID NO:96; for SEQ ID NO: 1, SEQ ID NO:16, SEQ ID NO:41, SEQ ID NO: 71, SEQ ID NO:81, SEQ ID NO:21, SEQ ID NO: 46, SEQ ID NO:91, and SEQ ID NO:96; for SEQ ID NO: 1, SEQ ID NO:6, SEQ ID NO:11, SEQ ID NO:21, SEQ ID NO: 31, SEQ ID NO:41, SEQ ID NO:51, SEQ ID NO: 61, SEQ ID NO:76, and SEQ ID NO:96; for all the genes of the six clusters 1, 5, 17, 10, 12 and 20; or for all the genes of the 10 clusters 2, 5, 8, 12, 13, 15, 16, 17, 18, and 21 if said microarray is intended to diagnose or prognose benign steatosis.

More advantageously, said nucleic acid microarray comprises or consists of nucleic acids specific for at least one bacterial gene chosen in the group consisting of: for SEQ ID NO:1, SEQ ID NO:91, SEQ ID NO:51 and SEQ ID NO:151.

Even more advantageously, said nucleic acid microarray comprises or consists of nucleic acids specific at least one gene of each of the clusters 1 and 31, of each of the clusters 1, 16, 13 and 14, or of each of the clusters 3, 16, 13, 15, 16, 11, 14, 7 and 4 (see table 1 below for the correspondence with the targeted sequences). They can be used for example to prognose or diagnose liver disease in patients suffering thereof.

Even more advantageously, said nucleic acid microarray comprises or consists of nucleic acids specific at least one gene of each of the clusters 3, 11, 17 and 10, of each of the clusters 2, 7, 11, 15, 17 and 18, or of each of the clusters 3, 11, 13, 15, 17 and 18, or of each of the clusters 3, 11, 12, 14, 17 and 18 (see table 1 below for the correspondence with the targeted sequences). They can be used for example to prognose or diagnose evolution of Crohn disease in patients suffering thereof.

Advantageously, said microarray comprises or consists of nucleic acids specific for at least: SEQ ID NO: 106, SEQ ID NO:111, SEQ ID NO:116, SEQ ID NO:121; SEQ ID NO:131, SEQ ID NO:136 and SEQ ID NO:151; for SEQ ID NO: 106, SEQ ID NO:111, SEQ ID NO:116, SEQ ID NO: 121, SEQ ID NO:126, SEQ ID NO:131, SEQ ID NO: 136, and SEQ ID NO:151; for all the genes of the six clusters 22, 23, 25, 27, 28 and 31; or for all the genes of the seven clusters 22, 23, 24, 25, 27, 28, and 31, if said microarray is intended to diagnose or prognose fibrosis-associated steatohepatitis.

Said nucleic acid microarray may comprise additional nucleic acids specific for additional genes and optionally one or more reference gene(s), but preferably consists of a maximum of 500, 400, 300, 200 preferably 100, 90, 80, 70 more preferably 60, 50, 45, 40, 35, 30, 25, 20, 15, 10, or even less (for instance 9, 8, 7, 6, 5, 4, 3, 2 or 1) distinct nucleic acids.

To determine the gene signature of a target nucleic sample, said sample is labelled, contacted with the nucleic acid microarray of the invention in hybridization conditions, leading to the formation of complexes between target nucleic acids that are complementary to probe sequences attached to the microarray surface. The presence of labelled hybridized complexes on the nucleic acid microarray is then detected. Many variants of the microarray hybridization technology are available to the man skilled in the art.

Suitable microarray oligonucleotides specific for any gene of SEQ ID NO: 1 to 155 may be designed, based on the genomic sequence of each gene, using any method of microarray oligonucleotide design known in the art. In particular, any available software developed for the design of microarray oligonucleotides may be used, such as, for instance, the OligoArray software (available at http://berry-.engin.umich.edu/oligoarray/), the GoArrays software (available at http://www.isima.fr/bioinfo/goarrays/), the Array Designer software (available at http://www.premier-biosoft.com/dnamicroarray/index.html), the Primer3 software (available at http://frodo.wi.mit.edu/primer3/primer3_code.html), or the Promide software (available at http://oligos.molgen.mpg.de/).

In another aspect, the invention thus relates to a method for the in vitro diagnosis or prognosis of an inflammatory disease in a subject, said method using the microarray of the invention, which is defined above. In a preferred embodiment, said method comprises the following steps:

a) determining from a biological sample of said subject a gene signature comprising or consisting of one bacterial gene, preferably of at least two bacterial genes, thereby using the microarray of the invention as defined above, b) comparing the obtained gene signature with at least one reference gene signature, c) determining the phenotype of said subject from said comparison.

In a preferred embodiment, the said method permits to determine whether a subject is suffering or will suffer from a liver disease or an inflammatory bowel disease, and, in particular, from benign steatosis, NASH or NASH-associated fibrosis, in the conditions defined above.

EXAMPLES

Material and Methods

1. A clustering approach was used, using the co-variance principle. A two-step hierarchical graph clustering was applied to 435 samples from the MetaHIT consortium mapped to the 3.3 million gene catalogue.

At a first step, all non-redundant pair wise Spearman correlations were calculated between all 3.3 million genes with abundance profiles from the 435 samples using the MetaProf software.

$5.4*10^{12}$ different correlations were computed in less than 20 minutes onto 288 cores at the French Curie supercomputer. A starting threshold rho=0.5 was used to group genes into clusters. When a cluster size was greater than 10,000 genes, the composing genes were re-clustered iteratively using increased correlation thresholds of 0.01 until its final size was smaller or equal than 10,000. This first step allowed for an exhaustive and deterministic exploration of the clustering problem, using an inflatable discrete threshold.

In a second step clusters size greater than 1,000 genes and whose genes had a non-null abundance signal in at least two samples underwent another partitioning procedure. This approach consists on a parametric partitioning method, using the DAPC algorithm. To assess the optimal number of cluster (i.e k) in a gene set, the [3]pam[2] function was used to estimate the optimal silhouette widths3. Then DAPC method was applied using the [3]adegenet[2] library in R programming environment. The minimal number of principal components including at least 90% of total variability was used to cluster the genes. This second step allowed grouping all genes into subunits, which corresponded to the identified clusters.

2. Identification of Clusters of Genes of Interest

The relative abundance of the predetermined clusters of genes was obtained by averaging the abundance of the genes in the cluster. Only the clusters with more than 500 items were used, as it corresponds to the minimal size of known bacteria. The log-transformed abundance profiles of the clusters of genes have been tested against the phenotypes (either benign steatosis versus NASH or NASH+fibrosis, or NASH versus NASH+fibrosis) using Kolmogorov-Smirnov and Wilcoxon non-parametric tests. The clusters that pass either test (p-value threshold: 0.05) were selected. They were split into sub-clusters using hierarchical clustering on the elements of the original cluster in order to enrich the cluster in elements highly correlated. The sub-clusters that contain more than 250 elements were tested using Kolmogorov-Smirnov and Wilcoxon tests. Only the sub-cluster that most significantly passes the test was selected.

3. These methods were applied on 102 fecal samples from liver patients having all a recent (<4 years) biopsy available.

TABLE 1

| cluster | Sequence name (internal reference code - mgs) | Equivalents | Associated to bacterial genus | Stage of liver-related metabolic disease |
|---|---|---|---|---|
| 1 | SEQ ID NO: 1 (10764_1_2) | SEQ ID NO: 2-5 | Not identified | Benign steatosis |
| 2 | SEQ ID NO: 6 (6639_2) | SEQ ID NO: 7-10 | Not identified | Benign steatosis |
| 3 | SEQ ID NO: 11 (6639_6) | SEQ ID NO: 12-15 | Not identified | Benign steatosis |
| 4 | SEQ ID NO: 16 (8091_7) | SEQ ID NO: 17-20 | Not identified | Benign steatosis |
| 5 | SEQ ID NO: 21 (1523_2) | SEQ ID NO: 22-25 | Not identified | NASH or NASH fibrosis |
| 6 | SEQ ID NO: 26 (9828_3) | SEQ ID NO: 27-30 | Not identified | Benign steatosis |
| 7 | SEQ ID NO: 31 (8091_5) | SEQ ID NO: 32-35 | Not identified | Benign steatosis |
| 8 | SEQ ID NO: 36 (6639_5) | SEQ ID NO: 37-40 | Not identified | Benign steatosis |
| 9 | SEQ ID NO: 41 (4373_12) | SEQ ID NO: 42-45 | Not identified | Benign steatosis |
| 10 | SEQ ID NO: 46 (1523_3) | SEQ ID NO: 47-50 | Not identified | NASH or NASH fibrosis |
| 11 | SEQ ID NO: 51 (6063_6) | SEQ ID NO: 52-55 | *Bifidobacterium* | Benign steatosis |
| 12 | SEQ ID NO: 56 (1523_1) | SEQ ID NO: 57-60 | Not identified | NASH or NASH fibrosis |
| 13 | SEQ ID NO: 61 (8091_1) | SEQ ID NO: 62-65 | Not identified | Benign steatosis |
| 14 | SEQ ID NO: 66 (8091_2) | SEQ ID NO: 67-70 | Not identified | Benign steatosis |
| 15 | SEQ ID NO: 71 (6063_3) | SEQ ID NO: 72-75 | *Bifidobacterium* | Benign steatosis |
| 16 | SEQ ID NO: 76 (5459_1) | SEQ ID NO: 77-80 | Not identified | Benign steatosis |
| 17 | SEQ ID NO: 81 (1731_5) | SEQ ID NO: 82-85 | *bacteroides* | Benign steatosis |
| 18 | SEQ ID NO: 86 (1731_14) | SEQ ID NO: 87-90 | *bacteroides* | NASH or NASH fibrosis |
| 19 | SEQ ID NO: 91 (6069_2_2) | SEQ ID NO: 92-95 | *Escherichia* | NASH or NASH fibrosis |
| 20 | SEQ ID NO: 96 (4381_2) | SEQ ID NO: 97-100 | *Paraprevotella* | NASH or NASH fibrosis |
| 21 | SEQ ID NO: 101 (274_3) | SEQ ID NO: 102-105 | Not identified | NASH or NASH fibrosis |
| 22 | SEQ ID NO: 106 (10769_1) | SEQ ID NO: 107-110 | *Haemophilus* | NASH |
| 23 | SEQ ID NO: 111 (8089_1) | SEQ ID NO: 112-115 | *Sutterella* | NASH |
| 24 | SEQ ID NO: 116 (5468_2) | SEQ ID NO: 117-120 | *Acidaminococcus* | NASH |
| 25 | SEQ ID NO: 121 (1786_2) | SEQ ID NO: 122-125 | Not identified | NASH |
| 26 | SEQ ID NO: 126 (6639_3) | SEQ ID NO: 127-130 | Not identified | NASH |
| 27 | SEQ ID NO: 131 (10769_2) | SEQ ID NO: 132-135 | *Haemophilus* | NASH |
| 28 | SEQ ID NO: 136 (289_1) | SEQ ID NO: 137-140 | *Desulfovibrio* | NASH |
| 29 | SEQ ID NO: 141 (4693_6) | SEQ ID NO: 142-145 | *Faecalibacterium* | NASH + fibrosis |
| 30 | SEQ ID NO: 146 (6069_3) | SEQ ID NO: 147-150 | *Escherichia* | NASH + fibrosis |
| 31 | SEQ ID NO: 151 (9828_3_1) | SEQ ID NO: 152-155 | Not identified | NASH |

Importantly, table 1 indicates the correspondence between:

the cluster numbers and the targeted sequences listed in the enclosed listing, the internal reference codes (also referred to hereafter as "mgs") and the cluster number.

Statistical Analysis of the Results

Example 1: Diagnosis of Benign Steatosis

True and false positive results, NPV, PPV, specificity and sensitivity are defined and calculated as follows:

| | | Diagnosis of benign steatosis (obtained by biopsy) | |
|---|---|---|---|
| | | Positive | Negative |
| Test outcome (association with a gene expression modulation) | Positive | True Positive (TP) | False positive (FP) |
| | Negative | False negative (FN) | True negative (TN) |

PPV (Positive Predictive Value)=TP/(TP+FP)

NPV (Negative Predictive Value)=TN/(TN+FN)

Specificity=TN/(TN+FP)

Sensitivity=TP/(TP+FN)

ER=error rate a) Combination of genes from 2, 3, 4, 5, 6, 7, 8, 9, 10 clusters of genes (k) for diagnosing benign steatosis (taking into account only the representative gene for each cluster)

| k | score | threshold | AUC | ER | SN (Benign) | SP (NASH) | PPV | NPV |
|---|---|---|---|---|---|---|---|---|
| 2 | (SEQ ID NO: 1 + SEQ ID NO: 51) | −13.218 | 0.76 | 0.21 | 0.55 | 0.9 | 0.7 | 0.82 |
| 3 | (SEQ ID NO: 1 + SEQ ID NO: 51)/(SEQ ID NO: 91) | 2.112 | 0.77 | 0.26 | 0.62 | 0.79 | 0.56 | 0.83 |
| **4** | **(SEQ ID NO: 1 + SEQ ID NO: 81)/(SEQ ID NO: 56 + SEQ ID NO: 96)** | **0.652** | **0.83** | **0.19** | **0.62** | **0.9** | **0.72** | **0.85** |
| 5 | (SEQ ID NO: 1 + SEQ ID NO: 71 + SEQ ID NO: 76)/(SEQ ID NO: 46 + SEQ ID NO: 91) | 1.362 | 0.8 | 0.21 | 0.55 | 0.9 | 0.7 | 0.82 |
| 6 | (SEQ ID NO: 1 + SEQ ID NO: 66 + SEQ ID NO: 71)/(SEQ ID NO: 46 + SEQ ID NO: 56 + SEQ ID NO: 91) | 0.778 | 0.8 | 0.2 | 0.38 | 0.99 | 0.92 | 0.79 |
| 7 | (SEQ ID NO: 11 + SEQ ID NO: 16 + SEQ ID NO: 26 + SEQ ID NO31 + SEQ ID NO: 76)/(SEQ ID NO: 56 + SEQ ID NO: 96) | 1.987 | 0.81 | 0.22 | 0.52 | 0.9 | 0.68 | 0.81 |
| 8 | (SEQ ID NO: 11 + SEQ ID NO: 36 + SEQ ID NO: 51 + SEQ ID NO: 81)/(SEQ ID NO: 56 + SEQ ID NO: 86 + SEQ ID NO: 91 + SEQ ID NO: 101) | 0.733 | 0.82 | 0.18 | 0.48 | 0.97 | 0.88 | 0.81 |
| **9** | **(SEQ ID NO: 1 + SEQ ID NO: 16 + SEQ ID NO: 41 + SEQ ID NO: 71 + SEQ ID NO: 81)/(SEQ ID NO: 21 + SEQ ID NO: 46 + SEQ ID NO: 91 + SEQ ID NO: 96)** | **1.041** | **0.86** | **0.18** | **0.66** | **0.9** | **0.73** | **0.86** |
| **10** | **(SEQ ID NO: 1 + SEQ ID NO: 6 + SEQ ID NO: 11 + SEQ ID NO: 26 + SEQ ID NO: 41 + SEQ ID NO: 51 + SEQ ID NO: 61 + SEQ ID NO: 76)/(SEQ ID NO: 21 + SEQ ID NO: 96)** | **2.998** | **0.83** | **0.2** | **0.59** | **0.9** | **0.71** | **0.83** |

The combinations in bold gave the most significant results.

b) Combination of 2, 3, 4, 5, 6, 7, 8, 9, 10 genes (k) for diagnosing benign steatosis (taking into account the 5 equivalent genes disclosed in table 1 and the listing for each cluster)

| k | score | threshold | AUC | ER | SN (benign) | SP (NASH) | PPV | NPV |
|---|---|---|---|---|---|---|---|---|
| 2 | (cluster 1 + cluster 2) | −12.370 | 0.72 | 0.22 | 0.34 | 0.97 | 0.83 | 0.77 |
| 3 | (cluster 1 + cluster 15)/(cluster 19) | 2.289 | 0.76 | 0.26 | 0.59 | 0.81 | 0.57 | 0.82 |
| 4 | (cluster 1 + cluster 6 + cluster 11 + cluster 16) | −27.419 | 0.76 | 0.24 | 0.45 | 0.9 | 0.65 | 0.79 |

-continued

| k | score | threshold | AUC | ER | SN (benign) | SP (NASH) | PPV | NPV |
|---|---|---|---|---|---|---|---|---|
| 5 | (cluster 2 + cluster 6)/(cluster 5 + cluster 18 + cluster 19) | 0.5724 | 0.76 | 0.23 | 0.62 | 0.84 | 0.62 | 0.84 |
| **6** | **(cluster 1 + cluster 17)/(cluster 5 + cluster 10 + cluster 12 + cluster 20)** | **0.321** | **0.81** | **0.2** | **0.48** | **0.94** | **0.78** | **0.81** |
| 7 | (cluster 1 + cluster 3 + cluster 4 + cluster 6 + cluster 11)/(cluster 10 + cluster 18) | 2.112 | 0.78 | 0.22 | 0.76 | 0.79 | 0.61 | 0.88 |
| 8 | (cluster 1 + cluster 3 + cluster 7 + cluster 11 + cluster 13 + cluster 16 + cluster 17)/(cluster 10) | 5.118 | 0.78 | 0.22 | 0.66 | 0.84 | 0.63 | 0.85 |
| 9 | (cluster 1 + cluster 2 + cluster 9 + cluster 14 + cluster 17)/(cluster 10 + cluster 12 + cluster 19 + cluster 20) | 0.9116 | 0.78 | 0.23 | 0.41 | 0.93 | 0.71 | 0.78 |
| **10** | **(cluster 2 + cluster 8 + cluster 13 + cluster 15 + cluster 16 + cluster 17)/(cluster 5 + cluster 12 + cluster 18 + cluster 21)** | **1.113** | **0.8** | **0.22** | **0.52** | **0.9** | **0.68** | **0.81** |

The combinations in bold gave the most significant results.

c) With all the representative genes of the clusters 1 to 21, one obtains:

AUC: 0.84

Sensitivity (identification of benign steatosis): 0.45

Specificity: 0.94

PPV: 0.76

NPV: 0.80

Error rate: 0.21 d) With the 5 equivalent and representative genes of the clusters 1 to 21, one obtains:

AUC: 0.80

Sensitivity (identification of benign steatosis): 0.38

Specificity: 0.93

PPV: 0.69

NPV: 0.78

Error rate: 0.24 e) Depending of the type of algorithm used, it may be necessary to determine a threshold for the determination of a binary test outcome from a continuous scoring variable provided by the test. The determination of this threshold is done to conform to the performance requirements. For instance, it may be important to build a test highly specific or sensitive. Area Under the Curve (AUC) is a measure of a classifier/test performance across all possible values of the thresholds. The higher the AUC, the better the performance of the test.

Performance of the test with all the representative genes of the clusters 1 to 21 for different values of the threshold:

| threshold | SN | SP | PPV | NPV | ER |
|---|---|---|---|---|---|
| 1.31 | 0.03 | 1.00 | 1.00 | 0.71 | 0.29 |
| 1.55 | 0.45 | 0.94 | 0.76 | 0.8 | 0.21 |
| 1.58 | 0.55 | 0.90 | 0.70 | 0.82 | 0.21 |
| 1.65 | 0.62 | 0.85 | 0.64 | 0.84 | 0.22 |
| 1.70 | 0.69 | 0.81 | 0.61 | 0.86 | 0.23 |

-continued

| threshold | SN | SP | PPV | NPV | ER |
|---|---|---|---|---|---|
| 1.71 | 0.72 | 0.75 | 0.55 | 0.86 | 0.26 |
| 1.74 | 0.83 | 0.70 | 0.55 | 0.90 | 0.26 |
| 1.76 | 0.83 | 0.66 | 0.51 | 0.90 | 0.29 |
| 1.83 | 0.93 | 0.60 | 0.50 | 0.95 | 0.30 |
| 1.88 | 0.93 | 0.55 | 0.47 | 0.95 | 0.33 |
| 1.92 | 0.93 | 0.51 | 0.45 | 0.94 | 0.36 |
| 1.95 | 0.93 | 0.45 | 0.42 | 0.94 | 0.41 |
| 1.99 | 0.93 | 0.40 | 0.40 | 0.93 | 0.44 |
| 2.00 | 0.93 | 0.36 | 0.39 | 0.92 | 0.47 |
| 2.05 | 0.97 | 0.30 | 0.37 | 0.95 | 0.50 |
| 2.08 | 0.97 | 0.25 | 0.36 | 0.94 | 0.53 |
| 2.12 | 1.00 | 0.21 | 0.35 | 1.00 | 0.55 |
| 2.26 | 1.00 | 0.15 | 0.34 | 1.00 | 0.59 |
| 2.30 | 1.00 | 0.10 | 0.33 | 1.00 | 0.63 |
| 2.40 | 1.00 | 0.06 | 0.32 | 1.00 | 0.66 |
| 2.77 | 1.00 | 0.01 | 0.31 | 1.00 | 0.69 |

Example 2: Diagnosis of NASH+Fibrosis

True and false positive results, NPV, PPV, specificity and sensitivity are defined and calculated as follows:

| | | Diagnosis of NASH + fibrosis (obtained by biopsy) | |
|---|---|---|---|
| | | Positive | Negative |
| Test outcome (association with a gene expression modulation) | Positive | True Positive (TP) | False positive (FP) |
| | Negative | False negative (FN) | True negative (TN) |

PPV (Positive Predictive Value)=TP/(TP+FP)

NPV (Negative Predictive Value)=TN/(TN-FEN)

Specificity=TN/(TN+FP)

Sensitivity=TP/(TP+FN)

ER=Error rate a) Combination of 2, 3, 4, 5, 6, 7, 8, and 9 (k) for diagnosing NASH and NASH with fibrosis (taking into account only the representative gene for each cluster)

| k | score | threshold | AUC | ER | SN | SP | PPV | NPV |
|---|---|---|---|---|---|---|---|---|
| 2 | (SEQ ID NO: 116)/(SEQ ID NO: 146) | 0.973 | 0.71 | 0.27 | 0.97 | 0.5 | 0.65 | 0.94 |
| 3 | (SEQ ID NO: 106 + SEQ ID NO: 116)/(SEQ ID NO: 146) | 2.356 | 0.73 | 0.3 | 0.94 | 0.47 | 0.63 | 0.89 |
| 4 | (SEQ ID NO: 106 + SEQ ID NO: 111 + SEQ ID NO: 116 + SEQ ID NO: 151) | −32.855 | 0.78 | 0.25 | 0.82 | 0.68 | 0.71 | 0.79 |
| 5 | (SEQ ID NO: 111 + SEQ ID NO: 121 + SEQ ID NO: 131 + SEQ ID NO: 136 + SEQ ID NO: 151) | −43.811 | 0.77 | 0.27 | 0.82 | 0.65 | 0.69 | 0.79 |
| 6 | (SEQ ID NO: 111 + SEQ ID NO: 116 + SEQ ID NO: 121 + SEQ ID NO: 126 + 10769__2 + SEQ ID NO: 136) | −53.877 | 0.75 | 0.27 | 0.76 | 0.71 | 0.71 | 0.75 |
| **7** | **(SEQ ID NO: 106 + SEQ ID NO: 111 + SEQ ID NO: 116 + SEQ ID NO: 121 + SEQ ID NO: 131 + SEQ ID NO: 136 + SEQ ID NO: 151)** | **−62.855** | **0.83** | **0.21** | **0.76** | **0.82** | **0.81** | **0.78** |
| **8** | **(SEQ ID NO: 106 + SEQ ID NO: 111 + SEQ ID NO: 116 + SEQ ID NO: 121 + SEQ ID NO: 126 + SEQ ID NO: 131 + SEQ ID NO: 136 + SEQ ID NO: 151)** | **−70.301** | **0.81** | **0.19** | **0.82** | **0.79** | **0.79** | **0.82** |
| 9 | (SEQ ID NO: 106 + SEQ ID NO: 111 + SEQ ID NO: 116 + SEQ ID NO: 121 + SEQ ID NO: 126 + SEQ ID NO: 131 + SEQ ID NO: 136 + SEQ ID NO: 151)/(SEQ ID NO: 146) | 10.904 | 0.72 | 0.3 | 0.94 | 0.47 | 0.63 | 0.89 |

b) Combination of 2, 3, 4, 5, 6, 7, 8, and 9 genes (k) for diagnosing NASH and NASH with fibrosis (taking into account the 5 equivalent genes disclosed in table 1 for each cluster)

| k | score | threshold | AUC | ER | SN (NASH) | SP (fibrosis) | PPV | NPV |
|---|---|---|---|---|---|---|---|---|
| 2 | (cluster 22 + cluster 23) | −16.231 | 0.73 | 0.27 | 0.71 | 0.76 | 0.75 | 0.71 |
| 3 | (cluster 22 + cluster 28 + cluster 31) | −27.258 | 0.8 | 0.25 | 0.85 | 0.64 | 0.71 | 0.81 |
| 4 | (cluster 22 + cluster 23 + cluster 24 + cluster 28) | −34.265 | 0.83 | 0.24 | 0.74 | 0.79 | 0.78 | 0.74 |
| 5 | (cluster 23 + cluster 25 + cluster 27 + cluster 28 + cluster 31) | −45.402 | 0.83 | 0.22 | 0.85 | 0.7 | 0.74 | 0.82 |
| **6** | **(cluster 22 + cluster 23 + cluster 25 + cluster 27 + cluster 28 + cluster 31)** | **−53.882** | **0.85** | **0.21** | **0.74** | **0.85** | **0.83** | **0.76** |
| **7** | **(cluster 22 + cluster 23 + cluster 24 + cluster 25 + cluster 27 + cluster 28 + cluster 31)** | **−62.595** | **0.85** | **0.21** | **0.88** | **0.7** | **0.75** | **0.85** |
| 8 | (cluster 22 + cluster 23 + cluster 24 + cluster 25 + cluster 26 + cluster 27 + cluster 28 + cluster 31) | −69.354 | 0.81 | 0.22 | 0.68 | 0.88 | 0.85 | 0.72 |

c) With all the representative genes of the clusters 1 to 10, one obtains:

AUC: 0.66

Sensitivity (identification of NASH+fibrosis): 0.61

Specificity: 0.82

PPV: 0.77

NPV: 0.68

Error rate: 0.28 d) With the 5 equivalent and representative genes of the clusters 1 to 10, one obtains:

AUC: 0.67

Sensitivity (identification of NASH+fibrosis): 0.52

Specificity: 0.82

PPV: 0.74

NPV: 0.64

Error rate: 0.33 e) Performance of the test with all the representative genes of the clusters 1 to 10 for different values of the threshold:

| threshold | SN | SP | PPV | NPV | ER |
|---|---|---|---|---|---|
| 3.84 | 1.00 | 0.08 | 0.52 | 1.00 | 0.49 |
| 4.52 | 0.91 | 0.28 | 0.56 | 0.77 | 0.43 |
| 4.68 | 0.85 | 0.42 | 0.58 | 0.79 | 0.39 |
| 4.71 | 0.82 | 0.44 | 0.59 | 0.76 | 0.39 |
| 4.79 | 0.76 | 0.50 | 0.60 | 0.72 | 0.39 |
| 4.87 | 0.70 | 0.50 | 0.58 | 0.67 | 0.42 |
| 4.94 | 0.67 | 0.50 | 0.56 | 0.64 | 0.43 |
| 4.97 | 0.61 | 0.50 | 0.54 | 0.60 | 0.46 |
| 5.21 | 0.55 | 0.58 | 0.56 | 0.60 | 0.45 |
| 5.69 | 0.52 | 0.81 | 0.74 | 0.66 | 0.34 |
| 5.83 | 0.45 | 0.83 | 0.75 | 0.64 | 0.36 |
| 5.93 | 0.42 | 0.86 | 0.78 | 0.63 | 0.36 |
| 6.04 | 0.36 | 0.86 | 0.75 | 0.61 | 0.39 |
| 6.06 | 0.30 | 0.89 | 0.71 | 0.60 | 0.40 |
| 6.11 | 0.27 | 0.89 | 0.69 | 0.59 | 0.42 |
| 6.25 | 0.24 | 0.94 | 0.80 | 0.60 | 0.40 |
| 6.33 | 0.21 | 0.97 | 0.88 | 0.59 | 0.40 |
| 6.40 | 0.15 | 0.97 | 0.83 | 0.57 | 0.43 |
| 6.55 | 0.12 | 0.97 | 0.80 | 0.56 | 0.45 |
| 6.86 | 0.06 | 0.97 | 0.67 | 0.55 | 0.48 |
| 7.41 | 0.00 | 0.97 | 0.00 | 0.53 | 0.51 |

Example 3: Validation of the Results Using Two Approaches (Threshold/Global)

3.1. Material and Methods

The "Global approach" has been disclosed previously (comparison of distributions using non parametric tests—usually the significance cutoff is set to 0.05).

The "Threshold Approach"

Several main arrangements of the gut microbiota have been reported. M, Raes J, Pelletier E et al. reported in their article from Nature, 2011 that there were three such arrangements. They reflect the different combinations of bacteria that can perform critical functions for their survival and the host, such as energy harvest and processing of metabolites. For instance, one of these arrangements, enterotype 1, is known to derive energy primarily from carbohydrates and proteins through fermentation. These enterotypes shape the microbes hosted in the gut and consequently the presence/absence/abundance of the different species. The marker of interest for the phenotype may be dependent of such arrangements of the microbiota.

To identify such markers, we searched for trends seen in part of samples only, and not in all samples as it is usually done. We used the binomial distribution in order to estimate if the samples in the subgroup, defined by a relative abundance of the gene, are enriched or not for one phenotype. A Chi-squared test is used for another evaluation of the enrichment.

Statistics

Chi-squared test is commonly used by statisticians to study the association between two categorical variables. Once the test of absence of independence is rejected, it is possible to estimate the strength of the association between the two variables using various methods, such as Tschuprow's T reported here. If Tschuprow's T is 0, there is no association between the variables, while if it is 1, the association is perfect.

The NASH1 Group of Patients ("NASH1 Patients")

A single-centre cross-sectional study has been conducted from November 2011 to January 2012 to determine the metagenotypes in stool samples of 96 adult subjects who have had a liver biopsy prior to enrollment. Exclusion criteria were: antibiotic therapy within previous 6 weeks, regular intake of probiotics during last 2 weeks, colonoscopy within previous 6 months, previous intestinal (bariatric) surgery, alcohol consumption >20 g/d (w)/>30 g/d (m), identifiable cause of liver disease (viral, autoimmune, genetic, toxic, drug-induced). Each subject received a kit (Fecotainer™+AnaeroGen™) for collecting faeces himself at home and a 30€ fee for participation. The stools were kept at 4° C. and transported within 36 h.

The NASH2 Group of Patients ("NASH2 Patients")

NASH2 patients were recruited with the same inclusion criteria as patients from NASH1. The recruitment was extended to several new centers (Amiens, Angers, Berne, Bordeaux, Nice and another center from Paris) to complement the recruitment from the original center. The collection method was slightly modified for practical reasons: one stool sample only was collected and stored in a fixative solution during transport at ambient temperature.

The Crohn-Suffering Patients ("Crohn Patients")

19 patients were recruited in St Louis and St Antoine hospitals in Paris. Several samples were collected for each patient, summing up to 118 samples collected.

Crohn disease evolves in time and the status of the patient may change at each sampling point. The criteria chosen for the description of the state of the disease for each sample is related to stability in time.

At the moment of the sampling, the patient is considered stable if:

- the patient estimates he is in good health condition (Harvey Bradshaw index strictly lower than 4),
- the patient has low calprotectin (strictly lower than 150),
- the patient was not asked to intensify his treatment:
  - introducing anti-TNF treatment,
  - introducing immunosuppressant or increasing dosage of immunosuppressant,
  - introducing antibiotics, or
  - introducing cortisone, and
- the patient is not taking any antibiotics.

A patient is "stable" in time if he is stable at the two next sampling times at least. Samples can be classified in two groups using this method: one group of samples collected from patients stable in time, one group of samples collected from patients whose state is evolutive.

Figure 1B:
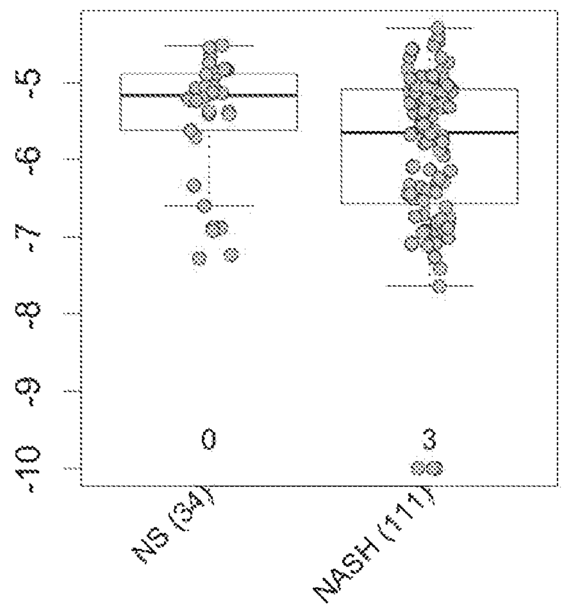
Figure 1C:
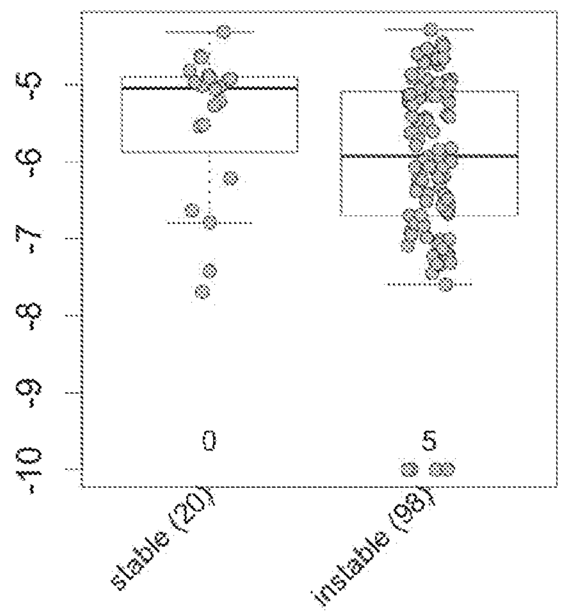

3.2. Results 3.2.1. The Mgs 10764_1_2 (SEQ ID NO: 1-5 and Cluster 1) is of High Interest on NASH1, NASH2 and Crohn Patients Global Approach:

The results of the global approach are disclosed on FIGS. 1A, 1B and 1C (the number of patients for whom the information is available in indicated between brackets).

Global statistics (comparison of median/distribution—usually the significance cutoff is set to 0.05):

Wilcoxon test:
- NASH1: 0.00056
- NASH2: 0.015
- Crohn: 0.034

Kolmogorov-Smirnov test:
- NASH1: 0.011
- NASH2: 0.013
- Crohn: 0.05

Figure 1D:
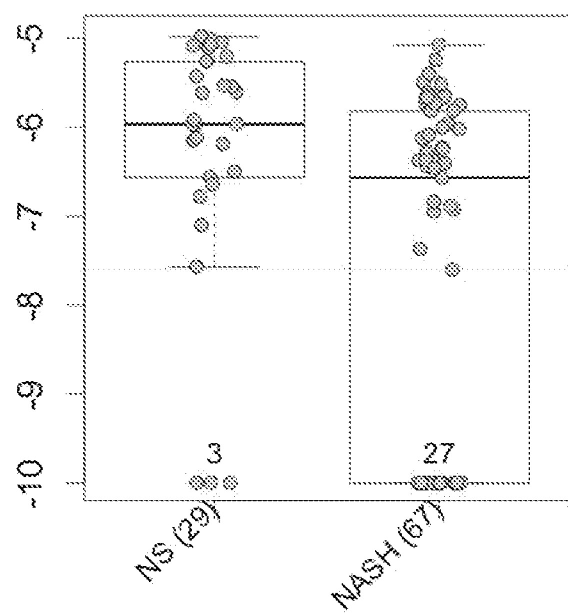
Figure 1E:
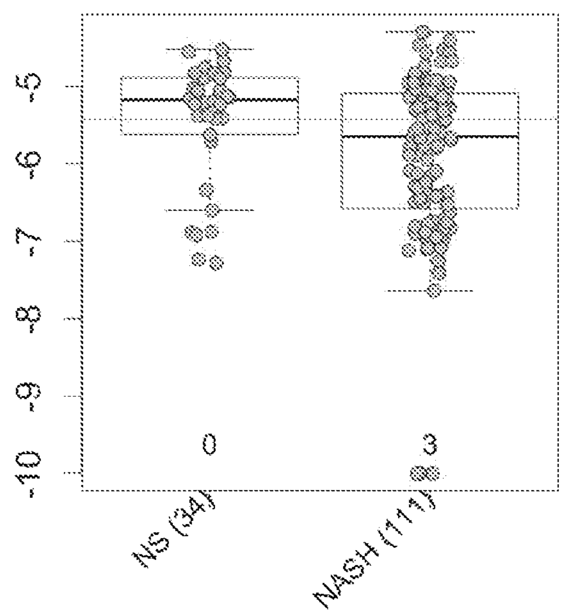
Figure 1F:
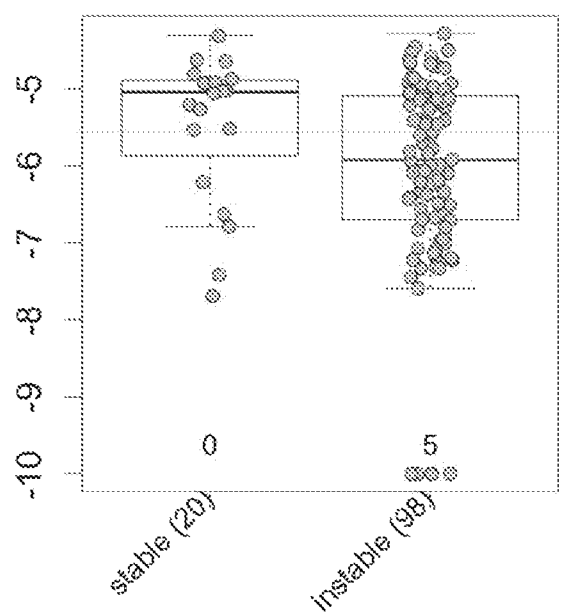

Threshold Approach:

Using an automatic procedure to determine threshold separating low and high abundance, FIGS. 1D), E) and F) have been obtained (the number of patients for whom the information is available in indicated between brackets).

N.B.—the relative abundances are log 10-transformed
"−10" is an artificial value introduced when the mgs is not detected The following tables show the NASH status versus low/high mgs relative abundance:

10764_1_2 low/high versus NASH status (NASH1)

| | Simple Steatosis | NASH |
|---|---|---|
| High | 26 | 39 |
| Low | 3 | 28 |

10764_1_2 low/high versus NASH status (NASH2)

| | Simple Steatosis | NASH |
|---|---|---|
| High | 25 | 47 |
| Low | 9 | 64 |

10764_1_2 low/high versus stability (Crohn)

| | stable | instable |
|---|---|---|
| High | 15 | 41 |
| Low | 5 | 57 |

Results of the Chi-squared test (comparing phenotypes with low and high mgs abundance—the lower the values, the larger the difference between the two partitions, the stronger the enrichment—usually the significance cutoff is set to 0.05):

NASH1: 0.0053 (coefficient Tschuprow: 0.28)
NASH2: 0.0028 (coefficient Tschuprow: 0.25)
Crohn: 0.014 (coefficient Tschuprow: 0.23)

N.B. The usual metrics (Error rate, Specificity, Sensitivity) do not apply here as the criteria apply for one status of the phenotype only, i.e. the prediction of NASH/instability for part of the population. Positive Predictive Value, alt. Negative Predictive Value, could be computed (but are highly dependent of the prior prevalence of the status).

Link with Other Variables:

gene richness (defined as the average number of genes detected when sequencing at a depth of 11M reads)
 Wilcoxon test NASH1 (96 samples): 1.37e-5
 Wilcoxon test NASH2 (137 samples): 4.4e-6
 Wilcoxon test Crohn (83 samples): 5.3e-7

Diabetes (diagnosed or fasting blood glucose >6.1 mmol/L)
 Chi-squared test NASH1 (96 samples): 0.0013 (coef.Tschuprow: 0.33)
 Chi-squared test NASH2 (145 samples): 0.0061 (coef.Tschuprow: 0.23)

Metformin

Metformin is an anti diabetic treatment that is known to modify the gut microbiota Chi-squared test NASH2 (145 samples): 0.00026 (coef.Tschuprow: 0.30)

N.B. For now, I do not know how to deal with these interconnected factors waist/height ratio
 Wilcoxon test NASH1 (94 samples): 0.0069
 Wilcoxon test NASH2 (137 samples): 0.085

Conclusion:

Samples where the mgs 10764_1_2 is not abundant tend to be less healthy, i.e., in NASH cohorts (NASH1, NASH2), patients are more prone to have the advanced state of the disease, i.e. NASH, and not Simple Steatosis, and in Crohn, patients are more prone to be instable.

Figure 2A:
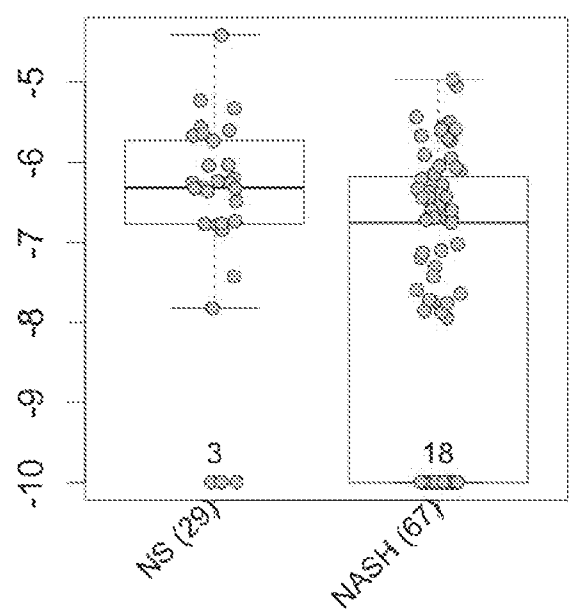
Figure 2B:
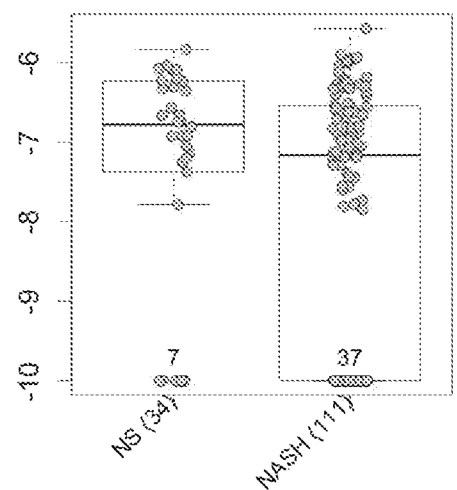
Figure 2C:
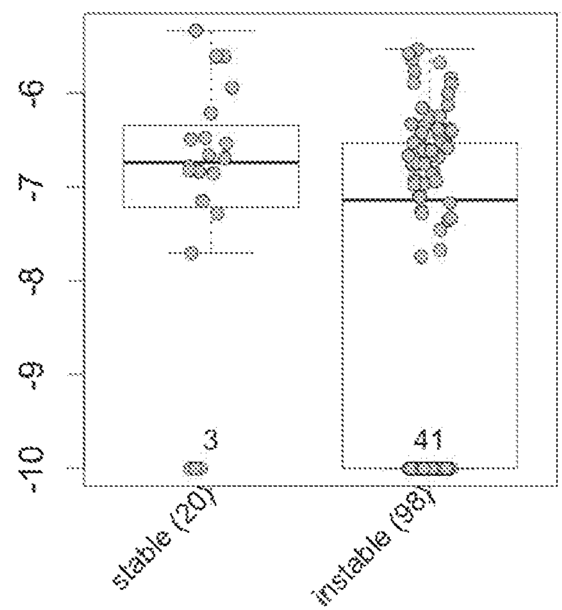

3.2.2. The Mgs 9828_3_1 (SEQ ID NO: 151-155—Cluster 31) is of High Interest on NASH1, NASH2 and Crohn Patients Global Approach:

The results of the global approach are disclosed on FIGS. 2A, 2B and 2C (the number of patients for whom the information is available in indicated between brackets).

Global statistics (comparison of median/distribution—usually the significance cutoff is set to 0.05):

Wilcoxon test:
 NASH1: 0.014
 NASH2: 0.064
 Crohn: 0.052

Kolmogorov-Smirnov test:
 NASH1: 0.032
 NASH2: 0.023
 Crohn: 0.14

Threshold Approach

Figure 2D:
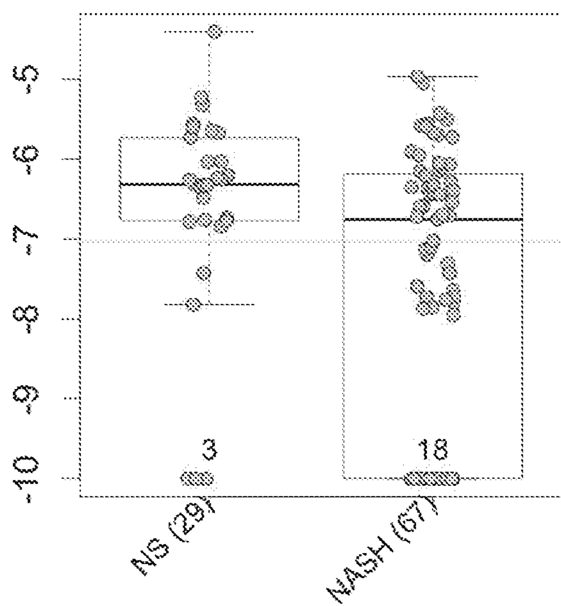
Figure 2E:
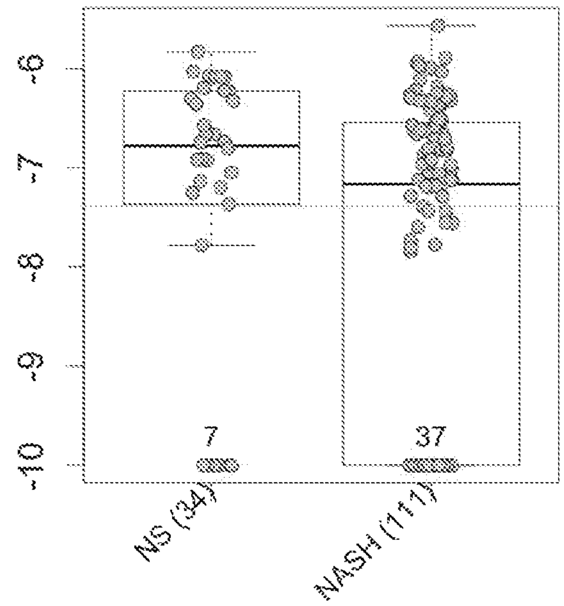
Figure 2F:
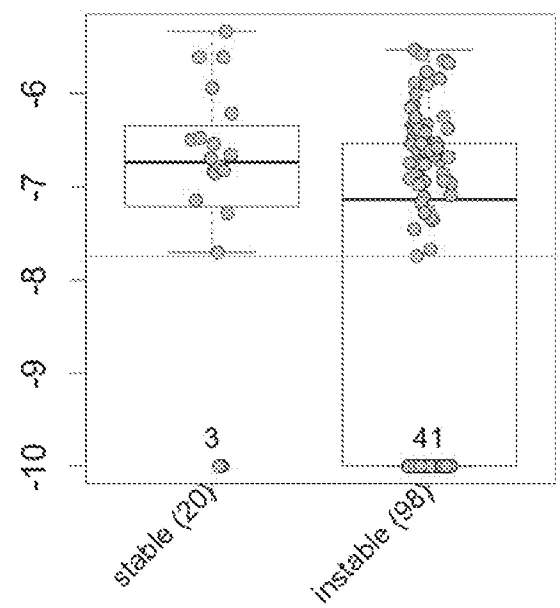
Figure 3A:
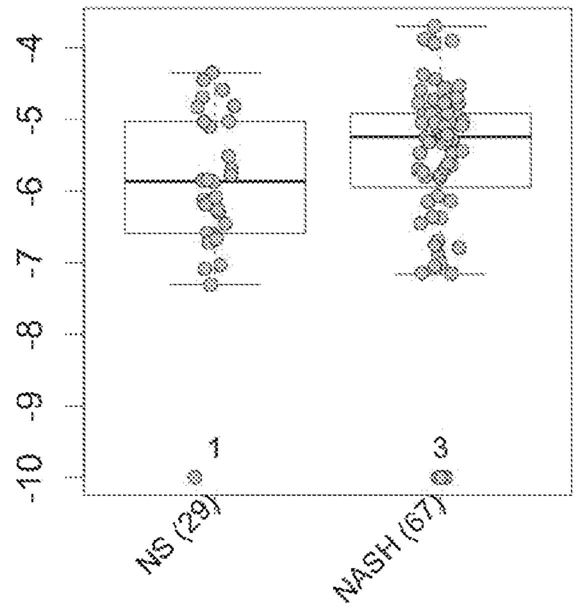
Figure 3B:
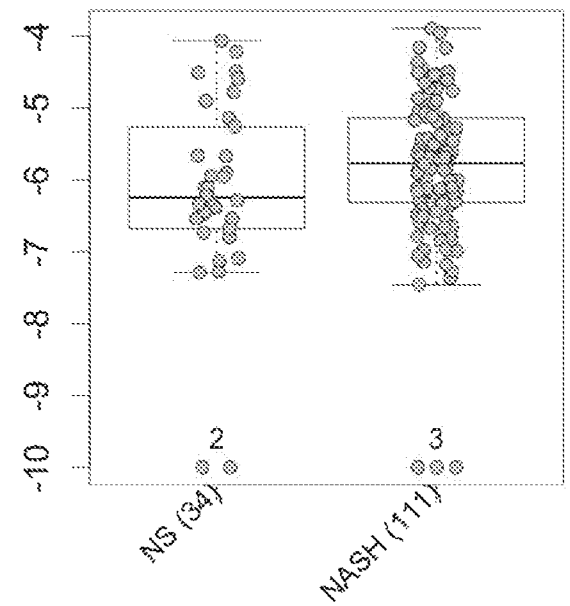
Figure 3C:
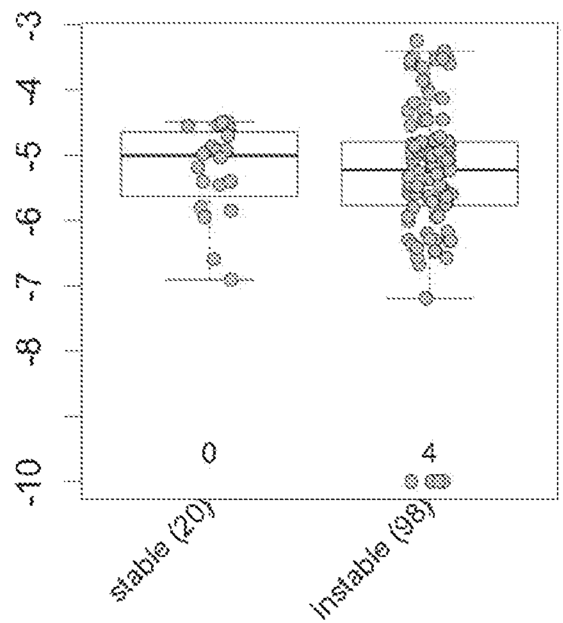
Figure 3D:
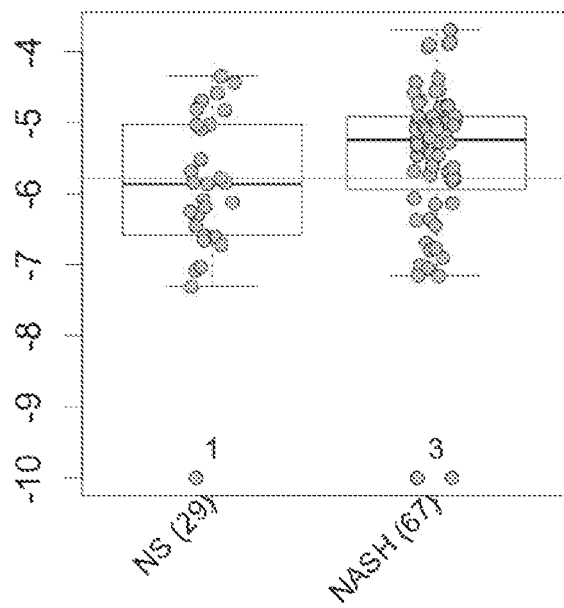
Figure 3E:
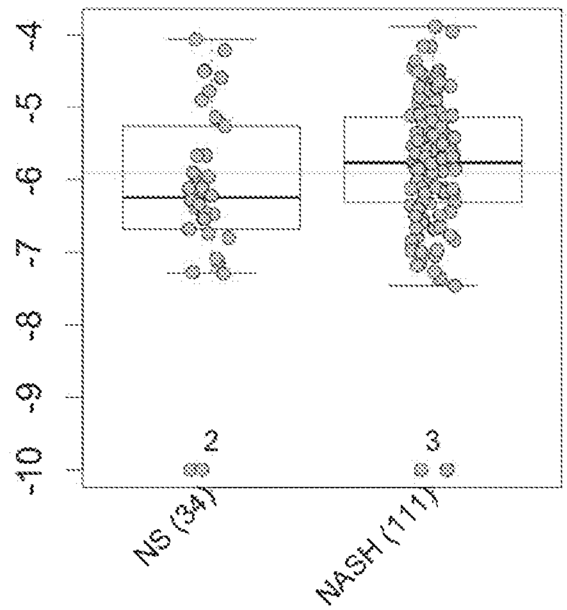
Figure 3F:
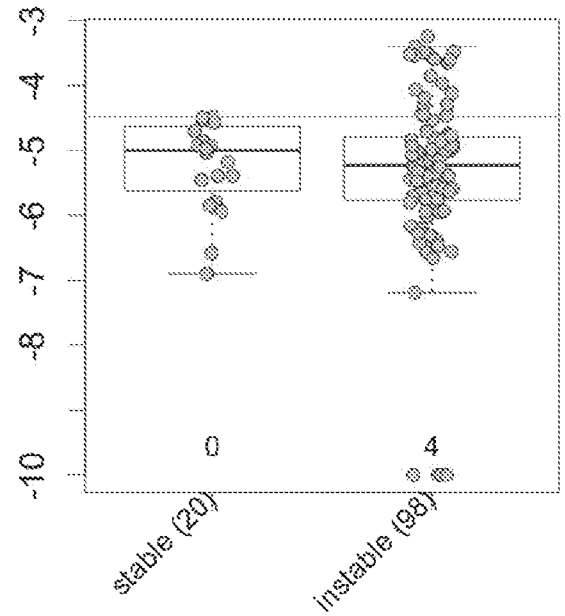

Using an automatic procedure to determine threshold separating low and high abundance, FIGS. 2D), 2E) and 2F) have been obtained (the number of patients for whom the information is available in indicated between brackets).

N.B.

the relative abundances are log 10-transformed
"−10" is an artificial value introduced when the mgs is not detected The following tables show the NASH status versus low/high mgs relative abundance:

9828_3_1 low/high versus NASH status (NASH1)

| | Simple Steatosis | NASH |
|---|---|---|
| High | 24 | 34 |
| Low | 5 | 33 |

9828_3_1 low/high versus NASH status (NASH2)

| | Simple Steatosis | NASH |
|---|---|---|
| High | 26 | 64 |
| Low | 8 | 47 |

9828_3_1 low/high versus stability (Crohn)

| | stable | instable |
|---|---|---|
| High | 17 | 56 |
| Low | 3 | 42 |

Results of the Chi-squared test (comparing phenotypes with low and high mgs abundance—the lower the values, the stronger the enrichment—usually the significance cutoff is set to 0.05):

NASH1: 0.0066 (coef.Tschuprow: 0.28)
NASH2: 0.076
Crohn: 0.037 (coef.Tschuprow: 0.19)

N.B. The usual metrics (Error rate, Specificity, Sensitivity) do not apply here as the criteria apply for one status of the phenotype only, i.e. the prediction of NASH/instability for part of the population. Positive Predictive Value, alt. Negative Predictive Value, could be computed (but are highly dependent of the prior prevalence of the status).

Link with Other Variables gene richness (defined as the average number of genes detected when sequencing at a depth of 11M reads)

Wilcoxon test NASH1 (96 samples): 0.0004

Wilcoxon test NASH2 (137 samples): 2.3e-6

Wilcoxon test Crohn (83 samples): 1.3e-7

Diabetes (diagnosed or fasting blood glucose >6.1 mmol/L)

Chi-squared test NASH1 (96 samples): 0.48

Chi-squared test NASH2 (145 samples): 0.0086 (coef.Tschuprow: 0.22)

Metformin

Metformin is an anti diabetic treatment that is known to modify the gut microbiota Chi-squared test NASH2 (145 samples): 0.0026 (coef.Tschuprow: 0.25)

waist/height ratio

Chi-squared test NASH1 (94 samples): 0.26

Chi-squared test NASH2 (137 samples): 0.042 (coef.Tschuprow: 0.17)

HOMA (<=3.5)

Chi-squared test NASH1 (80 samples): 0.048 (coef.Tschuprow: 0.21)

Chi-squared test NASH2 (137 samples): 0.019 (coef.Tschuprow: 0.20)

Hyper triglyceridemia (<=1.7 mmol/L or specific treatment)

Chi-squared test NASH1 (96 samples): 0.11

Chi-squared test NASH2 (145 samples): 0.044

Conclusion:

Samples where the mgs 9828_3_1 is not abundant tend to be less healthy, i.e. in NASH cohorts (NASH1, NASH2), patients are more prone to have the advanced state of the disease, i.e. NASH, and not Simple Steatosis, and in Crohn, patients are more prone to be instable.

3.2.3. The Mgs 6069_2_2 (SEQ ID NO: 91-95—Cluster 19) is of High Interest on NASH1, NASH2 and Crohn Patients Global Trends The results of the global approach are disclosed on FIGS. 3A, 3B and 3C (the number of patients for whom the information is available in indicated between brackets).

Global statistics (comparison of median/distribution—usually the significance cutoff is set to 0.05):

Wilcoxon test:

NASH1: 0.048

NASH2: 0.082

Crohn: 0.070

Kolmogorov-Smirnov test:

NASH1: 0.020

NASH2: 0.056

Crohn: 0.49

Threshold Approach

Using an automatic procedure to determine threshold separating low and high abundance, FIGS. 3 D, E, and F have been obtained (the number of patients for whom the information is avalailable in indicated between brackets).

N.B.

the relative abundances are log 10-transformed

"−10" is an artificial value introduced when the mgs is not detected

The following tables show the NASH status versus low/high mgs relative abundance:

| 9828_3_1 low/high versus NASH status (NASH1) | | |
|---|---|---|
| | Simple Steatosis | NASH |
| High | 11 | 48 |
| Low | 18 | 19 |

| 9828_3_1 low/high versus NASH status (NASH2) | | |
|---|---|---|
| | Simple Steatosis | NASH |
| High | 12 | 65 |
| Low | 22 | 46 |

| 9828_3_1 low/high versus stability (Crohn) | | |
|---|---|---|
| | stable | instable |
| High | 0 | 20 |
| Low | 20 | 78 |

Results of the Chi-squared test (comparing phenotypes with low and high mgs abundance—the lower the values, the stronger the enrichment—usually the significance cutoff is set to 0.05):

NASH1: 0.0039 (coef.Tschuprow: 0.29)

NASH2: 0.029 (coef.Tschuprow: 0.18)

Crohn: 0.059

N.B. The usual metrics (Error rate, Specificity, Sensitivity) do not apply here as the criteria apply for one status of the phenotype only, i.e. the prediction of NASH/instability for part of the population. Positive Predictive Value, alt. Negative Predictive Value, could be computed (but are highly dependent of the prior prevalence of the status).

Link with Other Variables

Diabetes (diagnosed or fasting blood glucose >6.1 mmol/L)

Chi-squared test NASH1 (96 samples): 0.015 (coef.Tschuprow: 0.25)

Chi-squared test NASH2 (145 samples): 0.00073 (coef.Tschuprow: 0.28)

Metformin

Metformin is an anti diabetic treatment that is known to modify the gut microbiota Chi-squared test NASH2 (145 samples): 0.00040 (coef.Tschuprow: 0.29)

HOMA (<=3.5)

Chi-squared test NASH1 (80 samples): 0.026 (coef.Tschuprow: 0.23)

Chi-squared test NASH2 (137 samples): 0.33

Hyper triglyceridemia (<=1.7 mmol/L or specific treatment)

Chi-squared test NASH1 (96 samples): 0.66

Chi-squared test NASH2 (145 samples): 0.0019 (coef.Tschuprow: 0.19)

Conclusion

Samples where the mgs 6069_2_2 is abundant tend to be less healthy, i.e. in NASH cohorts (NASH1, NASH2), patients are more prone to have the advanced state of the disease, i.e. NASH, and not Simple Steatosis, and in Crohn, patients are more prone to be instable.

3.2.4. The Three Mgs of High Interest Provide Different Information

In order to compare the three mgs of interest, we attempted two approaches:

1. Check for differences between low and high relative abundance (if there is no link between high/low relative abundance for two mgs, i.e., if the information provided by each mgs is complementary and not redundant, the chisq test should be significative),
2. Check for differences between low and high relative abundance with regard to the phenotype of interest (NASH in NASH cohorts or stability in Crohn cohort)

Using Low/High Relative Abundance Threshold:

NASH1

Comparison 10764_1_2 (row)/9828_3_1 (column)
Chi-squared p-value=0.0061

| | High | Low |
|---|---|---|
| High | 48 | 22 |
| Low | 12 | 20 |

Comparison 9828_3_1 (row)/6069_2_2 (column)
Chi-squared p-value=0.29

| | High | Low |
|---|---|---|
| High | 34 | 26 |
| Low | 29 | 13 |

Comparison 10764_1_2 (row)/6069_2_2 (column)
Chi-squared p-value=0.45

| | High | Low |
|---|---|---|
| High | 41 | 29 |
| Low | 22 | 10 |

NASH2

Comparison 10764_1_2 (row)/9828_3_1 (column)
Chi-squared p-value=8.26e-8

| | High | Low |
|---|---|---|
| High | 64 | 12 |
| Low | 31 | 45 |

Comparison 9828_3_1 (row)/6069_2_2 (column)
Chi-squared p-value=0.40

| | High | Low |
|---|---|---|
| High | 47 | 48 |
| Low | 33 | 24 |

Comparison 10764_1_2 (row)/6069_2_2 (column)
Chi-squared p-value=0.0058

| | High | Low |
|---|---|---|
| High | 31 | 45 |
| Low | 49 | 27 |

Crohn

Comparison 10764_1_2 (row)/9828_3_1 (column)
Chi-squared p-value=0.00020

| | High | Low |
|---|---|---|
| High | 46 | 11 |
| Low | 28 | 33 |

Comparison 9828_3_1 (row)/6069_2_2 (column)
Chi-squared p-value=1

| | High | Low |
|---|---|---|
| High | 13 | 61 |
| Low | 8 | 36 |

Comparison 10764_1_2 (row)/6069_2_2 (column)
Chi-squared p-value=0.025

| | High | Low |
|---|---|---|
| High | 5 | 52 |
| Low | 16 | 45 |

Using Low/High Relative Abundance Threshold+Phenotype of Interest:

10764_1_2×9828_3_1

NASH1 (Number of Simple Steatosis/Number of NASH)

| | 10764_1_2 low | 10764_1_2 high |
|---|---|---|
| 9828_3 high | 2/10 | 22/25 |
| 9828_3 low | 1/17 | 4/15 |

NASH2 (Number of Simple Steatosis/Number of NASH)

| | 10764_1_2 low | 10764_1_2 high |
|---|---|---|
| 9828_3 high | 5/24 | 21/40 |
| 9828_3 low | 6/39 | 2/8 |

Crohn (Number of Stable/Number of Instable)

| | 10764_1_2 low | 10764_1_2 high |
|---|---|---|
| 9828_3 high | 5/22 | 12/34 |
| 9828_3 low | 0/34 | 3/8 |

Figure 5A:
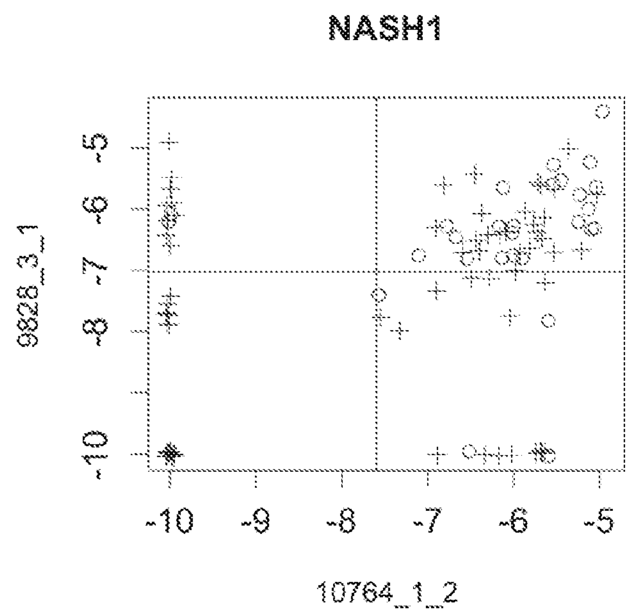
Figure 5B:
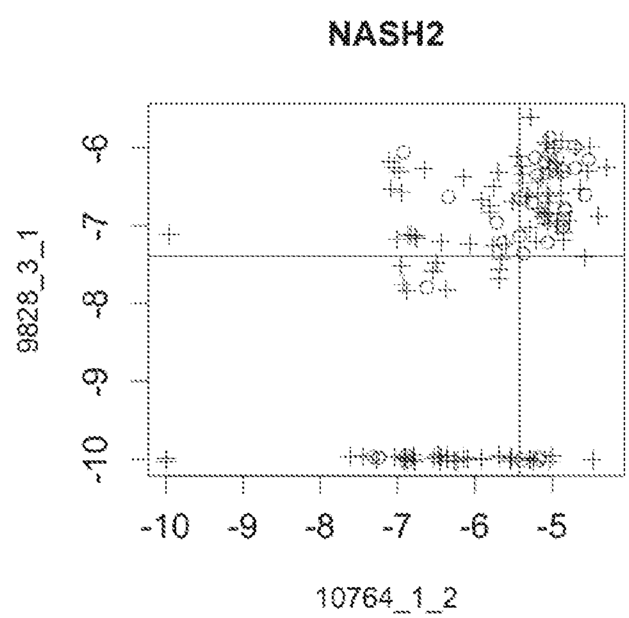
Figure 5C:
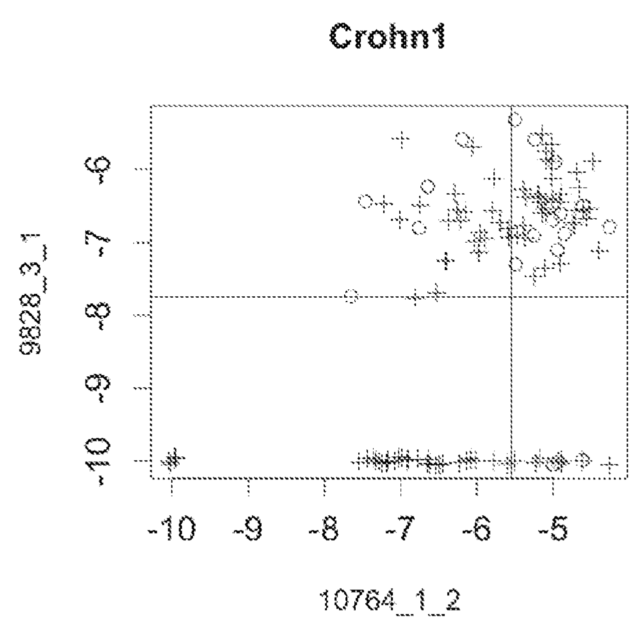

These results are reproduced on FIGS. 5A to 5C (circles represent simple steatosis or Crohn-stable status whereas crosses represent NASH or Crohn-instable status).

10764_21_2×6069_2_2

NASH1 (Number of Simple Steatosis/Number of NASH)

| | 10764_1_2 low | 10764_1_2high |
|---|---|---|
| 6069_2_2 high | 1/22 | 10/26 |
| 6069_2_2 low | 2/6 | 16/13 |

NASH2 (Number of Simple Steatosis/Number of NASH)

| | 10764_1_2low | 10764_1_2 high |
|---|---|---|
| 6069_2_2 high | 4/42 | 8/22 |
| 6069_2_2 low | 6/20 | 16/27 |

Crohn (Number of Stable/Number of Instable)

| | 10764_1_2low | 10764_1_2 high |
|---|---|---|
| 6069_2_2 high | 0/16 | 0/4 |
| 6069_2_2 low | 7/41 | 13/37 |

Figure 6A:
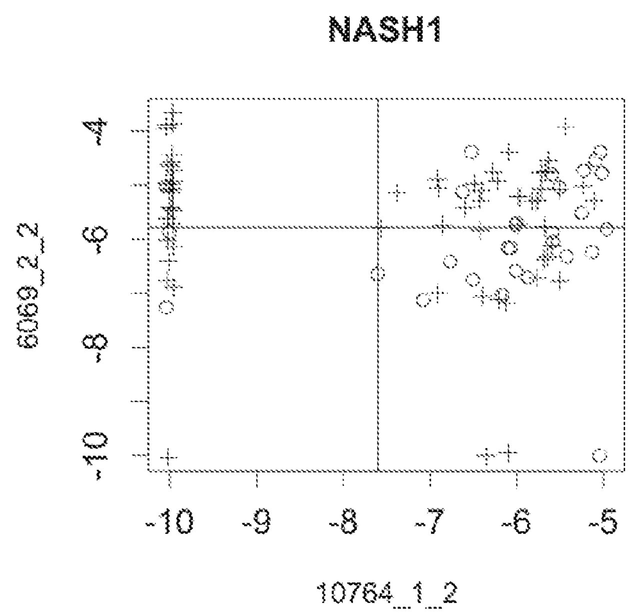
Figure 6B:
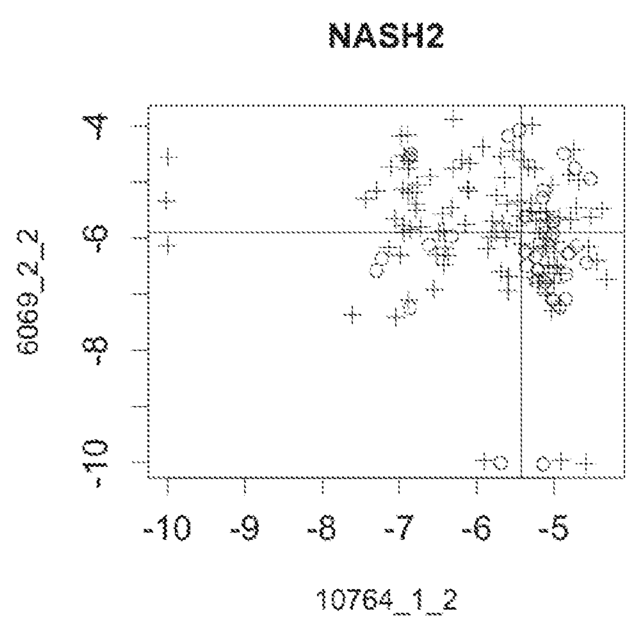
Figure 6C:
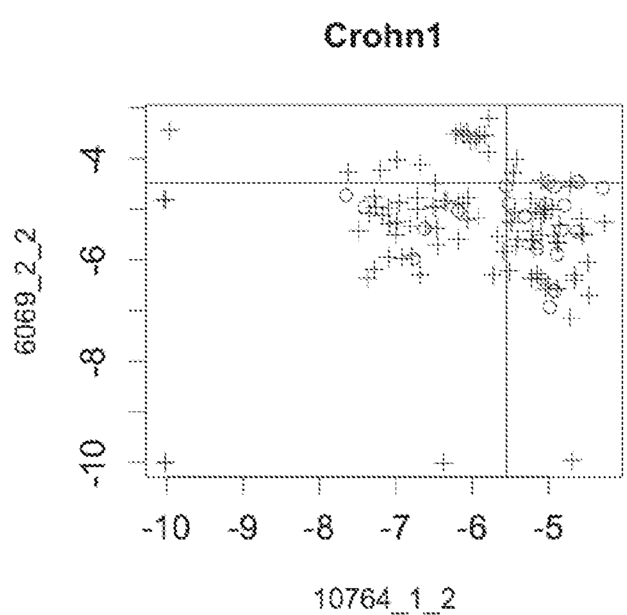

These results are reproduced on FIGS. 6A to 6C (circles represent simple steatosis or Crohn-stable status whereas crosses represent NASH or Crohn-instable status).

9828_3×6069_2_2

NASH1 (Number of Simple Steatosis/Number of NASH)

| | 9828_3 low | 9828_3 high |
|---|---|---|
| 6069_2_2 high | 2/24 | 9/24 |
| 6069_2_2 low | 3/8 | 15/11 |

NASH2 (Number of Simple Steatosis/Number of NASH)

| | 9828_3 low | 9828_3 high |
|---|---|---|
| 6069_2_2 high | 4/28 | 8/26 |
| 6069_2_2 low | 4/18 | 18/29 |

Crohn (Number of Stable/Number of Instable)

| | 9828_3 low | 9828_3 high |
|---|---|---|
| 6069_2_2 high | 0/7 | 1/12 |
| 6069_2_2 low | 3/34 | 16/45 |

Figure 7A:
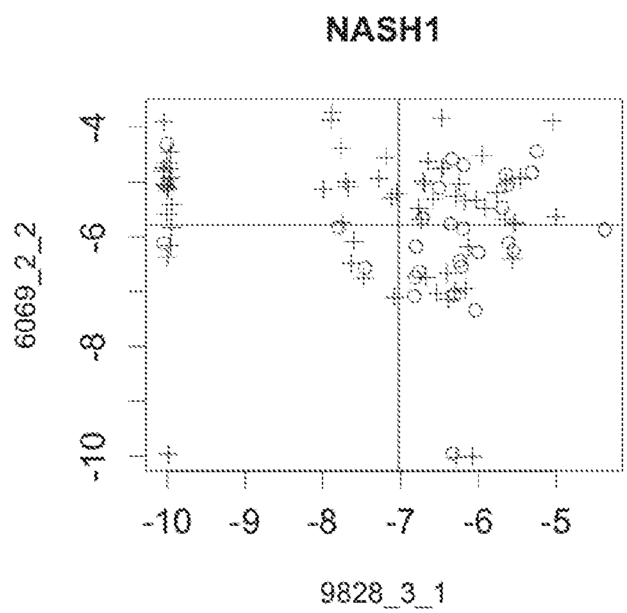
Figure 7B:
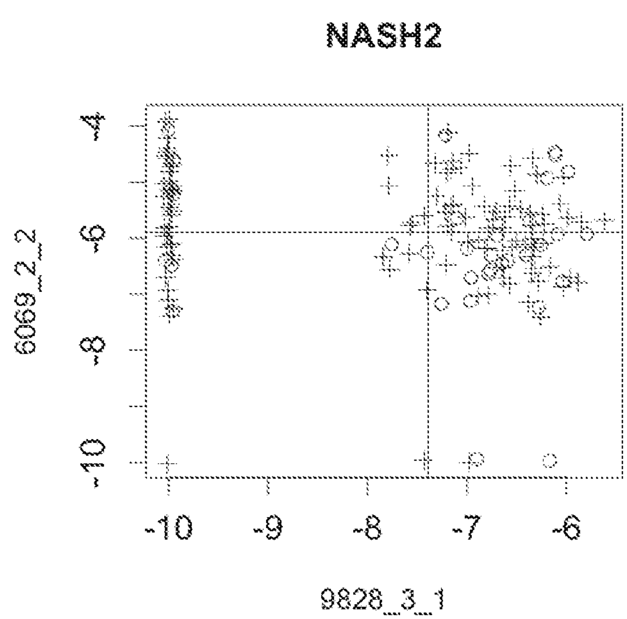
Figure 7C:
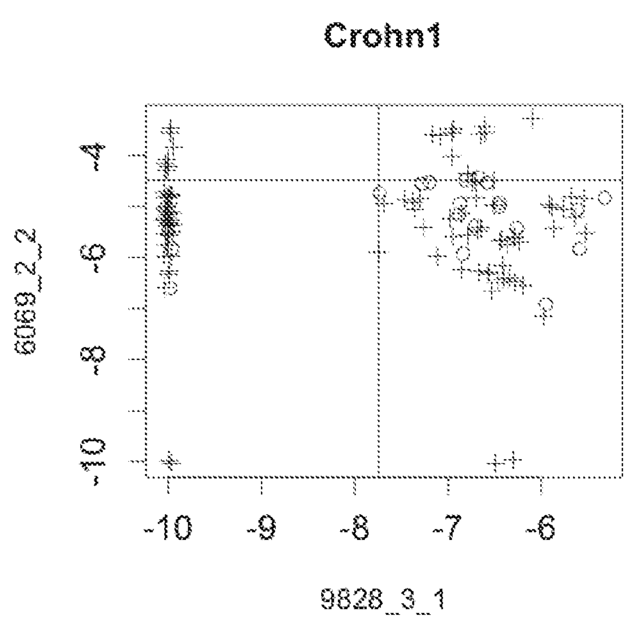

These results are reproduced on FIGS. 7A to 7C (circles represent simple steatosis or Crohn-stable status whereas crosses represent NASH or Crohn-instable status)

3.2.5. The Three Mgs of High Interest are Predictive of the Disease Independently of Each Other Thresholds were determined for each mgs of interest, so that patient samples could be split into a subset of interest that contains samples with low (alternatively, high) relative abundance of the mgs and another subset that contains the other samples (the probability of enrichment at the different thresholds is evaluated using the binomial distribution).

Results are provided on table 2 below:

TABLE 2

| | NASH1:PPV OR NPV (items analysed) | NASH2:PPV OR NPV (items analysed) | Crohn1:PPV OR NPV (items analysed) |
|---|---|---|---|
| 10764_1_2_status2 × low | 0.90 (31) | 0.87 (73) | 0.919 (62) |
| 1523_1_2_status2 × high | 1 (12) | 1 (9) | 1 (13) |
| 1523_2_4_status2 × high | 0.947 (19) | 0.84375 (32) | 1 (7) |
| 1523_3_3_status2 × high | 0.88 (27) | 0.8125 (32) | 1 (12) |
| 1731_14_2_status2 × high | 0.878 (33) | 0.77 (103) | NA |
| 1731_5_10_status2 × low | 0.88 (34) | 0.77 (117) | 0.85 (54) |
| 274_3_1_status2 × high | 1 (5) | 1 (11) | NA |
| 4373_12_3_status2 × low | 0.829 (41) | 0.76 (141) | 0.844 (109) |
| 4381_2_5_status2 × high | 0.86 (30) | 0.78 (112) | 1 (18) |
| 5459_1_3_status1 × high | 0.615 (13) | 0.588 (17) | 0.70 (34) |
| 6063_3_1_status1 × high | 0.625 (24) | 0.71 (102) | 0.8 (75) |
| 6063_6_3_status1 × high | 0.538 (26) | 0.72 (118) | 0.5 (6) |
| 6063_6_3_status2 × low | 0.82 (45) | 0.96 (27) | 0.848 (112) |
| 6069_2_2_status2 × high | 0.813 (59) | 0.844 (77) | 1 (20) |
| 6639_2_8_status1 × high | 0.5 (40) | 0.631 (19) | 0.8125 (16) |
| 6639_2_8_status2 × low | 0.85 (48) | 0.78 (126) | 0.83 (102) |
| 6639_5_9_status1 × high | 0.5 (30) | 0.76 (34) | 0.81 (11) |
| 6639_5_9_status2 × low | 0.85 (40) | 0.76 (141) | 0.83 (107) |
| 6639_6_1_status1 × high | 0.551 (29) | NA | NA |
| 6639_6_1_status2 × low | 0.8125 (64) | NA | NA |
| 8091_1_2_status1 × high | 0.535 (28) | 0.746 (67) | 0.764 (34) |
| 8091_1_2_status2 × low | 0.794 (68) | NA | 0.857 (84) |
| 8091_2_1_status1 × high | 0.555 (27) | 0.75 (60) | 0.722 (36) |
| 8091_2_1_status2 × low | 0.797 (69) | 0.773 (141) | 0.878 (82) |
| 8091_5_1_status1 × high | 0.590 (22) | 0.75 (48) | 0.714 (28) |
| 8091_5_1_status2 × low | 0.80 (63) | NA | 0.86 (90) |
| 8091_7_1_status1 × high | 0.53 (32) | 0.74 (58) | 0.82 (28) |
| 8091_7_1_status2 × low | 0.8125 (64) | NA | 0.83 (90) |
| 9828_3_1_status2 × low | 0.868 (38) | 0.854 (55) | 0.93 (45) |

Positive and Negative Predictive Values (PPV and NPV) estimate the number of good predictions made when a test is positive. In this case, PPV or NPV estimates the ratio of the number of good predictions when the relative abundance of the mgs is above (resp. below) the pre-determined threshold. The higher the PPV or NPV and the larger the subsets of selected samples, the more useful is the predictor.

Interestingly, the subset of interest was enriched in patients with one phenotype (for NASH cohort: Benign or NASH, for Crohn: stable or instable), in which case the relative abundance of the mgs could be used to identify patients with a specific phenotype (note that the other patient samples may not be associated with any status).

3.2.6. The Mgs 6063_6_3 (SEQ ID NO:51-55+Cluster 11) is of Intermediate Interest (NASH1+NASH2)

Figure 4A:
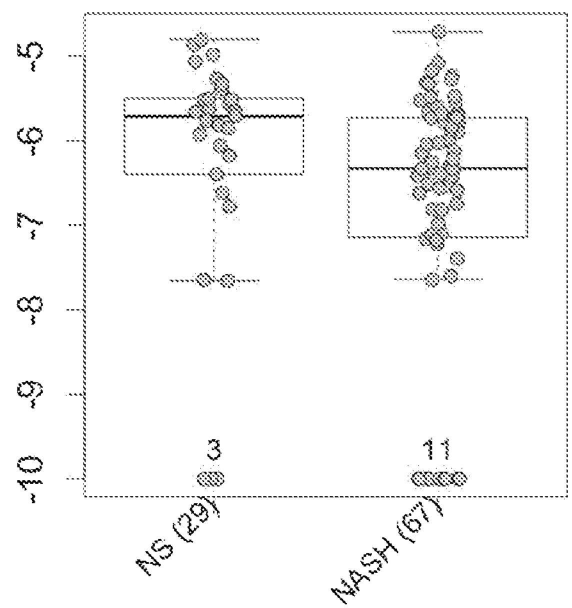
Figure 4B:
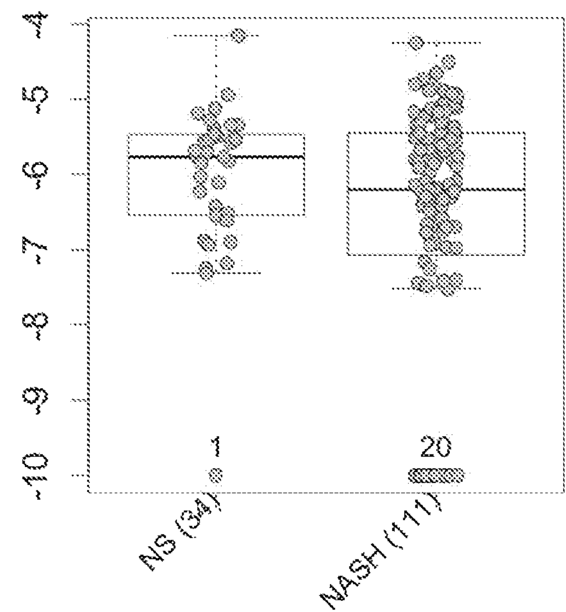
Figure 4C:
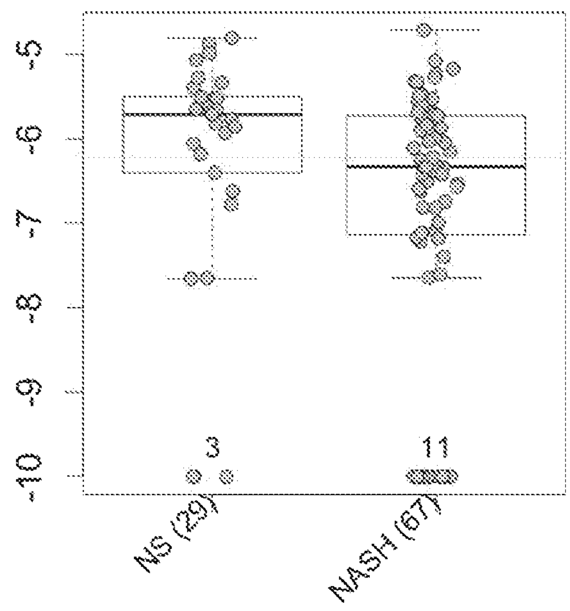
Figure 4D:
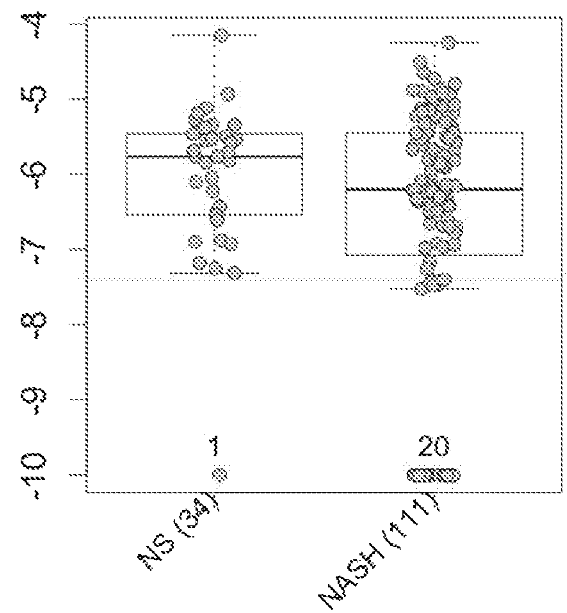

The results of the global approach for this mgs are disclosed on FIGS. 4 and 4B (the number of patients for whom the information is available in indicated between brackets).

Global Trends

Global statistics (comparison of median/distribution—usually the significance cutoff is set to 0.05):

Wilcoxon test:
- NASH1: 0.02
- NASH2: 0.21
- Crohn: 0.83

Kolmogorov-Smirnov test:
- NASH1: 0.048
- NASH2: 0.23
- Crohn: 0.97

Threshold Approach

Using an automatic procedure to determine threshold separating low and high abundance, FIGS. 4 C and D have been obtained (the number of patients for whom the information is avalailable in indicated between brackets):

N.B.

the relative abundances are log 10-transformed

"−10" is an artificial value introduced when the mgs is not detected

The following tables show the NASH status versus low/high mgs relative abundance:

6063_6 low/high versus NASH status (NASH1)

| | Simple Steatosis | NASH |
|---|---|---|
| High | 21 | 30 |
| Low | 8 | 37 |

6063_6 low/high versus NASH status (NASH2)

| | Simple Steatosis | NASH |
|---|---|---|
| High | 33 | 85 |
| Low | 1 | 26 |

Results of the Chi-squared test (comparing phenotypes with low and high mgs abundance—the lower the values, the larger the difference between the two partitions, the stronger the enrichment—usually the significance cutoff is set to 0.05):

NASH1: 0.023 (coefficient Tschuprow: 0.23)

NASH2: 0.015 (coefficient Tschuprow: 0.20)

N.B. The usual metrics (Error rate, Specificity, Sensitivity) do not apply here as the criteria apply for one status of the phenotype only, i.e. the prediction of NASH/instability for part of the population. Positive Predictive Value, alt. Negative Predictive Value, could be computed (but are highly dependent of the prior prevalence of the status).

Link with Other Variables gene richness (defined as the average number of genes detected when sequencing at a depth of 11M reads)

Wilcoxon test NASH1 (96 samples): 1.37e-5

Wilcoxon test NASH2 (137 samples): 4.4e-6

Wilcoxon test Crohn (83 samples): 5.3e-7 waist/height ratio

Wilcoxon test NASH1 (94 samples): 0.0069

Wilcoxon test NASH2 (137 samples): 0.085

Conclusion

Samples where the mgs 6063_6 is not abundant tend to be less healthy, i.e. in NASH cohorts (NASH1, NASH2), patients are more prone to have the advanced state of the disease, i.e. NASH, and not Simple Steatosis.

Example 4: Combinations of High Interest for the Crohn Disease 20 stable and 98 instable patients of the Crohn cohort have been studied.

The values have been calculated as disclosed above, taking into account all the equivalent genes for each cluster.

The mgs numbers referred to in the following table are related to the clusters disclosed the correspondence table 1.

| k | score | auc | er | sn (stable) | sp (instable) | ppv | npv |
|---|---|---|---|---|---|---|---|
| 3 | (1731__5__10 + 6063__3__1)/(1731__14__2) | 0.73 | 0.15 | 0.45 | 0.93 | 0.56 | 0.89 |
| 3 | (1731__5__10 + 6063__3__1)/(1731__14__2) | 0.73 | 0.15 | 0.45 | 0.93 | 0.56 | 0.89 |
| 3 | (10764__1__2 + 1731__5__10)/(1731__14__2) | 0.72 | 0.16 | 0.4 | 0.93 | 0.53 | 0.88 |
| 3 | (1731__5__10 + 6063__3__1)/(1731__14__2) | 0.73 | 0.15 | 0.45 | 0.93 | 0.56 | 0.89 |
| 4 | (1731__5__10 + 6063__3__1)/(1523__3__3 + 1731__14__2) | 0.72 | 0.15 | 0.45 | 0.93 | 0.56 | 0.89 |
| 4 | (1731__5__10 + 6063__3__1 + 8091__7__1)/(1731__14__2) | 0.73 | 0.15 | 0.45 | 0.93 | 0.56 | 0.89 |
| 4 | (1731__5__10 + 6063__3__1 + 8091__5__1)/(1731__14__2) | 0.74 | 0.14 | 0.45 | 0.94 | 0.6 | 0.89 |
| 4 | (1731__5__10 + 6063__3__1 + 8091__5__1)/(1731__14__2) | 0.74 | 0.14 | 0.45 | 0.94 | 0.6 | 0.89 |
| 4 | (1731__5__10 + 6063__6__3 + 9828__3__1)/(1731__14__2) | 0.71 | 0.14 | 0.35 | 0.96 | 0.64 | 0.88 |
| 5 | (1731__5__10 + 4373__12__3 + 6063__3__1)/(1731__14__2 + 4381__2__5) | 0.7 | 0.15 | 0.45 | 0.93 | 0.56 | 0.89 |
| 5 | (1731__5__10 + 4373__12__3 + 6063__3__1 + 9828__3__1)/(1731__14__2) | 0.72 | 0.15 | 0.45 | 0.93 | 0.56 | 0.89 |
| 5 | (1731__5__10 + 6063__3__1 + 6639__5__9)/(1731__14__2 + 274__3__1) | 0.73 | 0.15 | 0.45 | 0.93 | 0.56 | 0.89 |
| 5 | (1731__5__10 + 6063__6__3)/(1731__14__2 + 274__3__1 + 4381__2__5) | 0.7 | 0.14 | 0.4 | 0.96 | 0.67 | 0.89 |
| 5 | (10764__1__2 + 1731__5__10 + 6063__3__1 + 6063__6__3)/(1731__14__2) | 0.72 | 0.14 | 0.4 | 0.96 | 0.67 | 0.89 |
| 5 | (1731__5__10 + 4373__12__3 + 6063__3__1 + 6063__6__3)/(1731__14__2) | 0.72 | 0.14 | 0.4 | 0.96 | 0.67 | 0.89 |
| **5** | **(6639__6__1 + 1731__5__10 + 6063__6__3)/(1523__3__3 + 1731__14__2)** | **0.73** | **0.11** | **0.4** | **0.99** | **0.89** | **0.89** |
| 6 | (1731__5__10 + 6063__3__1 + 6639__2__8 + 6639__5__9)/(1523__3__3 + 1731__14__2) | 0.74 | 0.14 | 0.4 | 0.96 | 0.67 | 0.89 |
| 6 | (1731__5__10 + 4373__12__3 + 6063__3__1 + 6063__6__3)/(1523__2__4 + 1731__14__2) | 0.72 | 0.14 | 0.4 | 0.96 | 0.67 | 0.89 |
| 6 | (1731__5__10 + 6063__3__1 + 6639__2__8 + 8091__5__1 + 9828__3__1)/(1731__14__2) | 0.74 | 0.14 | 0.35 | 0.97 | 0.7 | 0.88 |
| 6 | (10764__1__2 + 6063__3__1 + 8091__2__1 + 8091__7__1)/(1731__14__2 + 274__3__1) | 0.7 | 0.14 | 0.25 | 0.98 | 0.71 | 0.86 |
| 6 | (6639__6__1 + 10764__1__2 + 6063__6__3 + 8091__2__1 + 8091__5__1)/(1731__14__2) | 0.7 | 0.12 | 0.4 | 0.98 | 0.8 | 0.89 |
| 6 | (6639__6__1 + 10764__1__2 + 1731__5__10 + 4373__12__3 + 8091__2__1)/(1731__14__2) | 0.74 | 0.13 | 0.35 | 0.98 | 0.78 | 0.88 |
| 6 | (1731__5__10 + 6063__3__1 + 6063__6__3 + 6639__5__9 + 8091__5__1)/(1731__14__2) | 0.73 | 0.14 | 0.25 | 0.99 | 0.83 | 0.87 |
| **6** | **(1731__5__10 + 6063__3__1 + 6063__6__3 + 6639__2__8 + 8091__5__1)/(1731__14__2)** | **0.74** | **0.11** | **0.4** | **0.99** | **0.89** | **0.89** |
| **6** | **(6639__6__1 + 1731__5__10 + 6063__3__1 + 6063__6__3 + 8091__1__2)/(1731__14__2)** | **0.74** | **0.11** | **0.4** | **0.99** | **0.89** | **0.89** |
| 7 | (6639__6__1 + 1731__5__10 + 6063__3__1)/(1523__1__2 + 1523__2__4 + 1731__14__2 + 274__3__1) | 0.73 | 0.14 | 0.4 | 0.96 | 0.67 | 0.89 |
| 7 | (1731__5__10 + 4373__12__3 + 5459__1__3 + 6063__6__3 + 6639__5__9)/(1731__14__2 + 274__3__1) | 0.73 | 0.14 | 0.4 | 0.96 | 0.67 | 0.89 |
| 7 | (1731__5__10 + 5459__1__3 + 6063__3__1 + 8091__2__1)/(1523__1__2 + 1523__3__3 + 1731__14__2) | 0.73 | 0.14 | 0.3 | 0.97 | 0.67 | 0.87 |
| 7 | (1731__5__10 + 6063__3__1 + 6639__2__8 + 8091__1__2 + 9828__3__1)/(1523__2__4 + 1731__14__2) | 0.74 | 0.14 | 0.35 | 0.97 | 0.7 | 0.88 |
| 7 | (6639__6__1 + 10764__1__2 + 4373__12__3 + 6063__6__3 + 8091__2__1 + 9828__3__1)/(1731__14__2) | 0.7 | 0.13 | 0.35 | 0.98 | 0.78 | 0.88 |
| 7 | (1731__5__10 + 4373__12__3 + 6063__3__1 + 6063__6__3 + 8091__1__2)/(1523__3__3 + 1731__14__2) | 0.72 | 0.14 | 0.25 | 0.99 | 0.83 | 0.87 |
| **7** | **(6639__6__1 + 1731__5__10 + 5459__1__3 + 6063__6__3 + 8091__2__1)/(1523__1__2 + 1731__14__2)** | **0.73** | **0.11** | **0.4** | **0.99** | **0.89** | **0.89** |
| 7 | (6639__6__1 + 10764__1__2 + 1731__5__10 + 5459__1__3 + 6063__6__3 + 8091__7__1)/(1731__14__2) | 0.73 | 0.14 | 0.25 | 0.99 | 0.83 | 0.87 |

-continued

| k | score | auc | er | sn (stable) | sp (instable) | ppv | npv |
|---|---|---|---|---|---|---|---|
| 8 | (10764_1_2 + 1731_5_10 + 6063_3_1 + 8091_2_1)/(1523_2_4 + 1523_3_3 + 1731_14_2 + 274_3_1) | 0.71 | 0.15 | 0.4 | 0.94 | 0.57 | 0.88 |
| 8 | (10764_1_2 + 1731_5_10 + 4373_12_3 + 5459_1_3 + 6063_6_3 + 6639_5_9 + 8091_5_1)/(1731_14_2) | 0.73 | 0.14 | 0.4 | 0.96 | 0.67 | 0.89 |
| 8 | (10764_1_2 + 1731_5_10 + 5459_1_3 + 6639_2_8 + 8091_7_1)/(1523_1_2 + 1523_3_3 + 1731_14_2) | 0.71 | 0.16 | 0.2 | 0.97 | 0.57 | 0.86 |
| 8 | (10764_1_2 + 1731_5_10 + 6639_2_8 + 8091_1_2 + 8091_5_1)/(1523_1_2 + 1523_3_3 + 1731_14_2) | 0.71 | 0.15 | 0.25 | 0.97 | 0.62 | 0.86 |
| 8 | (10764_1_2 + 1731_5_10 + 5459_1_3 + 6639_2_8 + 8091_7_1)/(1523_3_3 + 1731_14_2 + 4381_2_5) | 0.7 | 0.16 | 0.2 | 0.97 | 0.57 | 0.86 |
| 8 | (10764_1_2 + 1731_5_10 + 6063_6_3 + 6639_2_8 + 8091_7_1)/(1731_14_2 + 274_3_1 + 4381_2_5) | 0.7 | 0.14 | 0.25 | 0.99 | 0.83 | 0.87 |
| 8 | (6639_6_1 + 1731_5_10 + 6063_3_1 + 6063_6_3 + 8091_2_1 + 8091_5_1)/(1523_2_4 + 1731_14_2) | 0.74 | 0.11 | 0.4 | 0.99 | 0.89 | 0.89 |
| 8 | (1731_5_10 + 5459_1_3 + 6063_6_3 + 8091_1_2 + 8091_2_1)/(1523_1_2 + 1731_14_2 + 274_3_1) | 0.73 | 0.11 | 0.4 | 0.99 | 0.89 | 0.89 |
| 8 | (1731_5_10 + 4373_12_3 + 6063_3_1 + 6063_6_3 + 8091_1_2 + 8091_7_1)/(1731_14_2 + 274_3_1) | 0.74 | 0.11 | 0.4 | 0.99 | 0.89 | 0.89 |
| 8 | (6639_6_1 + 1731_5_10 + 6063_6_3 + 6639_2_8 + 8091_5_1 + 8091_7_1 + 9828_3_1)/(1731_14_2) | 0.73 | 0.12 | 0.35 | 0.99 | 0.88 | 0.88 |
| 9 | (10764_1_2 + 1731_5_10 + 4373_12_3 + 5459_1_3 + 6063_3_1 + 6639_5_9 + 8091_1_2)/(1523_2_4 + 1731_14_2) | 0.73 | 0.14 | 0.4 | 0.95 | 0.62 | 0.89 |
| 9 | (10764_1_2 + 1731_5_10 + 6063_6_3 + 6639_5_9 + 8091_1_2 + 8091_7_1)/(1523_2_4 + 1523_3_3 + 1731_14_2) | 0.71 | 0.14 | 0.4 | 0.96 | 0.67 | 0.89 |
| 9 | (6639_6_1 + 10764_1_2 + 1731_5_10 + 4373_12_3 + 5459_1_3 + 6639_5_9 + 8091_1_2)/(1523_3_3 + 1731_14_2) | 0.73 | 0.14 | 0.35 | 0.97 | 0.7 | 0.88 |
| 9 | (6639_6_1 + 1731_5_10 + 6063_3_1 + 6639_2_8 + 8091_2_1)/(1523_2_4 + 1731_14_2 + 274_3_1 + 4381_2_5) | 0.74 | 0.12 | 0.45 | 0.97 | 0.75 | 0.9 |
| 9 | (1731_5_10 + 5459_1_3 + 6063_3_1 + 6639_2_8 + 6639_5_9 + 8091_5_1)/(1523_1_2 + 1523_2_4 + 1731_14_2) | 0.74 | 0.12 | 0.45 | 0.97 | 0.75 | 0.9 |
| 9 | (6639_6_1 + 1731_5_10 + 4373_12_3 + 5459_1_3 + 6063_3_1 + 8091_7_1 + 9828_3_1)/(1523_3_3 + 1731_14_2) | 0.72 | 0.14 | 0.35 | 0.97 | 0.7 | 0.88 |
| 9 | (6639_6_1 + 10764_1_2 + 1731_5_10 + 4373_12_3 + 6639_2_8 + 8091_2_1)/(1523_2_4 + 1731_14_2 + 4381_2_5) | 0.72 | 0.13 | 0.4 | 0.97 | 0.73 | 0.89 |
| 9 | (10764_1_2 + 5459_1_3 + 6063_6_3 + 6639_5_9 + 8091_1_2 + 8091_2_1 + 8091_7_1)/(1731_14_2 + 274_3_1) | 0.71 | 0.12 | 0.4 | 0.98 | 0.8 | 0.89 |
| 9 | (1731_5_10 + 6063_6_3 + 6639_2_8 + 8091_5_1 + 8091_7_1)/(1523_1_2 + 1523_3_3 + 1731_14_2 + 4381_2_5) | 0.71 | 0.11 | 0.4 | 0.99 | 0.89 | 0.89 |
| 10 | (10764_1_2 + 1731_5_10 + 6063_3_1 + 6639_2_8 + 8091_5_1 + 9828_3_1)/(1523_1_2 + 1523_3_3 + 1731_14_2 + 274_3_1) | 0.7 | 0.14 | 0.4 | 0.95 | 0.62 | 0.89 |
| 10 | (10764_1_2 + 1731_5_10 + 6063_3_1 + 6063_6_3 + 6639_5_9 + 8091_1_2 + 8091_5_1)/(1731_14_2 + 274_3_1 + 4381_2_5) | 0.7 | 0.14 | 0.4 | 0.96 | 0.67 | 0.89 |
| 10 | (6639_6_1 + 1731_5_10 + 5459_1_3 + 6063_3_1 + 6639_5_9 + 8091_1_2 + 8091_5_1 + 8091_7_1)/(1731_14_2 + 274_3_1) | 0.76 | 0.13 | 0.4 | 0.97 | 0.73 | 0.89 |
| 10 | (6639_6_1 + 10764_1_2 + 1731_5_10 + 4373_12_3 + 5459_1_3 + 6639_2_8)/(1523_2_4 + 1731_14_2 + 274_3_1 + 4381_2_5) | 0.72 | 0.14 | 0.35 | 0.97 | 0.7 | 0.88 |
| 10 | (1731_5_10 + 6063_3_1 + 6063_6_3 + 6639_5_9 + 8091_1_2 + 8091_5_1 + 9828_3_1)/(1523_2_4 + 1731_14_2 + 274_3_1) | 0.72 | 0.12 | 0.35 | 0.99 | 0.88 | 0.88 |
| 10 | (1731_5_10 + 6063_6_3 + 6639_5_9 + 8091_5_1 + 8091_7_1 + 9828_3_1)/(1523_2_4 + 1523_3_3 + 1731_14_2 + 274_3_1) | 0.71 | 0.12 | 0.35 | 0.99 | 0.88 | 0.88 |
| 10 | (1731_5_10 + 5459_1_3 + 6063_3_1 + 6063_6_3 + 8091_2_1 + 8091_7_1)/(1523_2_4 + 1523_3_3 + 1731_14_2 + 4381_2_5) | 0.71 | 0.11 | 0.4 | 0.99 | 0.89 | 0.89 |
| 10 | (6639_6_1 + 1731_5_10 + 4373_12_3 + 6063_3_1 + 6063_6_3 + 6639_5_9 + 8091_2_1 + 8091_7_1)/(1523_3_3 + 1731_14_2) | 0.73 | 0.11 | 0.4 | 0.99 | 0.89 | 0.89 |
| 10 | (6639_6_1 + 1731_5_10 + 5459_1_3 + 6063_6_3 + 6639_5_9 + 8091_1_2)/(1523_1_2 + 1523_2_4 + 1731_14_2 + 274_3_1) | 0.73 | 0.11 | 0.4 | 0.99 | 0.89 | 0.89 |

These results show that the following combinations are of high interest for the Crohn disease:

Cluster 3+cluster 17+cluster 11+cluster 10+cluster 18

Cluster 17+cluster 11+cluster 15+cluster 2+cluster 7+cluster 18

Cluster 3+cluster 17+cluster 11+cluster 15+cluster 13+cluster 18

Cluster 3+cluster 17+cluster 16+cluster 11+cluster 14+cluster 18+cluster 12

Comments

These examples illustrate the discriminative potential of the clusters of genes identified in examples of test implementations/algorithms. The combinations were generated by a random sampling procedure and only the results with AUC above 0.7 were reported.

A simple combination of as little as two clusters of genes provides tests with significant predictive power (AUC >0.7). The more clusters are combined, the better the performance of the test. Other more sophisticated algorithms could be used to improve the performance of the test.

Using the clusters of genes identified, tests can be tuned with various levels of complexity and various performance outcomes by adjusting the number of clusters of genes combined and the threshold used, such as tests with high detection capability for patients with any of the phenotypes (benign steatosis or NASH or NASH+fibrosis) or balanced test with good and balanced performance.

Two options were considered for the development of tests based on the identified clusters of genes: one where only the representative gene of each cluster is used, another one where the arithmetic mean of the 5 most correlated genes of the clusters is used. Both these approaches led to tests with similar performance, which enables various practical implementations of the test. If a highly precise detection method is used for the evaluation of gene abundance, one gene per cluster may be sufficient. On the contrary, if the detection method lacks precision, a combination of genes of each cluster can be used to evaluate the abundance of the cluster and compensate for the low precision of the detection method.

The invention claimed is:

1. A method, comprising:

a) providing a stool sample of a human subject; and b) measuring the amount in the sample of the DNA of at least one bacterial gene selected from SEQ ID NO: 146, SEQ ID NO: 147, SEQ ID NO: 148, SEQ ID NO: 149, and SEQ ID NO: 150.

2. The method of claim 1, wherein the at least one bacterial gene is SEQ ID NO: 146.

3. The method of claim 2, further comprising measuring the amount in the sample of the DNA of at least one bacterial gene selected from SEQ ID NO: 147, SEQ ID NO: 148, SEQ ID NO: 149, and SEQ ID NO: 150.

4. The method of claim 1, wherein the at least one bacterial gene is SEQ ID NO: 147.

5. The method of claim 1, wherein the at least one bacterial gene is SEQ ID NO: 148.

6. The method of claim 1, wherein the at least one bacterial gene is SEQ ID NO: 149.

7. The method of claim 1, wherein the at least one bacterial gene is SEQ ID NO: 150.

8. The method of claim 1, wherein the amount in the sample of the DNA of each of the bacterial genes SEQ ID NO: 146, SEQ ID NO: 147, SEQ ID NO: 148, SEQ ID NO: 149, and SEQ ID NO: 150 is measured.

9. The method of claim 1, wherein the human subject has steatohepatitis without fibrosis.

10. The method of claim 2, wherein the human subject has steatohepatitis without fibrosis.

11. The method of claim 8, wherein the human subject has steatohepatitis without fibrosis.

12. The method of claim 1, wherein the human subject has NASH with fibrosis.

13. The method of claim 2, wherein the human subject has NASH with fibrosis.

14. The method of claim 8, wherein the human subject has NASH with fibrosis.

15. The method of claim 1, wherein the human subject suffers from an inflammatory disease selected from the group consisting of: benign steatosis, non alcoholic steatohepatitis, liver fibrosis, cirrhosis, liver failure, liver cancer, and inflammatory bowel disease.

16. The method of claim 2, wherein the human subject suffers from an inflammatory disease selected from the group consisting of: benign steatosis, non alcoholic steatohepatitis, liver fibrosis, cirrhosis, liver failure, liver cancer, and inflammatory bowel disease.

17. The method of claim 8, wherein the human subject suffers from an inflammatory disease selected from the group consisting of: benign steatosis, non alcoholic steatohepatitis, liver fibrosis, cirrhosis, liver failure, liver cancer, and inflammatory bowel disease.

18. The method of claim 1, wherein the amount in the sample of the DNA is measured by a process comprising DNA sequencing.

19. The method of claim 2, wherein the amount in the sample of the DNA is measured by a process comprising DNA sequencing.

20. The method of claim 8, wherein the amount in the sample of the DNA is measured by a process comprising DNA sequencing.

* * * * *